(12) United States Patent
Jansen et al.

(10) Patent No.: US 10,813,989 B2
(45) Date of Patent: Oct. 27, 2020

(54) NEISSERIA MENINGITIDIS COMPOSITIONS AND METHODS THEREOF

(71) Applicant: PFIZER INC., New York, NY (US)

(72) Inventors: Kathrin Ute Jansen, New York, NY (US); Annaliesa Sybil Anderson, Upper Saddle River, NJ (US); Judith Absalon, New York, NY (US); Jose Miguel Aste-Amezaga, Harleysville, PA (US); Johannes Frederik Beeslaar, Farnham (GB); David Cooper, Monroe, NY (US); John Erwin Farley, Chapel Hill, NC (US); Leah Diane Fletcher, Genesco, NY (US); Shannon Lea Harris, Nanuet, NY (US); Thomas Richard Jones, Bluffton, SC (US); Isis Kanevsky, New York, NY (US); Lakshmi Khandke, Nanuet, NY (US); Paul Liberator, Holmdel, NJ (US); John Lance Perez, Doylestown, PA (US); Lynn Marie Phelan, Lake Hiawatha, NJ (US); Gary Warren Zlotnick, San Antonio, TX (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/704,701

(22) Filed: Dec. 5, 2019

(65) Prior Publication Data

US 2020/0164056 A1 May 28, 2020

Related U.S. Application Data

(63) Continuation of application No. 16/196,150, filed on Nov. 20, 2018, now Pat. No. 10,543,267, which is a continuation of application No. 15/883,334, filed on Jan. 30, 2018, now Pat. No. 10,183,070.

(60) Provisional application No. 62/623,233, filed on Jan. 29, 2018, provisional application No. 62/613,945, filed on Jan. 5, 2018, provisional application No. 62/503,295, filed on May 8, 2017, provisional application No. 62/452,963, filed on Jan. 31, 2017.

(51) Int. Cl.
| | |
|---|---|
| *A61K 39/095* | (2006.01) |
| *A61K 31/7028* | (2006.01) |
| *A61K 47/10* | (2017.01) |
| *A61K 47/18* | (2017.01) |
| *C07K 14/22* | (2006.01) |
| *C07K 16/12* | (2006.01) |
| *A61K 47/26* | (2006.01) |
| *A61K 47/64* | (2017.01) |
| *A61P 31/00* | (2006.01) |
| *A61K 39/12* | (2006.01) |
| *A61K 39/00* | (2006.01) |

(52) U.S. Cl.
CPC ........ *A61K 39/095* (2013.01); *A61K 31/7028* (2013.01); *A61K 39/12* (2013.01); *A61K 47/10* (2013.01); *A61K 47/183* (2013.01); *A61K 47/26* (2013.01); *A61K 47/646* (2017.08); *A61K 47/6415* (2017.08); *A61P 31/00* (2018.01); *C07K 14/22* (2013.01); *C07K 16/1217* (2013.01); *A61K 2039/545* (2013.01); *A61K 2039/55* (2013.01); *A61K 2039/55505* (2013.01); *A61K 2039/6037* (2013.01); *A61K 2039/70* (2013.01); *C12N 2770/32434* (2013.01)

(58) Field of Classification Search
CPC ............ A61K 39/095; A61K 2039/545; A61K 2039/55505; A61K 2039/70; A61K 39/0016; A61K 39/12; A61K 39/295; A61K 2039/5252; A61K 2039/55511; A61K 39/13; A61K 39/39; A61K 2039/541; A61K 2039/55577; A61K 2039/6018; A61K 47/26; A61K 47/646; A61K 2039/6037; A61K 31/7028; A61K 47/02; A61K 47/10; A61K 47/183; A61K 47/22; A61K 47/6415; C07K 14/22; C07K 16/1217

See application file for complete search history.

(56) References Cited

U.S. PATENT DOCUMENTS

| | | | |
|---|---|---|---|
| 4,376,110 A | 3/1983 | David et al. | |
| 4,554,101 A | 11/1985 | Hopp | |
| 4,650,764 A | 3/1987 | Temin et al. | |
| 4,666,829 A | 5/1987 | Glenner et al. | |
| 4,708,871 A | 11/1987 | Geysen | |
| 4,797,368 A | 1/1989 | Carter et al. | |

(Continued)

FOREIGN PATENT DOCUMENTS

| | | |
|---|---|---|
| CA | 2012311 C | 9/1990 |
| EP | 0125023 B1 | 11/1984 |

(Continued)

OTHER PUBLICATIONS

Resinger, et al., "Safety, Tolerability, and Immunogenicity of Gardasil Given Concomitantly with Menactra and Adacel" Pediatrics; 125 (6):1142-1151 (2010).

(Continued)

*Primary Examiner* — Padmavathi Baskar
(74) *Attorney, Agent, or Firm* — Anna C. Chau

(57) ABSTRACT

In one aspect, the invention relates to a composition including a factor H binding protein (fHBP) and a *Neisseria meningitidis* non-serogroup B capsular polysaccharide. The invention further relates to uses of a composition that includes fHBP, such as, for example, uses to elicit an immune response against *N. meningitidis* serogroup B strains and non-serogroup B strains. The compositions and (Continued)

methods described herein are directed to administration in humans, including adults, adolescents, toddlers, and infants.

19 Claims, 16 Drawing Sheets

Specification includes a Sequence Listing.

(56) References Cited

U.S. PATENT DOCUMENTS

| | | |
|---|---|---|
| 4,861,719 A | 8/1989 | Miller |
| 4,912,094 A | 3/1990 | Myers et al. |
| 4,925,792 A | 5/1990 | Rappuoli |
| 4,980,289 A | 12/1990 | Temin et al. |
| 5,057,540 A | 10/1991 | Kensil et al. |
| 5,078,996 A | 1/1992 | Conlon, III et al. |
| 5,124,263 A | 6/1992 | Temin et al. |
| 5,139,941 A | 8/1992 | Muzyczka et al. |
| 5,254,339 A | 10/1993 | Morein |
| 5,399,346 A | 3/1995 | Anderson et al. |
| 5,459,127 A | 10/1995 | Felgner et al. |
| 5,514,581 A | 5/1996 | Ferrari et al. |
| 5,550,213 A | 8/1996 | Anderson et al. |
| 5,565,204 A | 10/1996 | Kuo et al. |
| 5,580,859 A | 12/1996 | Felgner et al. |
| 5,583,038 A | 12/1996 | Stover |
| 5,589,466 A | 12/1996 | Felgner et al. |
| 5,597,572 A | 1/1997 | Huergo et al. |
| 5,614,382 A | 3/1997 | Metcalf |
| 5,668,004 A | 9/1997 | O'Donnell |
| 5,723,127 A | 3/1998 | Scott et al. |
| 5,739,118 A | 4/1998 | Carrano et al. |
| 5,955,580 A | 9/1999 | Green et al. |
| 6,113,918 A | 9/2000 | Johnson et al. |
| 6,130,085 A | 10/2000 | Hamers et al. |
| 6,149,919 A | 11/2000 | Domenighini et al. |
| 6,165,995 A | 12/2000 | Hilgers |
| 6,207,646 B1 | 3/2001 | Krieg et al. |
| 6,245,892 B1 | 6/2001 | Oaks et al. |
| 6,270,775 B1 | 8/2001 | Cleary |
| 6,281,337 B1 | 8/2001 | Cannon-Carlson et al. |
| 6,299,884 B1 | 10/2001 | Van Nest et al. |
| 6,355,253 B1 | 3/2002 | Zlotnick |
| 6,355,255 B1 | 3/2002 | Cleary et al. |
| 6,610,310 B2 | 8/2003 | Hilgers |
| 6,951,653 B2 | 10/2005 | Cleary et al. |
| 7,115,730 B1 | 10/2006 | Pizza et al. |
| 7,118,757 B1 | 10/2006 | Seid et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,576,176 B1 | 8/2009 | Fraser et al. |
| 7,608,278 B2 | 10/2009 | Hoiseth et al. |
| 7,785,608 B2 | 8/2010 | Zlotnick et al. |
| 7,803,387 B2 | 9/2010 | Arico et al. |
| 7,820,789 B2 | 10/2010 | Kirkham et al. |
| 8,039,007 B2 | 10/2011 | Rappuoli et al. |
| 8,101,194 B2 | 1/2012 | Zlotnick et al. |
| 8,273,360 B2 | 9/2012 | Pizza et al. |
| 8,398,988 B2 | 3/2013 | Contori et al. |
| 8,563,006 B2 | 10/2013 | Zlotnick et al. |
| 8,563,007 B1 | 10/2013 | Zlotnick et al. |
| 8,574,597 B2 | 11/2013 | Zlotnick |
| 8,632,995 B2 | 1/2014 | Sun et al. |
| 8,834,888 B2 | 9/2014 | Contorni |
| 8,986,710 B2 | 3/2015 | Anderson et al. |
| 9,107,873 B2 | 8/2015 | Zlotnick et al. |
| 9,132,182 B2 | 9/2015 | Zlotnick et al. |
| 9,168,293 B2 | 10/2015 | Zlotnick et al. |
| 9,249,196 B2 | 2/2016 | Fraser et al. |
| 9,249,198 B2 | 2/2016 | Fraser et al. |
| 9,266,929 B2 | 2/2016 | Fraser et al. |
| 9,267,163 B2 | 2/2016 | Arico et al. |
| 9,486,515 B2 | 11/2016 | Biemans et al. |
| 9,556,240 B2 | 1/2017 | Khandke et al. |
| 9,561,269 B2 | 2/2017 | Zlotnick et al. |
| 9,623,101 B2 | 4/2017 | Zlotnick et al. |
| 9,724,402 B2 | 8/2017 | Anderson et al. |
| 9,757,443 B2 | 9/2017 | Anderson et al. |
| 9,757,444 B2 | 9/2017 | Zlotnick et al. |
| 9,789,179 B2 | 10/2017 | Biemans et al. |
| 9,802,987 B2 | 10/2017 | Dilts et al. |
| 9,822,150 B2 | 11/2017 | Anderson et al. |
| 10,183,070 B2 | 1/2019 | Jansen et al. |
| 10,195,264 B2 | 2/2019 | Contorni et al. |
| 10,196,429 B2 | 2/2019 | Anderson et al. |
| 10,300,122 B2 | 5/2019 | Zlotnick et al. |
| 10,328,142 B2 | 6/2019 | Comanducci |
| 10,512,681 B2 | 12/2019 | Anderson et al. |
| 10,543,267 B2 | 1/2020 | Jansen et al. |
| 10,550,159 B2 | 2/2020 | Anderson et al. |
| 2004/0110670 A1 | 6/2004 | Arico et al. |
| 2004/0167068 A1 | 8/2004 | Zlotnick et al. |
| 2004/0249125 A1 | 12/2004 | Pizza et al. |
| 2006/0251670 A1 | 11/2006 | Comanducci et al. |
| 2006/0257413 A1 | 11/2006 | Zlotnick et al. |
| 2007/0020622 A1 | 1/2007 | Lee et al. |
| 2007/0049532 A1 | 3/2007 | Feige et al. |
| 2007/0082007 A1 | 4/2007 | Zlotnick et al. |
| 2007/0148729 A1 | 6/2007 | Farley et al. |
| 2007/0253964 A1 | 11/2007 | Zlotnick et al. |
| 2009/0035328 A1 | 2/2009 | Granoff |
| 2009/0202593 A1 | 8/2009 | Zlotnick et al. |
| 2009/0252759 A1 | 10/2009 | Biemans et al. |
| 2011/0076299 A1 | 3/2011 | Zlotnick et al. |
| 2011/0189187 A1 | 8/2011 | Zlotnick |
| 2011/0312510 A1 | 12/2011 | Mak et al. |
| 2012/0034261 A1 | 2/2012 | Zlotnick et al. |
| 2012/0070457 A1 | 3/2012 | Daugherty et al. |
| 2012/0093852 A1 | 4/2012 | Anderson et al. |
| 2012/0107339 A1 | 5/2012 | Granoff et al. |
| 2012/0201844 A1 | 8/2012 | Zlotnick et al. |
| 2012/0294880 A1 | 11/2012 | Zlotnick et al. |
| 2012/0301496 A1 | 11/2012 | Zlotnick et al. |
| 2012/0308595 A1 | 12/2012 | Zlotnick et al. |
| 2013/0171194 A1 | 7/2013 | Khandke et al. |
| 2013/0243807 A1 | 9/2013 | Anderson et al. |
| 2013/0259889 A1 | 10/2013 | Zlotnick et al. |
| 2014/0113329 A1 | 4/2014 | Sun et al. |
| 2015/0071959 A1 | 3/2015 | Anderson et al. |
| 2015/0216960 A1 | 8/2015 | Zlotnick et al. |
| 2015/0335724 A1 | 11/2015 | Zlotnick et al. |
| 2016/0017006 A1 | 1/2016 | Dilts et al. |
| 2016/0030543 A1 | 2/2016 | Zlotnick et al. |
| 2016/0347797 A1 | 12/2016 | Anderson et al. |
| 2017/0065714 A1 | 3/2017 | Biemans et al. |
| 2017/0173140 A1 | 6/2017 | Zlotnick et al. |
| 2017/0032622 A1 | 11/2017 | Anderson et al. |
| 2018/0000923 A1 | 1/2018 | Jansen et al. |
| 2018/0022783 A1 | 1/2018 | Anderson et al. |
| 2018/0064806 A1 | 3/2018 | Biemans et al. |
| 2018/0214532 A1 | 8/2018 | Jansen et al. |
| 2018/0371030 A1 | 12/2018 | Anderson et al. |
| 2019/0127426 A1 | 5/2019 | Anderson et al. |
| 2019/0151431 A1 | 5/2019 | Zlotnick et al. |
| 2019/0231861 A1 | 8/2019 | Jansen et al. |
| 2020/0093914 A1 | 3/2020 | Anderson et al. |
| 2020/0123206 A1 | 4/2020 | Anderson et al. |
| 2020/0138933 A1 | 5/2020 | Zlotnick et al. |

FOREIGN PATENT DOCUMENTS

| | | |
|---|---|---|
| EP | 0171496 B1 | 2/1986 |
| EP | 0173494 A2 | 3/1986 |
| EP | 0184187 A2 | 6/1986 |
| EP | 0185573 B1 | 6/1986 |
| EP | 0467714 A1 | 7/1991 |
| EP | 0178220 B1 | 1/1992 |
| EP | 0488528 B1 | 11/1995 |
| EP | 0453242 B1 | 8/1996 |
| EP | 1296713 B1 | 9/2003 |
| EP | 1326634 B1 | 4/2006 |

(56) References Cited

FOREIGN PATENT DOCUMENTS

| | | |
|---|---|---|
| EP | 2351767 A2 | 8/2011 |
| GB | 0121591.2 | 11/1918 |
| JP | 1144977 A | 6/1989 |
| WO | 1986/01533 A1 | 3/1986 |
| WO | 1987/01130 A1 | 2/1987 |
| WO | 1987/002671 A1 | 5/1987 |
| WO | 1989/07150 A1 | 8/1989 |
| WO | 1990/02806 A1 | 3/1990 |
| WO | 1990/10458 A1 | 9/1990 |
| WO | 1991/18088 A1 | 11/1991 |
| WO | 1992/05263 A1 | 4/1992 |
| WO | 1992/19265 A1 | 11/1992 |
| WO | 1993/09239 A1 | 5/1993 |
| WO | 1994/12649 A2 | 6/1994 |
| WO | 1994/21807 A2 | 9/1994 |
| WO | 1994/26914 A1 | 11/1994 |
| WO | 1994/28152 A1 | 12/1994 |
| WO | 1994/28938 A1 | 12/1994 |
| WO | 1995/02697 A1 | 1/1995 |
| WO | 1995/07358 A1 | 3/1995 |
| WO | 1995/18863 A1 | 7/1995 |
| WO | 1995/21931 A1 | 8/1995 |
| WO | 1995/22617 A1 | 8/1995 |
| WO | 1995/26411 A2 | 10/1995 |
| WO | 1995/28494 A1 | 10/1995 |
| WO | 1996/10038 A1 | 4/1996 |
| WO | 1996/14086 A1 | 5/1996 |
| WO | 1996/17823 A1 | 6/1996 |
| WO | 1996/22378 A1 | 7/1996 |
| WO | 1996/25508 A1 | 8/1996 |
| WO | 1996/29412 A1 | 9/1996 |
| WO | 1996/39036 A1 | 12/1996 |
| WO | 1996/40718 A1 | 12/1996 |
| WO | 1997/19182 A1 | 5/1997 |
| WO | 1998/08543 A1 | 3/1998 |
| WO | 1998/08874 A1 | 3/1998 |
| WO | 1998/17805 A2 | 4/1998 |
| WO | 1999/01157 A1 | 1/1999 |
| WO | 1999/01158 A1 | 1/1999 |
| WO | 1999/01175 A1 | 1/1999 |
| WO | 1999/10372 A1 | 3/1999 |
| WO | 1999/24578 A2 | 5/1999 |
| WO | 1999/27944 A1 | 6/1999 |
| WO | 1999/36544 A2 | 7/1999 |
| WO | 1999/40200 A1 | 8/1999 |
| WO | 1999/48525 A1 | 9/1999 |
| WO | 1999/55730 A2 | 11/1999 |
| WO | 1999/55872 A1 | 11/1999 |
| WO | 1999/57280 A2 | 11/1999 |
| WO | 1999/61053 A1 | 12/1999 |
| WO | 2000/18434 A1 | 4/2000 |
| WO | 2000/22430 A2 | 4/2000 |
| WO | 2000/42192 A1 | 7/2000 |
| WO | 2000/43518 A1 | 7/2000 |
| WO | 2000/44890 A1 | 8/2000 |
| WO | 2000/45841 A2 | 8/2000 |
| WO | 2000/50075 A2 | 8/2000 |
| WO | 2000/57906 A1 | 10/2000 |
| WO | 2000/66741 A2 | 11/2000 |
| WO | 2000/66791 A1 | 11/2000 |
| WO | 2000/71574 A2 | 11/2000 |
| WO | 2000/71725 A2 | 11/2000 |
| WO | 2001/04316 A2 | 1/2001 |
| WO | 2001/31019 A2 | 5/2001 |
| WO | 2001/37863 A2 | 5/2001 |
| WO | 2001/38350 A2 | 5/2001 |
| WO | 2001/41800 A2 | 6/2001 |
| WO | 2001/52885 A1 | 7/2001 |
| WO | 2001/64920 A2 | 9/2001 |
| WO | 2001/64922 A2 | 9/2001 |
| WO | 2002/058737 A2 | 8/2002 |
| WO | 2002/079243 A2 | 10/2002 |
| WO | 2002/079246 A2 | 10/2002 |
| WO | 2002/083710 A2 | 10/2002 |
| WO | 2002/083711 A2 | 10/2002 |
| WO | 2002/098368 A2 | 12/2002 |
| WO | 2002/098369 A2 | 12/2002 |
| WO | 2003/007985 A2 | 1/2003 |
| WO | 2003/009869 A1 | 2/2003 |
| WO | 2003/020756 A2 | 3/2003 |
| WO | 2003/047619 A2 | 6/2003 |
| WO | 2003/063766 A2 | 8/2003 |
| WO | 2003/080678 A1 | 10/2003 |
| WO | 2003/094834 A2 | 11/2003 |
| WO | 2003/094960 A2 | 11/2003 |
| WO | 2004/019977 A2 | 3/2004 |
| WO | 2004/019992 A1 | 3/2004 |
| WO | 2004/032958 A1 | 4/2004 |
| WO | 2004/046177 A2 | 6/2004 |
| WO | 2004/048404 A2 | 6/2004 |
| WO | 2004/065603 A2 | 8/2004 |
| WO | 2004/067030 A2 | 8/2004 |
| WO | 2004/067033 A1 | 8/2004 |
| WO | 2004/083251 A2 | 9/2004 |
| WO | 2004/094596 A2 | 11/2004 |
| WO | 2005/000345 A2 | 1/2005 |
| WO | 2005/004908 A1 | 1/2005 |
| WO | 2005/020964 A1 | 3/2005 |
| WO | 2005/032583 A2 | 4/2005 |
| WO | 2005/033148 A1 | 4/2005 |
| WO | 2005/065708 A2 | 7/2005 |
| WO | 2005/090985 A1 | 9/2005 |
| WO | 2005/090986 A2 | 9/2005 |
| WO | 2005/102384 A2 | 11/2005 |
| WO | 2005/103230 A2 | 11/2005 |
| WO | 2005/105140 A2 | 11/2005 |
| WO | 2005/105141 A2 | 11/2005 |
| WO | 2005/108580 A1 | 11/2005 |
| WO | 2005/113607 A2 | 12/2005 |
| WO | 2006/000920 A2 | 1/2006 |
| WO | 2006/011060 A2 | 2/2006 |
| WO | 2006/024954 A2 | 3/2006 |
| WO | 2006/027685 A2 | 3/2006 |
| WO | 2006/046143 A2 | 5/2006 |
| WO | 2006/067632 A2 | 6/2006 |
| WO | 2006/075170 A1 | 7/2006 |
| WO | 2006/081259 A2 | 8/2006 |
| WO | 2006/096701 A2 | 9/2006 |
| WO | 2006/120576 A2 | 11/2006 |
| WO | 2007/000314 A2 | 1/2007 |
| WO | 2007/000341 A2 | 1/2007 |
| WO | 2007/000342 A2 | 1/2007 |
| WO | 2007/000343 A2 | 1/2007 |
| WO | 2007/026249 A2 | 3/2007 |
| WO | 2007/028408 A1 | 3/2007 |
| WO | 2007/060548 A2 | 5/2007 |
| WO | 2007/071786 A2 | 6/2007 |
| WO | 2007/127665 A2 | 8/2007 |
| WO | 2007/111940 A2 | 10/2007 |
| WO | 2007/127668 A2 | 11/2007 |
| WO | 2007/144316 A2 | 12/2007 |
| WO | 2007/144317 A2 | 12/2007 |
| WO | 2008/001222 A2 | 1/2008 |
| WO | 2008/001224 A2 | 1/2008 |
| WO | 2008/013943 A2 | 1/2008 |
| WO | 2008/079372 A2 | 7/2008 |
| WO | 2008/084411 A2 | 7/2008 |
| WO | 2008/149238 A2 | 12/2008 |
| WO | 2009/010877 A2 | 1/2009 |
| WO | 2009/016515 A2 | 2/2009 |
| WO | 2009/050586 A1 | 4/2009 |
| WO | 2009/104097 A2 | 8/2009 |
| WO | 2009/109550 A1 | 9/2009 |
| WO | 2009/114485 A2 | 9/2009 |
| WO | 2009/143168 A2 | 11/2009 |
| WO | 2009/158142 A1 | 12/2009 |
| WO | 2010/027872 A2 | 3/2010 |
| WO | 2010/028096 A2 | 3/2010 |
| WO | 2010/028859 A1 | 3/2010 |
| WO | 2010/067202 A2 | 6/2010 |
| WO | 2010/070453 A2 | 6/2010 |
| WO | 2010/077422 A2 | 7/2010 |
| WO | 2010/109323 A1 | 9/2010 |
| WO | 2010/109324 A1 | 9/2010 |

(56) References Cited

FOREIGN PATENT DOCUMENTS

| | | |
|---|---|---|
| WO | 2010/127172 A2 | 11/2010 |
| WO | 2011/024072 A2 | 3/2011 |
| WO | 2011/039631 A2 | 4/2011 |
| WO | 2011/042516 A2 | 4/2011 |
| WO | 2011/051893 A1 | 5/2011 |
| WO | 2011/080595 A2 | 7/2011 |
| WO | 2011/110531 A2 | 9/2011 |
| WO | 2011/110634 A1 | 9/2011 |
| WO | 2011/110635 A1 | 9/2011 |
| WO | 2011/126863 A1 | 10/2011 |
| WO | 2011/161653 A1 | 12/2011 |
| WO | 2012/020326 A1 | 2/2012 |
| WO | 2012/025873 A2 | 3/2012 |
| WO | 2012/031271 A1 | 3/2012 |
| WO | 2012/032169 A1 | 3/2012 |
| WO | 2012/032489 A1 | 3/2012 |
| WO | 2012/032498 A2 | 3/2012 |
| WO | 2012/035519 A1 | 3/2012 |
| WO | 2012/117377 A1 | 9/2012 |
| WO | 2012/134975 A1 | 10/2012 |
| WO | 2013/132452 A2 | 9/2013 |
| WO | 2014/136064 A2 | 9/2014 |
| WO | 2015/033251 A2 | 3/2015 |
| WO | 2016/132294 A1 | 8/2016 |

OTHER PUBLICATIONS

Richmond, et al, On Behalf of the 2001 Study Investigators, "Safety, immunogenicity, and tolerability of meningococcal serogroup B bivalent recombinant lipoprotein 2086 vaccine in healthy adolescents: a ranomised, single-blind, placebo-controlled, phase 2 trial", www.thelancet.com/infection, 13 pages, Published online May 7, 2012.
Rinaudo et al, "Vaccinology in the genome era", The Journal of Clinical Investigation, 119(9):2515-2525 (2009).
Rodriguez, A.P., et al., "The Epidemiological Impact of Antimeningococcal B Vaccination in Cuba", Mem Inst Oswaldo Cruz, Jul.-Aug. 1999, 94 (4): 433-440 (1999).
Romero et al, "Current Status of Meningococcal Group B Vaccine Candidates: Capsular or Noncapsular?" Clinical Microbiology Reviews 7(4):559-575 (1994).
Rose et al, "Pyruvic Acid is Attached Through Its Central Carbon Atom to the Amino Terminus of the Recombinant DNA-derived DNA-binding Protein Ner of Bacteriophage Mu", The Journal of Biological Chemistry 267 (27):19101-19106 (1992).
Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Rosenqvist, E., et al., "Effect of Aluminium Hydroxide and Meningococcal Serogroup C Capsular Polysaccharide on the Immunogenicity and Reactogenicity of a Group B Neisseria Meningitides Outer Membrane Vesicle Vaccine", Dev Biol Stand, 1998, 92: 323-333.
Rosenstein et al, "Meningococcal Vaccines", Infectious Disease Clinics of North America 15(1):155-169 (2001).
Ross, et al., "Identification of Vaccine Candidate Antigens from a Genomic Analysis of Porphyromonas gingivalis", Vaccine 19:4135-4142 (2001).
Sahagan et al, "A Genetically Engineered Murine/Human Chimeric Antibody Retains Specificity for Human Tumor-Associated Antigen", The Journal of Immunology 137(3):1066-1074 (1986).
Salzberg et al, "Microbial gene identification using interpolated Markov models", Nucleic Acids Research 26(2):544-548 (1998).
Sambrook et al, Molecular Cloning: A Laboratory Manual, Third Edition, Cold Spring Harbor Laboratory Press, Cold Spring Harbor, New York (2001).
Sambrook et al, "Analysis and Cloning of Eukaryotic Genomic DNA", Molecular Cloning: A Laboratory Manual, Second Edition, Cold Spring Harbor Laboratory Press, Cold Spring Harbor, New York, Chapter 9, pp. 9.1-9.62 (1989).
Sambrook et al, "Synthetic Oligonucleotide Probes", Molecular Cloning: A Laboratory Manual, Second Edition, Cold Spring Harbor Laboratory Press, Cold Spring Harbor, New York, Chapter 11, pp. 11.1-11.61 (1989).
Samulski et al, "A Recombinant Plasmid from Which an Infectious Adeno-Associated Virus Genome Can Be Excised In Vitro and Its Use to Study Viral Replication", Journal of Virology 61(10):3096-3101 (1987).
Samulski et al, "Helper-Free Stocks of Recombinant Adeno-Associated Viruses: Normal Integration Does Not Require Viral Gene Expression", Journal of Virology 63(9):3822-3828 (1989).
Sanger Centre FTP files [online] URL: ftp://ftp.sanger.ac.uk/pub/pathogens/nm/, dated Jul. 23, 2008.
Sanger Centre's "Projects" website as of Dec. 10, 1997 as retrievable via http://web.archive.org, accessed Mar. 15, 2010.
Sankaran et al, "Modification of Bacterial Lipoproteins", Methods in Enzymology 250:683-697 (1995).
Sankaran, K., et al., "Lipid Modification of Bacterial Prolipoprotein", The Journal of Biological Chemistry, 269(31):19701-19706 (1994).
Sastalla et al, "Codon-Optimized Fluorescent Proteins Designed for Expression in Low-GC Gram-Positive Bacteria", Applied and Environmental Microbiology, 75(7):2099-2110 (2009).
Saukkonen et al, "Protective efficacy of monoclonal antibodies to class 1 and class 3 outer membrane proteins of Neisseria meningitidis B:15:P1.16 in infant rat infection model: new prospects for vaccine development", Microbial Pathogenesis 3:261-267 (1987).
Sedegah et al, "Improving Protective Immunity Induced by DNA-Based Immunization: Priming with Antigen and GM-CSF-Encoding Plasmid DNA and Boosting witih Antigen-Expressing Recombinant Poxvirus", The Journal of Immunology 164:5905-5912 (2000).
Sedegah et al, "Protection against malaria by immunization with plasmid DNA encoding circumsporozoite protein", Proc. Natl. Acad. Sci. 91:9866-9870 (1994).
Seib et al, "Characterization of Diverse Subvariants of the Meningococcal Factor H (fH) Binding Protein for Their Ability to Bind fH, To Mediate Serum Resistance, and to Induce Bactericidal Antibodies", Infection and Immunity 79(2):970-981 (2011).
Sepelyak et al, "Adsorption of Pepsin by Aluminum Hydroxide I: Adsorption Mechanism", Journal of Pharmaceutical Sciences 73(11):1514-1517 (1984).
Sequence Analysis in Molecular Biology. Treasure Trove or Trivial Pursuit, Gunnar von Heijne, Academic Press (1987).
Sequence Analysis Primer, Gribskov and Devereux, eds., M Stockton Press, New York (1991).
Sequence for "Putative Lipoprotein [Neisseria Meningitidis Z2491]", NCBI Reference Sequence:YP_002342062.1, dated May 6, 2009, accessed Aug. 4, 2009.
Serruto et al, "Genome-based approaches to develop vaccines against bacterial pathogens", Vaccine 27:3245-3250 (2009).
Sierra, G.V.G., et al.,"Vaccine Against Group B Neisseria Meningitidis: Protection Trial and Mass Vaccination Results in Cuba" NIPH Annals, 14 (2): 195-210 (1991).
Smith et al., "Nucleotide sequence determination and genetic analysis of the bacteroides plasmid, pBI143," Plasmid 34(3):211-222 (1995).
Snape et al, "Immunogenicity of Two Investigational Serogroup B Meningococcal Vaccines in the First Year of Life", The Pediatric Infectious Disease Journal 29(11):e71-e79 (2010).
Snapper et al, "Bacterial Lipoproteins May Substitute for Cytokines in the Humoral Immune Response to T Cell-Independent Type II Antigens", The Journal of Immunology 155:5582-5589 (1995).
Snapper et al, "IL-3 and Granulocyte-Macrophage Colony-Stimulating Factor Strongly Induce Ig secretion by Sort-Purified Murine B Cells Activated Through the Membrane Ig, but Not the CD40, Signaling Pathway", The Journal of Immunology 154:5842-5850 (1995).
Sonnhammer et al, "Pfam: A Comprehensive Database of Protein Domain Families Based on Seed Alignments", Proteins: Structure, Function, and Genetics 28:405-420 (1997).
Stedman's Medical Dictionary, Illustrated, 24th Edition, Williams & Wilkins, Baltimore, Maryland, p. 707 (1982).

(56) References Cited

OTHER PUBLICATIONS

Stevens, "Streptococcal Toxic-Shock Syndrome: Spectrum of Disease, Pathogenesis, and New Concepts in Treatment", Emerging Infectious Diseases 1(3):69-78 (1995).
Stockbauer et al, "A natural variant of the cysteine protease virulence factor of group A *Streptococcus* with an arginine-glycine-aspartic acid (RGD) motif preferentially binds human integrins alphavbeta3 and alphaIIbbeta3", Proc. Natl. Acad. Sci. 96:242-247 (1999).
Stratford-Perricaudet et al, "Widespread Long-term Gene Transfer to Mouse Skeletal Muscles and Heart", J. Clin. Invest. 90:626-630 (1992).
Strauss, "Using DNA Fragments as Probes", Current Protocols in Molecular Biology, Supp. 24, 6.3.1-6.3.6 (1993).
Suhrbier, "Multi-epitope DNA vaccines", Immunology and Cell Biology, 75(4):402-408 (1997).
Sun et al, "Chimeric antibody with human constant regions and mouse variable regions directed against carcinoma-associated antigen 17-1A", Proc. Natl. Acad. Sci. 84:214-218 (1987).
Supplementary Declaration by Dr. Julian Parkhill submitted in Opposition Proceedings against Novartis EP1645631 on May 10, 2010.
Supplementary Submission in Opposition Proceedings against Novartis EP 1 645 631 submitted May 25, 2010.
Sutcliff et al, "Lipoproteins of Gram-Positive Bacteria", Journal of Bacteriology 177(5):1123-1128 (1995).
Sworn Statement from Dr. Giovanna Campanella submitted in Opposition Proceedings against Novartis EP1409013 on Nov. 10, 2011.
Sworn Statement from Dr. Rino Rappuoli submitted in Opposition Proceedings against Novartis EP1645631 on Oct. 14, 2011.
Tappero et al, "Immunogenicity of 2 Serogroup B Outer-Membrane Protein Meningococcal Vaccines", JAMA 281(16):1520-1527 (1999).
Opposition papers EP2343308 May 2-9, 2016; 274 pages; accessed https://register.epo.org/application?number=EP10183020&lng=en &tab=doclist on May 16, 2016.
Opposition papers EP2343308 Apr. 6-13, 2016; 30 pages; accessed https://register.epo.org/application?number=EP10183020&lng=en &tab=doclist on May 16, 2016.
Opposition notice EP2343308_(Nov. 13, 2015); 21 pages; accessed https://register.epo.org/application?number=EP10183020&lng=en &tab=doclist on Apr. 21, 2016.
Oudega et al, "A lipoprotein signal peptide plus a cysteine residue at the amino-terminal end of the periplasmic proteins beta-lactamase is sufficient for its lipid modification, processing and membrane localization in *Escherichia coli*", FEMS Microbiology Letters 108:353-360 (1993).
Oudega et al, "*Escherichia coli* SecB, SecA, and SecY Proteins are Required for Expression and Membrane Insertion of the Bacteriocin Release Protein, a Small Lipoprotein", Journal of Bacteriology 175(5):1543-1547 (1993).
Pajon et al, "Frequency of factor H-binding protein modular groups and susceptibility to cross-reactive bactericidal activity in invasive meningococcal isolates", Vaccine 28:2122-2129 (2010).
Pannekoek et al, "Construction of recombinant neisserial Hsp60 proteins and mapping of antigenic domains", Molecular Microbiology 15(2):277-285 (1995).
Paoletti et al, "Potency of clinical group B streptococcal conjugate vaccines", Vaccine, 19(15-16):2118-2126 (2001).
Park et al, "DIVCLUS: an automatic method in the GEANFAM-MER package that finds homologous domains in single- and multi-domain proteins", Bioinformatics 14(2):144-150 (1998).
Parkhill et al, "Complete DNA sequence of a serogroup A strain of Neisseria meningitidis Z2491", Nature 404:502-506 (2000).
Parkhill, "Campylobacter jejuni genome sequence at the Sanger Centre", (May 8, 1998), available at: http://www.bio.net/bionet/mm/ bionews/1997-May/00442.html.
Patel, M., "Outbreaks of Serogroup B Meningococcal Disease on University Campuses—2013", Medical Officer, Meningitis and Vaccine Preventable Diseases Branch, http://www.cdc.gov/vaccines/ acip/meetings/downloads/slides-2014-02/04-Mening-Patel.pdf, 16 Pages, Apr. 3, 2014.
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
PCT Annex to Form PCT/ISA/206 Communication Relating to the Results of the Partial International Search, PCT/US2007/026238.
PCT International Search Report for PCT/IB2011/053934 dated Jan. 20, 2012.
PCT International Search Report for PCT/US02/32369 dated Nov. 14, 2003.
PCT International Search Report for PCT/US2007/026238 dated Feb. 23, 2009.
Perrett et al, "Towards an improved serogroup B Neisseria meningitidis vaccine", Expert Opin. Biol. Ther. 5(12):1611-1625 (2005).
Pettersson et al., "Vaccine potential of the Neisseria meningitidis Lactoferrin-binding Proteins LbpA and LbpB", Vaccine, 24(17):3545-3557 (2006).
Pettersson, et al., "The meningococcal lactoferrin receptor", IPNC Abstract (1998).
Phase II clinical results for Novartis vaccine, Novartis Media Release (Oct. 9, 2008).
Phillips, "The challenge of gene therapy and DNA delivery", Journal of Pharmacy and Pharmacology 53:1169-1174 (2001).
Pierschbacher et al, "Influence of Stereochemistry of the Sequence Arg-Gly-Asp-Xaa on Binding Specificity in Cell Adhesion",The Journal of Biological Chemistry 262(36):17294-17298 (1987).
Pillai et al, "Outer membrane protein (OMP) based vaccine for Neisseria meningitidis serogroup B", Vaccine 23:2206-2209 (2005).
Pizza et al, "Factor H-binding protein, a unique meningococcal vaccine antigen", Vaccine 26(Supp8):I46-I48 (2008).
Pizza et al, "Identification of Vaccine Candidates Against Serogroup B Meningococcus by Whole-Genome Sequencing", Science 287:1816-1820 (2000).
Pizza, Preparation of Meningococcal Antigens (2005), available at: http://cordis.europa.eu/search/index.cfm?fuseaction=result.document &RS LANG=EN&RS RCN=7461241&q=.
Podbielski et al, "The Group A Streptococcal virR49 Gene Controls Expression of Four Structural vir Regulon Genes", Infection and Immunity 63(1):9-20 (1995).
Polakowski, L., "Pharmacovigilance Plan Review—Trumenba", XP055266007, Retrieved form the Internet: URL: http://www/fda. gov/downloads/BiologicsBlood/Vaccines/Vaccines/ApprovedProducts/ UCM424630: pp. 1-28, Nov. 23, 2014.
Pollitt et al, "Effect of Amino Acid Substitutions at the Signal Peptide Cleavage Site of the *Escherichia coli* Major Outer Membrane Lipoprotein", The Journal of Biological Chemistry 261(4):1835-1837 (1986).
Poolman et al, "Colony variants of Neisseria meningitidis strain 2996 (B-2b:P1.2): influence of class-5 outer membrane proteins and lipopolysaccharides", J Med Microbiol 19(2):203-209 (1985).
Poolman, "Bacterial Outer Membrane Protein Vaccines: The Meningococcal Example", Advances in Experimental Medicine & Biology 397:73-77 (1996).
Poolman, "Development of a meningococcal vaccine," Infectious Agents and Disease 4(1):13-28 (1995).
Preliminary Opinion of the Opposition Division in Opposition against Novartis EP 1 645 631 dated Jun. 24, 2011.
Proft et al, "Identification and Characterization of Novel Superantigens from *Streptococcus pyogenes*", J. Exp. Med. 189(1):89-101 (1999).
Progress through the Sanger Institute FTP Server, submitted in Opposition Proceedings against Novartis EP1645631 on May 8, 2009.
Prome et al, "Characterization of new amino-terminal blocking groups in the normal human adult hemoglobin Hb A1b", Eur. Mass Spectrom. 1(2):195-201 (1995).
Prome et al, "Structure of the Human Adult Hemoglobin Minor Fraction A1b bu Electrospray and Secondary Ion Mass Spectrom-

(56) References Cited

OTHER PUBLICATIONS etry. Pyruvic Acid as Amino-Terminal Blocking Group", The Journal of Biological Chemistry 266(20):13050-13054 (1991).
Prosecution history of U.S. Appl. No. 13/455,326, dated Apr. 26, 2013, (Third-party submission under 37 CFR 1.290).
PSORT analysis of 200 of the sequences disclosed in PCT/US99/09346, submitted in Opposition Proceedings against Novartis EP1645631 on May 25, 2010 Part 1.
PSORT analysis of 200 of the sequences disclosed in PCT/US99/09346, submitted in Opposition Proceedings against Novartis EP1645631 on May 25, 2010 Part 2.
PSORT analysis of SEQ ID Nos. 4 and 6, and of 'Contig295' 300mer, submitted in Opposition Proceedings against Novartis EP1645631 on May 8, 2009.
PSORT prediction result for SEQ ID No. 2, submitted in Opposition Proceedings against Novartis EP1645631 on May 25, 2010.
Pugsley, "The Complete General Secretory Pathway in Gram-Negative Bacteria", Microbiological Reviews 57(1):50-108 (1993).
Quinn et al, "Immunological Relationship between the Class I Epitope of Streptococcal M Protein and Myosin", Infection and Immunity 66(9):4418-4424 (1998).
Random House Dictionary, Random House, New York, p. 546 (1984).
Reda et al, "Phylogenetic Distribution of Streptococcal Superantigen SSA Allelic Variants Provides Evidence for Horizontal Transfer of ssa within *Streptococcus pyogenes*", Infection and Immunity 64(4):1161-1165 (1996).
Registration document for VA-MENGOC-BC® Vaccine Together with Translation Into English and Translation Certificate.
Fischetti et al, "Conservation of a hexapeptide sequence in the anchor region of surface proteins from Gram-positive cocci", Molecular Microbiology 4(9):1603-1605 (1990).
Fleischmann et al, "Whole-Genome Random Sequencing and Assembly of Haemophilus influenzae Rd", Science 269:496-501 (1995).
Fletcher et al, "Vaccine Potential of the Neisseria meningitidis 2086 Lipoprotein", Infection and Immunity 72(4):2088-2100 (2004).
Fogg et al, "Constitutive Expression of Fibronectin Binding in *Streptococcus pyogenes* as a Result of Anaerobic Activation of rofA", Journal of Bacteriology 179(19):6172-6180 (1997).
Fontana et al, "A genomic approach to identify vaccine candidates against gonococcus", Abstract from the 13th International Pathogenic Neisseria Conference, Oslo Norway, Sep. 1-6, 2002, p. 248 (http://neisseria.org/ipnc/history.shtml).
Foster et al, "Surface protein adhesins of *Staphylococcus aureus*", Trends in Microbiology 6(12):484-488 (1998).
Frankel et al, "Characterization of diphtheria fusion proteins targeted to the human interleukin-3 receptor", Protein Engineering 13(8):579-591 (2000).
Fraser et al, "Genomic sequence of a Lyme disease spirochaete, Borrelia burgdorferi", Nature 390:580-591 (1997).
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Fukasawa et al, "Neisseria meningitidis serogroup C polysaccharide and serogroup B outer membrane vesicle conjugate as a bivalent meningococcus vaccine candidate", Vaccine 17:2951-2958 (1999).
Gentz et al, "Bioassay for trans-activation using purified human immunodeficiency virus tat-encoded protein: Trans-activation requires mRNA synthesis", Proc. Natl. Acad. Sci. 86:821-824 (1989).
Geysen et al, "A Priori Delineation of a Peptide Which Mimics a Discontinuous Antigenic Determinant", Molecular Immunology, 23(7):709-715 (1986).
Geysen et al, "Use of peptide synthesis to probe viral antigens for epitopes to a resolution of a single amino acid", Proc. Natl. Acad. Sci. USA, 81(13):3998-4002 (1984).
Gil, J., et al., Proteomic Study via a Non-Gel Based Approach of Meningococcal Outer Membrane Vesicle Vaccine Obtained from Strain CU385 Human Vaccines, 5 (5): 347-356 (2009).

Giuliani et al, "The Region Comprising Amino Acids 100 to 255 of Neisseria meningitidis Lipoprotein GNA 1870 Elicits Bactericidal Antibodies", Infection and Immunity 73(2):1151-1160 (2005).
Giuliani et al, "A universal vaccine for serogroup B meningococcus" Proc Natl Acad Sci 103(29):10834-10839 (2006).
*GlaxoSmithKline UK Ltd v Wyeth Holdings LLC* [2016] EWHC 1045 (Ch) (May 12, 2016); Case No. HP-2015-000002; 66 pages; accessed http://www.bailii.org/ew/cases/EWHC/Ch/2016/1045.html on Jul. 11, 2016.
Gold et al., "Chapter 78. Translational Initiation", *Escherichia coli* and *Salmonella typhimurium*: Cellular and Molecular Biology, Ed. Neidhardt FC, vol. 2, pp. 1302-1307 (1987).
Goldschneider et al, "Human Immunity to the Meningococcus I. The Role of Humoral Antibodies", Journal of Experimental Medicine 129(6):1307-1326 (1969).
Goldschneider et al, "Human Immunity to the Meningococcus II. Development of Natural Immunity", Journal of Experimental Medicine 129(6):1327-1348 (1969).
Gomez et al, "The Bacillus subtilis lipoprotein LpIA causes cell lysis when expressed in *Escherichia coli*", Microbiology 140:1839-1845 (1994).
Gotschlich et al, "Human Immunity to the Meningococcus. IV. Immunogenicity of Group A and Group C Meningococcal Polysaccharides in Human Volunteers", Journal of Experimental Medicine 129(6):1367-1384 (1969).
Gotschlich et al, "Human Immunity to the Meningococcus. V. The Effect of Immunization with Meningococcal Group C Polysaccharide on the Carrier State", Journal of Experimental Medicine 129(6):1385-1395 (1969).
Graham et al, "Characteristics of a Human Cell Line Transformed by DNA from Human Adenovirus Type 5", J. Gen. Virology 36:59-72 (1977).
Graham, "Covalently closed circles of human adenovirus DNA are infectious", The EMBO Journal 3(12):2917-2922 (1984).
Grandi, "Reverse Vaccinology: A Critical Analysis", Encyclopedia of Genetics, Genomics, Proteomics and Bioinformatics, pp. 1320-1330 (2005).
Green et al, "The e (P4) Outer Membrane Protein of Haemophilus influenzae: Biologic Activity of Anti-e Serum and Cloning and Sequencing of the Structural Gene", Infection and Immunity 59(9):3191-3198 (1991).
Greenspan et al, "Defining epitopes: It's not as easy as it seems", Nature Biotechnology 17:936-937 (1999).
Griffin et al, "Computer Analysis of Sequence Data", Methods in Molecular Biology, vol. 24, Part 1, Chapter 1, Humana Press, New Jersey (1994).
Gupta, "Aluminum compounds as vaccine adjuvants", Advanced Drug Delivery Reviews 32(3):155-172 (1998).
Guzman et al, "Tight Regulation, Modulation, and High-Level Expression by Vectors Containing the Arabinose PBAD Promoter", Journal of Bacteriology 177(14):4121-4130 (1995).
Hacker et al, "Pathogenicity islands of virulent bacteria: structure, function and impact on microbial evolution", Molecular Microbiology 23(6):1089-1097 (1997).
Hanski et al, "Expression of protein F, the fibronectin-binding protein of *Streptococcus pyogenes* JRS4, in heterologous streptococcal and enterococcal strains promotes their adherence to respiratory epithelial cells", Infection and Immunity 60(12):5119-5125 (1992).
Hanski et al, "Protein F, a fibronectin-binding protein, is an adhesin of the group A *Streptococcus Streptococcus pyogenes*", Proc. Natl. Acad. Sci. 89:6172-6176 (1992).
Hansson et al, "Expression of Truncated and Full-Length Forms of the Lyme Disease Borrelia Outer Surface Protein A in *Escherichia coli*", Protein Expression and Purification 6:15-24 (1995).
Harris et al, "Preclinical evidence for the potential of a bivalent fHBP vaccine to prevent Neisseria meningitidis serogroup C disease", Human Vaccines 7(Supplement):68-74 (2011).
HAVRIX prescribing information, https://www.gsksource.com/pharma/content/dam/GlaxoSmithKline/US/en/Prescribing_Information/Havrix/pdf/HAVRIX.PDF, revised Jul. 2014, accessed Feb. 18, 2015.

(56) References Cited

OTHER PUBLICATIONS

Hayashi et al, "Lipoproteins in Bacteria", Journal of Bioenergetics and Biomembranes 22(3):451-471 (1990).
Hedari, et al., Meningococcal Serogroups A, C, W-135, and Y Tetanus Toxoid Conjugate Vaccine: A New Conjugate Vaccine Against Invasive Meningococcal Disease., Infect Drug Resist.;7:85-99 (2014).
Hem et al, "Chapter 9: Structure and Properties of Aluminum-Containing Adjuvants", Vaccine Design: The Subunit and Adjuvant Approach, Plenum Press, New York, pp. 249-276 (1995).
Hernandez-Sanchez et al, "lambda bar minigene-mediated inhibition of protein synthesis involves accumulation of peptidyl-tRNA and starvation for tRNA", The EMBO Journal 17(13):3758-3765 (1998).
Hornyik et al, "Cerebrospinal Fluid Shunt Infection by Neisseria sicca", Pediatr Neurosurg 21:189-191 (1994).
Houghten, "General Method for the rapid solid-phase synthesis of large numbers of peptides: Specificity of antigen-antibody interaction at the level of individual amino acids", Proceedings of the National Academy of Sciences of USA 82:5131-5135 (1985.
Huang et al, "The streptokinase gene of group A streptococci: cloning, expression in *Escherichia coli*, and sequence analysis", Molecular Microbiology 3(2):197-205 (1989).
Hung, "The Neisseria meningitidis Macrophage Infectivity Potentiator Protein Induces Cross-Strain Serum Bactericidal Activity and Is a Potential Serogroup B Vaccine Candidate", Infection and Immunity, 79(9):3784-3791 (2011).
Hynes et al, "Analysis of a Second Bacteriophage Hyaluronidase Gene from *Streptococcus pyogenes*: Evidence for a Third Hyaluronidase Involved in Extracellular Enzymatic Activity", Infection and Immunity 63(8):3015-3020 (1995).
Hynes et al, "The extracellular hyaluronidase gene (hylA) of *Streptococcus pyogenes*", FEMS Microbiology Letters 184:109-112 (2000).
Interlocutory Decision of the Opposition Division in Opposition against Novartis EP 1 645 631 dated May 21, 2012.
Isberg et al, "Binding and internalization of microorganisms by integrin receptors", Trends in Microbiology 2(1):10-14 (1994).
Jackson et al, U.S. Appl. No. 60/098,685, filed Sep. 1, 1998.
Aasel et al., "Most antibodies to PorB and Rmp do not bind to viable meningococci, but bind strongly to ethanol-killed bacteria", Abstract from the 11th International Pathogenic Neisseria Conference (Nice France, Nov. 1-6, 1998), pp. 37-38 (http://neisseria.org/ipnc/history.shtml).
Abdillahi et al, "Whole-cell ELISA for typing Neisseria meningitidis with monoclonal antibodies", FEMS Microbiology Letters 48:367-371 (1987).
Abdillahi et al, "Neisseria meningitidis group B serosubtyping using monoclonal antibodies in whole-cell Elisa", Microbial Pathogenesis 4:27-32 (1988).
Achtman et al, "Epidemic Spread and Anitgenic Variability of Neisseria Meningitidis", Trends in Microbiology 3(5):186-192 (1995).
Adacel Prescribing information, http://www.fda.gov/downloads/biologicsbloodvaccines/vaccines/approvedproducts/ucm142764.pdf, "Revised: [XX/201X]", accessed Feb. 14, 2015.
Alm et al, "Genomic-sequence comparison of two unrelated isolates of the human gastric pathogen Helicobacter pylori", Nature 397:176-180 (1999).
Altschul et al, "Basic Local Alignment Search Tool", J. Mol. Biol. 215:403-410 (1990).
Altschul et al, "Protein database searches for multiple alignments", Proc. Natl. Acad. Sci. 87:5509-5513 (1990).
Altschul et al, "Gapped BLAST and PSI-BLAST: a new generation of protein database search programs", Nucleic Acids Research 25(17): 3389-3402 (1997).
Ambrosch et al, "Immunogenicity and side-effects of a new tetravalent meningococcal polysaccharide vaccine", Bulletin of the World Health Organization 61(2):317-323 (1983).
Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Anderson, "Techniques for the preservation of three-dimensional structure in preparing specimens for the electron microscope", Transactions of the New York Academy of Sciences, 13:130-134 (1951).
Anderson et al; "Potential Impact of the Bivalent rLP2086 Vaccine on Neisseria meningitidis Invasive Disease and Carriage Isolates in Two Adolescent Populations"; poster presented at the 30th Annual Meeting of the European Society for Paediatric Infectious Diseases; May 8-12, 2012; Thessaloniki, Greece; http://epostersonline.s3.amazonaws.com/espid2012/espid2012.02400cf.NORMAL.pdf, May 12, 2012.
Anderson, "Elicitation of Functional Antibodies by a Group B Neisseria meningitidis Bivalent rLP2086 Vaccine in Non-Human Primates", NHP IPNC Poster Presentation 2008.
Ausubel et al, Current Protocols in Molecular Biology, Sections 2.10, 6.3 & 6.4 (1995).
Bambini et al, "Distribution and genetic variability of three vaccine components in a panel of strains representative of the diversity of serogroup B meningococcus", Vaccine 27:2794-2803 (2009).
Bantam Medical Dictionary, Third Edition, pp. 302-303 (2000).
Barbour et al, "New tricks of tick-borne pathogen", Nature 390:553 & 555 (1997).
Bateman et al, "The Pfam Protein Families Database", Nucleic Acids Research 28(1):263-266 (2000).
Beard et al, "Transcription Mapping of Mouse Adenovirus Type 1 Early Region 3", Virology 175:81-90 (1990).
Beernink et al, "Prevalence of Factor H-Binding Protein Variants and NadA among Meningococcal Group B Isolates from the United States: Implications for the Development of a Multicomponent Group B Vaccine", The Journal of Infectious Diseases 195:1472-1479 (2007).
Beernink, P.T., et al., "The modular architecture of meningococcal factor H-binding protein", Microbiology, 155:2873-2883 (2009).
Bender et al, "Evidence that the Packaging Signal of Moloney Murine Leukemia Virus Extends into the gag Region", Journal of Virology 61(5):1639-1646 (1987).
Benson, "Tandem repeats finder: a program to analyze DNA sequences", Nucleic Acids Research 27(2):573-580(1999).
Bergmann et al, "An endogenously synthesized decamer peptide efficiently primes cytotoxic T cells specific for the HIV-1 envelope glycoprotein", Eur. J. Immunol., 23(11):2777-2781 (1993).
Bergmann et al, "Flanking Residues Alter Antigenicity and Immunogenicity of Multi-Unit CTL Epitopes", The Journal of Immunology, 157:3242-3249 (1996).
Bernfield et al., "Identification of a novel vaccine candidate for group B Neisseria meningitidis", Abstracts of the Thirteenth International Pathogenic Neisseria Conference, (Ed) Caugant et al. Oslo, Norway, p. 116, Sep. 1-6, 2002.
Bernstein et al, "Gene Transfer with Retrovirus Vectors", Genet. Eng. 7:235-261 (1985).
Better et al, *Escherichia coli* Secretion of an Active Chimeric Antibody Fragment, Science 240:1041-1043 (1988).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Beuvery et al, "Preparation and Physicochemical and Immunological Characterization of Polysaccharide-Outer Membrane Protein Complexes of Neisseria meningitidis", Infection and Immunity 40(1):369-380 (1983).
Biocomputing: Informatics and Genome Projects, Smith D.W., ed., Academic Press, New York (1994).
Bjune, et al., "Effect of Outer Membrane Vesicle Vaccine Against Group B Meningococcal Disease in Norway", The Lancet, 338(8775):1093-1096 (1991).
Borrow et al, "Meningococcal surrogates of protection-serum bactericidal antibody activity", Vaccine 23:2222-2227 (2005).

(56) References Cited

OTHER PUBLICATIONS

Boslego et al, "Chapter 17: Gonorrhea Vaccines", Vaccines and Immunotherapy, SJ Cryz Jr. ed., Pergamon Press, pp. 211-223 (1991).
Boulianne et al, "Production of functional chimaeric mouse/human antibody", Nature 312:643-646 (1984).
Brown, "Hybridization Analysis of DNA Blots", Current Protocols in Molecular Biology, Supp. 21, 2.10.1-2.10.16 (1993).
Budroni, S. et al., "Neisseria Meningitidis is Structured in Clades Associated with Restriction Modification Systems that Modulate Homologous Recombination", PNAS, Mar. 15, 2011,108 (11): 4494-4499 and supporting information pp. 1-17 (2011).
Cabilly et al, "Generation of antibody activity from immunoglobulin polypeptide chains produced in Escherichia coli", Proc. Natl. Acad. Sci. 81:3273-3277 (1984).
Callahan, P.M., et al., "The Importance of Surface Charge in the Optimization of Antigen-Adjuvant Interactions", Pharmaceutical Research, 8(7):851-858 (1991).
Cannon, "Conserved Lipoproteins of Pathogenic Neisseria Species Bearing the H.8 Epitope: Lipid-Modified Azurin and H.8 Outer Membrane Protein", Clinical Microbiology Reviews 2(Suppl):S1-S4 (1989).
Cantini et al, "Solution Structure of the Immunodominant Domain of Protective Antigen GNA1870 of Neisseria meningitidis", The Journal of Biological Chemistry 281(11):7220-7227 (2006).
Carillo et al, "The Multiple Sequence Alignment Problem in Biology", SIAM J. Appl. Math. 48(5):1073-1082 (1988).
Chao et al, "Endocarditis due to Neisseria sicca: Report of One Case", Acta Paed Sin 38(3):229-231 (1997).
Chen et al, "Cloning and Expression of the Streptococcal C5a Peptidase Gene in Escherichia coli: Linkage to the Type 12 M Protein Gene", Infection and Immunity 57(6):1740-1745 (1989).
Chen et al., "Determination of the Optimal Aligned Spacing Between the Shine-Dalgarno Sequence and the Translation Initiation Codon of Escherichia coli mRNAs", Nucleic Acids Research 22(23):4953-4957 (1994).
Cheetham, et al., "An HPLC Method for the Determination of Acetyl and Pyruvyl Groups in Polysaccharides, Carbohydrade Polymers", School of Chemistry, The University of New South Wales, 5 (6): 399-406 (1985).
Chmouryguina et al, "Conservation of the C5a Peptidase Genes in Group A and B Streptococci", Infection and Immunity 64(7):2387-2390 (1996).
Cockerill et al, "Molecular, Serological, and Clinical Features of 16 Consecutive Cases of Invasive Streptococcal Disease", Clinical Infectious Diseases 26:1448-1458 (1998).
Coleman et al, "Virus Attenuation by Genome-Scale Changes in Codon Pair Bias", Science, 320:1784-1787 (2008).
Jiang et al, "Broad vaccine coverage predicted for a bivalent recombinant factor H binding protein based vaccine to prevent serogroup B meningococcal disease", Vaccine 28:6086-6093 (2010).
Johnson et al., "Analysis of the Human Ig Isotype Response to Lactoferrin Binding Protein A from Neisseria meningitidis", FEMS Immunology and Medical Microbiology 25(4):349-354 (1999).
Jones et al, "The Importance of the Location of Antibody Binding on the M6 Protein for Opsonization and Phagocytosis of Group A M6 Streptococci", J. Exp. Med. 167:1114-1123 (1988).
JVCI-CMR website showing 22491 Sanger sequence (http://cmr.jvci.org/tigr-scripts/CMR/shared/Genomes.cgi and links) printed on Jul. 1, 2010.
Kafri et al, "A Packaging Cell Line for Lentivirus Vectors", Journal of Virology 73(1):576-584 (1999).
Kaplitt et al, "Expression of a Functional Foreign Gene in Adult Mammalian Brain following in Vivo Transfer via a Herpes Simplex Virus Type 1 Defective Viral Vector", Molecular and Cellular Neurosciences 2:320-330 (1991).
Kihlberg et al, "Protein H, an Antiphagocytic Surface Protein in Streptococcus pyogenes", Infection and Immunity 67(4):1708-1714 (1999).
Klein et al, "Distinctive properties of signal sequences from bacterial lipoproteins", Protein Engineering 2(1):15-20 (1988).
Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).
Koebnik, "Proposal for a peptidoglycan-associating alpha-helical motif in the C-terminal regions of some bacterial cell-surface proteins", Molecular Microbiology 16(6):1269-1270 (1995).
Kohler et al, "Continuous cultures of fused cells secreting antibody of predefined specificity", Nature 256:495-497 (1975).
Kuipers et al, "Improved site-directed mutagenesis method using PCR", Nucleic Acids Research 19(16):4558 (1991).
Kuo et al, "Efficient Gene Transfer into Primary Murine Lymphocytes Obviating the Need for Drug Selection", Blood 82(3):845-852 (1993).
Kyte et al, "A Simple Method for Displaying the Hydropathic Character of a Protein", J. Mol. Biol. 157:105-132 (1982).
Landt et al, "A general method for rapid site-directed mutagenesis using the polymerase chain reaction", Gene 96:125-128 (1990).
Lasalle et al, "An Adenovirus Vector for Gene Transfer into Neurons and Glia in the Brain", Science 259:988-990 (1993).
Lebkowski et al, "Adeno-Associated Virus: a Vector System for Efficient Introduction and Integration of DNA into a Variety of Mammalian Cell Types", Molecular and Cellular Biology 8(10):3988-3996 (1988).
Lee, L., et al, "Clinical Review STN: 125549 Application Type Biologics License Application STN# 125549 CBER Received Date Division/Office DVRPA/OVRR Priority Review Yes Reviewer Name", XP055265361, Retrieved from the Internet: URL:http://www.fda.gov/downloads/BiologicsBloodVaccines/Vaccines/ApprovedProducts/UCM424626, Jun. 16, 2014.
Levrero et al, "Defective and nondefective adenovirus vectors for expressing foreign genes in vitro and in vivo", Gene 101:195-202 (1991).
Liu et al, "Chimeric mouse-human IgG1 antibody that can mediate lysis o f cancer cells", Proc. Natl. Acad. Sci. 84:3439-3443 (1987).
Liu et al, "High-throughput imaging of bacterial colonies grown on filter plates with application to serum bactericidal assays", Journal of Immunological Methods 292(1-2):187-193 (2004).
Loessner et al, "Evidence for a Holin-Like Protein Gene Fully Embedded Out of Frame in the Endolysin Gene of Staphylococcus aureus Bacteriophage 187", Journal of Bacteriology 181(15):4452-4460 (1999).
Lukashin et al, "GeneMark.hmm: new solutions for gene finding", Nucleic Acids Research 26(4):1107-1115 (1998).
Lukomski et al, "Extracellular Cysteine Protease Produced by Streptococcus pyogenes Participates in the Pathogenesis of Invasive Skin Infection and Dissemination in Mice", Infection and Immunity 67(4):1779-1788 (1999).
Lunn et al, "Effects of Prolipoprotein Signal Peptide Mutations on Secretion of Hybrid Prolipo-beta-lactamase in Escherichia coli", The Journal of Biological Chemistry 262(17):8318-8324 (1987).
Machy et al, "Gene transfer from targeted liposomes to specific lymphoid cells by electroporation", Proc. Natl. Acad. Sci. 85:8027-8031 (1988).
Madore, "Characterization of immune response as an indicator of Haemophilus influenzae type b vaccine efficacy", The Pediatric Infectious Disease Journal 17(9):Supplement:S207-S210 (1998).
Mann, et al, "Construction of a Retrovirus Packaging Mutant and Its Use to Produce Helper-Free Defective Retrovirus", Cell 33:153-159 (1983).
Markowitz et al, "A Safe Packaging Line for Gene Transfer: Separating Viral Genes on Two Different Plasmids", Journal of Virology 62(4):1120-1124 (1988).
Marshall, H.S., et al., "A phase 2 open-label safety and immunogenicity study of a meningococcal B bivalent rLP2086 vaccine in healthy adults", Vaccine, 31(12):1569-1575 (2013).
Martin et al, "Highly Conserved Neisseria meningitidis Surface Protein Confers Protection against Experimental Infection", J. Exp. Med. 185(7):1173-1183 (1997).

(56) References Cited

OTHER PUBLICATIONS

Mascioni et al, "Structural Basis for the Immunogenic Properties of the Meningococcal Vaccine Candidate LP2086", Journal of Biological Chemistry 284(13):8738-8746 (2009).
Masignani et al, "Vaccination against Neisseria meningitidis Using Three Variants of the Lipoprotein GNA1870", J. Exp. Med. 197(6):789-799 (2003).
Matsuka et al, "Fibrinogen Cleavage by the *Streptococcus pyogenes* Extracellular Cysteine Protease and Generation of Antibodies That Inhibit Enzyme Proteolytic Activity", Infection and Immunity 67(9):4326-4333 (1999).
Mazmanian et al, "*Staphylococcus aureus* Sortase, an Enzyme that Anchors Surface Proteins to the Cell Wall", Science 285:760-763 (1999).
McAtee et al, "Characterization of a Helicobacter pylori vaccine candidate by proteome techniques", Journal of Chromatography B, Biomedical Sciences and Applications 714:325-333 (1998).
McAtee et al, "Identification of Potential Diagnostic and Vaccine Candidates of Helicobacter pylori by "Proteome" Technologies", Helicobacter 3(3):163-169 (1998).
McAtee et al, "Identification of Potential Diagnostic and Vaccine Candidates of Helicobacter pylori by Two-Dimensional Gel Electrophoresis, Sequence Analysis, and Serum Profiling", Clinical and Diagnostic Laboratory Immunology 5(4):537-542 (1998).
McCormick, "Human Gene Therapy: The First Round", BioTechnology 3(8):689-693 (1985).
McGuiness et al, "Class 1 outer membrane protein of Neisseria meningitidis: epitope analysis of the antigenic diversity between strains, implications for subtype definition and molecular epidemiology", Molecular Microbiology 7 (4):505-514 (1993).
McNeil, et al, "Detection of LP2086 on the cell surface of Neisseria meningitidis and its accessibility in the presence of serogroup B capsular polysaccharide", Vaccine 27:3417-3421 (2009).
McNeil, L., "Role of Factor H Binding Protein in Neisseria Meningitidis Virulence and Its Potential as a Vaccine Candidate to Broadly Protect Against Meningococcal Disease" Microbiology and Molecular Biology Reviews, 77(2):234-252 (2013).
Mejlhede et al, "Ribosomal-1 Frameshifting during Decoding of Bacillus subtilis cdd Occurs at the Sequence CGA AAG", Journal of Bacteriology 181(9):2930-2937 (1999).
Menactra prescribing information, http://www.fda.gov/downloads/BiologicsBloodVaccines/Vaccines/ApprovedProducts/UCM131170.pdf, revised Aug. 26, 2014, accessed Feb. 14, 2015.
Menactra, Australian Public Assessment Report for Groups A, C, Y and W-135 Meningococcal Polysaccharide Diphtheria Toxoid Conjugate Vaccine, https://www.tga.gov.au/file/1277/download , Aug. 31, 2011, accessed Feb. 13, 2015 (part 1 and 2).
Mencevax, New Zealand data sheet, http://www.medsafe.govt.nz/profs/datasheet/m/Mencevaxacwyinj.pdf, date of preparation Mar. 25, 2014, accessed Feb. 14, 2015.
Menveo Package insert, http://www.fda.gov/downloads/BiologicsBloodVaccines/Vaccines/ApprovedProducts/UCM201349.pdf, accessed Feb. 19, 2015, revised Aug. 2013.
Milagres et al., "Specificity of Bactericidal Antibody Response to Serogroup B Miningococcal Strains in Brazilian Children after Immunization with an Outer Membrane Vaccine", Infection and Immunity 66(10):4755-4761 (1998).
Miller et al, "Improved Retroviral Vectors for Gene Transfer and Expression", BioTechniques 7(9):980-990 (1992).
Minutes of Oral Proceedings in Opposition against Novartis EP 1 645 631 dated Mar. 5, 2012.
Mir et al, "Long-term, high level in vivo gene expression after electric pulse-mediated gene transfer into skeletal muscle", Academie des sciences 321:893-899 (1998).
Moe, et al., "Sequential Immunization with Vesicles Prepared from Heterologous Neisseria meningitidis Strains Elicits Broadly Protective Serum Antibodies to Group B Strains", Infection and Immunity, Nov. 2002, 70:11, 6021-6031.
Molinari et al, "The Fibronectin-Binding Protein of *Streptococcus pyogenes*, Sfbl, Is Involved in the Internalization of Group A Streptococci by Epithelial Cells", Infection and Immunity 65(4):1357-1363 (1997).
Morbidity and Mortality Weekly Report (MMWR), Recommendations and Reports, Case Definitions for Infectious Conditions Under Public Health Surveillance, May 2, 1997, vol. 46, No. RR-10.
Moreno et al, "Immunity and Protection of Mice Against Neisseria meningitidis Group B by Vaccination, Using Polysaccharide Complexed with Outer Membrane Proteins: A Comparison with Purified B Polysaccharide", Infection and Immunity 47(2):527-533 (1985).
Morley et al, "Vaccine prevention of meningococcal disease, coming soon?", Vaccine 20:666-687 (2002).
Morrison et al, "Chimeric human antibody molecules: Mouse antigen-binding domains with human constant region domains", Proc. Natl. Acad. Sci. 81:6851-6855 (1984).
Mountzouros et al, "Detection of Complement-Mediated Antibody-Dependent Bactericidal Activity in a Fuorescence-Based Serum Bactericidal Assay for Group B Neisseria meningitidis", Journal of Clinical Microbiology 38(8):2878-2884 (2000).
Moxon, "Applications of molecular microbiology to vaccinology," Lancet 350(9086):1240-1244 (1997).
Munkley et al., "Blocking of Bactericidal Killing of Neisseria meningitidis by Antibodies Directed Against Class 4 Outer Membrane Protein", Microbial Pathogenesis 11:447-452 (1991).
Murphy et al, "Sequence Diversity of the Factor H Binding Protein Vaccine Candidate in Epidemiologically Relevant Strains of Serogroup B Neisseria meningitidis" The Journal of Infectious Diseases 200:379-389 (2009).
Murphy, E., "HM807466: Neisseria meningitidis strain M08452 factor H binding protein variant B153 (fhbp) gene, partial cds.", URL:http://getentry.ddbj.nig.ac.jp/getentry/na/HM807466/?filetype=html, Jul. 21, 2010.
Nakai et al, "Expert System for Predicting Protein Localization Sites in Gram-Negative Bacteria", PROTEINS: Structure, Function, and Genetics 11:95-110 (1991).
Naldini et al, "Lentiviruses as gene transfer agents for delivery to non-dividing cells", Current Opinion in Biotechnology 9:457-463 (1998).
Nassif, "A Furtive Pathogen Revealed", Science 287:1767-1768 (2000).
Navarre et al, "Surface Proteins of Gram-Positive Bacteria and Mechanisms of Their Targeting to the Cell Wall Envelope", Microbiology and Molecular Biology Reviews 63(1):174-229 (1999).
NCBI GenBank No. AAF42204.1, Tettelin, H. et al., "Hypothetical protein [Neisseria meningitidis]", Feb. 25, 2000, accessed Jul. 12, 2012.
NCBI GenBank : ACI46791, "Factor H binding protein variant A04_001, partial [Neisseria meningitidis]". Aug. 4, 2009.
NCBI GenBank No. EF108319.1, O'Leary, M. M. et al., Neisseria meningitidis strain NM452 FHBP/GNA1870 variant (GNA1870) gene, complete cds, Nov. 8, 2006, accessed Sep. 5, 2012.
NCBI GenBank: ACI46789.1; "Factor H binding protein variant A62_001, partial [Neisseria meningitidis]", Aug. 4, 2009.
NCBI GenBank: ACB38141.1, factor H-binding protein [Neisseria meningitidis] (Jun. 4, 2010).
NCBI GenBank: AY330365.1; "Neisseria meningitidis strain CDC1492 factor H binding protein variant A22_001 (fhbp) gene, partial cds"; Mar. 12, 2009; accessed Jun. 3, 2014.
NCBI GenBank: AY330400.1; "Neisseria meningitidis strain M982 factor H binding variant B09_001 (fhbp) gene, partial cds"; Mar. 12, 2009; accessed Jun. 3, 2014.
NCBI GenBank: AY330401.1; "Neisseria meningitidis strain 880049 factor H binding protein variant B03_001 (fhbp) gene, partial cds"; Mar. 12, 2009; accessed Jun. 3, 2014.
NCBI GenBank: FJ184103.1; "Neisseria meningitidis factor H binding protein variant A12_001 (fhbp) gene, partial cds"; Aug. 4, 2009; accessed Jun. 3, 2014.
NCBI GenBank: FJ184126.1; "Neisseria meningitidis factor H binding protein variant B02_001 (fhbp) gene, partial cds"; Aug. 4, 2009; accessed Jun. 3, 2014.

(56) References Cited

OTHER PUBLICATIONS

NCBI GenBank: FJ184157.1; "Neisseria meningitidis factor H binding protein variant B44_001 (fhbp) gene, partial cds"; Aug. 4, 2009; accessed Jun. 3, 2014.
NCBI GenBank: FJ184233.1, "Neisseria meningitidis factor H binding protein variant B09_004 (fhbp) gene, partial cds" (Aug. 4, 2009).
Neisseria gonorrhoeae FA 1090 chromosome Entire clone gono strain FA1090, complete sequence. GenBank Accession gono AE004969, 2153894 bp, Sep. 26, 2000.
Nielsen et al, "Identification of prokaryotic and eukaryotic signal peptides and prediction of their cleavage sites", Protein Engineering 10(1):1-6 (1997).
Nimenrix product monograph, gsk.com/media/673251/nimenrix. pdf, accessed Feb. 19, 2015, date of revision Jan. 9, 2015.
Nimenrix product monograph, http://webprod5.hc-sc.gc.ca/dpd-bdpp/item-iteme.do?pm-mp=00033642, accessed Mar. 2016. Date of revision Nov. 9, 2015.
Nizet et al, "Genetic Locus for Streptolysin S Production by Group A *Streptococcus*", Infection and Immunity 68(7):4245-4254 (2000).
Nordstrand et al, "Allele Substitution of the Streptokinase Gene Reduces the Nephritogenic Capacity of Group A Streptococcal Strain NZ131", Infection and Immunity 68(3):1019-1025 (2000).
Notice of Opposition against Novartis EP 1 645 631 submitted Jul. 23, 2008.
Novartis submits Bexsero®, a multi-component meningococcal B vaccine, for regulatory review in Europe, Novartis Media Release (Dec. 23, 2010).
Okuda et al, Lipoprotein sortingin bacteria, Annu. Rev. Microbiol., 65:239-259 (2011).
Olmsted et al, "High-Resolution Visualization by Field Emission Scanning Electron Microscopy of Enterococcus faecalis Surface Proteins Encoded by the Pheromone-Inducible Conjugative Plasmid pCF10", Journal of Bacteriology 175(19):6229-6237 (1993).
Opponent's Further Submission in Preparation of Oral Proceedings in Opposition against Novartis EP 1 645 631 submitted Nov. 3, 2011.
Opposition documents (part 1 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 2 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 3 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 4 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 5 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 6 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 7 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 8 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 9 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 10 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Opposition documents (part 11 of part 11) submitted to the European Patent Office in EP2343308 dated Nov. 13, 2015 to Dec. 23, 2015, https://register.epo.org/application?number=EP10183020&lng=en&tab=doclist, accessed Mar. 30, 2016.
Anderson, et al, "Potential Impact of the Bivalent rLP2806 Vaccine on Neisseria Meningitidis Carnage and Invasive Serogroup B Disease", Human Vaccines & Immunotherpeutics, 9(3):471-479 (2013).
Tarkka et al, "Antibody production to a meningococcal outer membrane protein cloned into live *Salmonella typhimurium* aroA vaccine strain", Micrb. Pathogen 6:327-335 (1989).
Telford et al., "Chapter 1: Genomics and Proteomics in Vaccine Design", New Bacterial Vaccines, Kleweur Academic/Plenum Publishers, USA, pp. 1-11 (2003).
Tettelin et al, "Complete Genome Sequence of Neisseria meningitidis Serogroup B Strain MC58", Science 287:1809-1815 (2000).
Tondella et al, "Distribution of Neisseria meningitidis Serogroup B Serosubtypes and Serotypes Circulating in the United States", Journal of Clinical Microbiology 38(9):3323-3328 (2000).
Ton-That et al, "Purification and characterization of sortase, the transpeptidase that cleaves surface proteins of *Staphylococcus aureus* at the LPXTG motif", Proc Natl Acad Sci 96(22):12424-12429 (1999).
Uli, et al., "Outer Membrane Vesicles of VA-MENGOC-BC Vaccine Against Serogroup B of Neisseria Meningitidis: Analysis of Protein Components by Two-Dimensional Gel Electrophoresis and Mass Spectrometry", Proteomics, 2006, 6, 3389-3399.
Ulmer et al, "Heterologous Protection Against Influenza by Injection of DNA Encoding a Viral Protein", Science 259:1745-1748 (1993).
University of Oklahoma—Neisseria gonorrhoeae webpage to retrieve genome [online] URL: http://dna1.chem.ou.edu/gono.html, Apr. 5, 2004, accessed Aug. 3, 2012.
U.S. Pat. No. 8,398,988 B2 Prosecution History (Feb. 23, 2012-Feb. 27, 2013).
Van Der Ende, A., et al., "Deletion of porA by Recombination between Clusters of Repetitive Extragenic Palindromic Sequences in Neisseria meningitidis", Infection and Immunity, 67(6):2928-2934 (1999).
Van Der Ende, A., et al., "Multiple Mechanisms of Phase Variation of PorA in Neisseria meningitidis", Infection and Immunity 68(12):6685-6690 (2000).
Van Der Ley et al., "Construction of Neisseria meningitidis Strains Carrying Multiple Chromosomal Copies of the porA gene for Use in the production of a Multivalent Outer Membrane Vesicle Vaccine", Vaccine 13(4):401-407 (1995).
Wahl et al, "Improved Radioimaging and Tumor Localization with Monoclonal F(ab')2", J Nucl Med 24:316-325 (1983).
Webster's II New Riverside University Dictionary, The Riverside Publishing Company, p. 933 (1984).
Weldingh et al, "Two-Dimensional Electrophoresis for Analysis of *Mycobacterium tuberculosis* Culture Filtrate and Purification and Characterization of Six Novel Proteins", Infection and Immunity 66(8):3492-3500 (1998).
Welsch et al, "Factor H and Neisserial pathogenesis", Vaccine 26(Supp8):I40-I45 (2008).
Welsch et al, "Protective Activity of Monoclonal Antibodies to Genome-Derived Neisserial Antigen 1870, a Neisseria meningitidis Candidate Vaccine", The Journal of Immunology 172:5606-5615 (2004).
Wiertz et al, "T-Cell Responses to Outer Membrane Proteins of Neisseria meningitidis: Comparative Study of the Opa, Opc, and Por A Proteins", Infection and Immunity 64(1) 298-304 (1996).

(56) References Cited

OTHER PUBLICATIONS

Williams et al, "Introduction of foreign genes into tissues of living mice by DNA-coated microprojectiles", Proc. Natl. Acad. Sci. 88:2726-2730 (1991).

Wilson et al, "Hepatocyte-directed Gene Transfer in Vivo Leads to Transient Improvement of Hypercholesterolemia in Low Density Lipoprotein Receptor-deficient Rabbits", The Journal of Biological Chemistry 267(2):963-967 (1992).

Witze et al, Mapping Protein Post-Translational Modifcations with Mass Spectrometry, Nat Methods, Oct.; 4(10):798-806 (2007).

Wolf et al, "Conditions Affecting Direct Gene Transfer into Rodent Muscle In Vivo", Biotechniques, 11(4):474-485 (1991).

Wolff et al, "Direct Gene Transfer into Mouse Muscle in Vivo", Science 247:1465-1468 (1990).

Woods et al., "Resistance to Meningococcemia Apparently Conferred by Anti-H.8 Monoclonal Antibody Is Due to Contaminating Endotoxin and Not to Specific Immunoprotection", Infection and Immunity 55(8):1927-1928 (1987).

Wu et al, "Receptor-mediated Gene Delivery and Expression in Vivo", The Journal of Biological Chemistry 263(29):14621-14624 (1988).

Wu et al, "Receptor-mediated in Vitro Gene Transformation by a Soluble DNA Carrier System", The Journal of Biological Chemistry 262(10):4429-4432 (1987).

Wyeth Neisseria Meningitidis Serogroup B Vaccine, Vaccine and Related Biological Products Advisory Committee Pre-Meeting Background Document, URL:http://www.fda.gov/downloads/AdvisoryCommittees/CommitteesMeetingMaterials/BloodVaccinesandOtherBiologics/VaccinesandRelatedBiologicalProductsAdvisoryCommittee/UCM249479.pdf, Mar. 4, 2011.

Yakushi et al, "A new ABC transporter mediating the detachment of lipid-modified proteins from membranes", Nature Cell Biology 2:212-218 (2000).

Yakushi et al, "Lethality of the Covalent Linkage between Mislocalized Major Outer Membrane Lipoprotein and the Peptidoglycan of *Escherichia coli*", Journal of Bacteriology 179(9):2857-2862 (1997).

York, "Pfizer's Investigational Vaccine, rLP2086, for Invasive Meningococcal Serogroup B Disease", Sabin Vaccine Institute, http://www.sabin.org/sites/sabin.org/files/Laura%20J%20York.pdf, accessed Aug. 1, 2014.

Yutsudo et al, "The Gene Encoding a New Mitogenic Factor in a *Streptococcus pyogenes* Strain Is Distributed Only in Group A Streptococci", Infection and Immunity 62(9):4000-4004 (1994).

Zagursky et al, "Bioinformatics: Use in Bacterial Vaccine Delivery", BioTechniques 31(3):636-659 (2001).

Zavascki et al, "First Case Report of Neisseria lactamica Causing Cavitary Lung Disease in an Adult Organ Transplant Recipient", Journal of Clinical Microbiology 44(7):2666-2668 (2006).

Zhu et al, "Evaluation of Recombinant Lipidated P2086 Protein as a Vaccine Candidate for Group B Neisseria meningitidis in a Murine Nasal Challenge Model", Infection and Immunity 73(10):6838-6845 (2005).

Zollinger, "New and Improved Vaccines Against Meningococcal Disease", New Generation Vaccines, 2nd Ed., Myron M. Levine, et al. eds., Marcel Dekker, Inc., New York, NY pp. 469-488 (1997).

Zufferey et al, "Self-Inactivating Lentivirus Vector for Safe and Efficient In Vivo Gene Delivery", Journal of Virology 72(12):9873-9880 (1998).

Deasy et al, Challenges for Development of Meningococcal Vaccines in Infants and Children, Expert Review of Vaccines 10(3): 335-343 (2011).

Computational Molecular Biology: Sources and Methods for Sequence Analysis, Lesk A.M. et., Oxford University Press, New York, 1988.

Courtney et al, "Cloning, Sequencing, and Expression of a Fibronectin/Fibrinogen-Binding Protein from Group A Streptococci", Infection and Immunity 62(9):3937-3946 (1994).

Cserzo et al, "Prediction of transmembrane alpha-helices in prokaryotic membrane proteins: the dense alignment surface method", Protein Engineering 10(6):673-676 (1997).

Cunningham et al, "Immunological Crossreactivity Between the Class I Epitope of Streptococcal M Protein and Myosin", Adv Exp Med Biol 418:887-892 (1997).

Curiel et al, "High-Efficiency Gene Transfer Mediated by Adenovirus Coupled to DNA-Polylysine Complexes", Human Gene Therapy 3:147-154 (1992).

Curriculum Vitae of Professor Paul M. Dunman, Ph.D., submitted in Opposition Proceedings against Novartis EP 1 645 631 on Sep. 14, 2011.

Curriculum Vitae of Lakshmi Khandke, Ph.D., submitted in Opposition Proceedings against Novartis EP1409013 on Nov. 18, 2011.

Dale et al, "Hyaluronate Capsule and Surface M Protein in Resistance to Opsonization of Group A Streptococci", Infection and Immunity 64(5):1495-1501 (1996).

Dale et al, "Passive Protection of Mice Against Group A Streptococcal Pharyngeal Infection by Lipoteichoic Acid", The Journal of Infectious Diseases 169:319-323 (1994).

Dale et al, "Recombinant, octavalent group A streptococcal M protein vaccine", Vaccine 14(10):944-948 (1996).

Database EMBL [Online] EBI, Kohara, Y., "Caenorhabditis elegans cDNA clone yk26f2: 5' end, single read," Database accession No. D35881 (Aug. 13, 1994).

Database Geneseq 'Online', "N. gonorrhoeae amino acid sequence SEQ ID 1586", XP002320505, Mar. 7, 2003.

Database Geneseq 'Online', "Neisseria meningitidis ORF 741 protein sequence SEQ ID No. 2536", XP002320506, Mar. 21, 2000.

Database Geneseq Online, "N. meningitidis NL096 fHBP protein fragment SEQ ID 76", XP002703350, Database accession No. AXQ90374, Nov. 26, 2009.

Database Geneseq Online, "Neisseria meningitides ORF2086 protein-encoding gene SedID61" AAY75530, Jan. 29, 2004.

Database Geneseq Online, "Neisseria meningitides ORF2086 protein-encoding gene SedID61" AAZ54292-NT, Jan. 29, 2004.

Database Geneseq Online, "Neisseria meningitidis modified fHBP fusion protein SEQ:140", XP002703351, Database accession No. AZG10689, Apr. 28, 2011.

Database Geneseq Online, "Neisseria meningitidis modified fHBP NL096 SEQ:76", XP002703352,Database accession No. AZG10625, Apr. 28, 2011.

Database UniPro 'Online', "Hypothetical Protein NMB1870", XP002308111, Oct. 1, 2000.

Database UniProt 'Online', "Putative lipoprotein N meningitidis (Serotype A)", XP002320503, Oct. 1, 2000.

"Database Uniprot [Online] Jul. 4, 2004, "SubName: Full=Factor H binding protein variant A05_001";Flags: Fragment, retrieved from EBI; UNIPROT database accession No. Q6VS29; Database entry from Oct. 28, 2014, entry version 29, sequence version 1See strains Neisseria meningitidis M98-250732 & M98250771".

"Database Uniprot [Online] Jul. 5, 2004, "Factor H binding protein variant A22_001"; Flags: Fragment,retrieved from EBI; UNIPROT database accession No. Q6VS35; Database entry from Oct. 28, 2014, entryversion 28, sequence version 2 updated on Sep. 23, 2008See strains Neisseria meningitidis: CDC-1034 and L4-891".

Database UniProt Online, "Subname: Full=Factor H binding protein variant A62_001; Subname: Full=Factor H binding protein variant A62_002; Flags: Fragment", XP002703353, Database accession No. C0JF81, May 5, 2009.

Datasheet for MENCEVAX™, International Data Sheet version 2.1 (May 15, 2000).

Datasheet for MENOMUNE™, product information as of Feb. 2001.

Datasheet for MeNZB® vaccine product prepared Jun. 23, 2009.

De et al, "Purification and characterization of *Streptococcus pneumoniae* palmitoylated pneumococcal surface adhesin A expressed in *Escherichia coli*", Vaccine 18:1811-1821 (2000).

Declaration by Dr. Julian Parkhill, submitted in Opposition Proceedings against Novartis EP1645631 on Jul. 23, 2008.

Declaration by Professor Paul Dunman, submitted in Opposition Proceedings against Novartis EP1645631 on Sep. 14, 2011.

Declaration of Dr. Ellen Murphy, submitted in Opposition Proceedings against Novartis EP 1 645 631 on Sep. 14, 2011.

Declaration of Emilio A. Emini, Ph.D., submitted in Opposition Proceedings against Novartis EP1645631 on Nov. 3, 2011.

(56) References Cited

OTHER PUBLICATIONS

Declaration of Lakshmi Khandke, Ph.D., submitted in Opposition Proceedings against Novartis EP1409013 on Dec. 21, 2011.
Definition of "epitope" from Henderson's Dictionary of Biological Terms, 11th edition, Eleanor Lawrence ed., pp. 37, 184 and cover pages (1997).
Delgado et al., "Lipoprotein NMB0928 from Neisseria meningitidis Serogroup B as a Novel Vaccine Candidate", Vaccine 25:8420-8431 (2007).
Dempsey et al., "The physical map of the chromosome of A serogroup A strain of Neisseria meningitidis shows complex rearrangements relative to the chromosomes of the two mapped strains of the closely related species N. gonorrhoeae," Journal of Bacteriology 177(22):6390-6400 (1995).
Devereux et al, "A comprehensive set of sequence analysis programs for the VAX", Nucleic Acids Research 12(1):387-395 (1984).
Duby et al, "Using Synthetic Oligonucleotides as Probes", Current Protocols in Molecular Biology, Supp. 2, 6.4.1-6.4.10 (1993).
Eddy, "Hidden Markov models", Current Opinion in Structural Biology 6:361-365 (1996).
Ellen et al, "M Protein-Associated Adherence of *Streptococcus pyogenes* to Epithelial Surfaces: Prerequisite for Virulence", Infection and Immunity 5(5):826-830 (1972).
Ellis, "New Technologies for Making Vaccines", Vaccines, Plotkin et al. editors, W.B. Saunders Company, Philadelphia, Chapter 29, pp. 568-575 (1988).
Eng et al, "An Approach to Correlate Tandem Mass Spectral Data of Peptides with Amino Acid Sequences in a Protein Database", J Am Soc Mass Spectrom 5:976-989 (1994).
EP Application No. 07075161.5 Response to Communication dated Oct. 28, 2009.
Erdile et al, "Role of Attached Lipid in Immunogenicity of Borrelia burgdorferi OspA", Infection and Immunity 61(1):81-90 (1993).
Farley et al., "Characterization, cloning and expression of different subfamilies of the ORF2086 gene from Neisseria meningitidis", Abstracts of the Thirteenth International Pathogenic Neisseria Conference, (Ed) Caugant et al., Oslo, Norway, p. 124, Sep. 1-6, 2002.
Farley, J., et al. poster entitled "Characterization, Cloning and Expression of Different Subfamlies of the ORF 2086 gene Neisseria Meningitidis", presented at the Thirteenth International Pathogenic Neisseria Conference (the 'IPNC Oslo 2002'), hosted at the Norwegian Institute of Public Health, Oslo, Norway between Sep. 1, 2002 and Sep. 6, 2002, as evidenced by photographs and transcript thereof.
Feavers et al, "Meningococcal protein antigens and vaccines", Vaccine 275:B42-B50 (2009).
Felgner et al, "Cationic liposome-mediated transfection", Nature 337:387-388 (1989).
Felgner et al, "Lipofection: A highly efficient, lipid-mediated DNA-transfection procedure", Proc. Natl. Acad. Sci. 84:7413-7417 (1987).
Final Written Submission in Preparation of Oral Proceedings in Opposition against Novartis EP 1 645 631 submitted Sep. 14, 2011.
Findlow et al, "Multicenter, Open-Label, Randomized Phase II Controlled Trial of an Investigational Recombinant Meningococcal Serogroup B Vaccine With and Without Outer Membrane Vesicles, Administered in Infance", Clinical Infectious Diseases 51(10):1127-1137 (2010).
Assaf-Casals and Dbaibo, Meningococcal Quadrivalent Tetanus Toxoid Conjugate Vaccine (MenACWY-TT, Nimenrix): A review of Its Immunogenicity, Safety, Co-Adminstration, and Antibody Persistence, Human Vaccines and Immunotherapeutics, 12(7):1825-1837 (2016).
Baker, "Prevention of Meningococcal Infection in the United States Current Recommendations and Future Considerations", Journal of Adolescent Health, 59(2): S29-S37 (2016).
Biagini, et al., "Expression of Factor H Binding Protein in Meningococcal Strains Can Vary at Least 15-Fold and is Genetically Determined", Preceedings of the National Academy of Sciences, 113:1 (2016).
Gandhi, et al., Characteristics of A New Meningococcal Serogroup B Vaccine, Bivalent rLP2086 (MenB-FHbp: Trumenba) (2016).
Saez-Llorens, et al., "Immunogenicity and Safety of Investigational Vaccine Formulations Against Meningococcal Serogroups A, B, C, W, and Y in Healthy Adolescents" Human Vaccines and Immunotherapeutics, 11(6):1507-1517 (2015).
Sonnenberg et al, "Definition of *Mycobacterium tuberculosis* Culture Filtrate Proteins by Two-Dimensional Polyacrylamide Gel Electrophoresis, N-Terminal Amino Acid Sequencing, and Electrospray Mass Spectrometry", Infection and Immunity 65(11):4515-4524 (1997).
Vesikari, et al., "Immunogenicity, Safety, and Tolerability of Bivalent rLP2086 Meningococcal Group B Vaccine Administered Concomitantly With Diphteria, Tetans, and Acellular Pertussis", Journal of the Pediatric Infectious Diseases Society, 5(2): 180-187.
Vidor, E., "The nature and consequences of intra- and inter-vaccine interference." J Comp Pathol. Jul. 2007;137 Suppl 1:S62-6.

```
  1 CGSSGGGGVA ADIGTGLADA LTAPLDHKDK GLKSLTLEDS ISQNGTLTLS
 51 AQGAEKTFKV GDKDNSLNTG KLKNDKISRF DFVQKIEVDG QTITLASGEF
101 QIYKQDHSAV VALQIEKINN PDKIDSLINQ RSFLVSGLGG EHTAFNQLPS
151 GKAEYHGKAF SSDDAGGKLT YTIDFAAKQG HGKIEHLKTP EQNVELASAE
201 LKADEKSHAV ILGDTRYGSE EKGTYHLALF GDRAQEIAGS ATVKIREKVH
251 EIGIAGKQ (SEQ ID NO: 1)
```

```
  1 CGSSGGGGSG GGGVTADIGT GLADALTAPL DHKDKGLKSL TLEDSISQNG
 51 TLTLSAQGAE KTYGNGDSLN TGKLKNDKVS RFDFIRQIEV DGQLITLESG
101 EFQVYKQSHS ALTALQTEQE QDPEHSEKMV AKRRFRIGDI AGEHTSFDKL
151 PKDVMATYRG TAFGSDDAGG KLTYTIDFAA KQGHGKIEHL KSPELNVDLA
201 VAYIKPDEKH HAVISGSVLY NQDEKGSYSL GIFGEKAQEV AGSAEVETAN
251 GIHHIGLAAK Q (SEQ ID NO: 2)
```

FIG. 6A

CSSGGGGVAA DIGAGLADAL TAPLDHKDKS LQSLTLDQSV RKNEKLKLAA
QGAEKTYGNG DSLNTGKLKN DKVSRFDFIR QIEVDGQLIT LESGEFQVYK
QSHSALTALQ TEQVQDSEHS GKMVAKRQFR IGDIAGEHTS FDKLPEGGRA
TYRGTAFGSD DASGKLTYTI DFAAKQGHGK IEHLKSPELN VDLAASDIKP
DKKRHAVISG SVLYNQAEKG SYSLGIFGGQ AQEVAGSAEV ETANGIRHIG
LAAKQ (SEQ ID NO: 26)

FIG. 6B

CSSGGGGVAA DIGAGLADAL TAPLDHKDKS LQSLTLDQSV RKNEKLKLAA
QGAEKTYGNG DSLNTGKLKN DKVSRFDFIR QIEVDGQLIT LESGEFQIYK
QDHSAVVALQ IEKINNPDKI DSLINQRSFL VSGLGGEHTA FNQLPSGKAE
YHGKAFSSDD PNGRLHYSID FTKKQGYGRI EHLKTPEQNV ELASAELKAD
EKSHAVILGD TRYGGEEKGT YHLALFGDRA QEIAGSATVK IREKVHEIGI
AGKQ (SEQ ID NO: 27)

FIG. 6C

CSSGGGGVAA DIGAGLADAL TAPLDHKDKS LQSLTLDQSV RKNEKLKLAA
QGAEKTYGNG DSLNTGKLKN DKVSRFDFIR QIEVDGQLIT LESGEFQIYK
QDHSAVVALQ IEKINNPDKI DSLINQRSFL VSGLGGEHTA FNQLPDGKAE
YHGKAFSSDD AGGKLTYTID FAAKQGHGKI EHLKTPEQNV ELAAAELKAD
EKSHAVILGD TRYGSEEKGT YHLALFGDRA QEIAGSATVK IGEKVHEIGI
AGKQ (SEQ ID NO: 28)

FIG. 6D

CSSGGGGVAA DIGAGLADAL TAPLDHKDKS LQSLTLDQSV RKNEKLKLAA
QGAEKTYGNG DSLNTGKLKN DKVSRFDFIR QIEVDGQLIT LESGEFQIYK
QDHSAVVALQ IEKINNPDKI DSLINQRSFL VSGLGGEHTA FNQLPSGKAE
YHGKAFSSDD PNGRLHYSID FTKKQGYGRI EHLKTPEQNV ELASAELKAD
EKSHAVILGD TRYGGEEKGT YHLALFGDRA QEIAGSATVK IREKVHEIGI
AGKQ (SEQ ID NO: 27)

FIG. 6E

CSSGGGGSGG GGVAADIGTG LADALTAPLD HKDKGLQSLM LDQSVRKNEK
LKLSAQGAEK TYGNGDSLNT GKLKNDKISR FDFIHQIEVD GQLITLESGE
FQVYKQSHSA LTALQTEQVQ DSEHSEKMVA KRRFKIGDIA GEHTSFDKLP
KDVMATYRGT AFGSDDAGGK LTYTIDFAAK QGHGKIEHLK SPELNVELAA
AYIKPDEKRH AVISGSVLYN QDEKGSYSLG IFGGQAQEVA GSAEVETANG
IHHIGLAAKQ (SEQ ID NO: 29)

```
CSSGGGGVAA DIGAGLADAL TAPLDHKDKG LQSLTLDQSV RKNEKLKLAA
QGAEKTYGNG DSLNTGKLKN DKVSRFDFIR QIEVDGQLIT LESGEFQVYK
QSHSALTALQ TEQEQDPEHS GKMVAKRRFK IGDIAGEHTS FDKLPKDVMA
TYRGTAFGSD DAGGKLTYTI DFAAKQGHGK IEHLKSPELN VDLAVAYIKP
DEKHHAVISG SVLYNQDEKG SYSLGIFGEK AQEVAGSAEV KTANGIHHIG
LAAKQ
```
(SEQ ID NO: 30)

FIG. 9

| | | Month 0<br>Vaccine 1 | Month 2<br>Vaccine 2 | Month 6<br>Vaccine 3 | |
|---|---|---|---|---|---|
| ▷ | Group A | Saline +<br>Tdap + MCV4 | saline | saline | Positive control<br>group for<br>current study |
| ▷ | Group B | rLP2086+<br>Saline + Saline | rLP2086 | rLP2086 | Test group for<br>current study |

SEQUENCE LISTING

```
<160> NUMBER OF SEQ ID NOS: 62

<210> SEQ ID NO 1
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 1

Cys Gly Ser Ser Gly Gly Gly Val Ala Ala Asp Ile Gly Thr Gly
1               5                   10                  15

Leu Ala Asp Ala Leu Thr Ala Pro Leu Asp His Lys Asp Lys Gly Leu
            20                  25                  30

Lys Ser Leu Thr Leu Glu Asp Ser Ile Ser Gln Asn Gly Thr Leu Thr
        35                  40                  45

Leu Ser Ala Gln Gly Ala Glu Lys Thr Phe Lys Val Gly Asp Lys Asp
    50                  55                  60

Asn Ser Leu Asn Thr Gly Lys Leu Lys Asn Asp Lys Ile Ser Arg Phe
65                  70                  75                  80
```

```
Asp Phe Val Gln Lys Ile Glu Val Asp Gly Gln Thr Ile Thr Leu Ala
                85                  90                  95

Ser Gly Glu Phe Gln Ile Tyr Lys Gln Asp His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Ser Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ser Ala Glu Leu Lys Ala Asp Glu Lys Ser His
        195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 2
<211> LENGTH: 261
<212> TYPE: PRT
<213> ORGANISM: Artificial Sequence
<220> FEATURE:
<223> OTHER INFORMATION: Synthetic amino acid sequence

<400> SEQUENCE: 2

Cys Gly Ser Ser Gly Gly Gly Ser Gly Gly Gly Gly Val Thr Ala
1               5                   10                  15

Asp Ile Gly Thr Gly Leu Ala Asp Ala Leu Thr Ala Pro Leu Asp His
            20                  25                  30

Lys Asp Lys Gly Leu Lys Ser Leu Thr Leu Glu Asp Ser Ile Ser Gln
        35                  40                  45

Asn Gly Thr Leu Thr Leu Ser Ala Gln Gly Ala Glu Lys Thr Tyr Gly
    50                  55                  60

Asn Gly Asp Ser Leu Asn Thr Gly Lys Leu Lys Asn Asp Lys Val Ser
65                  70                  75                  80

Arg Phe Asp Phe Ile Arg Gln Ile Glu Val Asp Gly Gln Leu Ile Thr
                85                  90                  95

Leu Glu Ser Gly Glu Phe Gln Val Tyr Lys Gln Ser His Ser Ala Leu
            100                 105                 110

Thr Ala Leu Gln Thr Glu Gln Glu Gln Asp Pro Glu His Ser Glu Lys
        115                 120                 125

Met Val Ala Lys Arg Arg Phe Arg Ile Gly Asp Ile Ala Gly Glu His
    130                 135                 140

Thr Ser Phe Asp Lys Leu Pro Lys Asp Val Met Ala Thr Tyr Arg Gly
145                 150                 155                 160

Thr Ala Phe Gly Ser Asp Asp Ala Gly Gly Lys Leu Thr Tyr Thr Ile
                165                 170                 175

Asp Phe Ala Ala Lys Gln Gly His Gly Lys Ile Glu His Leu Lys Ser
```

```
                    180                 185                 190
Pro Glu Leu Asn Val Asp Leu Ala Val Ala Tyr Ile Lys Pro Asp Glu
            195                 200                 205

Lys His His Ala Val Ile Ser Gly Ser Val Leu Tyr Asn Gln Asp Glu
        210                 215                 220

Lys Gly Ser Tyr Ser Leu Gly Ile Phe Gly Lys Ala Gln Glu Val
225                 230                 235                 240

Ala Gly Ser Ala Glu Val Glu Thr Ala Asn Gly Ile His His Ile Gly
                245                 250                 255

Leu Ala Ala Lys Gln
            260

<210> SEQ ID NO 3
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 3

Cys Gly Ser Ser
1

<210> SEQ ID NO 4
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 4

Cys Gly Ser Ser Gly Gly Gly Gly Val Ala Ala Asp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic amino acid sequence

<400> SEQUENCE: 5

Cys Ser Ser Gly Ser Gly Ser Gly Gly Gly Val Ala Ala Asp
1               5                   10                  15

<210> SEQ ID NO 6
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 6

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
```

```
                65                  70                  75                  80
        Gln Ile Glu Val Asp Gly Gln Leu Ile Thr Leu Glu Ser Gly Glu Phe
                        85                  90                  95
        Gln Val Tyr Lys Gln Ser His Ser Ala Leu Thr Ala Leu Gln Thr Glu
                    100                 105                 110
        Gln Val Gln Asp Ser Glu Asp Ser Gly Lys Met Val Ala Lys Arg Gln
                    115                 120                 125
        Phe Arg Ile Gly Asp Ile Ala Gly Glu His Thr Ser Phe Asp Lys Leu
            130                 135                 140
        Pro Lys Gly Gly Ser Ala Thr Tyr Arg Gly Thr Ala Phe Gly Ser Asp
        145                 150                 155                 160
        Asp Ala Gly Gly Lys Leu Thr Tyr Thr Ile Asp Phe Ala Ala Lys Gln
                        165                 170                 175
        Gly His Gly Lys Ile Glu His Leu Lys Ser Pro Glu Leu Asn Val Asp
                    180                 185                 190
        Leu Ala Ala Ala Tyr Ile Lys Pro Asp Glu Lys His His Ala Val Ile
                    195                 200                 205
        Ser Gly Ser Val Leu Tyr Asn Gln Asp Glu Lys Gly Ser Tyr Ser Leu
            210                 215                 220
        Gly Ile Phe Gly Gly Lys Ala Glu Glu Val Ala Gly Ser Ala Glu Val
        225                 230                 235                 240
        Lys Thr Val Asn Gly Ile Arg His Ile Gly Leu Ala Ala Lys Gln
                        245                 250                 255

<210> SEQ ID NO 7
<211> LENGTH: 259
<212> TYPE: PRT
<213> ORGANISM: Neisseria meningitidis (group B)

<400> SEQUENCE: 7

Cys Ser Ser Gly Gly Gly Gly Gly Val Ala Ala Asp Ile Gly Thr
        1               5                   10                  15
        Gly Leu Ala Asp Ala Leu Thr Ala Pro Leu Asp His Lys Asp Lys Gly
                    20                  25                  30
        Leu Lys Ser Leu Thr Leu Glu Asp Ser Ile Pro Gln Asn Gly Thr Leu
                35                  40                  45
        Thr Leu Ser Ala Gln Gly Ala Glu Lys Thr Phe Lys Ala Gly Asp Lys
            50                  55                  60
        Asp Asn Ser Leu Asn Thr Gly Lys Leu Lys Asn Asp Lys Ile Ser Arg
        65                  70                  75                  80
        Phe Asp Phe Val Gln Lys Ile Glu Val Asp Gly Gln Thr Ile Thr Leu
                        85                  90                  95
        Ala Ser Gly Glu Phe Gln Ile Tyr Lys Gln Asp His Ser Ala Val Val
                    100                 105                 110
        Ala Leu Gln Ile Glu Lys Ile Asn Asn Pro Asp Lys Ile Asp Ser Leu
                    115                 120                 125
        Ile Asn Gln Arg Ser Phe Leu Val Ser Gly Leu Gly Gly Glu His Thr
            130                 135                 140
        Ala Phe Asn Gln Leu Pro Gly Asp Lys Ala Glu Tyr His Gly Lys Ala
        145                 150                 155                 160
        Phe Ser Ser Asp Asp Ala Gly Gly Lys Leu Thr Tyr Thr Ile Asp Phe
                        165                 170                 175
        Ala Ala Lys Gln Gly His Gly Lys Ile Glu His Leu Lys Thr Pro Glu
                    180                 185                 190
```

```
Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln

<210> SEQ ID NO 8
<211> LENGTH: 261
<212> TYPE: PRT
<213> ORGANISM: Neisseria meningitidis (group B)

<400> SEQUENCE: 8

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 9
<211> LENGTH: 254
<212> TYPE: PRT
<213> ORGANISM: Neisseria meningitidis (group B)
```

<400> SEQUENCE: 9

```
Cys Ser Ser Gly Gly Gly Gly Val Ala Ala Asp Ile Gly Ala Gly Leu
1               5                   10                  15
Ala Asp Ala Leu Thr Ala Pro Leu Asp His Lys Asp Lys Ser Leu Gln
            20                  25                  30
Ser Leu Thr Leu Asp Gln Ser Val Arg Lys Asn Glu Lys Leu Lys Leu
        35                  40                  45
Ala Ala Gln Gly Ala Glu Lys Thr Tyr Gly Asn Gly Asp Ser Leu Asn
    50                  55                  60
Thr Gly Lys Leu Lys Asn Asp Lys Val Ser Arg Phe Asp Phe Ile Arg
65                  70                  75                  80
Gln Ile Glu Val Asp Gly Gln Thr Ile Thr Leu Ala Ser Gly Glu Phe
                85                  90                  95
Gln Ile Tyr Lys Gln Asn His Ser Ala Val Val Ala Leu Gln Ile Glu
            100                 105                 110
Lys Ile Asn Asn Pro Asp Lys Ile Asp Ser Leu Ile Asn Gln Arg Ser
        115                 120                 125
Phe Leu Val Ser Gly Leu Gly Gly Glu His Thr Ala Phe Asn Gln Leu
    130                 135                 140
Pro Asp Gly Lys Ala Glu Tyr His Gly Lys Ala Phe Ser Ser Asp Asp
145                 150                 155                 160
Pro Asn Gly Arg Leu His Tyr Ser Ile Asp Phe Thr Lys Lys Gln Gly
                165                 170                 175
Tyr Gly Arg Ile Glu His Leu Lys Thr Pro Glu Gln Asn Val Glu Leu
            180                 185                 190
Ala Ser Ala Glu Leu Lys Ala Asp Glu Lys Ser His Ala Val Ile Leu
        195                 200                 205
Gly Asp Thr Arg Tyr Gly Glu Glu Lys Gly Thr Tyr His Leu Ala
    210                 215                 220
Leu Phe Gly Asp Arg Ala Gln Glu Ile Ala Gly Ser Ala Thr Val Lys
225                 230                 235                 240
Ile Arg Glu Lys Val His Glu Ile Gly Ile Ala Gly Lys Gln
                245                 250
```

<210> SEQ ID NO 10
<211> LENGTH: 254
<212> TYPE: PRT
<213> ORGANISM: Neisseria meningitidis (group B)

<400> SEQUENCE: 10

```
Cys Ser Ser Gly Gly Gly Gly Val Ala Ala Asp Ile Gly Ala Gly Leu
1               5                   10                  15
Ala Asp Ala Leu Thr Ala Pro Leu Asp His Lys Asp Lys Ser Leu Gln
            20                  25                  30
Ser Leu Thr Leu Asp Gln Ser Val Arg Lys Asn Glu Lys Leu Lys Leu
        35                  40                  45
Ala Ala Gln Gly Ala Glu Lys Thr Tyr Gly Asn Gly Asp Ser Leu Asn
    50                  55                  60
Thr Gly Lys Leu Lys Asn Asp Lys Val Ser Arg Phe Asp Phe Ile Arg
65                  70                  75                  80
Gln Ile Glu Val Asp Gly Gln Leu Ile Thr Leu Glu Ser Gly Glu Phe
                85                  90                  95
Gln Ile Tyr Lys Gln Asp His Ser Ala Val Val Ala Leu Gln Ile Glu
            100                 105                 110
```

```
Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 11
<211> LENGTH: 263
<212> TYPE: PRT
<213> ORGANISM: Neisseria meningitidis (group B)

<400> SEQUENCE: 11

Cys Ser Ser Gly Gly Gly Gly Ser Gly Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Asp Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240
```

-continued

```
Glu Val Ala Gly Ser Ala Val Glu Thr Ala Asn Gly Ile Arg His
                245                 250                 255

Ile Gly Leu Ala Ala Lys Gln
            260

<210> SEQ ID NO 12
<211> LENGTH: 255
<212> TYPE: PRT
<213> ORGANISM: Neisseria meningitidis (group B)

<400> SEQUENCE: 12

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Glu Gln Asp Pro Glu His Ser Gly Lys Met Val Ala Lys Arg Arg
            115                 120                 125

Phe Lys Ile Gly Asp Ile Ala Gly Glu His Thr Ser Phe Asp Lys Leu
        130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 13
<211> LENGTH: 255
<212> TYPE: PRT
<213> ORGANISM: Neisseria meningitidis (group B)

<400> SEQUENCE: 13

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45
```

```
Ala Ala Gln Gly Ala Glu Lys Thr Tyr Gly Asn Gly Asp Ser Leu Asn
         50                  55                  60

Thr Gly Lys Leu Lys Asn Asp Lys Val Ser Arg Phe Asp Phe Ile Arg
 65                  70                  75                  80

Gln Ile Glu Val Asp Gly Lys Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
            195                 200                 205

Ser Gly Ser Val Leu Tyr Asn Gln Asp Glu Lys Gly Ser Tyr Ser Leu
210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 14
<211> LENGTH: 255
<212> TYPE: PRT
<213> ORGANISM: Neisseria meningitidis (group B)

<400> SEQUENCE: 14

Cys Ser Ser Gly Gly Gly Gly Val Ala Ala Asp Ile Gly Ala Val Leu
 1               5                  10                  15

Ala Asp Ala Leu Thr Ala Pro Leu Asp His Lys Asp Lys Ser Leu Gln
                 20                  25                  30

Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
         50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
```

165                 170                 175
Gly His Gly Lys Ile Glu His Leu Lys Ser Pro Glu Leu Asn Val Asp
            180                 185                 190

Leu Ala Ala Ser Asp Ile Lys Pro Asp Lys Arg His Ala Val Ile
        195                 200                 205

Ser Gly Ser Val Leu Tyr Asn Gln Ala Glu Lys Gly Ser Tyr Ser Leu
        210                 215                 220

Gly Ile Phe Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 15
<211> LENGTH: 255
<212> TYPE: PRT
<213> ORGANISM: Neisseria meningitidis (group B)

<400> SEQUENCE: 15

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
        210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 16
<211> LENGTH: 263
<212> TYPE: PRT
<213> ORGANISM: Neisseria meningitidis (group B)

<400> SEQUENCE: 16

```
Cys Ser Ser Gly Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Arg Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Ile Arg Gln Ile Glu Val Asp Gly Gln Leu
                85                  90                  95

Ile Thr Leu Glu Ser Gly Glu Phe Gln Val Tyr Lys Gln Ser His Ser
            100                 105                 110

Ala Leu Thr Ala Leu Gln Thr Glu Gln Val Gln Asp Ser Glu His Ser
        115                 120                 125

Gly Lys Met Val Ala Lys Arg Gln Phe Arg Ile Gly Asp Ile Val Gly
    130                 135                 140

Glu His Thr Ser Phe Gly Lys Leu Pro Lys Asp Val Met Ala Thr Tyr
145                 150                 155                 160

Arg Gly Thr Ala Phe Gly Ser Asp Asp Ala Gly Gly Lys Leu Thr Tyr
                165                 170                 175

Thr Ile Asp Phe Ala Ala Lys Gln Gly His Gly Lys Ile Glu His Leu
            180                 185                 190

Lys Ser Pro Glu Leu Asn Val Asp Leu Ala Ala Ala Asp Ile Lys Pro
        195                 200                 205

Asp Glu Lys His His Ala Val Ile Ser Gly Ser Val Leu Tyr Asn Gln
    210                 215                 220

Ala Glu Lys Gly Ser Tyr Ser Leu Gly Ile Phe Gly Gly Gln Ala Gln
225                 230                 235                 240

Glu Val Ala Gly Ser Ala Glu Val Glu Thr Ala Asn Gly Ile Arg His
                245                 250                 255

Ile Gly Leu Ala Ala Lys Gln
            260
```

<210> SEQ ID NO 17
<211> LENGTH: 255
<212> TYPE: PRT
<213> ORGANISM: Neisseria meningitidis (group B)

<400> SEQUENCE: 17

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

Gln Val Tyr Lys Gln Ser His Ser Ala Leu Thr Ala Leu Gln Thr Glu
                100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255

<210> SEQ ID NO 18
<211> LENGTH: 254
<212> TYPE: PRT
<213> ORGANISM: Neisseria meningitidis (group B)

<400> SEQUENCE: 18

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
            245                 250

<210> SEQ ID NO 19

<400> SEQUENCE: 19

000

<210> SEQ ID NO 20
<211> LENGTH: 257
<212> TYPE: PRT
<213> ORGANISM: Neisseria meningitidis (group B)

<400> SEQUENCE: 20

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
                20                  25                  30

Ser Leu Thr Leu Glu Asp Ser Ile Ser Gln Asn Gly Thr Leu Thr Leu
            35                  40                  45

Ser Ala Gln Gly Ala Glu Lys Thr Phe Lys Val Gly Asp Lys Asp Asn
50                  55                  60

Ser Leu Asn Thr Gly Lys Leu Lys Asn Asp Lys Ile Ser Arg Phe Asp
65                  70                  75                  80

Phe Val Gln Lys Ile Glu Val Asp Gly Gln Thr Ile Thr Leu Ala Ser
                85                  90                  95

Gly Glu Phe Gln Ile Tyr Lys Gln Asn His Ser Ala Val Val Ala Leu
            100                 105                 110

Gln Ile Glu Lys Ile Asn Asn Pro Asp Lys Ile Asp Ser Leu Ile Asn
        115                 120                 125

Gln Arg Ser Phe Leu Val Ser Gly Leu Gly Gly Glu His Thr Ala Phe
130                 135                 140

Asn Gln Leu Pro Gly Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
            180                 185                 190

Val Glu Leu Ala Ala Ala Glu Leu Lys Ala Asp Glu Lys Ser His Ala
        195                 200                 205

Val Ile Leu Gly Asp Thr Arg Tyr Gly Ser Glu Glu Lys Gly Thr Tyr
210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln

<210> SEQ ID NO 21
<211> LENGTH: 254
<212> TYPE: PRT
<213> ORGANISM: Neisseria meningitidis (group B)

<400> SEQUENCE: 21

```
Cys Ser Ser Gly Gly Gly Val Ala Ala Asp Ile Gly Ala Gly Leu
1               5                  10                  15

Ala Asp Ala Leu Thr Thr Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
                100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 22
<211> LENGTH: 262
<212> TYPE: PRT
<213> ORGANISM: Neisseria meningitidis (group B)

<400> SEQUENCE: 22

Cys Ser Ser Gly Gly Gly Ser Gly Gly Gly Val Ala Ala Asp
1               5                  10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
                100                 105                 110

Ala Val Val Ala Leu Gln Ile Glu Lys Ile Asn Asn Pro Asp Lys Ile
```

```
            115                 120                 125
Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
                180                 185                 190

Thr Pro Glu Leu Asn Val Asp Leu Ala Ser Ala Glu Leu Lys Ala Asp
                195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 23
<211> LENGTH: 255
<212> TYPE: PRT
<213> ORGANISM: Neisseria meningitidis (group B)

<400> SEQUENCE: 23

Cys Ser Ser Gly Gly Gly Gly Val Ala Ala Asp Ile Gly Ala Gly Leu
1               5                  10                  15

Ala Asp Ala Leu Thr Ala Pro Leu Asp His Lys Asp Lys Gly Leu Gln
                20                  25                  30

Ser Leu Ile Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
                180                 185                 190

Leu Ala Ala Ala Asp Ile Lys Pro Asp Glu Lys His His Ala Val Ile
            195                 200                 205

Ser Gly Ser Val Leu Tyr Asn Gln Ala Glu Lys Gly Ser Tyr Ser Leu
    210                 215                 220
```

-continued

```
Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 24
<211> LENGTH: 17
<212> TYPE: PRT
<213> ORGANISM: Artificial Sequence
<220> FEATURE:
<223> OTHER INFORMATION: Synthetic amino acid sequence

<400> SEQUENCE: 24

Cys Gly Ser Ser Gly Gly Gly Gly Ser Gly Gly Gly Gly Val Thr Ala
1               5                   10                  15

Asp

<210> SEQ ID NO 25
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 25

Cys Ser Ser Gly Gly Gly Gly Ser Gly Gly Gly Gly Val Thr Ala Asp
1               5                   10                  15

<210> SEQ ID NO 26
<211> LENGTH: 255
<212> TYPE: PRT
<213> ORGANISM: Neisseria meningitidis

<400> SEQUENCE: 26

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
```

|    |     |     |     | 195 |     |     |     | 200 |     |     |     | 205 |     |     |     |
|----|-----|-----|-----|-----|-----|-----|-----|-----|-----|-----|-----|-----|-----|-----|-----|

Ser Gly Ser Val Leu Tyr Asn Gln Ala Glu Lys Gly Ser Tyr Ser Leu
     210                   215               220

Gly Ile Phe Gly Gly Gln Ala Gln Glu Val Ala Gly Ser Ala Glu Val
225               230               235               240

Glu Thr Ala Asn Gly Ile Arg His Ile Gly Leu Ala Ala Lys Gln
     245                   250               255

<210> SEQ ID NO 27
<211> LENGTH: 254
<212> TYPE: PRT
<213> ORGANISM: Neisseria meningitidis

<400> SEQUENCE: 27

Cys Ser Ser Gly Gly Gly Gly Val Ala Ala Asp Ile Gly Ala Gly Leu
1               5                   10               15

Ala Asp Ala Leu Thr Ala Pro Leu Asp His Lys Asp Lys Ser Leu Gln
             20                   25               30

Ser Leu Thr Leu Asp Gln Ser Val Arg Lys Asn Glu Lys Leu Lys Leu
           35                   40               45

Ala Ala Gln Gly Ala Glu Lys Thr Tyr Gly Asn Gly Asp Ser Leu Asn
    50                   55               60

Thr Gly Lys Leu Lys Asn Asp Lys Val Ser Arg Phe Asp Phe Ile Arg
65              70               75               80

Gln Ile Glu Val Asp Gly Gln Leu Ile Thr Leu Glu Ser Gly Glu Phe
             85                   90               95

Gln Ile Tyr Lys Gln Asp His Ser Ala Val Val Ala Leu Gln Ile Glu
           100                 105             110

Lys Ile Asn Asn Pro Asp Lys Ile Asp Ser Leu Ile Asn Gln Arg Ser
        115                 120               125

Phe Leu Val Ser Gly Leu Gly Gly Glu His Thr Ala Phe Asn Gln Leu
130               135               140

Pro Ser Gly Lys Ala Glu Tyr His Gly Lys Ala Phe Ser Ser Asp Asp
145              150               155               160

Pro Asn Gly Arg Leu His Tyr Ser Ile Asp Phe Thr Lys Lys Gln Gly
           165                 170             175

Tyr Gly Arg Ile Glu His Leu Lys Thr Pro Glu Gln Asn Val Glu Leu
        180                 185               190

Ala Ser Ala Glu Leu Lys Ala Asp Glu Lys Ser His Ala Val Ile Leu
           195                 200             205

Gly Asp Thr Arg Tyr Gly Gly Glu Glu Lys Gly Thr Tyr His Leu Ala
     210                   215               220

Leu Phe Gly Asp Arg Ala Gln Glu Ile Ala Gly Ser Ala Thr Val Lys
225               230               235               240

Ile Arg Glu Lys Val His Glu Ile Gly Ile Ala Gly Lys Gln
           245                 250

<210> SEQ ID NO 28
<211> LENGTH: 254
<212> TYPE: PRT
<213> ORGANISM: Neisseria meningitidis

<400> SEQUENCE: 28

Cys Ser Ser Gly Gly Gly Gly Val Ala Ala Asp Ile Gly Ala Gly Leu
1               5                   10               15

Ala Asp Ala Leu Thr Ala Pro Leu Asp His Lys Asp Lys Ser Leu Gln

```
                 20                  25                  30
Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
         50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Ala Leu Gln Ile Glu
            100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
            130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
            195                 200                 205

Gly Asp Thr Arg Tyr Gly Ser Glu Glu Lys Gly Thr Tyr His Leu Ala
            210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 29
<211> LENGTH: 260
<212> TYPE: PRT
<213> ORGANISM: Neisseria meningitidis

<400> SEQUENCE: 29

Cys Ser Ser Gly Gly Gly Gly Ser Gly Gly Gly Gly Val Ala Ala Asp
  1               5                  10                  15

Ile Gly Thr Gly Leu Ala Asp Ala Leu Thr Ala Pro Leu Asp His Lys
                 20                  25                  30

Asp Lys Gly Leu Gln Ser Leu Met Leu Asp Gln Ser Val Arg Lys Asn
             35                  40                  45

Glu Lys Leu Lys Leu Ser Ala Gln Gly Ala Glu Lys Thr Tyr Gly Asn
         50                  55                  60

Gly Asp Ser Leu Asn Thr Gly Lys Leu Lys Asn Asp Lys Ile Ser Arg
 65                  70                  75                  80

Phe Asp Phe Ile His Gln Ile Glu Val Asp Gly Gln Leu Ile Thr Leu
                 85                  90                  95

Glu Ser Gly Glu Phe Gln Val Tyr Lys Gln Ser His Ser Ala Leu Thr
                100                 105                 110

Ala Leu Gln Thr Glu Gln Val Gln Asp Ser Glu His Ser Glu Lys Met
            115                 120                 125

Val Ala Lys Arg Arg Phe Lys Ile Gly Asp Ile Ala Gly Glu His Thr
            130                 135                 140
```

```
Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
            165                 170                 175

Phe Ala Ala Lys Gln Gly His Gly Lys Ile Glu His Leu Lys Ser Pro
        180                 185                 190

Glu Leu Asn Val Glu Leu Ala Ala Ala Tyr Ile Lys Pro Asp Glu Lys
    195                 200                 205

Arg His Ala Val Ile Ser Gly Ser Val Leu Tyr Asn Gln Asp Glu Lys
210                 215                 220

Gly Ser Tyr Ser Leu Gly Ile Phe Gly Gly Gln Ala Gln Glu Val Ala
225                 230                 235                 240

Gly Ser Ala Glu Val Glu Thr Ala Asn Gly Ile His His Ile Gly Leu
            245                 250                 255

Ala Ala Lys Gln
        260

<210> SEQ ID NO 30
<211> LENGTH: 255
<212> TYPE: PRT
<213> ORGANISM: Neisseria meningitidis

<400> SEQUENCE: 30

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
            85                  90                  95

Gln Val Tyr Lys Gln Ser His Ser Ala Leu Thr Ala Leu Gln Thr Glu
        100                 105                 110

Gln Glu Gln Asp Pro Glu His Ser Gly Lys Met Val Ala Lys Arg Arg
    115                 120                 125

Phe Lys Ile Gly Asp Ile Ala Gly Glu His Thr Ser Phe Asp Lys Leu
130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
            165                 170                 175

Gly His Gly Lys Ile Glu His Leu Lys Ser Pro Glu Leu Asn Val Asp
        180                 185                 190

Leu Ala Val Ala Tyr Ile Lys Pro Asp Glu Lys His His Ala Val Ile
    195                 200                 205

Ser Gly Ser Val Leu Tyr Asn Gln Asp Glu Lys Gly Ser Tyr Ser Leu
210                 215                 220

Gly Ile Phe Gly Glu Lys Ala Gln Glu Val Ala Gly Ser Ala Glu Val
225                 230                 235                 240

Lys Thr Ala Asn Gly Ile His His Ile Gly Leu Ala Ala Lys Gln
            245                 250                 255
```

<210> SEQ ID NO 31
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 31

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250

<210> SEQ ID NO 32
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 32

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr

```
            50                  55                  60
Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Ile Tyr Lys Gln Asp His Ser Ala Val Ala Leu Gln Ile Glu Lys
                100                 105                 110

Ile Asn Asn Pro Asp Lys Ile Asp Ser Leu Ile Asn Gln Arg Ser Phe
                115                 120                 125

Leu Val Ser Gly Leu Gly Gly Glu His Thr Ala Phe Asn Gln Leu Pro
            130                 135                 140

Gly Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
                180                 185                 190

Ser Ala Glu Leu Lys Ala Asp Glu Lys Ser His Ala Val Ile Leu Gly
            195                 200                 205

Asp Thr Arg Tyr Gly Ser Glu Glu Lys Gly Thr Tyr His Leu Ala Leu
210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 33
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 33

Ser Ser Gly Gly Gly Val Ala Ala Asp Ile Gly Ala Gly Leu Ala
 1               5                  10                  15

Asp Ala Leu Thr Ala Pro Leu Asp His Lys Asp Lys Ser Leu Gln Ser
                 20                  25                  30

Leu Thr Leu Asp Gln Ser Val Arg Lys Asn Glu Lys Leu Lys Leu Ala
             35                  40                  45

Ala Gln Gly Ala Glu Lys Thr Tyr Gly Asn Gly Asp Ser Leu Asn Thr
 50                  55                  60

Gly Lys Leu Lys Asn Asp Lys Val Ser Arg Phe Asp Phe Ile Arg Gln
 65                  70                  75                  80

Ile Glu Val Asp Gly Gln Leu Ile Thr Leu Glu Ser Gly Glu Phe Gln
                 85                  90                  95

Ile Tyr Lys Gln Asp His Ser Ala Val Ala Leu Gln Ile Glu Lys
                100                 105                 110

Ile Asn Asn Pro Asp Lys Ile Asp Ser Leu Ile Asn Gln Arg Ser Phe
                115                 120                 125

Leu Val Ser Gly Leu Gly Gly Glu His Thr Ala Phe Asn Gln Leu Pro
            130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
```

```
                    165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250

<210> SEQ ID NO 34
<211> LENGTH: 256
<212> TYPE: PRT
<213> ORGANISM: Artificial Sequence
<220> FEATURE:
<223> OTHER INFORMATION: Synthetic amino acid sequence

<400> SEQUENCE: 34

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Lys Ser
            20                  25                  30

Leu Thr Leu Glu Asp Ser Ile Ser Gln Asn Gly Thr Leu Thr Leu Ser
        35                  40                  45

Ala Gln Gly Ala Glu Lys Thr Phe Lys Val Gly Asp Lys Asp Asn Ser
    50                  55                  60

Leu Asn Thr Gly Lys Leu Lys Asn Asp Lys Ile Ser Arg Phe Asp Phe
65                  70                  75                  80

Val Gln Lys Ile Glu Val Asp Gly Gln Thr Ile Thr Leu Ala Ser Gly
                85                  90                  95

Glu Phe Gln Ile Tyr Lys Gln Asn His Ser Ala Val Val Ala Leu Gln
            100                 105                 110

Ile Glu Lys Ile Asn Asn Pro Asp Lys Ile Asp Ser Leu Ile Asn Gln
        115                 120                 125

Arg Ser Phe Leu Val Ser Gly Leu Gly Gly Glu His Thr Ala Phe Asn
    130                 135                 140

Gln Leu Pro Gly Gly Lys Ala Glu Tyr His Gly Lys Ala Phe Ser Ser
145                 150                 155                 160

Asp Asp Ala Gly Gly Lys Leu Thr Tyr Thr Ile Asp Phe Ala Ala Lys
                165                 170                 175

Gln Gly His Gly Lys Ile Glu His Leu Lys Thr Pro Glu Gln Asn Val
            180                 185                 190

Glu Leu Ala Ala Ala Glu Leu Lys Ala Asp Glu Lys Ser His Ala Val
        195                 200                 205

Ile Leu Gly Asp Thr Arg Tyr Gly Ser Glu Lys Gly Thr Tyr His
    210                 215                 220

Leu Ala Leu Phe Gly Asp Arg Ala Gln Glu Ile Ala Gly Ser Ala Thr
225                 230                 235                 240

Val Lys Ile Gly Glu Lys Val His Glu Ile Ser Ile Ala Gly Lys Gln
                245                 250                 255

<210> SEQ ID NO 35
<211> LENGTH: 253
<212> TYPE: PRT
```

<213> ORGANISM: Artificial Sequence
<220> FEATURE:
<223> OTHER INFORMATION: Synthetic amino acid sequence

<400> SEQUENCE: 35

```
Ser Ser Gly Gly Gly Val Ala Ala Asp Ile Gly Ala Gly Leu Ala
1               5                   10                  15

Asp Ala Leu Thr Thr Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
50                  55                  60

Gly Lys Leu Lys Asn Asp Lys Val Ser Arg Phe Asp Phe Ile Arg Gln
65                  70                  75                  80

Ile Glu Val Asp Gly Gln Thr Ile Thr Leu Ala Ser Gly Glu Phe Gln
                85                  90                  95

Ile Tyr Lys Gln Asn His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Asp Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
                180                 185                 190

Ser Ala Glu Leu Lys Ala Asp Glu Lys Ser His Ala Val Ile Leu Gly
            195                 200                 205

Asp Thr Arg Tyr Gly Gly Glu Glu Lys Gly Thr Tyr His Leu Ala Leu
        210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250
```

<210> SEQ ID NO 36
<211> LENGTH: 261
<212> TYPE: PRT
<213> ORGANISM: Artificial Sequence
<220> FEATURE:
<223> OTHER INFORMATION: Synthetic amino acid sequence

<400> SEQUENCE: 36

```
Ser Ser Gly Gly Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Pro Gln Asn Gly
        35                  40                  45

Thr Leu Thr Leu Ser Ala Gln Gly Ala Glu Lys Thr Phe Lys Ala Gly
    50                  55                  60

Asp Lys Asp Asn Ser Leu Asn Thr Gly Lys Leu Lys Asn Asp Lys Ile
65                  70                  75                  80
```

Ser Arg Phe Asp Phe Val Gln Lys Ile Glu Val Asp Gly Gln Thr Ile
            85                  90                  95

Thr Leu Ala Ser Gly Glu Phe Gln Ile Tyr Lys Gln Asn His Ser Ala
        100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
        130                 135                 140

His Thr Ala Phe Asn Gln Leu Pro Gly Asp Lys Ala Glu Tyr His Gly
145                 150                 155                 160

Lys Ala Phe Ser Ser Asp Asp Pro Asn Gly Arg Leu His Tyr Thr Ile
                165                 170                 175

Asp Phe Thr Asn Lys Gln Gly Tyr Gly Arg Ile Glu His Leu Lys Thr
            180                 185                 190

Pro Glu Leu Asn Val Asp Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Gly Glu Lys Val His Glu Ile Gly
                245                 250                 255

Ile Ala Gly Lys Gln
            260

<210> SEQ ID NO 37
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 37

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Ile Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
            85                  90                  95

Val Tyr Lys Gln Ser His Ser Ala Leu Thr Ala Leu Gln Thr Glu Gln
        100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Ser Ser Asp Asp
145                 150                 155                 160

Ala Gly Gly Lys Leu Ile Tyr Thr Ile Asp Phe Ala Ala Lys Gln Gly
                165                 170                 175

```
His Gly Lys Ile Glu His Leu Lys Ser Pro Glu Leu Asn Val Asp Leu
            180                 185                 190

Ala Ala Ala Asp Ile Lys Pro Asp Glu Lys His His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250
```

<210> SEQ ID NO 38
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 38

```
Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
            20                  25                  30

Leu Thr Leu Asp Gln Ser Val Arg Lys Asn Glu Lys Leu Lys Leu Ala
        35                  40                  45

Ala Gln Gly Ala Glu Lys Thr Tyr Gly Asn Gly Asp Ser Leu Asn Thr
    50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
            100                 105                 110

Val Gln Asp Ser Glu His Ser Gly Lys Met Val Ala Lys Arg Gln Phe
        115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250
```

<210> SEQ ID NO 39
<211> LENGTH: 253
<212> TYPE: PRT
<213> ORGANISM: Artificial Sequence
<220> FEATURE:

<223> OTHER INFORMATION: Synthetic amino acid sequence

<400> SEQUENCE: 39

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Ile Tyr Lys Gln Asp His Ser Ala Val Val Ala Leu Gln Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Ser Gly Lys Ala Glu Tyr His Gly Lys Ala Phe Ser Ser Asp Asp Pro
145                 150                 155                 160

Asn Gly Arg Leu His Tyr Ser Ile Asp Phe Thr Lys Lys Gln Gly Tyr
                165                 170                 175

Gly Arg Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Gly Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 40
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 40

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

```
Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
130                 135                 140

Asp Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250
```

<210> SEQ ID NO 41
<211> LENGTH: 259
<212> TYPE: PRT
<213> ORGANISM: Artificial Sequence
<220> FEATURE:
<223> OTHER INFORMATION: Synthetic amino acid sequence

<400> SEQUENCE: 41

```
Ser Ser Gly Gly Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Gln Ser Leu Met Leu Asp Gln Ser Val Arg Lys Asn Glu
        35                  40                  45

Lys Leu Lys Leu Ser Ala Gln Gly Ala Glu Lys Thr Tyr Gly Asn Gly
    50                  55                  60

Asp Ser Leu Asn Thr Gly Lys Leu Lys Asn Asp Lys Ile Ser Arg Phe
65                  70                  75                  80

Asp Phe Ile His Gln Ile Glu Val Asp Gly Gln Leu Ile Thr Leu Glu
                85                  90                  95

Ser Gly Glu Phe Gln Val Tyr Lys Gln Ser His Ser Ala Leu Thr Ala
                100                 105                 110

Leu Gln Thr Glu Gln Val Gln Asp Ser Glu His Ser Lys Met Val
            115                 120                 125

Ala Lys Arg Arg Phe Lys Ile Gly Asp Ile Ala Gly Glu His Thr Ser
        130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Ala Ala Tyr Ile Lys Pro Asp Glu Lys Arg
        195                 200                 205
```

His Ala Val Ile Ser Gly Ser Val Leu Tyr Asn Gln Asp Glu Lys Gly
        210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 42
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 42

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Glu Gln Asp Pro Glu His Ser Gly Lys Met Val Ala Lys Arg Arg Phe
            115                 120                 125

Lys Ile Gly Asp Ile Ala Gly Glu His Thr Ser Phe Asp Lys Leu Pro
130                 135                 140

Lys Asp Val Met Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Val Ala Tyr Ile Lys Pro Asp Glu Lys His His Ala Val Ile Ser
        195                 200                 205

Gly Ser Val Leu Tyr Asn Gln Asp Glu Lys Gly Ser Tyr Ser Leu Gly
    210                 215                 220

Ile Phe Gly Glu Lys Ala Gln Glu Val Ala Gly Ser Ala Glu Val Lys
225                 230                 235                 240

Thr Ala Asn Gly Ile His His Ile Gly Leu Ala Ala Lys Gln
                245                 250

<210> SEQ ID NO 43
<211> LENGTH: 262
<212> TYPE: PRT
<213> ORGANISM: Artificial Sequence
<220> FEATURE:
<223> OTHER INFORMATION: Synthetic amino acid sequence

<400> SEQUENCE: 43

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Arg Thr Phe Lys Ala Gly
50                  55                  60

Asp Lys Asp Asn Ser Leu Asn Thr Gly Lys Leu Lys Asn Asp Lys Ile
65                  70                  75                  80

Ser Arg Phe Asp Phe Ile Arg Gln Ile Glu Val Asp Gly Gln Leu Ile
                85                  90                  95

Thr Leu Glu Ser Gly Glu Phe Gln Val Tyr Lys Gln Ser His Ser Ala
            100                 105                 110

Leu Thr Ala Leu Gln Thr Glu Gln Val Gln Asp Ser Glu His Ser Gly
            115                 120                 125

Lys Met Val Ala Lys Arg Gln Phe Arg Ile Gly Asp Ile Val Gly Glu
            130                 135                 140

His Thr Ser Phe Gly Lys Leu Pro Lys Asp Val Met Ala Thr Tyr Arg
145                 150                 155                 160

Gly Thr Ala Phe Gly Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Ser Pro Glu Leu Asn Val Asp Leu Ala Ala Asp Ile Lys Pro Asp
            195                 200                 205

Glu Lys His His Ala Val Ile Ser Gly Ser Val Leu Tyr Asn Gln Ala
210                 215                 220

Glu Lys Gly Ser Tyr Ser Leu Gly Ile Phe Gly Gly Gln Ala Gln Glu
225                 230                 235                 240

Val Ala Gly Ser Ala Glu Val Glu Thr Ala Asn Gly Ile Arg His Ile
                245                 250                 255

Gly Leu Ala Ala Lys Gln
            260

<210> SEQ ID NO 44
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 44

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu Asp Ser Gly Lys Met Val Ala Lys Arg Gln Phe
        115                 120                 125

Arg Ile Gly Asp Ile Ala Gly Glu His Thr Ser Phe Asp Lys Leu Pro
130                 135                 140

Lys Gly Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Glu Leu
            180                 185                 190

Ala Thr Ala Tyr Ile Lys Pro Asp Glu Lys Arg His Ala Val Ile Ser
        195                 200                 205

Gly Ser Val Leu Tyr Asn Gln Asp Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile His His Ile Gly Leu Ala Ala Lys Gln
                245                 250

<210> SEQ ID NO 45
<211> LENGTH: 259
<212> TYPE: PRT
<213> ORGANISM: Artificial Sequence
<220> FEATURE:
<223> OTHER INFORMATION: Synthetic amino acid sequence

<400> SEQUENCE: 45

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
                20                  25                  30

Lys Gly Leu Gln Ser Leu Thr Leu Asp Gln Ser Val Arg Lys Asn Glu
            35                  40                  45

Lys Leu Lys Leu Ala Ala Gln Gly Ala Glu Lys Thr Tyr Gly Asn Gly
        50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Lys Leu Ile Thr Leu Glu
                85                  90                  95

Ser Gly Glu Phe Gln Val Tyr Lys Gln Ser His Ser Ala Leu Thr Ala
                100                 105                 110

Leu Gln Thr Glu Gln Val Gln Asp Ser Glu Asp Ser Gly Lys Met Val
            115                 120                 125

Ala Lys Arg Gln Phe Arg Ile Gly Asp Ile Ala Gly Glu His Thr Ser
        130                 135                 140

Phe Asp Lys Leu Pro Lys Gly Gly Ser Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Glu Leu Ala Thr Ala Tyr Ile Lys Pro Asp Glu Lys Arg
        195                 200                 205

```
His Ala Val Ile Ser Gly Ser Val Leu Tyr Asn Gln Asp Glu Lys Gly
            210                 215                 220

Ser Tyr Ser Leu Gly Ile Phe Gly Gly Gln Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln

<210> SEQ ID NO 46
<211> LENGTH: 260
<212> TYPE: PRT
<213> ORGANISM: Artificial Sequence
<220> FEATURE:
<223> OTHER INFORMATION: Synthetic amino acid sequence

<400> SEQUENCE: 46

Ser Ser Gly Ser Gly Ser Gly Gly Gly Val Ala Ala Asp Ile Gly
1               5                   10                  15

Thr Gly Leu Ala Asp Ala Leu Thr Ala Pro Leu Asp His Lys Asp Lys
                20                  25                  30

Gly Leu Lys Ser Leu Thr Leu Glu Asp Ser Ile Ser Gln Asn Gly Thr
            35                  40                  45

Leu Thr Leu Ser Ala Gln Gly Ala Glu Lys Thr Phe Lys Val Gly Asp
50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
130                 135                 140

Thr Ala Phe Asn Gln Leu Pro Ser Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ser Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Arg Glu Lys Val His Glu Ile Gly Ile
                245                 250                 255

Ala Gly Lys Gln
            260

<210> SEQ ID NO 47
<211> LENGTH: 259
<212> TYPE: PRT
<213> ORGANISM: Artificial Sequence
<220> FEATURE:
```

<223> OTHER INFORMATION: Synthetic amino acid sequence

<400> SEQUENCE: 47

```
Ser Ser Gly Gly Gly Ser Gly Gly Gly Val Thr Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Tyr Gly Asn Gly
        50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Leu Ile Thr Leu Glu
                85                  90                  95

Ser Gly Glu Phe Gln Val Tyr Lys Gln Ser His Ser Ala Leu Thr Ala
            100                 105                 110

Leu Gln Thr Glu Gln Glu Gln Asp Pro Glu His Ser Glu Lys Met Val
        115                 120                 125

Ala Lys Arg Arg Phe Arg Ile Gly Asp Ile Ala Gly Glu His Thr Ser
    130                 135                 140

Phe Asp Lys Leu Pro Lys Asp Val Met Ala Thr Tyr Arg Gly Thr Ala
145                 150                 155                 160

Phe Gly Ser Asp Asp Ala Gly Gly Lys Leu Thr Tyr Thr Ile Asp Phe
                165                 170                 175

Ala Ala Lys Gln Gly His Gly Lys Ile Glu His Leu Lys Ser Pro Glu
            180                 185                 190

Leu Asn Val Asp Leu Ala Val Ala Tyr Ile Lys Pro Asp Glu Lys His
        195                 200                 205

His Ala Val Ile Ser Gly Ser Val Leu Tyr Asn Gln Asp Glu Lys Gly
    210                 215                 220

Ser Tyr Ser Leu Gly Ile Phe Gly Glu Lys Ala Gln Glu Val Ala Gly
225                 230                 235                 240

Ser Ala Glu Val Glu Thr Ala Asn Gly Ile His His Ile Gly Leu Ala
                245                 250                 255

Ala Lys Gln
```

<210> SEQ ID NO 48
<211> LENGTH: 260
<212> TYPE: PRT
<213> ORGANISM: Artificial Sequence
<220> FEATURE:
<223> OTHER INFORMATION: Synthetic amino acid sequence

<400> SEQUENCE: 48

```
Cys Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80
```

Phe Asp Phe Ile Arg Gln Ile Glu Val Asp Gly Gln Leu Ile Thr Leu
            85                  90                  95

Glu Ser Gly Glu Phe Gln Val Tyr Lys Gln Ser His Ser Ala Leu Thr
        100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
                180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
        210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
        260

<210> SEQ ID NO 49
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 49

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Ile Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Ser Ser Asp
145                 150                 155                 160

Asp Ala Gly Gly Lys Leu Ile Tyr Thr Ile Asp Phe Ala Ala Lys Gln
                165                 170                 175

```
Gly His Gly Lys Ile Glu His Leu Lys Ser Pro Glu Leu Asn Val Asp
            180                 185                 190

Leu Ala Ala Asp Ile Lys Pro Asp Glu Lys His His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
            245                 250                 255

<210> SEQ ID NO 50
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 50

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
            165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
            195                 200                 205

Ser Gly Ser Val Leu Tyr Asn Gln Ala Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
            245                 250                 255

<210> SEQ ID NO 51
<211> LENGTH: 255
<212> TYPE: PRT
<213> ORGANISM: Artificial Sequence
<220> FEATURE:
```

<223> OTHER INFORMATION: Synthetic amino acid sequence

<400> SEQUENCE: 51

```
Gly Ser Ser Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255
```

<210> SEQ ID NO 52
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 52

```
Gly Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

```
Gln Ile Tyr Lys Gln Asp His Ser Ala Val Val Ala Leu Gln Ile Glu
                100                 105                 110

Lys Ile Asn Asn Pro Asp Lys Ile Asp Ser Leu Ile Asn Gln Arg Ser
            115                 120                 125

Phe Leu Val Ser Gly Leu Gly Glu His Thr Ala Phe Asn Gln Leu
    130                 135                 140

Pro Ser Gly Lys Ala Glu Tyr His Gly Lys Ala Phe Ser Ser Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
            195                 200                 205

Gly Asp Thr Arg Tyr Gly Gly Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 53
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 53

Ser Ser Gly Gly Gly Ser Gly Gly Gly Val Ala Ala Asp Ile
1               5                   10                  15

Gly Ala Gly Leu Ala Asp Ala Leu Thr Ala Pro Leu Asp His Lys Asp
            20                  25                  30

Lys Ser Leu Gln Ser Leu Thr Leu Asp Gln Ser Val Arg Lys Asn Glu
        35                  40                  45

Lys Leu Lys Leu Ala Ala Gln Gly Ala Glu Lys Thr Tyr Gly Asn Gly
    50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Thr Ile Thr Leu Ala
                85                  90                  95

Ser Gly Glu Phe Gln Ile Tyr Lys Gln Asn His Ser Ala Val Val Ala
                100                 105                 110

Leu Gln Ile Glu Lys Ile Asn Asn Pro Asp Lys Ile Asp Ser Leu Ile
            115                 120                 125

Asn Gln Arg Ser Phe Leu Val Ser Gly Leu Gly Glu His Thr Ala
    130                 135                 140

Phe Asn Gln Leu Pro Asp Gly Lys Ala Glu Tyr His Gly Lys Ala Phe
145                 150                 155                 160

Ser Ser Asp Asp Pro Asn Gly Arg Leu His Tyr Ser Ile Asp Phe Thr
                165                 170                 175

Lys Lys Gln Gly Tyr Gly Arg Ile Glu His Leu Lys Thr Pro Glu Gln
            180                 185                 190

Asn Val Glu Leu Ala Ser Ala Glu Leu Lys Ala Asp Glu Lys Ser His
        195                 200                 205
```

```
Ala Val Ile Leu Gly Asp Thr Arg Tyr Gly Gly Glu Glu Lys Gly Thr
        210                 215                 220

Tyr His Leu Ala Leu Phe Gly Asp Arg Ala Gln Glu Ile Ala Gly Ser
225                 230                 235                 240

Ala Thr Val Lys Ile Arg Glu Lys Val His Glu Ile Gly Ile Ala Gly
                245                 250                 255

Lys Gln

<210> SEQ ID NO 54
<211> LENGTH: 253
<212> TYPE: PRT
<213> ORGANISM: Artificial Sequence
<220> FEATURE:
<223> OTHER INFORMATION: Synthetic amino acid sequence

<400> SEQUENCE: 54

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Ser Gly Glu Phe Gln
                85                  90                  95

Ile Tyr Lys Gln Asp His Ser Ala Val Val Ala Leu Gln Ile Glu Lys
                100                 105                 110

Ile Asn Asn Pro Asp Lys Ile Asp Ser Leu Ile Asn Gln Arg Ser Phe
            115                 120                 125

Leu Val Ser Gly Leu Gly Gly Glu His Thr Ala Phe Asn Gln Leu Pro
        130                 135                 140

Ser Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ser Ala Glu Leu Lys Ala Asp Glu Lys Ser His Ala Val Ile Leu Gly
        195                 200                 205

Asp Thr Arg Tyr Gly Gly Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Arg Glu Lys Val His Glu Ile Gly Ile Ala Gly Lys Gln
                245                 250

<210> SEQ ID NO 55
<211> LENGTH: 255
<212> TYPE: PRT
<213> ORGANISM: Artificial Sequence
<220> FEATURE:
<223> OTHER INFORMATION: Synthetic amino acid sequence

<400> SEQUENCE: 55
```

```
Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
                35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
                115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
                180                 185                 190

Leu Ala Ser Ala Glu Leu Lys Ala Asp Glu Lys Ser His Ala Val Ile
                195                 200                 205

Leu Gly Asp Thr Arg Tyr Gly Gly Glu Lys Gly Thr Tyr His Leu
                210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255

<210> SEQ ID NO 56
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 56

Ser Ser Gly Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
            20                  25                  30

Leu Thr Leu Asp Gln Ser Val Arg Lys Asn Glu Lys Leu Lys Leu Ala
                35                  40                  45

Ala Gln Gly Ala Glu Lys Thr Tyr Gly Asn Gly Asp Ser Leu Asn Thr
50                  55                  60

Gly Lys Leu Lys Asn Asp Lys Val Ser Arg Phe Asp Phe Ile Arg Gln
65                  70                  75                  80

Ile Glu Val Asp Gly Lys Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110
```

Val Gln Asp Ser Glu Asp Ser Gly Lys Met Val Ala Lys Arg Gln Phe
            115                 120                 125

Arg Ile Gly Asp Ile Ala Gly Glu His Thr Ser Phe Asp Lys Leu Pro
        130                 135                 140

Lys Gly Ser Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 57
<211> LENGTH: 262
<212> TYPE: PRT
<213> ORGANISM: Artificial Sequence
<220> FEATURE:
<223> OTHER INFORMATION: Synthetic amino acid sequence

<400> SEQUENCE: 57

Cys Ser Ser Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Asp Lys Ala Glu Tyr His
145                 150                 155                 160

Gly Lys Ala Phe Ser Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Leu Asn Val Asp Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

```
Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260
```

<210> SEQ ID NO 58
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 58

```
Ser Ser Gly Gly Gly Val Ala Ala Asp Ile Gly Ala Val Leu Ala
1               5                   10                  15

Asp Ala Leu Thr Ala Pro Leu Asp His Lys Asp Lys Ser Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Leu Gln Thr Glu Gln
                100                 105                 110

Val Gln Asp Ser Glu His Ser Gly Lys Met Val Ala Lys Arg Gln Phe
            115                 120                 125

Arg Ile Gly Asp Ile Ala Gly Glu His Thr Ser Phe Asp Lys Leu Pro
130                 135                 140

Glu Gly Gly Arg Ala Thr Tyr Arg Gly Thr Ala Phe Gly Ser Asp Asp
145                 150                 155                 160

Ala Ser Gly Lys Leu Thr Tyr Thr Ile Asp Phe Ala Ala Lys Gln Gly
                165                 170                 175

His Gly Lys Ile Glu His Leu Lys Ser Pro Glu Leu Asn Val Asp Leu
            180                 185                 190

Ala Ala Ser Asp Ile Lys Pro Asp Lys Lys Arg His Ala Val Ile Ser
        195                 200                 205

Gly Ser Val Leu Tyr Asn Gln Ala Glu Lys Gly Ser Tyr Ser Leu Gly
    210                 215                 220

Ile Phe Gly Gly Gln Ala Gln Glu Val Ala Gly Ser Ala Glu Val Glu
225                 230                 235                 240

Thr Ala Asn Gly Ile Arg His Ile Gly Leu Ala Ala Lys Gln
                245                 250
```

<210> SEQ ID NO 59
<211> LENGTH: 258
<212> TYPE: PRT
<213> ORGANISM: Artificial Sequence
<220> FEATURE:
<223> OTHER INFORMATION: Synthetic amino acid sequence

<400> SEQUENCE: 59

```
Cys Gly Ser Ser Gly Gly Gly Gly Val Ala Ala Asp Ile Gly Thr Gly
```

```
                1               5                  10                 15
            Leu Ala Asp Ala Leu Thr Ala Pro Leu Asp His Lys Asp Lys Gly Leu
                            20                  25                 30
            Lys Ser Leu Thr Leu Glu Asp Ser Ile Ser Gln Asn Gly Thr Leu Thr
                            35                  40                 45
            Leu Ser Ala Gln Gly Ala Glu Lys Thr Phe Lys Val Gly Asp Lys Asp
                        50                  55                 60
            Asn Ser Leu Asn Thr Gly Lys Leu Lys Asn Asp Lys Ile Ser Arg Phe
            65                  70                  75                 80
            Asp Phe Val Gln Lys Ile Glu Val Asp Gly Gln Thr Ile Thr Leu Ala
                                85                  90                 95
            Ser Gly Glu Phe Gln Ile Tyr Lys Gln Asp His Ser Ala Val Val Ala
                            100                 105                110
            Leu Gln Ile Glu Lys Ile Asn Asn Pro Asp Lys Ile Asp Ser Leu Ile
                        115                 120                125
            Asn Gln Arg Ser Phe Leu Val Ser Gly Leu Gly Gly Glu His Thr Ala
                        130                 135                140
            Phe Asn Gln Leu Pro Ser Gly Lys Ala Glu Tyr His Gly Lys Ala Phe
            145                 150                 155                160
            Ser Ser Asp Asp Ala Gly Gly Lys Leu Thr Tyr Thr Ile Asp Phe Ala
                            165                 170                175
            Ala Lys Gln Gly His Gly Lys Ile Glu His Leu Lys Thr Pro Glu Gln
                        180                 185                190
            Asn Val Glu Leu Ala Ser Ala Glu Leu Lys Ala Asp Glu Lys Ser His
                        195                 200                205
            Ala Val Ile Leu Gly Asp Thr Arg Tyr Gly Ser Glu Glu Lys Gly Thr
                    210                 215                 220
            Tyr His Leu Ala Leu Phe Gly Asp Arg Ala Gln Glu Ile Ala Gly Ser
            225                 230                 235                240
            Ala Thr Val Lys Ile Arg Glu Lys Val His Glu Ile Gly Ile Ala Gly
                            245                 250                255
            Lys Gln

<210> SEQ ID NO 60
<211> LENGTH: 257
<212> TYPE: PRT
<213> ORGANISM: Artificial Sequence
<220> FEATURE:
<223> OTHER INFORMATION: Synthetic amino acid sequence

<400> SEQUENCE: 60

Gly Ser Ser Gly Gly Gly Val Ala Ala Asp Ile Gly Thr Gly Leu
            1               5                  10                 15

Ala Asp Ala Leu Thr Ala Pro Leu Asp His Lys Asp Lys Gly Leu Lys
                            20                  25                 30

Ser Leu Thr Leu Glu Asp Ser Ile Ser Gln Asn Gly Thr Leu Thr Leu
                        35                  40                 45

Ser Ala Gln Gly Ala Glu Lys Thr Phe Lys Val Gly Asp Lys Asp Asn
                    50                  55                 60

Ser Leu Asn Thr Gly Lys Leu Lys Asn Asp Lys Ile Ser Arg Phe Asp
            65                  70                  75                 80

Phe Val Gln Lys Ile Glu Val Asp Gly Gln Thr Ile Thr Leu Ala Ser
                                85                  90                 95

Gly Glu Phe Gln Ile Tyr Lys Gln Asp His Ser Ala Val Val Ala Leu
                            100                 105                110
```

Gln Ile Glu Lys Ile Asn Asn Pro Asp Lys Ile Asp Ser Leu Ile Asn
                115                 120                 125

Gln Arg Ser Phe Leu Val Ser Gly Leu Gly Glu His Thr Ala Phe
    130                 135                 140

Asn Gln Leu Pro Ser Gly Lys Ala Glu Tyr His Gly Lys Ala Phe Ser
145                 150                 155                 160

Ser Asp Asp Ala Gly Gly Lys Leu Thr Tyr Thr Ile Asp Phe Ala Ala
                165                 170                 175

Lys Gln Gly His Gly Lys Ile Glu His Leu Lys Thr Pro Glu Gln Asn
                180                 185                 190

Val Glu Leu Ala Ser Ala Glu Leu Lys Ala Asp Glu Lys Ser His Ala
                195                 200                 205

Val Ile Leu Gly Asp Thr Arg Tyr Gly Ser Glu Glu Lys Gly Thr Tyr
                210                 215                 220

His Leu Ala Leu Phe Gly Asp Arg Ala Gln Glu Ile Ala Gly Ser Ala
225                 230                 235                 240

Thr Val Lys Ile Arg Glu Lys Val His Glu Ile Gly Ile Ala Gly Lys
                245                 250                 255

Gln

<210> SEQ ID NO 61
<211> LENGTH: 254
<212> TYPE: PRT
<213> ORGANISM: Artificial Sequence
<220> FEATURE:
<223> OTHER INFORMATION: Synthetic amino acid sequence

<400> SEQUENCE: 61

Ser Ser Gly Gly Gly Val Ala Ala Asp Ile Gly Ala Gly Leu Ala
1               5                   10                  15

Asp Ala Leu Thr Ala Pro Leu Asp His Lys Asp Lys Gly Leu Gln Ser
                20                  25                  30

Leu Thr Leu Asp Gln Ser Val Arg Lys Asn Glu Lys Leu Lys Leu Ala
            35                  40                  45

Ala Gln Gly Ala Glu Lys Thr Tyr Gly Asn Gly Asp Ser Leu Asn Thr
        50                  55                  60

Gly Lys Leu Lys Asn Asp Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Phe Gln Thr Glu Gln
                100                 105                 110

Ile Gln Asp Ser Glu His Ser Gly Lys Met Val Ala Lys Arg Gln Phe
                115                 120                 125

Arg Ile Gly Asp Ile Ala Gly Glu His Thr Ser Phe Asp Lys Leu Pro
    130                 135                 140

Glu Gly Gly Arg Ala Thr Tyr Arg Gly Thr Ala Phe Gly Ser Asp Asp
145                 150                 155                 160

Ala Gly Gly Lys Leu Thr Tyr Thr Ile Asp Phe Ala Ala Lys Gln Gly
                165                 170                 175

Asn Gly Lys Ile Glu His Leu Lys Ser Pro Glu Leu Asn Val Asp Leu
                180                 185                 190

Ala Ala Ala Asp Ile Lys Pro Asp Gly Lys Arg His Ala Val Ile Ser
                195                 200                 205

```
Gly Ser Val Leu Tyr Asn Gln Ala Glu Lys Gly Ser Tyr Ser Leu Gly
        210                 215                 220

Ile Phe Gly Gly Lys Ala Gln Glu Val Ala Gly Ser Ala Glu Val Lys
225                 230                 235                 240

Thr Val Asn Gly Ile Arg His Ile Gly Leu Ala Ala Lys Gln
                245                 250

<210> SEQ ID NO 62
<211> LENGTH: 252
<212> TYPE: PRT
<213> ORGANISM: Artificial Sequence
<220> FEATURE:
<223> OTHER INFORMATION: Synthetic amino acid sequence

<400> SEQUENCE: 62

Gly Gly Gly Gly Val Ala Ala Asp Ile Gly Ala Gly Leu Ala Asp Ala
1               5                   10                  15

Leu Thr Ala Pro Leu Asp His Lys Asp Lys Gly Leu Gln Ser Leu Thr
            20                  25                  30

Leu Asp Gln Ser Val Arg Lys Asn Glu Lys Leu Lys Leu Ala Ala Gln
            35                  40                  45

Gly Ala Glu Lys Thr Tyr Gly Asn Gly Asp Ser Leu Asn Thr Gly Lys
50                  55                  60

Leu Lys Asn Asp Lys Val Ser Arg Phe Asp Phe Ile Arg Gln Ile Glu
65                  70                  75                  80

Val Asp Gly Gln Leu Ile Thr Leu Glu Ser Gly Glu Phe Gln Val Tyr
                85                  90                  95

Lys Gln Ser His Ser Ala Leu Thr Ala Phe Gln Thr Glu Gln Ile Gln
            100                 105                 110

Asp Ser Glu His Ser Gly Lys Met Val Ala Lys Arg Gln Phe Arg Ile
            115                 120                 125

Gly Asp Ile Ala Gly Glu His Thr Ser Phe Asp Lys Leu Pro Glu Gly
130                 135                 140

Gly Arg Ala Thr Tyr Arg Gly Thr Ala Phe Gly Ser Asp Asp Ala Gly
145                 150                 155                 160

Gly Lys Leu Thr Tyr Thr Ile Asp Phe Ala Ala Lys Gln Gly Asn Gly
                165                 170                 175

Lys Ile Glu His Leu Lys Ser Pro Glu Leu Asn Val Asp Leu Ala Ala
            180                 185                 190

Ala Asp Ile Lys Pro Asp Gly Lys Arg His Ala Val Ile Ser Gly Ser
            195                 200                 205

Val Leu Tyr Asn Gln Ala Glu Lys Gly Ser Tyr Ser Leu Gly Ile Phe
        210                 215                 220

Gly Gly Lys Ala Gln Glu Val Ala Gly Ser Ala Glu Val Lys Thr Val
225                 230                 235                 240

Asn Gly Ile Arg His Ile Gly Leu Ala Ala Lys Gln
                245                 250
```

NEISSERIA MENINGITIDIS COMPOSITIONS AND METHODS THEREOF

CROSS REFERENCE TO RELATED APPLICATIONS

The present application is a continuation of and claims the benefit of U.S. patent application Ser. No. 16/196,150, filed on Nov. 20, 2018 (now allowed), which claims the benefit of U.S. patent application Ser. No. 15/883,334, filed on Jan. 30, 2018 (now U.S. Pat. No. 10,183,070), which claims the benefit of U.S. Provisional Patent Application 62/452,963, filed on Jan. 31, 2017, U.S. Provisional Patent Application 62/503,295, filed on May 8, 2017, U.S. Provisional Patent Application 62/613,945, filed on Jan. 5, 2018, and U.S. Provisional Patent Application No. 62/623,233, filed on Jan. 29, 2018. All of the foregoing applications are hereby incorporated by reference in their entireties.

FIELD OF THE INVENTION

The present invention relates to *Neisseria meningitidis* compositions and methods thereof.

BACKGROUND OF THE INVENTION

*Neisseria meningitidis* is a Gram-negative encapsulated bacterium that can cause sepsis, meningitis, and death. *N. meningitidis* can be classified into at least 12 serogroups (including serogroups A, B, C, 29E, H, I, K, L, W-135 (mostly now referred to as W), X, Y and Z) based on chemically and antigenically distinctive polysaccharide capsules. Strains with five of the serogroups (A, B, C, Y, and W135) are responsible for the majority of disease.

Meningococcal meningitis is a devastating disease that can kill children and young adults within hours despite the availability of antibiotics. There is a need for improved immunogenic compositions against meningococcal serogroups A, B, C, Y, and W135 and/or X.

Currently, a cross-protective vaccine or composition effective against a wide range of MnB and meningococcal serogroups A, C, Y, and W and/or X isolates is not yet commercially available. For example, published results-to-date relating to a licensed multi-component composition for protection against serogroup B disease has not demonstrated a direct bactericidal immune response against multiple meningococcal strains that express non-serogroup B capsular polysaccharides, at least in adolescents. Accordingly, a cross-protective vaccine or composition effective against diverse MnB and meningococcal serogroups A, C, Y, and W and/or X isolates is needed as is determining real-world vaccine coverage against a panel of diverse or heterologous meningococcal strains (e.g., representing different geographical regions).

It is a further object of the invention to provide improved schedules for administering a meningococcal vaccine, in particular to children. While incidence rates of invasive meningococcal disease (IMD) vary with age, incidence is often highest during infancy from age 1 month to 1 year, with a second peak in incidence during adolescence. In the United States, during 1998 to 2007, the overall rate of meningococcal disease in infants aged less than 2 years was 3.9 per 100,000. In children aged 2 to 10 years, the incidence was 0.68 per 100,000, with 41% of cases in this age group occurring in children aged 2 to 3 years. National surveillance data from Australia show the peak incidence of disease in children aged 4 years or less, with a secondary peak in adolescents and young adults; approximately 85% of all cases are attributed to serogroup B disease.

SUMMARY OF THE INVENTION

To meet these and other needs, the present invention relates to *Neisseria meningitidis* compositions and methods thereof.

The inventors surprisingly discovered a composition including at least one factor H binding protein (fHBP) and at least one *N. meningitidis* capsular saccharide conjugate. The composition is surprisingly stable and elicited an immune response against strains that express fHBP variants that are homologous to the fHBP variant in the multi-component composition and an immune response against strains that express fHBP variants that are heterologous to the fHBP variant in the multi-component composition.

The composition includes a first lipidated polypeptide including the amino acid sequence set forth in SEQ ID NO: 1; a second lipidated polypeptide including the amino acid sequence set forth in SEQ ID NO: 2; a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W135 (MenW) capsular saccharide conjugated to tetanus toxoid carrier protein (TT); and a *Neisseria meningitidis* serogroup Y (MenY) capsular saccharide conjugated to tetanus toxoid carrier protein (TT).

In one embodiment, the composition includes a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); and a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).

In one aspect, the invention relates to a kit including (a) a first composition including a lipidated MenB rLP2086 subfamily A polypeptide and a lipidated MenB rLP2086 subfamily B polypeptide; and (b) a second composition including a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W$_{135}$ (MenW) capsular saccharide conjugated to tetanus toxoid carrier protein (TT); and a *Neisseria meningitidis* serogroup Y (MenY) capsular saccharide conjugated to tetanus toxoid carrier protein (TT). In one embodiment, the first composition is a liquid composition and the second composition is a lyophilized composition. In another embodiment, the kit does not further include any one of the following immunogenic compositions: MENACTRA®, MENVEO®, ADACEL®, HAVRIX®, GARDASIL®, REPEVAX, or any combination thereof. In one embodiment, the kit includes any one of ibuprofen, paracetamol, and amoxicillin.

In one aspect, the invention relates to an immunogenic composition including a liquid composition including (i) a first lipidated polypeptide including the amino acid sequence set forth in SEQ ID NO: 1; and (ii) a second lipidated polypeptide including the amino acid sequence set forth in SEQ ID NO: 2; and a lyophilized composition including a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); and a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate). In one embodiment, the lyophilized composition is reconstituted with the liquid composition.

In another aspect, the invention relates to a method of inducing a bactericidal immune response against a *Neisseria meningitidis* serogroup X strain. In some embodiments, the method includes administering to the human a composition including a fHBP protein. In some embodiments, the method includes administering to the human a composition comprising a polypeptide comprising an amino acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the amino acid sequence set forth in any one of SEQ ID NO: 1, SEQ ID NO: 2, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62. In some embodiments, the method includes administering to the human a composition including a first lipidated polypeptide including the amino acid sequence set forth in SEQ ID NO: 1; a second lipidated polypeptide including the amino acid sequence set forth in SEQ ID NO: 2.

In another aspect, the invention relates to a method of inducing a bactericidal immune response against a *Neisseria meningitidis* serogroup X strain. The method includes administering to the human a composition that includes a first lipidated polypeptide including the amino acid sequence set forth in SEQ ID NO: 1; a second lipidated polypeptide including the amino acid sequence set forth in SEQ ID NO: 2; a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W135 (MenW) capsular saccharide conjugated to tetanus toxoid carrier protein (TT); and a *Neisseria meningitidis* serogroup Y (MenY) capsular saccharide conjugated to tetanus toxoid carrier protein (TT).

In one aspect, the invention relates to a method for eliciting an immune response in a patient of any age. The method includes administering to the human a composition including a first lipidated polypeptide including the amino acid sequence set forth in SEQ ID NO: 1; a second lipidated polypeptide including the amino acid sequence set forth in SEQ ID NO: 2. In one embodiment, the composition further includes polysorbate-80. In one embodiment, the composition further includes aluminum. In one embodiment, the composition further includes histidine. In one embodiment, the composition further includes sodium chloride. In one embodiment, the composition further includes polysorbate-80, aluminum, histidine, and sodium chloride. In yet another embodiment, the composition further includes a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W135 (MenW) capsular saccharide conjugated to tetanus toxoid carrier protein (TT); and a *Neisseria meningitidis* serogroup Y (MenY) capsular saccharide conjugated to tetanus toxoid carrier protein (TT).

BRIEF DESCRIPTION OF THE DRAWINGS

FIG. 6A—Amino acid sequences for a factor H binding protein (fHBP) B16 (SEQ ID NO: 26) from a *N. meningitidis* serogroup A strain (fHBP variant B16 (PMB3257, MenA);

FIG. 6B—a fHBP A10 (SEQ ID NO: 27) from a *N. meningitidis* serogroup C strain (fHBP variant A10 (PMB5208, MenC and PMB5523, MenW);

FIG. 6C—a fHBP A19 (SEQ ID NO: 28) from a *N. meningitidis* serogroup W strain (fHBP variant A19 (PMB5248, MenW);

FIG. 6D—a fHBP A10 (SEQ ID NO: 27) from a *N. meningitidis* serogroup W strain (fHBP variant A10 (PMB5523, MenW);

FIG. 6E—a fHBP B47 (SEQ ID NO: 29) from a *N. meningitidis* serogroup Y strain (fHBP variant B47 (PMB5187, MenY);

FIG. 6F—a fHBP B49 (SEQ ID NO: 30) from a *N. meningitidis* serogroup X strain (fHBP variant B49 (PMB5540, MenX).

FIG. 7—Serum Bactericidal Activity, the Correlate of Protection for Meningococcal Disease. A titer of ≥4 in serum bactericidal assays using human complement (hSBA) is the established correlate of protection for meningococcal disease.

FIG. 8—MenA, C, W, Y, and X Test Strain Selection

FIG. 9—Schematic of the Relevant Groups of the Clinical Trial From Which a Subset of Test Sera Were Randomly Selected FIG. 10—Distribution of FHbp Surface Expression Levels (MFI) Determined From Flow Cytometric Experiments Using the FHbp Reactive mAb MN 994-11. The FHbp surface expression for each of the strains within a serogroup is noted with a black dot while the FHbp surface expression levels for the selected test strains within each serogroup are noted with a colored star.

FIG. 11—hSBA Response Rate (Percentage of Subjects With hSBA Titers ≥8) for MenA PMB3257 (B16). Response rates and 95% confidence intervals for sera collected at preimmunization (month 0) and 1 month after doses 1, 2, and 3 for MenBFHbp are shown. The geometric mean titers (GMTs) obtained were 2, 3, 4, and 5, respectively. The response rates for subjects in the positive control group were 3% prior to vaccination and 97% one month after receiving MCV4. The GMTs for the positive control group were 2 and 95, respectively.

FIG. 12—hSBA Response Rate (Percentage of Subjects With hSBA Titers ≥8) for MenC PMB5208 (A10). Response rates and 95% confidence intervals for sera collected at preimmunization (month 0) and 1 month after doses 1, 2, and 3 for MenBFHbp are shown. The GMTs obtained were 4, 8, 12, and 29, respectively. The response rates for subjects in the positive control group were 20% prior to vaccination and 90% one month after receiving MCV4. The GMTs for the positive control group were 3 and 119, respectively.

FIG. 13—hSBA Response Rate (Percentage of Subjects With hSBA Titers ≥8) for MenW PMB5248 (A19). Response rates and 95% confidence intervals for sera collected at preimmunization (month 0) and 1 month after doses 1, 2, and 3 for MenBFHbp are shown. The GMTs obtained were 4, 18, 47, and 77, respectively. The response rates for subjects in the positive control group were 40% prior to vaccination and 97% one month after receiving MCV4. The GMTs for the positive control group were 5 and 88, respectively.

FIG. 14—hSBA Response Rate (Percentage of Subjects With hSBA Titers ≥8) for MenW PMB5523 (A10). Response rates and 95% confidence intervals for sera collected at preimmunization (month 0) and 1 month after doses 1, 2, and 3 for MenBFHbp are shown. The GMTs obtained were 7, 15, 21, and 42, respectively. The response rates for subjects in the positive control group were 55% prior to vaccination and 97% one month after receiving MCV4. The GMTs for the positive control group were 8 and 60, respectively.

FIG. 15—hSBA Response Rate (Percentage of Subjects With hSBA Titers ≥8) for MenY PMB5187 (B47). Response rates and 95% confidence intervals for sera collected at preimmunization (month 0) and 1 month after doses 1, 2, and 3 for MenBFHbp are shown. The GMTs obtained were 3, 7, 31, and 58, respectively. The response rates for subjects in the positive control group were 13% prior to vaccination and 97% one month after receiving MCV4. The GMTs for the positive control group were 3 and 79, respectively.

FIG. 16—hSBA Response Rate (Percentage of Subjects With hSBA Titers ≥8) for MenX PMB5540 (B49). Response rates and 95% confidence intervals for sera collected at preimmunization (month 0) and 1 month after doses 1, 2, and 3 for MenBFHbp are shown. The GMTs obtained were 2, 3, 7, and 20, respectively. The response rates for subjects in the positive control group were 0% prior to vaccination and 0% one month after receiving MCV4 vaccine. The GMTs for the positive control group were 2 and 2, respectively.

SEQUENCE IDENTIFIERS

SEQ ID NO: 1 sets forth the amino acid sequence for a recombinant *N. meningitidis*, serogroup B, 2086 variant A05 polypeptide antigen.

SEQ ID NO: 2 sets forth the amino acid sequence for a recombinant *N. meningitidis*, serogroup B, 2086 variant B01 polypeptide antigen.

SEQ ID NO: 3 sets forth the amino acid residues at positions 1-4 of SEQ ID NO: 1 and SEQ ID NO: 2.

SEQ ID NO: 4 sets forth the amino acid sequence of the N-terminus of a recombinant Neisserial Subfamily A LP2086 polypeptide (rLP2086) (A05) polypeptide.

SEQ ID NO: 5 sets forth the amino acid sequence of the N-terminus of Neisserial Subfamily A LP2086 M98250771 polypeptide (A05) polypeptide.

SEQ ID NO: 6 sets forth the amino acid sequence for *N. meningitidis*, serogroup B, 2086 variant B153.

SEQ ID NO: 7 sets forth the amino acid sequence for *N. meningitidis*, serogroup B, 2086 variant A04.

SEQ ID NO: 8 sets forth the amino acid sequence for *N. meningitidis*, serogroup B, 2086 variant A05

SEQ ID NO: 9 sets forth the amino acid sequence for *N. meningitidis*, serogroup B, 2086 variant A12.

SEQ ID NO: 10 sets forth the amino acid sequence for *N. meningitidis*, serogroup B, 2086 variant A22.

SEQ ID NO: 11 sets forth the amino acid sequence for *N. meningitidis*, serogroup B, 2086 variant B02.

SEQ ID NO: 12 sets forth the amino acid sequence for *N. meningitidis*, serogroup B, 2086 variant B03.

SEQ ID NO: 13 sets forth the amino acid sequence for *N. meningitidis*, serogroup B, 2086 variant B09.

SEQ ID NO: 14 sets forth the amino acid sequence for *N. meningitidis*, serogroup B, 2086 variant B22.

SEQ ID NO: 15 sets forth the amino acid sequence for *N. meningitidis*, serogroup B, 2086 variant B24.

SEQ ID NO: 16 sets forth the amino acid sequence for *N. meningitidis*, serogroup B, 2086 variant B44.

SEQ ID NO: 17 sets forth the amino acid sequence for *N. meningitidis*, serogroup B, 2086 variant B16.

SEQ ID NO: 18 sets forth the amino acid sequence for *N. meningitidis*, serogroup B, 2086 variant A07.

SEQ ID NO: 19 sets forth the amino acid sequence for *N. meningitidis*, serogroup B, 2086 variant A19.

SEQ ID NO: 20 sets forth the amino acid sequence for *N. meningitidis*, serogroup B, 2086 variant A06.

SEQ ID NO: 21 sets forth the amino acid sequence for *N. meningitidis*, serogroup B, 2086 variant A15.

SEQ ID NO: 22 sets forth the amino acid sequence for *N. meningitidis*, serogroup B, 2086 variant A29.

SEQ ID NO: 23 sets forth the amino acid sequence for *N. meningitidis*, serogroup B, 2086 variant B15.

Figure 1:
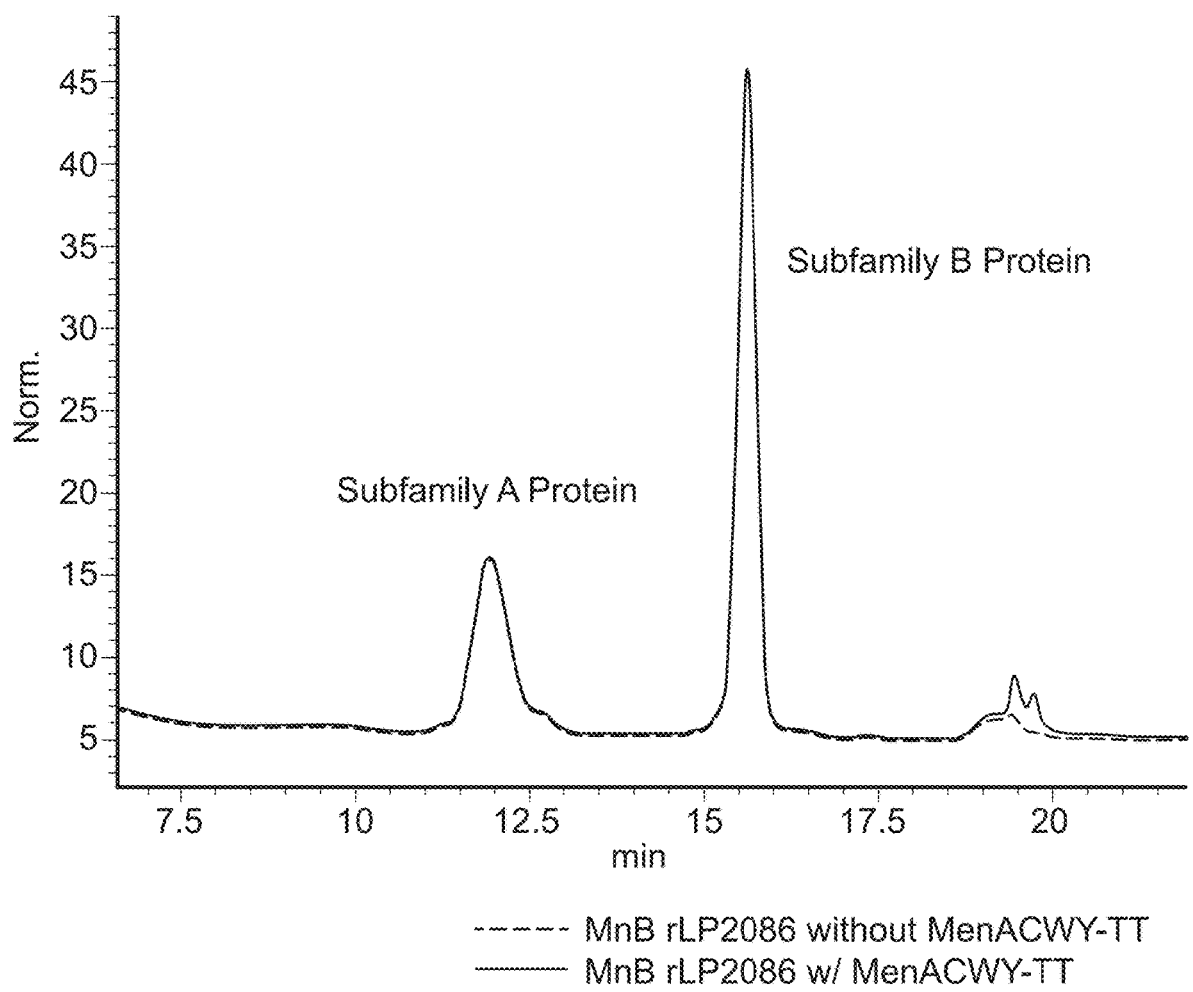
FIG. 1—Overlaid IEX-HPC Chromatograms for the MnB bivalent rLP2086 composition in the Absence and Presence of the MenACWY-TT composition, described in Example 6.

SEQ ID NO: 24 sets forth the amino acid sequence of the N-terminus of a recombinant Neisserial Subfamily B LP2086 polypeptide (rLP2086) (B01) polypeptide.

SEQ ID NO: 25 sets forth the amino acid sequence of the N-terminus of Neisserial Subfamily B LP2086 CDC-1573 polypeptide (B01) polypeptide.

SEQ ID NO: 26 sets forth the amino acid sequence for *N. meningitidis* serogroup A strain expressing factor H binding protein (fHBP) B16.

SEQ ID NO: 27 sets forth the amino acid sequence for a *N. meningitidis* serogroup C strain expressing fHBP A10. SEQ ID NO: 27 also sets forth the amino acid sequence for a *N. meningitidis* serogroup W strain expressing fHBP A10.

SEQ ID NO: 28 sets forth the amino acid sequence for a *N. meningitidis* serogroup W strain expressing fHBP A19.

SEQ ID NO: 29 sets forth the amino acid sequence for a *N. meningitidis* serogroup Y strain expressing fHBP B47.

SEQ ID NO: 30 sets forth the amino acid sequence for a *N. meningitidis* serogroup X strain expressing fHBP B49.

SEQ ID NO: 31 sets forth the amino acid sequence for a non-lipidated *N. meningitidis*, serogroup B, 2086 variant B16.

SEQ ID NO: 32 sets forth the amino acid sequence for a non-lipidated *N. meningitidis*, serogroup B, 2086 variant A07.

SEQ ID NO: 33 sets forth the amino acid sequence for a non-lipidated *N. meningitidis*, serogroup B, 2086 variant A19.

SEQ ID NO: 34 sets forth the amino acid sequence for a non-lipidated *N. meningitidis*, serogroup B, 2086 variant A06.

SEQ ID NO: 35 sets forth the amino acid sequence for a non-lipidated *N. meningitidis*, serogroup B, 2086 variant A15.

SEQ ID NO: 36 sets forth the amino acid sequence for a non-lipidated *N. meningitidis*, serogroup B, 2086 variant A29.

SEQ ID NO: 37 sets forth the amino acid sequence for a non-lipidated *N. meningitidis*, serogroup B, 2086 variant B15.

SEQ ID NO: 38 sets forth the amino acid sequence for a non-lipidated *N. meningitidis* serogroup A strain expressing factor H binding protein (fHBP) B16.

SEQ ID NO: 39 sets forth the amino acid sequence for a non-lipidated *N. meningitidis* serogroup C strain expressing fHBP A10. SEQ ID NO: 39 also sets forth the amino acid sequence for a non-lipidated *N. meningitidis* serogroup W strain expressing fHBP A10.

SEQ ID NO: 40 sets forth the amino acid sequence for a non-lipidated *N. meningitidis* serogroup W strain expressing fHBP A19.

SEQ ID NO: 41 sets forth the amino acid sequence for a non-lipidated *N. meningitidis* serogroup Y strain expressing fHBP B47.

SEQ ID NO: 42 sets forth the amino acid sequence for a non-lipidated *N. meningitidis* serogroup X strain expressing fHBP B49.

SEQ ID NO: 43 sets forth the amino acid sequence for a non-lipidated *N. meningitidis*, serogroup B, 2086 variant B44.

SEQ ID NO: 44 sets forth the amino acid sequence for a non-lipidated *N. meningitidis*, serogroup B, 2086 variant B09.

SEQ ID NO: 45 sets forth the amino acid sequence for a *N. meningitidis*, serogroup B, 2086 variant B09.

SEQ ID NO: 46 sets forth the amino acid sequence for a non-lipidated *N. meningitidis*, serogroup B, 2086 variant A05.

SEQ ID NO: 47 sets forth the amino acid sequence for a non-lipidated *N. meningitidis*, serogroup B, 2086 variant B01.

SEQ ID NO: 48 sets forth the amino acid sequence for a *N. meningitidis*, serogroup B, 2086 variant B01, which includes an N-terminal Cys at amino acid position 1.

SEQ ID NO: 49 sets forth the amino acid sequence for a *N. meningitidis*, serogroup B, 2086 variant B15, which includes an N-terminal Cys at amino acid position 1.

SEQ ID NO: 50 sets forth the amino acid sequence for a *N. meningitidis*, serogroup B, 2086 variant B16, which includes an N-terminal Cys at amino acid position 1.

SEQ ID NO: 51 sets forth the amino acid sequence for a *N. meningitidis*, serogroup B, 2086 variant B22.

SEQ ID NO: 52 sets forth the amino acid sequence for a *N. meningitidis*, serogroup B, 2086 variant A22.

SEQ ID NO: 53 sets forth the amino acid sequence for a non-lipidated *N. meningitidis*, serogroup B, 2086 variant A12.

SEQ ID NO: 54 sets forth the amino acid sequence for a non-lipidated *N. meningitidis*, serogroup B, 2086 variant A22.

SEQ ID NO: 55 sets forth the amino acid sequence for a *N. meningitidis* serogroup B, 2086 variant A62, which includes an N-terminal Cys at amino acid position 1. SEQ ID NO: 56 sets forth the amino acid sequence for a non-lipidated *N. meningitidis*, serogroup B, 2086 variant A62.

SEQ ID NO: 57 sets forth the amino acid sequence for a *N. meningitidis*, serogroup B, 2086 variant A29, which includes an N-terminal Cys at amino acid position 1. SEQ ID NO: 58 sets forth the amino acid sequence for a non-lipidated *N. meningitidis*, serogroup B, 2086 variant B22.

SEQ ID NO: 59 sets forth the amino acid sequence for a *N. meningitidis*, serogroup B, 2086 variant A05.

SEQ ID NO: 60 sets forth the amino acid sequence for a non-lipidated *N. meningitidis*, serogroup B, 2086 variant A05.

SEQ ID NO: 61 sets forth the amino acid sequence for a *N. meningitidis*, serogroup B, 2086 variant B24.

SEQ ID NO: 62 sets forth the amino acid sequence for a *N. meningitidis*, serogroup B, 2086 variant B24.

DETAILED DESCRIPTION OF THE INVENTION

The inventors surprisingly discovered a composition including at least one factor H binding protein (fHBP) and at least one *N. meningitidis* capsular saccharide conjugate. The composition is surprisingly stable and elicited an immune response against strains that express fHBP variants that are homologous to the fHBP variant in the multi-component composition and an immune response against strains that express fHBP variants that are heterologous to the fHBP variant in the multi-component composition. The inventors further surprisingly discovered that an fHBP polypeptide effectively elicited an immune response in children, such as, for example, humans aged 12 months and above. Moreover, the inventors surprisingly discovered that an fHBP polypeptide effectively elicited an immune response against a *N. meningitidis* serogroup X strain.

The inventors surprisingly discovered a composition that includes (a) a first lipidated polypeptide including the amino acid sequence set forth in SEQ ID NO: 1; (b) a second lipidated polypeptide including the amino acid sequence set forth in SEQ ID NO: 2; (c) a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); (d) a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); (e) a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); (f) a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate). The composition includes a lyophilized MenACWY-TT composition that surprisingly is readily reconstituted with a liquid MnB bivalent rLP2086 composition, wherein the composition is in a single vial. The inventors discovered that the lyophilized MenACWY-TT composition and the liquid MnB bivalent rLP2086 composition were compatible and stable, following reconstitution, for at least 24 hours at room temperature.

Moreover, the inventors further discovered that the MnB bivalent rLP2086 composition elicited bactericidal antibodies not only against *N. meningitidis* serogroup B, but also *N. meningitidis* serogroups other than B. For example, the MnB bivalent rLP2086 composition elicited bactericidal antibodies against at least *N. meningitidis* serogroups A, C, W, Y, and X. The surprising discovery that the MnB bivalent rLP2086 composition elicited bactericidal antibodies against *N. meningitidis* serogroup X indicates that the MnB bivalent rLP2086 composition elicits a broadly cross-reactive bactericidal immune response in humans against at least two diverse *Neisseria meningitidis* serogroups.

Furthermore, the inventors surprisingly discovered an immune response as measured by serum bactericidal assay using human complement (hSBA) performed with 4 primary *Neisseria meningitidis* serogroup B (MnB) test strains, 2 expressing an LP2086 subfamily A protein and 2 expressing an LP2086 subfamily B protein, measured 1 month after the third vaccination with bivalent rLP2086, in healthy subjects aged ≥24 months to <4 years at study entry. The inventors also surprisingly discovered an immune response as measured by hSBA performed with 4 primary MnB test strains, 2 expressing an LP2086 subfamily A protein and 2 expressing an LP2086 subfamily B protein, measured 1 month after the third vaccination with bivalent rLP2086, in healthy subjects aged A years to <10 years at study entry. The inventors further surprisingly discovered an immune response as measured by hSBA performed with 4 primary MnB test strains, 2 expressing an LP2086 subfamily A protein and 2 expressing an LP2086 subfamily B protein, measured 1 month after the third vaccination with bivalent rLP2086, in healthy subjects aged ≥24 months to <10 years at study entry (ie, in the combined age stratum). The inventors also surprisingly discovered an immune response as measured by hSBA performed with 4 primary MnB test strains, 2 expressing an LP2086 subfamily A protein and 2 expressing an LP2086 subfamily B protein, measured 1 month after the second vaccination and 6 months after the third vaccination with bivalent rLP2086, in healthy subjects aged ≥24 months to <4 years at study entry, in healthy subjects aged ≥4 years to <10 years at study entry, and in the combined age stratum. The immune response was further described through additional endpoints, as measured by hSBA performed with 4 primary MnB test strains, 2 expressing an LP2086 subfamily A protein and 2 expressing an LP2086 subfamily B protein, at specified time points, in healthy subjects aged ≥24 months to <4 years at study entry, in healthy subjects aged ≥4 years to <10 years at study entry, and in the combined age stratum.

In addition, the inventors surprisingly discovered an immune response as measured by serum bactericidal assay using human complement (hSBA) performed with 4 primary *Neisseria meningitidis* serogroup B (MnB) strains, 2 expressing an LP2086 subfamily A protein and 2 expressing an LP2086 subfamily B protein, measured 1 month after the third vaccination with bivalent rLP2086, in healthy toddlers aged 12 to <18 months at study entry. The inventors also surprisingly discovered an immune response as measured by hSBA performed with 4 primary MnB strains, 2 expressing an LP2086 subfamily A protein and 2 expressing an LP2086 subfamily B protein, measured 1 month after the third vaccination with bivalent rLP2086, in healthy toddlers aged 18 to <24 months at study entry. The inventors further surprisingly discovered an immune response as measured by hSBA performed with 4 primary MnB test strains, 2 expressing an LP2086 subfamily A protein and 2 expressing an LP2086 subfamily B protein, measured 1 month after the third vaccination with bivalent rLP2086, in healthy toddlers aged 12 to <24 months at study entry (ie, both age strata combined). The inventors also surprisingly discovered an immune response as measured by hSBA performed with 4 primary MnB test strains, 2 expressing an LP2086 subfamily A protein and 2 expressing an LP2086 subfamily B protein, measured 1 month after the second vaccination and at least 6 months after the third vaccination in healthy toddlers aged 12 to <18 months and 18 to <24 months at study entry, and in both age strata combined. For example, the hSBA may be measured at any time, including 12, 24, 36, and 48 months after the third vaccination in healthy toddlers aged 12 to <18 months and 18 to <24 months at study entry, and in both age strata combined. The immune response was further described through additional endpoints, as measured by hSBA performed with 4 primary MnB test strains, 2 expressing an LP2086 subfamily A protein and 2 expressing an LP2086 subfamily B protein, measured 1 month after the second vaccination and at least 1 month after the third vaccination with bivalent rLP2086 in healthy toddlers aged 12 to <18 months and 18 to <24 months at study entry, and in both age strata combined. For example, the hSBA may be measured at any time, including 6, 12, 24, 36, and 48 months after the third vaccination with bivalent rLP2086 in healthy toddlers aged 12 to <18 months and 18 to <24 months at study entry, and in both age strata combined. The immune response was also described through additional endpoints, as measured by hSBA to secondary MnB test strains expressing LP2086 subfamily A and B proteins, at 1 month after the second vaccination and at least 1 month after the third vaccination in healthy toddlers aged 12 to <18 months and 18 to <24 months at study entry, and in both age strata combined. For example, the hSBA may be measured at any time, including 6, 12, 24, 36, and 48 months after the third vaccination in healthy toddlers aged 12 to <18 months and 18 to <24 months at study entry, and in both age strata combined. Accordingly, in one aspect, the invention relates to a method for eliciting an immune response in a patient of any age. In some embodiments, the human is aged at least 4 weeks, 5 weeks, 6 weeks, 7 weeks, 8 weeks, 9 weeks, 10 weeks, 11 weeks, or 12 weeks old. For example, in a preferred embodiment, the human is aged at least 6 weeks. As is known in the art, a Meningococcal Group A, C, W-135, and Y Conjugate Vaccine, such as NIMENRIX®, is suitable for infants as early as six weeks of age, and can be administered to any human aged six weeks and above. In some embodiments, the human is aged at least 6 months, 7 months, 8 months, 9 months, 10 months, 11 months, or 12 months. For example, in a preferred embodiment, the human is aged at least 12 months. In one embodiment, the human is aged between 12 and 18 months. In another aspect, the invention relates to a method for eliciting an immune response in a patient aged at least 18 months. In one embodiment, the human is aged between 18 and 24 months. In yet another aspect, the invention relates to a method for eliciting an immune response in a patient aged at least 24 months. In one embodiment, the human is aged between 24 months and 10 years. In another aspect, the invention relates to a method for eliciting an immune response in a patient aged 10 years and above. In a further aspect, the invention relates to a method for eliciting an immune response in a patient aged between 10 years and 25 years. The method includes administering to the human a composition including a first lipidated polypeptide including the amino acid sequence set forth in SEQ ID NO: 1; a second lipidated polypeptide including the amino acid sequence set forth in SEQ ID NO: 2. In one embodiment, the composition further includes polysorbate-80. In one embodiment, the composition further includes aluminum. In one embodiment, the composition further includes histidine. In one embodiment, the composition further includes sodium chloride. In one embodiment, the composition further includes polysorbate-80, aluminum, histidine, and sodium chloride. In yet another embodiment, the composition further includes a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W135 (MenW) capsular saccharide conjugated to tetanus toxoid carrier protein (TT); and a *Neisseria meningitidis* serogroup Y (MenY) capsular saccharide conjugated to tetanus toxoid carrier protein (TT). As is known in the art, a Meningococcal Group A, C, W-135, and Y Conjugate Vaccine, such as NIMENRIX®, is suitable for infants as early as six weeks of age, and can be administered to any human aged six weeks and above.

Further descriptions of exemplary compositions are described below.

Composition and Vaccine

The inventors further discovered that a composition including fHBP elicits an effective immune response in humans aged at least 12 months. The composition also elicits an immune response against a *N. meningitidis* serogroup X strain. In addition, the inventors surprisingly discovered a composition including at least one factor H binding polypeptide (fHBP) and at least one *N. meningitidis* capsular saccharide conjugate. The composition is surprisingly stable and elicited an immune response against strains that express fHBP variants that are homologous to the fHBP variant in the multi-component composition and an immune response against strains that express fHBP variants that are heterologous to the fHBP variant in the multi-component composition. In one embodiment, the composition includes any fHBP, such as, for example, any one of the following polypeptides: B24, B16, B44, A22, B03, B09, A12, A19, A05, A07, A06, A15, A29, B01, A62, B15, and any combination thereof. Preferably, the composition includes a combination of A05 and B01 polypeptides. In another preferred embodiment, the composition includes a combination of B24 and A05 polypeptides. In another embodiment, the composition includes a combination of A05, A12, B09, and B44 polypeptides. In one embodiment, the composition includes a lipidated fHBP. In one embodiment, the composition does not include a non-lipidated fHBP.

In another embodiment, the composition includes a non-lipidated fHBP, such as any one of the non-lipidated fHBP described in International Patent Publication No. WO2012/032489, US Patent Publication No. US20120093852, International Patent Publication No. WO2013/132452, and US Patent Publication No. US20160030543, which are each incorporated herein by reference in their entirety. In one embodiment, the composition includes at least one non-lipidated fHBP and at least one lipidated fHBP.

In some embodiments, the composition includes a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.9% identity to the amino acid sequence set forth in any one of SEQ ID NO: 1, SEQ ID NO: 2, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

The inventors further surprisingly discovered that a liquid MnB bivalent rLP2086 composition can readily reconstitute a lyophilized MenACWY-TT composition and that the combined composition is compatible and stable.

In one aspect, the invention relates to a composition against *Neisseria meningitidis*. The composition includes (a) a first lipidated polypeptide including the amino acid sequence set forth in SEQ ID NO: 1; (b) a second lipidated polypeptide including the amino acid sequence set forth in SEQ ID NO: 2; (c) a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); (d) a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); (e) a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); (f) a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).

In another aspect, the invention relates to a composition that includes a combination of a MnB bivalent rLP2086 composition and a MenACWY-TT composition. The MnB bivalent rLP2086 composition refers to a composition that includes a single N. meningitidis polypeptide component that induces an effective broadly protective immune response against multiple strains of N. meningitidis serogroup B. Specifically, in one embodiment, the MnB bivalent rLP2086 composition includes a MnB rLP2086 subfamily A protein (SEQ ID NO: 1) and MnB rLP2086 subfamily B protein (SEQ ID NO: 2). In one embodiment, the composition does not include a fusion protein. In one embodiment, the composition does not include a chimeric protein. In one embodiment, the composition does not include a hybrid protein. In one embodiment, the composition does not further include a peptide fragment. In another embodiment, the composition does not further include a Neisserial polypeptide that is not fHBP. For example, in one embodiment, the composition does not include a PorA protein. In another embodiment, the composition does not include a NadA protein. In another embodiment, the composition does not further include a Neisserial heparin binding antigen (NHBA). In another embodiment, the composition does not further include a Neisserial outer membrane vesicle (OMV). In a preferred embodiment, the composition does not further include antigens, other than the first polypeptide and the second polypeptide. In a preferred embodiment, the MnB bivalent rLP2086 composition further includes polysorbate-80. In one embodiment, the MnB bivalent rLP2086 composition further includes histidine buffer. In one embodiment, the MnB bivalent rLP2086 composition further includes sodium chloride. In one embodiment, the MnB bivalent rLP2086 composition further includes aluminum phosphate. In one embodiment, the MnB bivalent rLP2086 composition further includes polysorbate-80, histidine buffer, sodium chloride, and aluminum phosphate. Preferably, the MnB bivalent rLP2086 composition is a liquid formulation, wherein the polypeptides are formulated as 120 mcg/mL/subfamily in 10 mM histidine buffer, pH 6.0, 150 mM sodium chloride (NaCl) with 0.5 mg/mL aluminum phosphate ($AlPO_4$), and further includes 0.018 mg polysorbate-80 in a 0.5 mL dose.

The MenACWY-TT composition refers to a composition that includes purified capsular polysaccharides of Neisseria meningitidis Serogroup A, C, W-135 and Y, each independently conjugated to TT at ratios (TT to polysaccharide) of ~3, ~3, ~1.5 and ~1.3, respectively. Specifically, the composition includes (c) a Neisseria meningitidis serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate); (d) a Neisseria meningitidis serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate); (e) a Neisseria meningitidis serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); (f) a Neisseria meningitidis serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate). Preferably, the MenACWY-TT composition is presented as a lyophilized powder.

MenA$_{AH}$-TT, MenC$_{AH}$-TT, MenW-TT, and MenY-TT conjugates are prepared through the following steps: manufacture of the polysaccharide drug substance intermediate, manufacture of the TT drug substance intermediate, microfluidization of the polysaccharide, derivatization of the polysaccharide (for the MenAAH-TT and MenCAH-TT processes only), additional purification of the TT, and conjugation of the individual polysaccharides to TT.

Regarding the MenA$_{AH}$-TT conjugate, the MenA polysaccharide is first microfluidized to reduce molecular size and viscosity, then activated via cyanylation with 1-cyano-4-dimethylamino-pyridinium tetrafluoroborate (CDAP). Activated MenA is derivatized with adipic acid dihydrazide (ADH) to form the MenA$_{AH}$. MenAAH and Tetanus Toxoid (TT) are coupled through carbodiimide-mediated condensation (1-ethyl-3-(3-dimethylaminopropyl)carbodiimide (EDAC) coupling technology) to form MenAAH-Tetanus Toxoid Conjugate (MenA$_{AH}$-TT).

Regarding the MenC$_{AH}$-TT conjugate, the MenC polysaccharide is first microfluidized to reduce molecular size and viscosity, then activated via cyanylation with CDAP. Activated MenC is derivatized with adipic acid dihydrazide (ADH) to form the MenC$_{AH}$. MenC$_{AH}$ and TT are coupled through carbodiimide-mediated condensation EDAC coupling technology) to form MenC$_{AH}$-Tetanus Toxoid (MenC$_{AH}$-TT).

Regarding the MenW-TT conjugate, MenW polysaccharide is first microfluidized to reduce molecular size and viscosity, then activated via cyanylation with CDAP. Activated MenW is directly coupled to TT to form MenW-Tetanus Toxoid (MenW-TT).

Regarding the MenY-TT conjugate, MenY polysaccharide is first microfluidized to reduce molecular size and viscosity, then activated via cyanylation with CDAP. Activated MenY is directly coupled to TT to form MenY-Tetanus Toxoid (MenY-TT).

In another aspect, the inventors surprisingly discovered that polypeptide antigens derived from at most two N. meningitidis serogroup B strains induces an effective broadly protective immune response against multiple strains of N. meningitidis serogroup B. Accordingly, in one embodiment, the composition does not further include a polypeptide that is not derived from N. meningitidis serogroup B fHBP subfamily A M98250771 strain and/or N. meningitidis serogroup B fHBP subfamily B CDC1573 strain.

In one embodiment, the composition does not further include a polypeptide having less than 100% sequence identity to SEQ ID NO: 1. In another embodiment, the composition does not further include a polypeptide having less than 100% sequence identity to SEQ ID NO: 2. For example, the composition does not further include a polypeptide having less than 100% sequence identity to the full length of SEQ ID NO: 1 and/or SEQ ID NO: 2.

In one embodiment, the composition further includes polysorbate-80, aluminum, histidine, and sodium chloride. In one embodiment, the composition includes about 60 µg of a first lipidated polypeptide including the amino acid sequence set forth in SEQ ID NO: 1, about 60 µg of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride, wherein the composition preferably has a total volume of about 0.5 ml.

In another aspect, the composition includes about 120 µg/ml of a first lipidated polypeptide including the amino acid sequence set forth in SEQ ID NO: 1, about 120 µg/ml of a second lipidated polypeptide including the amino acid sequence set forth in SEQ ID NO: 2, 2.8 molar ratio of polysorbate-80 to each polypeptide, 0.5 mg aluminum/ml as aluminum phosphate, 10 mM histidine, and 150 mM sodium chloride.

In a further aspect, the composition includes a) 60 µg of a first lipidated polypeptide including the amino acid sequence set forth in SEQ ID NO: 1; b) 60 µg of a second lipidated polypeptide including the amino acid sequence set forth in SEQ ID NO: 2; c) 18 µg polysorbate-80; d) 250 µg aluminum; e) 780 µg histidine, and; f) 4380 µg sodium chloride.

In an exemplary embodiment, the composition includes about 60 µg of a first lipidated polypeptide consisting of the amino acid sequence set forth in SEQ ID NO: 1, about 60 µg of a second lipidated polypeptide consisting of the amino acid sequence set forth in SEQ ID NO: 2, 2.8 molar ratio of polysorbate-80 to first lipidated polypeptide and to second lipidated polypeptide, 0.5 mg/ml aluminum phosphate, 10 mM histidine, and 150 mM sodium chloride, wherein the composition has a total volume of about 0.5 ml. In the exemplary embodiment, the composition is a sterile isotonic buffered liquid suspension. In the exemplary embodiment, the composition has a pH 6.0. In the exemplary embodiment, the first polypeptide and the second polypeptide are adsorbed to aluminum.

In one embodiment, the composition includes a MenA$_{AH}$-TT conjugate having a mean TT/polysaccharide ratio 3; a MenC$_{AH}$-TT conjugate having a mean TT/polysaccharide ratio 3; a MenW-TT conjugate having a mean TT/polysaccharide ratio 1.5; and a MenY-TT conjugate having a mean TT/polysaccharide ratio 1.3. In a preferred embodiment, the composition includes a MenA$_{AH}$-TT conjugate having 5 mcg MenA polysaccharide and ~15 mcg TT; a MenC$_{AH}$-TT conjugate having 5 mcg MenC polysaccharide and ~15 mcg TT; a MenW-TT conjugate having 5 mcg MenW polysaccharide and ~7.5 mcg TT; and a MenY-TT conjugate having 5 mcg MenY polysaccharide and ~6.5 mcg TT. The composition may further include Tris-HCl, sucrose, and sodium chloride.

In another embodiment, the composition includes a MenA$_{AH}$-TT conjugate; MenC$_{AH}$-TT conjugate; MenW-TT conjugate; and MenY-TT conjugate, which includes MenA polysaccharide; MenC polysaccharide; MenW polysaccharide; and MenY polysaccharide and TT carrier protein. The composition may further include sucrose and Trometanol. For example, in one embodiment, the composition includes 10 µg/mL MenA polysaccharide; 10 µg/mL MenC polysaccharide; 10 µg/mL MenW polysaccharide; and 10 µg/mL MenY polysaccharide; 88 µg/mL TT carrier protein; 164 mM sucrose; and 1.6 mM Trometanol.

In one embodiment, the composition has a total volume of about 0.5 ml. In one embodiment, a first dose of the composition has a total volume of about 0.5 ml. A "first dose" refers to the dose of the composition that is administered on Day 0. A "second dose" or "third dose" refers to the dose of the composition that is administered subsequently to the first dose, which may or may not be the same amount as the first dose.

In one aspect, the invention relates to a liquid immunogenic composition resulting from the lyophilized MenACWY-TT composition having been reconstituted with the liquid MnB bivalent rLP2086 composition. Reconstitution refers to restoring a dry lyophilized composition to a liquid form by the addition of a liquid diluent. In one preferred embodiment, the liquid MnB bivalent rLP2086 composition is not concomitantly administered, is not coadministered with, and is not simultaneously administered with the lyophilized MenACWY-TT composition, wherein the lyophilized MenACWY-TT composition has been reconstituted with a liquid composition that is not the liquid MnB bivalent rLP2086 composition. For example, in one preferred embodiment, the lyophilized MenACWY-TT composition is not reconstituted with an aqueous diluent consisting of sodium chloride and water and is not subsequently concomitantly administered, is not coadministered with, and is not simultaneously administered with with the liquid MnB bivalent rLP2086 composition.

Rather, in a preferred embodiment, the lyophilized MenACWY-TT composition is administered with the MnB bivalent rLP2086 composition in one, i.e., a single, administration to the human. The resulting single administration (e.g., the MenABCWY composition) may result from the MnB bivalent rLP2086 composition, from a first container, being mixed with the lyophilized MenACWY-TT composition, from a second container. Alternatively, single administration of the MenABCWY composition may result from one (single) container that includes the MnB bivalent rLP2086 composition and the lyophilized MenACWY-TT composition. Delivery devices for vaccine or immunogenic compositions are known in the art. In one embodiment, the MenABCWY composition is administered concomitantly with any one of ibuprofen, paracetamol, and amoxicillin.

The composition is immunogenic after administration of a first dose to a human. In one embodiment, the first dose is about 0.5 ml in total volume.

The composition induces a bactericidal titer of serum immunoglobulin that is at least greater than 1-fold higher, preferably at least 2-fold higher, in the human after receiving the first dose than a bactericidal titer of serum immunoglobulin in the human prior to receiving the first dose, when measured under identical conditions in a serum bactericidal assay using human complement (hSBA).

The bactericidal titer or bactericidal immune response is against N. meningitidis serogroup B. In a preferred embodiment, the bactericidal titer or bactericidal immune response is against a N. meningitidis serogroup B fHBP subfamily A strain and against a N. meningitidis serogroup B fHBP subfamily B strain. Most preferably, the bactericidal titer or bactericidal immune response is at least against N. meningitidis serogroup B, fHBP subfamily B, B01 strain.

In one embodiment, the composition induces a bactericidal titer of serum immunoglobulin that is at least greater than 1-fold, such as, for example, at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition than a bactericidal titer of serum immunoglobulin in the human prior to receiving said dose, when measured under identical conditions in a serum bactericidal assay using human complement.

In one embodiment, the composition is an immunogenic composition. In one embodiment, the composition is an immunogenic composition for a human. In another embodiment, the composition is a vaccine. A "vaccine" refers to a composition that includes an antigen, which contains at least one epitope that induces an immune response that is specific for that antigen. The vaccine may be administered directly into the subject by subcutaneous, oral, oronasal, or intranasal routes of administration. Preferably, the vaccine is administered intramuscularly. In one embodiment, the composition is a human vaccine. In one embodiment, the composition is an immunogenic composition against N. meningitidis.

In one embodiment, the composition is a liquid composition. In a preferred embodiment, the composition is a liquid suspension composition. In another preferred embodiment, the composition is not lyophilized.

First Polypeptide; MnB rLP2086 Subfamily A (A05) Protein

In one embodiment, the composition includes a first polypeptide having the amino acid sequence set forth in SEQ ID NO: 1. The polypeptide is a modified factor H binding protein (fHBP) from *N. meningitidis* strain M98250771. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The first polypeptide includes a total of 258 amino acids.

The representative primary structure of the MnB rLP2086 A05 protein is presented in FIG. 4. The primary structure of the protein is illustrated in FIG. 4 using a single letter notation for all amino acids except for the N-terminal cysteine and glyceryl moieties (illustrated using full chemical formula). This structure includes the primary structure of the protein sequence in which the N-terminal cysteine residue is lipidated. The amino group of the N-terminal cysteine residue at the protein N-terminus is attached to a fatty acid (R1) forming an amide linkage and the cysteinyl sulfhydryl group is attached to a glycerol moiety containing two ester-bound fatty acids (R2). The structure of R1 is deduced to be hexadecanoic acid (C16:0) and the structures of R2 vary depending on the MnB rLP2086 isoforms.

The first polypeptide includes two modifications introduced in the N-terminal region of the polypeptide, as compared to the corresponding wild-type sequence from *N. meningitidis* strain M98250771. A glycine in the second position is added as a consequence of introducing a cloning site. A second modification includes the deletion of four amino acids. Accordingly, in one embodiment, the first polypeptide includes a C-G-S-S sequence (SEQ ID NO: 3) at the N-terminus. See SEQ ID NO: 1, first four amino acid residues.

The N-terminal differences between the first polypeptide sequence and the wild-type Neisserial sequence is shown below. Accordingly, in one embodiment, the first polypeptide includes at least the first 2, 3, 4, 5, 6, 7, 8, 9, 10, 11, 12, 13, or more amino acid residues of the amino acid sequence set forth in SEQ ID NO: 1. Preferably, the first polypeptide includes at least the first 4, more preferably at least the first 6, and most preferably, at least the first 8 amino acid residues of SEQ ID NO: 1.

Comparison of Predicted N-Terminal Sequences of Recombinant and Neisserial Subfamily A LP2086 Polypeptide

```
rLP2086 M98250771
                                    (SEQ ID NO: 4)
CGSS-----GGGGVAAD

Neisserial LP2086 M98250771
                                    (SEQ ID NO: 5)
C-SSGS-GSGGGGVAAD >A05
                                    (SEQ ID NO: 1)
CGSSGGGGVAADIGTGLADALTAPLDHKDKGLKSLTLEDSISQNGTLTLSA

QGAEKTFKVGDKDNSLNTGKLKNDKISRFDFVQKIEVDGQTITLASGEFQI

YKQDHSAVVALQIEKINNPDKIDSLINQRSFLVSGLGGEHTAFNQLPSGKA
```

-continued

```
EYHGKAFSSDDAGGKLTYTIDFAAKQGHGKIEHLKTPEQNVELASAELKAD

EKSHAVILGDTRYGSEEKGTYHLALFGDRAQEIAGSATVKIREKVHEIGIA

GKQ
```

In one embodiment, the first polypeptide includes the amino acid sequence set forth in SEQ ID NO: 1. In one embodiment, the first polypeptide has a total of 258 amino acids. In one embodiment, the first polypeptide does not include an amino acid sequence having less than 100% sequence identity to SEQ ID NO: 1. In another embodiment, the first polypeptide consists of the amino acid sequence set forth in SEQ ID NO: 1. In another embodiment, the first polypeptide includes the amino acid sequence KDN. See for example, amino acid residues 73-75 of SEQ ID NO: 1. In another embodiment, the first polypeptide includes the amino acid sequence set forth in SEQ ID NO: 3 at the N-terminus of the polypeptide. In another embodiment, the first polypeptide includes the amino acid sequence set forth in SEQ ID NO: 4 at the N-terminus of the polypeptide.

In a preferred embodiment, the first polypeptide is readily expressed in a recombinant host cell using standard techniques known in the art. In another preferred embodiment, the first polypeptide includes a bactericidal epitope on the N- and/or C-domain of SEQ ID NO: 1. In one embodiment, the first polypeptide includes at least the first 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1. Preferably, the first polypeptide includes at least the first 2, more preferably at least the first 4, and most preferably, at least the first 8 amino acid residues of SEQ ID NO: 1.

In another embodiment, the first polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 1.

In one embodiment, the composition includes about 30 μg/ml of a first polypeptide including the amino acid sequence set forth in SEQ ID NO: 1. In one preferred embodiment, the composition includes about 60 μg of a first polypeptide including the amino acid sequence set forth in SEQ ID NO: 1. In one preferred embodiment, the composition includes about 60 μg of a first polypeptide including the amino acid sequence set forth in SEQ ID NO: 1, wherein the composition preferably has a total volume of 0.5 ml. In another embodiment, the composition includes about 120 μg/ml of a first polypeptide including the amino acid sequence set forth in SEQ ID NO: 1.

Second Polypeptide; MnB rLP2086 Subfamily B (B01) Protein

In one embodiment, the composition includes a second polypeptide having the amino acid sequence set forth in SEQ ID NO: 2. The polypeptide is a factor H binding protein (fHBP) from *N. meningitidis* strain CDC1573. A description of fHBP is disclosed in WO2012032489 and US patent publication US 2012/0093852, which are each incorporated by reference in their entirety. The polypeptide is N-terminally lipidated with three predominant fatty acids C16:0, C16:1, and C18:1 covalently linked at three positions of the polypeptide. The second polypeptide includes a total of 261 amino acids.

Figures 5A, 5B:
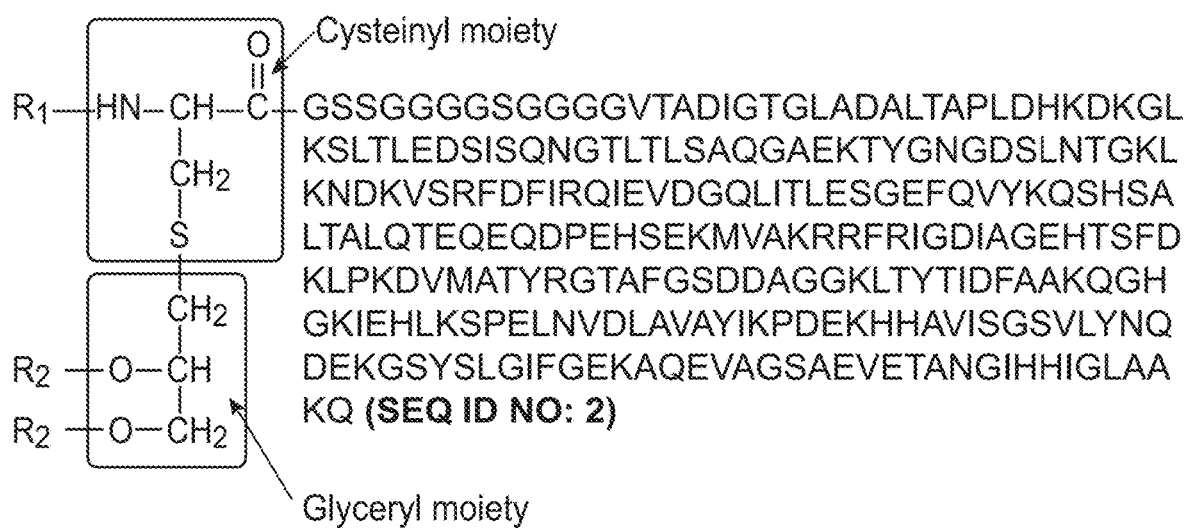
FIG. 5A—Primary Amino Acid Sequence of MnB rLP2086 Subfamily B B01 Protein.
FIG. 5B—Primary Structure of MnB rLP2086 Subfamily B B01 Protein

The representative primary structure of the MnB rLP2086 B01 protein is presented in FIG. 5. The primary structure of the protein is illustrated in FIG. 5 using a single letter notation for all amino acids except for the N-terminal cysteine and glyceryl moieties (illustrated using full chemical formula). This structure includes the primary structure of the protein sequence in which the N-terminal cysteine residue is lipidated. The amino group of the N-terminal cysteine residue at the protein N-terminus is attached to a fatty acid (R1) forming an amide linkage and the cysteinyl sulfhydryl group is attached to a glycerol moiety containing two-ester bound fatty acids (R2). The structure of R1 is deduced to be hexadecanoic acid (C16:0) and the structures of R2 vary depending on the rLP2086 isoforms.

The second polypeptide includes one modification introduced in the N-terminal region for the rLP2086 subfamily B protein, as compared to the corresponding wild-type sequence from N. meningitidis strain CDC-1573. A glycine in the second position is a consequence of introducing a cloning site.

The N-terminal differences from the original Neisserial sequences are shown below.

Comparison of Predicted N-Terminal Sequences of Recombinant and Neisserial Subfamily B LP2086 Protein

```
rLP2086 CDC-1573
                                         (SEQ ID NO: 24)
CGSSGGGGSGGGGVTAD

Neisserial LP2086 CDC-1573
                                         (SEQ ID NO: 25)
C-SSGGGGSGGGGVTAD
```

In one embodiment, the second polypeptide includes a C-G-S-S sequence (SEQ ID NO: 3) at the N-terminus. See the first four amino acid residues of SEQ ID NO: 2.

```
>B01
                                          (SEQ ID NO: 2)
CGSSGGGGSGGGGVTADIGTGLADALTAPLDHKDKGLKSLTLEDSISQNGT

LTLSAQGAEKTYGNGDSLNTGKLKNDKVSRFDFIRQIEVDGQLITLESGEF

QVYKQSHSALTALQTEQEQDPEHSEKMVAKRRFRIGDIAGEHTSFDKLPKD

VMATYRGTAFGSDDAGGKLTYTIDFAAKQGHGKIEHLKSPELNVDLAVAYI

KPDEKHHAVISGSVLYNQDEKGSYSLGIFGEKAQEVAGSAEVETANGIHHI

GLAAKQ
```

In one embodiment, the second polypeptide includes the amino acid sequence set forth in SEQ ID NO: 2. In one embodiment, the second polypeptide has a total of 261 amino acids. In one embodiment, the second polypeptide consists of the amino acid sequence set forth in SEQ ID NO: 2. In another embodiment, the second polypeptide does not further include a polypeptide having less than 100% sequence identity to SEQ ID NO: 2. In a preferred embodiment, the first polypeptide and the second polypeptide includes a C-G-S-S(SEQ ID NO: 3) sequence at the N-terminus of the respective polypeptide.

In a preferred embodiment, the second polypeptide is readily expressed in a recombinant host cell using standard techniques known in the art. In another preferred embodiment, the second polypeptide includes a bactericidal epitope on the N- and/or C-domain of SEQ ID NO: 2. In one embodiment, the second polypeptide includes at least the first 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2. Preferably, the second polypeptide includes at least the first 2, more preferably at least the first 4, and most preferably, at least the first 8 amino acid residues of SEQ ID NO: 2.

In another embodiment, the second polypeptide includes at least the last 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues of the amino acid sequence set forth in SEQ ID NO: 2.

In one embodiment, the composition includes about 30 µg/ml of a first polypeptide including the amino acid sequence set forth in SEQ ID NO: 2. In one preferred embodiment, the composition includes about 60 µg of a first polypeptide including the amino acid sequence set forth in SEQ ID NO: 2. In one preferred embodiment, the composition includes about 60 µg of a second polypeptide including the amino acid sequence set forth in SEQ ID NO: 2, wherein the composition preferably has a total volume of 0.5 ml. In another embodiment, the composition includes 120 µg/ml of a second polypeptide including the amino acid sequence set forth in SEQ ID NO: 2.

Saccharides

The term "saccharide" throughout this specification may indicate polysaccharide or oligosaccharide and includes both. Polysaccharides are isolated from bacteria or isolated from bacteria and sized to some degree by known methods and optionally by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

Each N. meningitidis capsular saccharide may be conjugated to a carrier protein independently selected from the group consisting of TT, DT, CRM197, fragment C of TT and protein D. Although one or more N. meningitidis capsular saccharide may be conjugated to different carrier proteins from the others, in one embodiment they are all conjugated to the same carrier protein. For instance they may all be conjugated to the same carrier protein selected from the group consisting of TT, DT, CRM197, fragment C of TT and protein D. In this context CRM197 and DT may be considered to be the same carrier protein as they differ by only one amino acid. In a preferred embodiment all the N. meningitidis capsular saccharides present are conjugated to TT.

If the protein carrier is the same for 2 or more saccharides in the composition, the saccharide could be conjugated to the same molecule of the protein carrier (carrier molecules having 2 more different saccharides conjugated to it) [see for instance WO 04/083251; for example, a single carrier protein might be conjugated to MenA and MenC; MenA and MenW; MenA and MenY; MenC and MenW; MenC and MenY; Men W and MenY; MenA, MenC and MenW; MenA, MenC and MenY; MenA, MenW and MenY; MenC, MenW and MenY; MenA, MenC, MenW and MenY. Alternatively the saccharides may each be separately conjugated to different molecules of the protein carrier (each molecule of protein carrier only having one type of saccharide conjugated to it).

In one embodiment, at least 2 different saccharide conjugates are conjugated separately to the same type of carrier protein, wherein one or more saccharide(s) is/are conjugated to the carrier protein via a first type of chemical group on the protein carrier, and one or more saccharide(s) is/are conjugated to the carrier protein via a second (different) type of chemical group on the protein carrier.

In one embodiment the 2 conjugates involve the same saccharide linked to the same carrier, but by different conjugation chemistries. In an alternative embodiment 2 different saccharides are conjugated to different groups on the protein carrier.

By "conjugated separately to the same type of carrier protein" it is meant that the saccharides are conjugated to the same carrier individually (for example, MenA is conjugated to tetanus toxoid through an amine group on the tetanus toxoid and MenC is conjugated to tetanus toxoid through a carboxylic acid group on a different molecule of tetanus toxoid.)

The capsular saccharide(s) may be conjugated to the same carrier protein independently selected from the group consisting of TT, DT, CRM197, fragment C of TT and protein D. A more complete list of protein carriers that may be used in the conjugates of the invention is presented below. In this context CRM197 and DT may be considered to be the same carrier protein as they differ by only one amino acid. In an embodiment all the capsular saccharides present are conjugated to TT.

The saccharides may include any one of: *N. meningitidis* serogroup A capsular saccharide (MenA), *N. meningitidis* serogroup C capsular saccharide (MenC), *N. meningitidis* serogroup Y capsular saccharide (MenY), and *N. meningitidis* serogroup W capsular saccharide (MenW), or any combination thereof.

The first and second chemical groups present on the protein carrier are different from each other and are ideally natural chemical groups that may be readily used for conjugation purposes. They may be selected independently from the group consisting of: carboxyl groups, amino groups, sulfhydryl groups, Hydroxyl groups, Imidazolyl groups, Guanidyl groups, and Indolyl groups. In one embodiment the first chemical group is carboxyl and the second is amino, or vice versa. These groups are explained in greater detail below.

In a specific embodiment the immunogenic composition comprises at least 2 different *N. meningitidis* capsular saccharides, wherein one or more is/are selected from a first group consisting of MenA and MenC which is/are conjugated to the carrier protein via the first type of chemical group on the protein carrier (for instance carboxyl), and one or more different saccharides is/are selected from a second group consisting of MenC, MenY and MenW which is/are conjugated to the carrier protein via the second type of chemical group on the protein carrier (for instance amino).

In a further embodiment the immunogenic composition of the invention comprises MenA conjugated via the first type of chemical group (for instance carboxyl), and MenC conjugated via the second type of chemical group (for instance amino).

In another embodiment the immunogenic composition comprises MenC conjugated via the first type of chemical group (for instance carboxyl), and MenY conjugated via the second type of chemical group (for instance amino).

In another embodiment the immunogenic composition comprises MenA conjugated via the first type of chemical group (for instance carboxyl), and MenC, MenY and MenW conjugated via the second type of chemical group (for instance amino).

In another embodiment the immunogenic composition comprises MenA and MenC conjugated via the first type of chemical group (for instance carboxyl), and MenY and MenW conjugated via the second type of chemical group (for instance amino).

The saccharides of the invention included in pharmaceutical (immunogenic) compositions of the invention are conjugated to a carrier protein such as tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from *N. meningitidis* serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761) or Protein D (EP594610 and WO 00/56360).

In an embodiment, the immunogenic composition of the invention uses the same type of carrier protein (independently) in at least two, three, four or each of the saccharides contained therein.

In an embodiment, the immunogenic composition of the invention comprises a *N. meningitidis* saccharide conjugated to a carrier protein selected from the group consisting of TT, DT, CRM197, fragment C of TT and protein D.

The immunogenic composition of the invention optionally comprises at least one meningococcal saccharide (for example MenA; MenC; MenW; MenY; MenA and MenC; MenA and MenW; MenA and MenY; MenC and Men W; Men C and MenY; Men W and MenY; MenA, MenC and MenW; MenA, MenC and MenY; MenA, MenW and MenY; MenC, MenW and MenY or MenA, MenC, MenW and MenY) conjugate having a ratio of Men saccharide to carrier protein of between 1:5 and 5:1, between 1:2 and 5:1, between 1:0.5 and 1:2.5 or between 1:1.25 and 1:2.5 (w/w). In one preferred embodiment, the composition includes MenA, MenC, MenW and MenY each conjugated to tetanus toxoid at ratios (toxoid to polysaccharide) of about 3, about 3, about 1.5 and about 1.3, respectively.

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the immunogenic composition of the invention comprises N. meningitidis saccharide conjugate(s) wherein the N. meningitidis saccharide(s) is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286).

The saccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a holoacetylated carrier protein (for example using iodoacetimide or N-succinimidyl bromoacetatebromoacetate). Optionally, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid hydrazide (ADH) to the protein carrier by Carbodiimide condensation (Chu C. et al Infect. Immunity, 1983 245 256), for example using EDAC.

In an embodiment, a hydroxyl group (optionally an activated hydroxyl group for example a hydroxyl group activated by a cyanate ester) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, N. meningitidis capsular saccharide(s) (or saccharide in general) is conjugated to the linker first before the linker is conjugated to the carrier protein. Alternatively the linker may be conjugated to the carrier before conjugation to the saccharide.

In general the following types of chemical groups on a protein carrier can be used for coupling/conjugation:
A) Carboxyl (for instance via aspartic acid or glutamic acid). In one embodiment this group is linked to amino groups on saccharides directly or to an amino group on a linker with carbodiimide chemistry e.g. with EDAC.
B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.
C) Sulphydryl (for instance via cysteine). In one embodiment this group is linked to a bromo or chloro acetylated saccharide or linker with maleimide chemistry. In one embodiment this group is activated/modified with bis diazobenzidine.
D) Hydroxyl group (for instance via tyrosine). In one embodiment this group is activated/modified with bis diazobenzidine.
E) Imidazolyl group (for instance via histidine). In one embodiment this group is activated/modified with bis diazobenzidine.
F) Guanidyl group (for instance via arginine).
G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.
Direct Coupling Approaches:
Saccharide-OH+CNBr or CDAP----->cyanate ester+NH2-Prot---->conjugate
Saccharide-aldehyde+NH2-Prot---->Schiff base+ NaCNBH3---->conjugate
Saccharide-COOH+NH2-Prot+EDAC---->conjugate
Saccharide-NH2+COOH-Prot+EDAC---->conjugate
Indirect Coupling Via Spacer (Linker) Approaches:

Saccharide-OH+CNBr or CDAP--->cyanate ester+NH2----NH2---->saccharide----NH2+COOH-Prot+EDAC----->conjugate Saccharide-OH+CNBr or CDAP---->cyanate ester+NH2-----SH----->saccharide----SH+SH-Prot (native Protein with an exposed cysteine or obtained after modification of amino groups of the protein by SPDP for instance)----->saccharide-S—S-Prot Saccharide-OH+CNBr or CDAP--->cyanate ester+NH2----SH----->saccharide----SH+maleimide-Prot (modification of amino groups)---->conjugate Saccharide-COOH+EDAC+NH2-----NH2--->saccharide------NH2+EDAC+COOH-Prot---->conjugate Saccharide-COOH+EDAC+NH2----SH----->saccharide----SH+SH-Prot (native Protein with an exposed cysteine or obtained after modification of amino groups of the protein by SPDP for instance)----->saccharide-S—S-Prot Saccharide-COOH+EDAC+NH2----SH----->saccharide----SH+maleimide-Prot (modification of amino groups)---->conjugate Saccharide-Aldehyde+NH2-----NH2---->saccharide---NH2+EDAC+COOH-Prot---->conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues).

In an embodiment, at least one of the $N.$ $meningitidis$ capsular saccharides (or saccharide in general) is directly conjugated to a carrier protein; optionally Men W and/or MenY and/or MenC saccharide(s) is directly conjugated to a carrier protein. For example MenW; MenY; MenC; MenW and MenY; MenW and MenC; MenY and MenC; or MenW, MenY and MenC are directly linked to the carrier protein. Optionally, at least one of the $N.$ $meningitidis$ capsular saccharides is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094). In an embodiment, all $N.$ $meningitidis$ capsular saccharides are conjugated to tetanus toxoid.

In an embodiment, the ratio of Men W and/or Y saccharide to carrier protein is between 1:0.5 and 1:2 (w/w) and/or the ratio of MenC saccharide to carrier protein is between 1:0.5 and 1:4 or 1:0.5 and 1:1.5 (w/w), especially where these saccharides are directly linked to the protein, optionally using CDAP.

In an embodiment, at least one of the $N.$ $meningitidis$ capsular saccharide(s) (or saccharide in general) is conjugated to the carrier protein via a linker, for instance a bifunctional linker. The linker is optionally heterobifunctional or homobifunctional, having for example a reactive amine group and a reactive carboxylic acid group, 2 reactive amine groups or 2 reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein (for example tetanus toxoid) via a linker.

In an embodiment, at least one $N.$ $meningitidis$ saccharide is conjugated to a carrier protein via a linker using CDAP and EDAC. For example, MenA; MenC; or MenA and MenC are conjugated to a protein via a linker (for example those with two hydrazino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of saccharide to carrier protein of between 1:0.5 and 1:6; 1:1 and 1:5 or 1:2 and 1:4, for MenA; MenC; or MenA and MenC.

In an embodiment, the MenA capsular saccharide, where present is at least partially O-acetylated such that at least 50%, 60%, 70%, 80%, 90%, 95% or 98% of the repeat units are O-acetylated at at least one position. O-acetylation is for example present at least at the O-3 position of at least 50%, 60%, 70%, 80%, 90%, 95% or 98% of the repeat units.

In an embodiment, the MenC capsular saccharide, where present is at least partially O-acetylated such that at least 30%, 40%, 50%, 60%, 70%, 80%, 90%, 95% or 98% of ($\alpha2\rightarrow9$)-linked NeuNAc repeat units are O-acetylated at at least one or two positions. O-acetylation is for example present at the O-7 and/or O-8 position of at least 30%, 40%, 50%, 60%, 70%, 80%, 90%, 95% or 98% of the repeat units.

In an embodiment, the MenW capsular saccharide, where present is at least partially O-acetylated such that at least 30%, 40%, 50%, 60%, 70%, 80%, 90%, 95% or 98% of the repeat units are O-acetylated at at least one or two positions. O-acetylation is for example present at the O-7 and/or O-9 position of at least 30%, 40%, 50%, 60%, 70%, 80%, 90%, 95% or 98% of the repeat units.

In an embodiment, the MenY capsular saccharide, where present is at least partially O-acetylated such that at least 20%, 30%, 40%, 50%, 60%, 70%, 80%, 90%, 95% or 98% of the repeat units are O-acetylated at at least one or two positions. 0-acetylation is present at the 7 and/or 9 position of at least 20%, 30%, 40%, 50%, 60%, 70%, 80%, 90%, 95% or 98% of the repeat units.

The percentage of O-acetylation refers to the percentage of the repeat units containing O-acetylation. This may be measured in the saccharide prior to conjugate and/or after conjugation.

In one embodiment of the invention the immunogenic composition, saccharide present, or each $N.$ $meningitidis$ capsular saccharide present, is conjugated to TT. In a further embodiment each $N.$ $meningitidis$ capsular saccharide is separately conjugated to a separate carrier protein. In a further embodiment each $N.$ $meningitidis$ capsular saccharide conjugate has a saccharide:carrier ratio of 1:5-5:1 or 1:1-1:4 (w/w). In a further embodiment at least one, two or three $N.$ $meningitidis$ capsular saccharide conjugate(s) is directly conjugated to a carrier protein. In a further embodiment Men W and/or MenY, MenW and/or MenC, MenY and/or MenC, or MenW and MenC and MenY are directly conjugated to a carrier protein. In a further embodiment at least one, two or three $N.$ $meningitidis$ saccharide conjugate(s) is directly conjugated by CDAP chemistry. In a further embodiment the ratio of Men W and/or Y saccharide to carrier protein is between 1:0.5 and 1:2 (w/w). In a further embodiment the ratio of MenC saccharide to carrier protein is between 1:0.5 and 1:2 (w/w). In a further embodiment at least one, two or three $N.$ $meningitidis$ capsular saccharide(s) are conjugated to the carrier protein via a linker (which may be bifunctional such as having two reactive amino groups (such as ADH) or two reactive carboxyl groups, or a reactive amino group at one end and a reactive carboxyl group at the other). The linker can have between 4 and 12 carbon atoms. In a further embodiment the or each $N.$ $meningitidis$ capsular saccharide(s) conjugated via a linker are conjugated to the linker with CDAP chemistry. In a further embodiment the carrier protein is conjugated to the linker using carbodiimide chemistry, for example using EDAC. In a further embodiment the or each *N. meningitidis* capsular saccharide is conjugated to the linker before the carrier protein is conjugated to the linker. In a further embodiment MenA is conjugated to a carrier protein via a linker (the ratio of MenA saccharide to carrier protein may be between 1:2 and 1:5 (w/w)). In a further embodiment MenC is conjugated to a carrier protein via a linker (the ratio of MenC saccharide to carrier protein may be between 1:2 and 1:5 (w/w)).

By using native or slightly sized polysaccharide conjugates, one or more of the following advantages may be realised: 1) a conjugate having high immunogenicity which is filterable through a 0.2 micron filter; 2) immune memory may be enhanced (as in example three); 3) the alteration of the ratio of polysaccharide to protein in the conjugate such that the ratio of polysaccharide to protein (w/w) in the conjugate may be increased (this can result in a reduction of the carrier suppression effect); 4) immunogenic conjugates prone to hydrolysis (such as MenA conjugates) may be stabilised by the use of larger polysaccharides for conjugation. The use of larger polysaccharides can result in more cross-linking with the conjugate carrier and may lessen the liberation of free saccharide from the conjugate. The conjugate vaccines described in the prior art tend to depolymerise the polysaccharides prior to conjugation in order to improve conjugation. Meningococcal (or saccharide) conjugate vaccines retaining a larger size of saccharide can provide a good immune response against meningococcal disease.

The immunogenic composition of the invention may thus comprise one or more saccharide conjugates wherein the average size of each saccharide before conjugation is above 50 kDa, 75 kDa, 100 kDa, 110 kDa, 120 kDa or 130 kDa. In one embodiment the conjugate post conjugation should be readily filterable through a 0.2 micron filter such that a yield of more than 50, 60, 70, 80, 90 or 95% is obtained post filtration compared with the pre filtration sample.

In particular, the immunogenic composition of the invention comprises *N. meningitidis* capsular saccharides from at least one, two, three or four of serogroups A, C, W and Y conjugated to a carrier protein, wherein the average size (weight-average molecular weight; Mw) of at least one, two, three or four or each *N. meningitidis* saccharide is above 50 kDa, 60 kDa, 75 kDa, 100 kDa, 110 kDa, 120 kDa or 130 kDa.

In a preferred embodiment, the average Mw of the MenA$_{AH}$-TT conjugate is at least 250 kDa, 260 kDa, 270 kDa, 280 kDa, or 290 kDa, most preferably about 300 kDa, and at most 350 kDa or 330 kDa. In a preferred embodiment, the average Mw of the MenC$_{AH}$-TT conjugate is at least 150 kDa, 160 kDa, 170 kDa, 180 kDa, or 190 kDa, most preferably about 200 kDa, and at most 250 kDa or 230 kDa. In a preferred embodiment, the average Mw of the MenW-TT conjugate is at least 240, 250 kDa, 260 kDa, or 270 kDa, most preferably about 280 kDa, and at most 330 kDa or 310 kDa. In a preferred embodiment, the average Mw of the MenY-TT conjugate is at least 220 kDa, 230 kDa, 240 kDa, or 250 kDa, most preferably about 270 kDa, and at most 320 kDa or 300 kDa.

The immunogenic composition may comprise *N. meningitidis* capsular saccharides from at least one, two, three or four of serogroups A, C, W and Y conjugated to a carrier protein, wherein at least one, two, three or four or each *N. meningitidis* saccharide is either a native saccharide or is sized by a factor up to ×2, ×3, ×4, ×5, ×6, ×7, ×8, ×9 or ×10 relative to the weight average molecular weight of the native polysaccharide.

For the purposes of the invention, "native polysaccharide" refers to a saccharide that has not been subjected to a process, the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native.

For the purposes of the invention, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

In an aspect of the invention, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is native polysaccharide.

In an aspect of the invention, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is sized by a factor up to ×1.5, ×2, ×3, ×4, ×5, ×6, ×7, ×8, ×9 or ×10.

The immunogenic compositions of the invention optionally comprise conjugates of: *N. meningitidis* serogroup C capsular saccharide (MenC), serogroup A capsular saccharide (MenA), serogroup W135 capsular saccharide (MenW), serogroup Y capsular saccharide (MenY), serogroup C and Y capsular saccharides (MenCY), serogroup C and A capsular saccharides (MenAC), serogroup C and W capsular saccharides (MenCW), serogroup A and Y capsular saccharide (MenAY), serogroup A and W capsular saccharides (MenAW), serogroup W and Y capsular saccharides (MenWY), serogroup A, C and W capsular saccharide (MenACW), serogroup A, C and Y capsular saccharides (MenACY); serogroup A, W135 and Y capsular saccharides (MenAWY), serogroup C, W135 and Y capsular saccharides (MenCWY); or serogroup A, C, W135 and Y capsular saccharides (MenACWY). This is the definition of "one, two, three or four", or "at least one of" of serogroups A, C, W and Y, or of each *N. meningitidis* saccharide where mentioned herein.

In an embodiment, the average size of at least one, two, three, four or each *N. meningitidis* saccharide is between 50 KDa and 1500 kDa, 50 kDa and 500 kDa, 50 kDa and 300 KDa, 101 kDa and 1500 kDa, 101 kDa and 500 kDa, 101 kDa and 300 kDa as determined by MALLS.

In an embodiment, the MenA saccharide, where present, has a molecular weight of 50-500 kDa, 50-100 kDa, 100-500 kDa, 55-90 KDa, 60-70 kDa or 70-80 kDa or 60-80 kDa.

In an embodiment, the MenC saccharide, where present, has a molecular weight of 100-200 kDa, 50-100 kDa, 100-150 kDa, 101-130 kDa, 150-210 kDa or 180-210 kDa.

In an embodiment the MenY saccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa.

In an embodiment the MenW saccharide, where present, has a molecular weight of 60-190 kDa, 70-180 kDa, 80-170 kDa, 90-160 kDa, 100-150 kDa, 110-140 kDa, 50-100 kDa or 120-140 kDa.

The molecular weight or average molecular weight of a saccharide herein refers to the weight-average molecular weight (Mw) of the saccharide measured prior to conjugation and is measured by MALLS.

The MALLS technique is well known in the art and is typically carried out as described in example 2. For MALLS analysis of meningococcal saccharides, two columns (TSKG6000 and 5000PWxI) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the N. meningitidis saccharides are native polysaccharides or native polysaccharides which have reduced in size during a normal extraction process.

In an embodiment, the N. meningitidis saccharides are sized by mechanical cleavage, for instance by microfluidisation or sonication. Microfluidisation and sonication have the advantage of decreasing the size of the larger native polysaccharides sufficiently to provide a filterable conjugate (from example through a 0.2 micron filter). Sizing is by a factor of no more than ×20, ×10, ×8, ×6, ×5, ×4, ×3, ×2 or ×1.5.

In an embodiment, the immunogenic composition comprises N. meningitidis conjugates that are made from a mixture of native polysaccharides and saccharides that are sized by a factor of no more than ×20. For example, saccharides from MenC and/or MenA are native. For example, saccharides from MenY and/or MenW are sized by a factor of no more than ×20, ×10, ×8, ×6, ×5, ×4, ×3 or ×2. For example, an immunogenic composition contains a conjugate made from MenY and/or MenW and/or MenC and/or MenA which is sized by a factor of no more then ×10 and/or is microfluidised. For example, an immunogenic composition contains a conjugate made from native MenA and/or MenC and/or MenW and/or MenY. For example, an immunogenic composition comprises a conjugate made from native MenC. For example, an immunogenic composition comprises a conjugate made from native MenC and MenA which is sized by a factor of no more then ×10 and/or is microfluidised. For example, an immunogenic composition comprises a conjugate made from native MenC and MenY which is sized by a factor of no more then ×10 and/or is microfluidised.

In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

Saccharides are optionally sized up to 1.5, 2, 4, 6, 8, 10, 12, 14, 16, 18 or 20 times from the size of the polysaccharide isolated from bacteria.

In one embodiment each N. meningitidis saccharide is either a native polysaccharide or is sized by a factor of no more than ×10. In a further embodiment each N. meningitidis capsular saccharide is a native polysaccharide. In a further embodiment at least one, two, three or four N. meningitidis capsular saccharide(s) is sized by microfluidization. In a further embodiment each N. meningitidis capsular saccharide is sized by a factor of no more than ×10. In a further embodiment the N. meningitidis conjugates are made from a mixture of native polysaccharides and saccharides that are sized by a factor of no more than ×10. In a further embodiment the capsular saccharide from serogroup Y is sized by a factor of no more than ×10. In a further embodiment capsular saccharides from serogroups A and C are native polysaccharides and saccharides from serogroups W135 and Y are sized by a factor of no more than ×10. In a further embodiment the average size of each N. meningitidis capsular saccharide is between 50 kDa and 300 KDa or 50 kDa and 200 kDa. In a further embodiment the immunogenic composition comprises a MenA capsular saccharide having an average size of above 50 kDa, 75 kDa, 100 kDa or an average size of between 50-100 kDa or 55-90 KDa or 60-80 kDa. In a further embodiment the immunogenic composition comprises a MenC capsular saccharide having an average size of above 50 kDa, 75 kDa, 100 kDa or between 100-200 kDa, 100-150 kDa, 80-120 kDa, 90-110 kDa, 150-200 kDa, 120-240 kDa, 140-220 kDa, 160-200 kDa or 190-200 kDa. In a further embodiment the immunogenic composition comprises a MenY capsular saccharide, having an average size of above 50 kDa, 75 kDa, 100 kDa or between 60-190 kDa or 70-180 kDa or 80-170 kDa or 90-160 kDa or 100-150 kDa, 110-145 kDa or 120-140 kDa. In a further embodiment the immunogenic composition comprises a MenW capsular saccharide having an average size of above 50 kDa, 75 kDa, 100 kDa or between 60-190 kDa or 70-180 kDa or 80-170 kDa or 90-160 kDa or 100-150 kDa, 140-180 kDa, 150-170 kDa or 110-140 kDa.

In an embodiment of the invention, the saccharide dose of each of the at least two, three, four or each of the N. meningitidis saccharide conjugates is optionally the same, or approximately the same.

In an embodiment, the immunogenic composition of the invention is adjusted to or buffered at, or adjusted to between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

For the N. meningitidis saccharide combinations discussed above, it may be advantageous not to use any aluminium salt adjuvant or any adjuvant at all.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained.

In another embodiment, the composition includes a conjugate of a *Neisseria meningitidis* serogroup X capsular polysaccharide and a carrier molecule. The structure of the group X capsular polysaccharide consists of N-acetylglucosamine-4-phosphate residues held together by al-4 phosphodiester bonds without O-acetyl groups. The carrier molecule may be a diphtheria or tetanus toxoid, CRM 197 or protein D. In a preferred embodiment, as exemplified in the Examples, the composition does not include a conjugate of a N. meningitidis serogroup X capsular polysaccharide.

Stability

The terms "stable" and "stability" refer the ability of an antigen to remain immunogenic over a period of time. Stability may be measured in potency over time. The terms "stable" and "stability" further refer to the physical, chemical, and conformational stability of the immunogenic composition. Instability of a protein composition may be caused by chemical degradation or aggregation of the protein molecules to form higher order polymers, by dissociation of the heterodimers into monomers, deglycosylation, modification of glycosylation, or any other structural modification that reduces at least one biological activity of the protein composition included in the present invention. Stability may be assessed by methods well-known in the art, including measurement of a sample's light scattering, apparent attenuation of light (absorbance, or optical density), size (e.g. by size exclusion chromatography), in vitro or in vivo biological activity and/or properties by differential scanning calorimetry (DSC). Other methods for assessing stability are known in the art and can also be used according to the present invention.

In some embodiments, an antigen in a stable formulation of the invention may maintain at least 50%, 60%, 70%, 75%, 80%, 85%, 90%, 95%, 96%, 97%, 98%, 99% or 100% potency, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, an antigen in a stable formulation of the invention may maintain at least 50% potency, as compared to a reference standard, for at least 1 year, 2 years, 3 years, 4 years or 5 years. The terms "stable" and "stability" also refer to the ability of an antigen to maintain epitopes or immunoreactivity over a period of time. For example, an antigen in a stable formulation of the invention may maintain at least 50%, 60%, 70%, 75%, 80%, 85%, 90%, 95%, 96%, 97%, 98%, 99%/0 or 100% of its epitopes or immunoreactivity, as compared to a reference standard, for at least 1 month, 2 months, 3 months, 4 months, 5 months, 6 months, 9 months, 12 months, 18 months, 24 months, 30 months, 36 months, 42 months, 48 months, 54 months, or 60 months. In some embodiments, stability is measured with respect to an environmental condition. Non-limiting examples of environmental conditions include light, temperature, freeze/thaw cycles, agitation, and pH. One of skill in the art would be able to determine the presence of antigenic epitopes or immunoreactivity using the methods disclosed herein or other methods known in the art. In some embodiments, the stability of an antigen is measured from the date of its formulation. In some embodiments, the stability of an antigen is measured from the date of a change in its storage conditions. Non-limiting examples of changes in storage conditions include changing from frozen to refrigerated, changing from frozen to room temperature, changing from refrigerated to room temperature, changing from refrigerated to frozen, changing from room temperature to frozen, changing from room temperature to refrigerated, changing from light to dark, or introduction of agitation.

In one embodiment, the terms "stable" and "stability" includes the ability of an antigen to be bound to aluminum. For example, a stable formulation of the invention includes at least 50%, 60%, 70%, 75%, 80%, 85%, 90%, 95%, 96%, 97%, 98%, 99% or 100% of a protein that is bound to aluminum (e.g., aluminum phosphate) in the formulation, as compared to a reference standard, for at least 1 hour, 6 hours, 12 hours, 18 hours, 24 hours, 1 month, 2 months, 3 months, 4 months, 5 months, 6 months, 9 months, 12 months, 18 months, 24 months, 30 months, 36 months, 42 months, 48 months, 54 months, or 60 months. See, for Example 13. In a preferred embodiment, at least 90%, more preferably at least 95%, and most preferably at least 99% of the total Subfamily A rLP2086 polypeptide (e.g., a polypeptide that includes the amino acid sequence set forth in SEQ ID NO: 1) is bound to aluminum in the composition. In a preferred embodiment, at least 90%, more preferably at least 95%, and most preferably at least 99% of the total Subfamily B rLP2086 polypeptide (e.g., a polypeptide that includes the amino acid sequence set forth in SEQ ID NO: 2) is bound to aluminum in the composition.

Determination of Aluminum Binding.

A composition comprising aluminum and at least one protein antigen was centrifuged such that the aluminum was pelleted. Centrifugation of aluminum absorbed proteins is known in the art. See e.g., Egan et al., Vaccine, Vol. 27(24): 3175-3180 (2009). Aluminum-bound protein was also pelleted, while non-aluminum-bound protein remained in the supernatant. Total protein in the supernatant and pellet were determined by Lowry Assay. The percentage bound protein was calculated by dividing the total protein in the supernatant by the total protein added to the composition and multiplying by 100%. Similarly, the percentage unbound protein was calculated by dividing the total protein in the supernatant by the total protein added to the composition and multiplying by 100%. For compositions comprising both Subfamily A and Subfamily B antigens, the individual Subfamily A and B protein concentrations in the supernatant were determined by ion-exchange chromatography. The separation and elution of Subfamily A and B proteins was carried out using a strong anion column and a high salt concentration eluent. Both Subfamily A and B proteins were detected and quantified using a fluorescence detector set at Excitation=280 run and Emission=310 run. Subfamily A and Subfamily B proteins elute at distinct retention times and were quantified using a standard curve generated against a rLP2086 protein reference material. The percentage unbound protein was calculated by dividing the total protein in the supernatant by the total protein added to the composition and multiplying by 100%. The percentage bound protein was calculated by subtracting the percentage unbound protein from 100%.

Polysorbate-80

Polysorbate 80 (PS-80) is a non-ionic surfactant. Accelerated stability studies using an in vitro monoclonal antibody based potency assay demonstrated instability of the subfamily B protein at higher molar ratios of PS-80 to MnB rLP2086 protein in the final formulation. Further experiments with varying ratios of PS-80 have demonstrated that the optimal molar ratio of PS-80 to MnB rLP2086 protein is approximately 2.8±1.4 to retain potency.

The concentration of PS-80 in the composition is dependent on a molar ratio of PS-80 to the polypeptide. In one embodiment, the composition includes a 2.8±1.4 molar ratio of PS-80 to the first polypeptide and to the second polypeptide. In one embodiment, the composition includes a 2.8±1.1 molar ratio of PS-80 to the first polypeptide and to the second polypeptide. In one embodiment, the composition includes at least 1.9, 2.0, 2.1, 2.2, 2.3, 2.4, 2.5, 2.6, 2.7, 2.8, 2.9, 3.0, 3.1, 3.2, or 3.3 molar ratio of PS-80 to polypeptide. In one embodiment, the composition includes at most 4.0, 3.9, 3.8, 3.7, 3.6, 3.5, 3.4, 3.3, 3.2, 3.1, 3.0, or 2.9 molar ratio of PS-80 to polypeptide. Any minimum value may be combined with any maximum value described herein to define a range. Preferably, the composition includes a 2.8 molar ratio of PS-80 to polypeptide.

The PS-80 to polypeptide molar ratio is determined by calculation from the measured concentration of PS-80 and the measured total polypeptide concentration, in which both values are expressed in moles. For example, PS-80 to Protein molar ratio is determined by calculation of the measured concentration of PS-80 (e.g., by reverse phase high pressure liquid chromatography (RP-HPLC)) to the measured total protein concentration (e.g., by ion exchangehigh pressure liquid chromatography (IEX-HPLC)) in the final drug substance, where both values are expressed in moles.

A RP-HPLC is used to quantitate the concentration of Polysorbate 80 in vaccine formulations. The concentration of detergent is determined by saponification of the fatty acid moiety; Polysorbate 80 is converted to free oleic acid by alkaline hydrolysis at 40° C. The sample is separated by RP-HPLC using a C18 column and quantitated using a UV detector at a wavelength of 200 nm.

The first and the second polypeptides are resolved by anion-exchange HPLC. rLP2086(fHBP) Subfamily A and B proteins elute at distinct retention times and are quantitated using a standard curve generated against the respective rLP2086 protein reference material.

The term "molar ratio" and a description of an immunogenic composition including a fHBP and PS-80 is further disclosed in WO2012025873 and US patent publication US 2013/0171194, which are each incorporated by reference in their entirety.

The term "molar ratio" as used herein refers to the ratio of the number of moles of two different elements in a composition. In some embodiments, the molar ratio is the ratio of moles of detergent to moles of polypeptide. In some embodiments, the molar ratio is the ratio of moles of PS-80 to moles of protein. In one embodiment, based on the protein and Polysorbate 80 concentrations, the Molar Ratio may be calculated using the following equation:

$$\text{Molar Ratio} = \frac{\% \text{ PS-80}}{\text{mg/ml protein}} \times 216$$

In one embodiment, the composition includes a molar ratio of PS-80 to MnB rLP2086 protein between 1.4 to 4.2 to retain potency. In one embodiment, the composition includes at least 1.2, 1.3, 1.4, 1.5, 1.6, 1.7, 1.8, 1.9, 2.0, 2.1, 2.2, 2.3, 2.4, 2.5, 2.6, 2.7, or 2.8. In one embodiment, the composition includes at most 4.2, 4.1, 4.0, 3.9, 3.8, 3.7, 3.7, 3.6, 3.5, 3.4, 3.3, 3.2, 3.1, 3.0, 2.9, or 2.8. Any minimum value may be combined with any maximum value described herein to define a range.

In one embodiment, the composition includes about 0.0015, 0.0017, 0.0019, 0.0021, 0.0023, 0.0025, 0.0027, 0.0029, 0.0031, 0.0033, 0.0035, 0.0037, 0.0039, 0.0041, 0.0043, 0.0045, 0.0047, 0.0049, 0.0051 mg/mL PS-80. Preferably, the composition includes about 0.0035 mg/mL PS-80.

In another embodiment, the composition includes at least 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, or 25 µg PS-80. In another embodiment, the composition includes at most 30 µg, 29 µg, 28 µg, 27 µg, 26 µg, 25 µg, 24 µg, 23 µg, 22 µg, 21 µg, 20 µg, 19 µg, or 18 µg PS-80. Any minimum value may be combined with any maximum value described herein to define a range. In a preferred embodiment, the composition includes at least 10 µg and at most 20 µg PS-80. In a most preferred embodiment, the composition includes about 18 µg PS-80.

In another embodiment, the composition includes a PS-80 concentration ranging from 0.0005% to 1%. For example, the PS-80 concentration in the composition may be at least 0.0005%, 0.005%, 0.01%, 0.02%, 0.03%, 0.04%, 0.05%, 0.06%, 0.07%, 0.08%, 0.09%, 0.10%, 0.2%, 0.3%, 0.4%, 0.5%, 0.6%, 0.7%, 0.8%, 0.9%, 1%, or 1.1% PS-80. In one embodiment, the PS-80 concentration in the composition may be at most 2.0%, 1.9%, 1.8%, 1.7%, 1.6%, 1.5%, 1.4%, 1.3%, 1.2%, 1.1%, 1.0%, 0.9%, 0.8%, or 0.7% PS-80. In a preferred embodiment, the composition includes about 0.07% PS-80. Any minimum value may be combined with any maximum value described herein to define a range.

The inventors surprisingly discovered that while a composition that includes a combination of the first composition and the second composition may have a different molar ratio of polysorbate-80 in relation to the MnB rLP2086 polypeptides, as compared to the molar ratio of polysorbate-80 in relation to the MnB rLP2086 polypeptides in the first composition, additional surfactant for the combined composition was surprisingly not necessary to maintain solubility and stability of the MnB rLP2086 polypeptides in the combined composition. Accordingly, in one embodiment, the kit does not comprise greater than 0.02 mg polysorbate-80.

Aluminum

The composition includes aluminum as aluminum phosphate. $AlPO_4$ is added as a stabilizer to provide enhanced manufacturability and stability. The process for producing an aluminum phosphate is described in US patent publication US 2009/0016946, which is incorporated by reference in its entirety. In one embodiment, the composition does not further include a multivalent cation, other than aluminum. In one embodiment, the composition does not further include $Al(OH)_3$ or $Al(SO_4)_3$.

In one embodiment, the composition includes at least 50 µg, 60 µg, 70 µg, 80 µg, 90 µg, 100 µg, 110 µg, 120 µg, 130 µg, 140 µg, 150 µg, 160 µg, 170 µg, 180 µg, 190 µg, 200 µg, 210 µg, 220 µg, 230 µg, 240 µg, or 250 µg aluminum. In one embodiment, the composition includes at most 500 µg, 490 µg, 480 µg, 470 µg, 460 µg, 450 µg, 440 µg, 430 µg, 420 µg, 410 µg, 400 µg, 390 µg, 380 µg, 370 µg, 360 µg, 350 µg, 340 µg, 330 µg, 320 µg, 310 µg, 300 µg, 290 µg, 280 µg, 270 µg, 260 µg, or 250 µg aluminum. Any minimum value may be combined with any maximum value described herein to define a range. In a most preferred embodiment, the composition includes 250 µg aluminum.

In one embodiment, the composition includes at least 0.005 mg/ml, 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.10 mg/ml, 0.2 mg/ml, 0.3 mg/ml, 0.4 mg/ml, or 0.5 mg/ml aluminum phosphate. In one embodiment, the composition includes at most 2.0 mg/ml, 1.9 mg/ml, 1.8 mg/ml, 1.7 mg/ml, 1.6 mg/ml, 1.5 mg/ml, 1.4 mg/ml, 1.3 mg/ml, 1.2 mg/ml, 1.1 mg/ml, 1.0 mg/ml, 0.9 mg/ml, 0.8 mg/ml, or 0.7 mg/ml PS-80. In a preferred embodiment, the composition includes about 0.07 mg/ml PS-80. Any minimum value may be combined with any maximum value described herein to define a range. In a preferred embodiment, the composition includes 0.5 mg/ml aluminum phosphate. In a most preferred embodiment, the composition includes 0.5 mg aluminum/ml as aluminum phosphate ($AlPO_4$). This concentration maintains binding (at least 90% binding or better) of the subfamily A and B proteins to aluminum.

The inventors surprisingly discovered that while a composition that a combination of the first composition and the second composition could change the percentage of MnB rLP2086 polypeptides bound to the aluminum, when compared to the percentage of MnB rLP2086 polypeptides bound to the aluminum in the first composition, the combination of the first and second compositions surprisingly maintained binding of at least 90% of the total MnB rLP2086 polypeptides to the aluminum. Accordingly, in one embodiment, the percentage of total MnB rLP2086 polypeptides to the aluminum in the combined composition is at least 80%, 81%, 82%, 83%, 84%, 85%, 86%, 87%, 88%, 89%, 90%, 91%, 92%, 93%, 94%, 95%, 96%, 97%, 98%, 99%, or 100%. Preferably, the percentage of total MnB rLP2086 polypeptides to the aluminum in the combined composition is at least 90%, more preferably at least 95%, and most preferably at least 100%.

In another embodiment, the concentration of polypeptides bound to the aluminum in the immunogenic composition is not decreased after 24 hours, as compared to the concentration of polypeptides bound to the aluminum in the liquid composition prior to reconstituting the lyophilized composition. In another embodiment, the concentration of MenA$_{AH}$-TT conjugate in the immunogenic composition is not decreased after 24 hours, as compared to the concentration of the MenA$_{AH}$-TT conjugate in the lyophilized composition. In one embodiment, the concentration is decreased by at most 1%, 2%, 3%, 4%, 5%, 6%, 7%, 8%, 9%, 10%, 11%, 12%, 13%, 14%, 15%, 16%, 17%, 18%, 19%, or 20% after 24 hours, as compared to the respective concentration in the liquid composition prior to reconstitution.

In another embodiment, the concentration of MenC$_{AH}$-TT conjugate in the immunogenic composition is not decreased after 24 hours, as compared to the concentration of the MenC$_{AH}$-TT conjugate in the lyophilized composition. In another embodiment, the concentration of MenW-TT conjugate in the immunogenic composition is not decreased after 24 hours, as compared to the concentration of the MenW-TT conjugate in the lyophilized composition. In another embodiment, the concentration of MenY-TT conjugate in the immunogenic composition is not decreased after 24 hours, as compared to the concentration of the MenY-TT conjugate in the lyophilized composition. In one embodiment, the concentration is decreased by at most 1%, 2%, 3%, 4%, 5%, 6%, 7%, 8%, 9%, 10%, 11%, 12%, 13%, 14%, 15%, 16%, 17%, 18%, 19%, or 20% after 24 hours, as compared to the respective concentration in the lyophilized composition prior to reconstitution.

Excipients

In one embodiment, the composition includes histidine. In one embodiment, the composition includes at least 650 µg, 660 µg, 670 µg, 680 µg, 690 µg, 700 µg, 710 µg, 720 µg, 730 µg, 740 µg, 750 µg, 760 µg, 770 µg, 780 µg, 790 µg, 800 µg, 810 µg, 820 µg, 830 µg, 840 µg, or 850 µg of histidine. In one embodiment, the composition includes at most 1560 µg, 1500 µg, 1400 µg, 1300 µg, 1200 µg, 1100 µg, 1000 µg, 950 µg, 900 µg, 890 µg, 880 µg, 870 µg, 860 µg, 850 µg, 840 µg, 830 µg, 820 µg, 810 µg, 800 µg, 790 µg, or 780 µg of histidine. Any minimum value may be combined with any maximum value described herein to define a range. Preferably, the composition includes 780 µg histidine.

In one embodiment, the composition includes a tris, phosphate, or succinate buffer. In a preferred embodiment, the composition does not include tris buffer. In a preferred, the composition does not include phosphate buffer. In one preferred embodiment, the composition does not include succinate buffer. In a preferred embodiment, the composition includes histidine buffer.

In one embodiment, the composition includes sodium chloride. Sodium chloride concentration in MenABCWY composition may vary between 160.5-161.1 mM.

In one embodiment, the pH of the composition is between 5.5 and 7.5. In a preferred embodiment, the pH of the composition is between 5.8 and 7.0, most preferably pH 5.8 to pH 6.0. In one embodiment, the pH of the composition is at most 6.1. In one embodiment, the pH of the composition is 5.8.

Kits

A further aspect of the invention is a kit for administering a dose of a composition for eliciting bactericidal antibodies against Neisseria meningitidis in a mammal.

In one aspect, the kit includes a first composition including a first polypeptide as described above and a second polypeptide as described above. In a preferred embodiment, the first polypeptide comprises the amino acid sequence set forth in SEQ ID NO: 1. In another preferred embodiment, the second polypeptide comprises the amino acid sequence set forth in SEQ ID NO: 2. The kit further includes a second composition including a MenA$_{AH}$-TT conjugate, a MenC$_{AH}$-TT conjugate, a MenW-TT conjugate, and a MenY-TT conjugate. In one embodiment, the kit includes at least two containers, wherein a first container includes the first composition, a second container includes the second composition.

In one embodiment, the kit includes a liquid first composition and a lyophilized second composition. Preferably, the kit includes a liquid MnB bivalent rLP2086 composition and a lyophilized MenACWY-TT composition.

The inventors surprisingly discovered that while a composition that includes a combination of the first composition and the second composition changes the molar ratio of polysorbate-80 in relation to the MnB rLP2086 polypeptides in the first composition, additional surfactant for the combined composition was surprisingly not necessary to maintain solubility and stability of the MnB rLP2086 polypeptides in the combined composition. Accordingly, in one embodiment, the kit does not comprise greater than 0.02 mg polysorbate-80.

In one embodiment of the invention, the kit does not further comprise any one of the following commercial immunogenic compositions: MENACTRA®, MENVEO®, ADACEL®, HAVRIX®, GARDASIL®, REPEVAX, or any combination thereof. For example, the kit preferably does not further include a meningococcal A, C, Y and W-135 polysaccharide conjugate (MCV4) composition, wherein the carrier protein is diphtheria toxoid. In one embodiment, the kit does not further include a meningococcal A, C, Y and W-135 polysaccharide conjugate (MCV4) composition, wherein the carrier protein is CRM197. In one embodiment, the kit does not further comprise NIMENRIX vaccine, wherein NIMENRIX comprises a diluent consisting of sodium chloride and water.

Bactericidal Activity

Disease incidence of MnB is approximately 1 in 100,000, meaning that extremely large numbers of subjects (400,000 to over 6 million) would be required to support a statistically significant assessment of efficacy. Thus, a serum bactericidal assay using human complement (hSBA), which is a surrogate of protection and vaccine efficacy, is used to assess immunogenicity in clinical trials.

Pfizer has built an extensive MnB strain collection (N=at least 1263) comprising IMD-causing isolates from Years 2000 to 2006. The MnB isolates were systematically collected from the US Centers for Disease Control and Prevention (CDC) and health and reference laboratories from European countries.

In one embodiment, immune response induced by administering the composition to a human is determined using a serum bactericidal assay using human complement (hSBA) against four N. meningitidis serogroup B (MnB) strains. The MnB strains used in the hSBA were selected from the strain pool. The strain pool represented a collection of systematically collected clinically relevant N. meningitidis strains.

The high proportion of hSBA response to all test strains, especially strains expressing lipoprotein 2086 variants with sequences heterologous to both the first polypeptide and the second polypeptide suggests that the composition is a broadly protective vaccine are sufficient to confer high seroprotection against *N. meningitidis* strains expressing rLP2086 (FHBP) from at least serogroup B, including additional serogroups, such as serogroup X.

Subfamily A Strains

In one embodiment, the hSBA strain is an *N. meningitidis* strain that expresses LP2086 (fHBP) subfamily A protein. In one embodiment, the hSBA strain is an LP2086 (fHBP) subfamily A strain that expresses a lipoprotein 2086 variant that is heterologous to a *N. meningitidis* strain expressing A05. For example, in one embodiment, the hSBA strain is an LP2086 (fHBP) subfamily A strain that expresses a lipoprotein 2086 variant that is heterologous to strain M98250771.

In one embodiment, the hSBA strain is a *N. meningitidis* strain expressing fHBP A10. In one embodiment, the hSBA strain is a *N. meningitidis* strain expressing LP2086 (fHBP) A22. In one embodiment, the hSBA strain is a *N. meningitidis* strain expressing LP2086 (fHBP) A56. In a further embodiment, the hSBA strains are LP2086 (fHBP) A22 and LP2086 (fHBP) A56 strains. In another embodiment, the hSBA strain is a *N. meningitidis* strain expressing LP2086 A04. In one embodiment, the hSBA strain is a *N. meningitidis* strain expressing LP2086 A05. In one embodiment, the hSBA strain is a *N. meningitidis* strain expressing LP2086 A12. In one embodiment, the hSBA strain is a *N. meningitidis* strain expressing LP2086 A22. In one embodiment, the hSBA strain is a *N. meningitidis* strain expressing LP2086 A12. In one embodiment, the hSBA strain is a *N. meningitidis* strain expressing LP2086 A04. In one embodiment, the hSBA strain is a *N. meningitidis* strain expressing LP2086 A19. In one embodiment, the hSBA strain is a *N. meningitidis* strain expressing LP2086 A07. In a further embodiment, the hSBA strain includes any one of an A22-, A12-, A19-, A05-, and A07-expressing strain. In one embodiment, the hSBA strains include any one of an A06-, A15-, and A29-expressing strain.

In one embodiment, the immune response is bactericidal against a *N. meningitidis* serogroup B fHPB subfamily A strain that is heterologous to a *N. meningitidis* strain expressing A05. In one embodiment, the immune response is against *N. meningitidis* serogroup B A22 strain. In one embodiment, the immune response is against *N. meningitidis* serogroup B A56 strain. In one embodiment, the immune response is against *N. meningitidis* serogroup B A06 strain. In one embodiment, the immune response is against *N. meningitidis* serogroup B A15 strain. In one embodiment, the immune response is against *N. meningitidis* serogroup B A29 strain. In one embodiment, the immune response is against *N. meningitidis* serogroup B A62 strain. In one embodiment, the immune response is bactericidal against a *N. meningitidis* serogroup B subfamily A strain that is heterologous to *N. meningitidis* strain M98250771.

In one embodiment, the immune response is bactericidal against a *N. meningitidis* serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a *N. meningitidis* serogroup B subfamily A strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain M98250771. In a preferred embodiment, the immune response is bactericidal against a *N. meningitidis* serogroup B subfamily A strain that expresses a factor H binding protein including an amino acid sequence that has at least 80%, more preferably at least 84%, identity to a factor H binding protein expressed by *N. meningitidis* strain M98250771.

In another embodiment, the immune response is bactericidal against a *N. meningitidis* serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the first polypeptide. In another embodiment, the immune response is bactericidal against a *N. meningitidis* serogroup B subfamily A strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain M98250771. In a preferred embodiment, the immune response is bactericidal against a *N. meningitidis* serogroup B subfamily A strain that expresses a factor H binding protein including an amino acid sequence that has at most 85%, more preferably at most 99%, identity to a factor H binding protein expressed by *N. meningitidis* strain M98250771. Any minimum value may be combined with any maximum value described herein to define a range.

In one embodiment, the immune response elicited by the composition is bactericidal not only against a *N. meningitidis* serogroup B fHPB subfamily A strain but also a *N. meningitidis* strain expressing an fHBP subfamily A polypeptide, wherein the serogroup is not serogroup B. For example, in one preferred embodiment, the immune response elicited by the composition is bactericidal against a *N. meningitidis* serogroup B subfamily A strain and against a *N. meningitidis* serogroup C strain that expresses an fHBP subfamily A polypeptide heterologous to fHBP A05. For example, in one embodiment, the immune response is against a *N. meningitidis* serogroup C strain expressing fHBP A10. In another embodiment, the immune response is against a *N. meningitidis* serogroup W strain expressing fHBP A19. In one embodiment, the immune response is bactericidal against a *N. meningitidis* strain that expresses an fHBP subfamily A polypeptide, wherein the strain is heterologous to *N. meningitidis* strain M98250771.

Subfamily B Strains

In one embodiment, the hSBA strain is an LP2086 (fHBP) subfamily B strain. In one embodiment, the hSBA strain is an LP2086 (fHBP) subfamily B strain that expresses a lipoprotein 2086 variant that is heterologous to a *N. meningitidis* strain expressing B01. For example, in one embodiment, the hSBA strain is an LP2086 (fHBP) subfamily B strain that expresses a lipoprotein 2086 variant that is heterologous to strain CDC1127. In a preferred embodiment, the hSBA strain is an LP2086 (fHBP) subfamily B strain that expresses a lipoprotein 2086 variant that is heterologous to strain CDC1573.

In one embodiment, the immune response is bactericidal against a *N. meningitidis* serogroup B fHPB subfamily B strain that is heterologous to a *N. meningitidis* strain expressing B01. In one embodiment, the immune response is against *N. meningitidis* serogroup B B24 strain. In one embodiment, the immune response is against *N. meningitidis* serogroup B B44 strain. In one embodiment, the immune response is against *N. meningitidis* serogroup B B16 strain. In one embodiment, the immune response is against *N. meningitidis* serogroup B B03 strain. In one embodiment, the immune response is against *N. meningitidis* serogroup B B09 strain. In one embodiment, the immune response is against *N. meningitidis* serogroup B B15 strain. In one embodiment, the immune response is against *N. meningitidis* serogroup B B153 strain. In one embodiment, the immune response is bactericidal against a *N. meningitidis* serogroup B subfamily B strain that is heterologous to *N. meningitidis* strain CDC1573.

In one embodiment, the immune response is bactericidal against a *N. meningitidis* serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a *N. meningitidis* serogroup B subfamily B strain that expresses a factor H binding protein including an amino acid sequence that has at least 80%, 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain CDC1573. In a preferred embodiment, the immune response is bactericidal against a *N. meningitidis* serogroup B subfamily B strain that expresses a factor H binding protein including an amino acid sequence that has at least 80% identity, more preferably at least 87% identity, to a factor H binding protein expressed by *N. meningitidis* strain CDC1573. In another preferred embodiment, the immune response is bactericidal against a *N. meningitidis* serogroup B subfamily B strain that expresses a factor H binding protein including an amino acid sequence that has 100% identity to a factor H binding protein expressed by *N. meningitidis* strain CDC1573.

In another embodiment, the immune response is bactericidal against a *N. meningitidis* serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to the second polypeptide. In another embodiment, the immune response is bactericidal against a *N. meningitidis* serogroup B subfamily B strain that expresses a factor H binding protein including an amino acid sequence that has at most 81%, 82%, 83%, 84%, 85%, 86%, 87%, 88%, 89%, 90%, 91%, 92%, 93%, 94%, 95%, 96%, 97%, 98%, 99%, or 100% identity to a factor H binding protein expressed by *N. meningitidis* strain CDC1573. In a preferred embodiment, the immune response is bactericidal against a *N. meningitidis* serogroup B subfamily B strain that expresses a factor H binding protein including an amino acid sequence that has at most 88% identity, more preferably at least 99% identity, to a factor H binding protein expressed by *N. meningitidis* strain CDC1573. Any minimum value may be combined with any maximum value described herein to define a range.

In one embodiment, the hSBA strain is an LP2086 (fHBP) B24 strain. In another embodiment, the hSBA strains is an LP2086 (fHBP) B44 strain. In a further embodiment, the hSBA strains includes LP2086 (fHBP) B24 and LP2086 (fHBP) B44 strains. In one embodiment, the hSBA strains includes LP2086 (fHBP) A22, LP2086 (fHBP) A56, LP2086 (fHBP) B24, and LP2086 (fHBP) B44 strains. In one embodiment, the hSBA strain includes B15. In one embodiment, the hSBA strain includes B153. In another embodiment, the hSBA strain is an LP2086 B16 strain. In one embodiment, the hSBA strain is an LP2086 B03 strain. In one embodiment, the hSBA strain is an LP2086 B09 strain. In a further embodiment, the hSBA strains include B24, B16, B44, B03, and B09, or any combination thereof. In another embodiment, the hSBA strains include B24, B16, B44, A22, B03, B09, A12, A19, A05, and A07, or any combination thereof. In another embodiment, the hSBA strains include A06, A07, A12, A15, A19, A29, B03, B09, B15, and B16, or any combination thereof.

In one embodiment, the method induces an immune response against a *N. meningitidis* serogroup B fHPB subfamily A strain and against a *N. meningitidis* serogroup B fHPB subfamily B strain. Preferably, the immune response is bactericidal against a *N. meningitidis* serogroup B fHPB subfamily A strain and against a *N. meningitidis* serogroup B fHPB subfamily B strain.

In one embodiment, the immune response elicited by the composition is bactericidal not only against a *N. meningitidis* serogroup B fHPB subfamily B strain but also a *N. meningitidis* strain expressing an fHBP subfamily B polypeptide, wherein the serogroup is not serogroup B. For example, in one preferred embodiment, the immune response elicited by the composition is bactericidal against a *N. meningitidis* serogroup B subfamily B strain and against a *N. meningitidis* serogroup Y strain that expresses an fHBP subfamily B polypeptide heterologous to fHBP B01. For example, in one embodiment, the immune response is against a *N. meningitidis* serogroup A strain expressing fHBP B16. In another embodiment, the immune response is against a *N. meningitidis* serogroup Y strain expressing fHBP B47. In another embodiment, the immune response is against a *N. meningitidis* serogroup X strain expressing fHBP B49. In one embodiment, the immune response is bactericidal against a *N. meningitidis* strain that expresses an fHBP subfamily B polypeptide, wherein the strain is heterologous to *N. meningitidis* serogroup B strain CDC1573.

Titers

In one embodiment, the composition induces an increase in bactericidal titer in the human, as compared to the bactericidal titer in the human prior to administration of a dose of the composition, when measured under identical conditions in an hSBA. In one embodiment, the increase in bactericidal titer is compared to the bactericidal titer in the human before administration of the first dose of the composition, as compared to the bactericidal titer in the human prior to administration of the first dose of the composition, when measured under identical conditions in an hSBA. In one embodiment, the increase in titer is observed after a second dose of the composition, as compared to the bactericidal titer in the human prior to administration of the second dose of the composition, when measured under identical conditions in an hSBA. In another embodiment, the increase in bactericidal titer is observed after a third dose of the composition, as compared to the bactericidal titer in the human prior to administration of the third dose of the composition, when measured under identical conditions in an hSBA.

In one embodiment, the composition induces a bactericidal titer in the human after administration of a dose, wherein the bactericidal titer is at least greater than 1-fold higher than the bactericidal titer in the human prior to administration of the dose, when measured under identical conditions in an hSBA. For example, the bactericidal titer may be at least 1.01-fold, 1.1-fold, 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, or 16-fold higher in the human after receiving a dose of the composition, as compared to the bactericidal titer in the human prior to administration of the dose, when measured under identical conditions in an hSBA.

In one embodiment, a "responder" refers to a human, wherein the composition induces a bactericidal titer in the human after administration of a dose, wherein the bactericidal titer is at least greater than 1-fold higher than the bactericidal titer in the human prior to administration of the dose. In a preferred embodiment, the responder achieves at least a 4-fold rise in hSBA titer, as compared to a bactericidal titer in the human prior to administration of the dose. Such a responder may be referred to as having a protective titer. In some embodiments, a protective titer is one that is greater than 1:4.

In one embodiment, the hSBA titer is the reciprocal of the highest dilution of a serum sample that produces a measurable effect. For example, in one embodiment, the hSBA titer is the reciprocal of the highest 2-fold dilution of a test serum that results in at least a 50% reduction of MnB bacteria (50% bacterial survival) compared to the T30 CFU value (i.e., the number of bacteria surviving after incubation in assay wells containing all assay components except test serum; 100% bacterial survival).

In one embodiment, the composition induces a bactericidal titer in the human after receiving the first dose that is at least 2-fold higher than the bactericidal titer in the human prior to receiving the first dose (e.g., higher than the bactericidal titer in the human in the absence of the first dose), when measured under identical conditions in the hSBA. In one embodiment, the composition induces a bactericidal titer in the human that is at least 4-fold higher than the bactericidal titer in the human prior to receiving the first dose, when measured under identical conditions in a human serum bactericidal assay that utilizes human complement (hSBA). In one embodiment, the composition induces a bactericidal titer in the human that is at least 8-fold higher than the bactericidal titer in the human prior to receiving the first dose, when measured under identical conditions in a human serum bactericidal assay that utilizes human complement (hSBA).

In a preferred embodiment, the human serum complement is derived from a human having low intrinsic bactericidal activity for a given hSBA test strain. Low intrinsic bactericidal activity refers to, for example, a bactericidal titer that is at least less than a 1:4 dilution against the given hSBA test strain. In one embodiment, the human complement is derived from a human having an hSBA titer that is at least less than 1:4, such as a 1:2 dilution, against the given hSBA test strain, wherein the composition was not administered to the human.

A human may exhibit an hSBA titer of less than 1:4 prior to administration of a composition, such as the bivalent rLP2086 composition, or a human may exhibit an hSBA titer of ≥4 prior to administration of the composition. Accordingly, in preferred embodiments and examples, administration of at least one dose of the composition to the human results in an hSBA titer that is at least 4-fold greater than the titer in the human prior to the administration. In some embodiments, administration of at least one dose of the composition to the human results in an hSBA titer that is at least greater than 1:4, such as, for example, an hSBA titer of ≥1:8, an hSBA titer of ≥1:16, and an hSBA titer of ≥1:32. The respective Examples described herein include assessments of the proportion of human subjects having an hSBA titer ≥1:8 and/or ≥1:16, wherein the bivalent rLP2086 composition was administered to the human. In some embodiments, a 4-fold rise in titer in the human after administration of the composition as compared to before administration of the composition show that protection is associated with the composition. In some embodiments, such preferred assessments of hSBA titers greater than 1:4 show that the protection, i.e., the bactericidal immune response induced in the human, is associated with the composition.

In one embodiment, the human has an hSBA titer equal to or greater than the hSBA's lower limit of quantitation (LLOQ) after administration of the first dose of the composition. In another embodiment, the human has an hSBA titer equal to or greater than the hSBA's LLOQ after administration of the second dose of the composition. In another embodiment, the human has an hSBA titer equal to or greater than the hSBA's LLOQ after administration of the third dose of the composition.

Methods and Administration

In one aspect, the invention relates to a method of inducing an immune response against N. meningitidis in a human. In another aspect, the invention relates to a method of vaccinating a human. In one embodiment, the method includes administering to the human at least one dose of the composition described above. In a preferred embodiment, the method includes administering to the human at most one dose of the composition described above. In another embodiment, the method includes administering to the human at least a first dose and a second dose of the composition described above.

In one embodiment, the second dose is administered at least 20, 30, 50, 60, 100, 120, 160, 170, or 180 days after the first dose, and at most 250, 210, 200, or 190 days after the first dose. Any minimum value may be combined with any maximum value described herein to define a range.

In another embodiment, the second dose is administered about 30 days after the first dose. In another embodiment, the second dose is administered about 60 days after the first dose, such as, for example, in a 0, 2 month immunization schedule. In another embodiment, the second dose is administered about 180 days after the first dose, such as, for example, in a 0, 6 month immunization schedule. In yet another embodiment, the second dose is administered about 120 days after the first dose, such as, for example, in a 2, 6 month immunization schedule.

In one embodiment, the method includes administering to the human two doses of the composition and at most two doses. In one embodiment, the two doses are administered within a period of about 6 months after the first dose. In one embodiment, the method does not include further administration of a booster to the human. A "booster" as used herein refers to an additional administration of the composition to the human. Administering to the human at most two doses of the composition may be advantageous. Such advantages include, for example, facilitating a human to comply with a complete administration schedule and facilitating cost-effectiveness of the schedule.

In one embodiment, the first dose and the second dose are administered to the human over a period of about 25, 30, 40, 50, 60, 70, 80, 90, 100, 110, 120, 130, 140, 150, 160, 170, 180, 190, or 200 days, and most 400, 390, 380, 370, 365, 350, 340, 330, 320, 310, 300, 290, 280, 270, 260, 250, 240, 230, 220, 210, or 200 days after the first dose. Any minimum value may be combined with any maximum value described herein to define a range. Preferably, the first and second doses will be administered at least 4 weeks apart e.g. ≥8 weeks apart, ≥2 months apart, ≥3 months apart, ≥6 months apart, etc.

In one embodiment, the first dose and the second dose are administered to the human over a period of about 30 days. In another embodiment, the first dose and the second dose are administered to the human over a period of about 60 days. In another embodiment, the first dose and the second dose are administered to the human over a period of about 180 days.

Conveniently, the first dose can be administered at substantially the same time as (e.g. during the same medical consultation or visit to a healthcare professional or within 24 hours of the first dose of the meningococcal vaccine) another vaccine e.g. at substantially the same time as a hepatitis B virus vaccine, a diphtheria vaccine, a tetanus vaccine, a pertussis vaccine (either cellular or, preferably, acellular), a *Haemophilus influenzae* type b vaccine, a *Streptococcus pneumoniae* vaccine, and/or a polio vaccine (preferably in inactivated poliovirus vaccine). Each of these optionally co-administered vaccines may be a monovalent vaccine or may be part of a combination vaccine (e.g. as part of a DTP vaccine).

Conveniently, the second dose can be administered at substantially the same time as (e.g. during the same medical consultation or visit to a healthcare professional or within 24 hours of the second dose of the meningococcal vaccine) another vaccine e.g. at substantially the same time as a hepatitis B virus vaccine, a diphtheria vaccine, a tetanus vaccine, a pertussis vaccine (either cellular or acellular), a *Haemophilus influenzae* type b vaccine, a *Streptococcus pneumoniae* vaccine, a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of an MMR vaccine).

Conveniently, the third dose can be administered at substantially the same time as (e.g. during the same medical consultation or visit to a healthcare professional or within 24 hours of the third dose of the meningococcal vaccine) another vaccine e.g. at substantially the same time as a hepatitis B virus vaccine, a diphtheria vaccine, a tetanus vaccine, a pertussis vaccine (either cellular or acellular), a *Haemophilus influenzae* type b vaccine, a *Streptococcus pneumoniae* vaccine, a polio vaccine (preferably in inactivated poliovirus vaccine), an influenza vaccine, a chickenpox vaccine, a measles vaccine, a mumps vaccine, and/or a rubella vaccine. Each of these optionally co-administered vaccines may be a monovalent vaccine or may be part of a combination vaccine (e.g. as part of an MMR vaccine).

Three Doses

In one embodiment, a three-dose schedule of the composition induces a bactericidal titer against multiple strains expressing LP2086 (fHBP) heterologous to the first and/or second polypeptide in a greater percentage of humans than a two-dose schedule.

In one embodiment, the method includes administering to the human three doses of the composition. In another embodiment, the method includes administering at most three doses of the composition. In one embodiment, the three doses are administered within a period of about 6 months after the first dose. In one embodiment, the method includes an administration of a booster dose to the human after the third dose. In another embodiment, the method does not include administration of a booster dose to the human after the third dose. In another embodiment, the method does not further include administering a fourth or booster dose of the composition to the human. In a further embodiment, at most three doses within a period of about 6 months are administered to the human.

In an exemplary embodiment, the second dose is administered about 30 days after the first dose, and the third dose is administered about 150 days after the second dose, such as, for example, in a 0, 1, 6 month immunization schedule. In another exemplary embodiment, the second dose is administered about 60 days after the first dose, and the third dose is administered about 120 days after the second dose, such as, for example, in a 0, 2, 6 month immunization schedule.

In one embodiment, the first dose, second dose, and third dose are administered to the human over a period of about 150, 160, 170, or 180 days, and at most 240, 210 200, or 190 days. Any minimum value may be combined with any maximum value described herein to define a range. Preferably, the first dose, second dose, and third dose is administered to the human over a period of about 180 days or 6 months. For example, the second dose may be administered to the human about 60 days after the first dose, and the third dose may be administered to the human about 120 days after the second dose. Accordingly, an exemplary schedule of administration includes administering a dose to the human at about months 0, 2, and 6.

As described above, multiple doses of the immunogenic composition may be administered to the human, and the number of days between each dose may vary. An advantage of the method includes, for example, flexibility for a human to comply with the administration schedules.

In one embodiment, the method includes administering to the human at most three doses of the identical immunogenic composition. For example, in a preferred embodiment, the method does not include administering to the human a first dose of a first composition, administering to the human a second dose of a second composition, and administering to the human a third dose of a third composition, wherein the first, second, and third compositions are not identical. In another embodiment, the method includes administering to the human at most four doses of the identical immunogenic composition.

EXAMPLES

The following Examples illustrate embodiments of the invention. Unless noted otherwise herein, reference is made in the following Examples to a MnB bivalent rLP2086 composition, at the 120-µg bivalent rLP2086 dose level, which is a preferred exemplary embodiment of a composition including: 60 µg of a first lipidated polypeptide including the amino acid sequence set forth in SEQ ID NO: 1 per 0.5 mL dose, 60 µg of a second lipidated polypeptide including the amino acid sequence set forth in SEQ ID NO: 2 per 0.5 mL dose, 2.8 molar ratio polysorbate-80 to the first polypeptide, 2.8 molar ratio polysorbate-80 to the second polypeptide, 0.5 mg $Al^{3+}$/ml of the composition, 10 mM histidine, and 150 mM sodium chloride.

More specifically, the investigational bivalent recombinant rLP2086 vaccine at the 120-µg bivalent rLP2086 dose level includes (a) 60 µg of a first lipidated polypeptide including the amino acid sequence set forth in SEQ ID NO: 1; (b) 60 µg of a second lipidated polypeptide including the amino acid sequence set forth in SEQ ID NO: 2; (c) 18 µg polysorbate-80; (d) 250 µg aluminum; (e) 780 µg histidine, and (f) 4380 µg sodium chloride. Each dose is 0.5 mL.

Unless noted otherwise herein, reference is made in the following Examples to a MenACWY-TT composition, which is a preferred exemplary embodiment of a tetravalent meningococcal polysaccharide conjugated composition that includes *Neisseria meningitidis* capsular polysaccharides A, C, W-135 and Y each coupled to tetanus toxoid as a carrier protein. The *Neisseria meningitidis* serogroups A and C polysaccharides are conjugated with an adipic dihydrazide (AH) spacer and indirectly conjugated to the tetanus toxoid whereas the W-135 and Y polysaccharides are conjugated directly to tetanus toxoid. The composition does not contain any preservatives or adjuvants.

More specifically, the lyophilized MenACWY-TT composition described in the examples below includes 5 micrograms of *Neisseria meningitidis* serogroup A polysaccharide conjugated to tetanus toxoid carrier protein; 5 micrograms of *Neisseria meningitidis* serogroup C polysaccharide conjugated to tetanus toxoid carrier protein; 5 micrograms of *Neisseria meningitidis* serogroup W-135 polysaccharide conjugated to tetanus toxoid carrier protein; 5 micrograms of *Neisseria meningitidis* serogroup Y polysaccharide conjugated to tetanus toxoid carrier protein; 28 mg sucrose; 97 μg trometamol, per dose (0.5 mL).

Example 1: The MenABCWY Composition

The final MenABCWY composition is prepared by reconstituting the lyophilized MenACWY-TT Drug Product (described in Example 2 below) vial with 0.67 mL of MnB Bivalent rLP2086 Drug Product (described in Example 3 below) in order to withdraw 0.5 mL dose of MenABCWY vaccine for intramuscular injection. All components used in the preparation of the MenABCWY vaccine and their functions are provided in Table 1 below.

TABLE 1

Composition of MenABCWY vaccine

| Ingredients | Amount/dose |
|---|---|
| MnB rLP2086 subfamily A (SEQ ID NO: 1) | 60 mcg |
| MnB rLP2086 subfamily B (SEQ ID NO: 2) | 60 mcg |
| $MenA_{AH}$-TT conjugate | 5 mcg MenA |
| (mean TT/polysaccharide ratio: ~3) | ~7.5 mcg TT |
| $MenC_{AH}$-TT conjugate | 5 mcg MenC |
| (mean TT/polysaccharide ratio: ~3) | ~7.5 mcg TT |
| MenW-TT conjugate | 5 mcg MenW |
| (mean TT/polysaccharide ratio: ~1.5) | ~3.75 mcg TT |
| MenY-TT conjugate | 5 mcg MenY |
| (mean TT/polysaccharide ratio: ~1.3) | ~3.25 mcg TT |
| Tris-HCl | 97 mcg |
| Sodium Chloride[a] | 4.69-4.71 mg |
| Sucrose | 28 mg |
| L-Histidine | 0.78 mg |
| Polysorbate 80 (PS80) | 0.02 mg |
| Aluminum phosphate | 0.25 mg aluminum |
| Water for injection | qs to 0.5 mL |

[a]Sodium chloride concentration in MenABCWY Vaccine may vary between 160.5-161.1 mM based on the composition of the clinical and commercial NIMENRIX Drug Product (DP) lots.

Example 2: Description and Composition of the MnB Bivalent rLP2086 Drug Product MnB bivalent rLP2086 drug product is a sterile liquid formulation composed of rLP2086 subfamily A and B proteins formulated at 120 μg/mL/subfamily in 10 mM histidine buffer, 150 mM sodium chloride (NaCl) at pH 6.0 with 0.5 mg/mL aluminum as aluminum phosphate (AlPO4). Polysorbate 80 (PS-80) is added to drug substance to obtain the target PS-80 to protein molar ratio. Therefore, PS-80 is not added during the drug product formulation but is present in the final drug product at the same ratio. The drug product is filled into 1 mL syringes. A single dose of vaccine is 0.5 mL with no preservatives.

TABLE 2

Composition of MnB Bivalent rLP2086 Drug Product

| Ingredients | Quantity/dose |
|---|---|
| MnB rLP2086 subfamily A (SEQ ID NO: 1) | 120 μg/mL |
| MnB rLP2086 subfamily B (SEQ ID NO: 2) | 120 μg/mL |
| Sodium chloride | 150 mM |
| L-Histidine | 10 mM |
| Aluminum phosphate | 0.50 mg Aluminum phosphate/mL |
| Water for injection | qs to 1 mL |

[a] Polysorbate 80 (PS-80) is part of drug substance. PS-80 functions as a surfactant in the drug product.
[b] Equivalent to 0.25 mg aluminum per dose The Effect of Polysorbate 80 Concentration Polysorbate 80 (PS-80) is a non-ionic surfactant. It is used to stabilize and solubilize MnB rLP2086 subfamily A and B proteins in the formulation by preventing aggregation and adsorption that may be caused by temperature, filter, tubing, container/closure contact and process mixing. Stability studies using an in vitro monoclonal antibody based potency assay demonstrated instability of the subfamily B protein at higher molar ratios of PS-80 to MnB rLP2086 protein in the final formulation. Experiments with varying molar ratios of PS-80 to protein have demonstrated that the optimal molar ratio of PS-80 to MnB rLP2086 protein is approximately between 1.4 to 4.2 to retain potency.

Example 3: Description and Composition of the MenACWY-TT Composition

MenACWY-TT drug product is composed of the purified polysaccharides of *Neisseria meningitidis* serogroups A, C, W and Y, each conjugated to Tetanus Toxoid (TT) at ratios to polysaccharide of ~3, ~3, ~1.5 and ~1.3, respectively.

The MenACWY-TT drug product is presented as a lyophilized powder, supplied in a 3 mL glass vial with bromobutyl rubber closures suitable for lyophilization and aluminum flip-off caps. All components used in the manufacture of the MenACWY-TT Drug product and their functions are provided in Table 3.

TABLE 3

Composition of MenACWY-TT Drug product

| Ingredients | Quantity/dose |
|---|---|
| $MenA_{AH}$-TT conjugate | 5 mcg MenA |
| (mean TT/polysaccharide ratio: ~3) | ~15 mcg TT |
| $MenC_{AH}$-TT conjugate | 5 mcg MenC |
| (mean TT/polysaccharide ratio: ~3) | ~15 mcg TT |
| MenW-TT conjugate | 5 mcg MenW |
| (mean TT/polysaccharide ratio: ~1.5) | ~7.5 mcg TT |
| MenY-TT conjugate | 5 mcg MenY |
| (mean TT/polysaccharide ratio: ~1.3) | ~6.5 mcg TT |
| Tris-HCl | 97 mcg |
| Sucrose | 28 mg |
| Sodium Chloride[a] | 306.0-325.0 mg |

[a]Lyophilized cake also contains sodium chloride resulting from the salt present in each of the bulk purified TT conjugates. Sodium chloride concentration varies between 10.5-11.1 mM based on the composition of the clinical and commercial lots.

Example 4: Preparation of the MenABCWY Composition

The final MenABCWY composition is prepared in the clinic by reconstituting the lyophilized MenACWY-TT drug product vial with 0.67 mL of MnB Bivalent rLP2086. The resulting MenABCWY composition (a vaccine liquid drug product) contains rLP2086 subfamily A and B proteins at 120 mcg/mL/subfamily, purified polysaccharides of *Neisseria meningitis* types A, C, W and Y at concentration of 10 mcg/mL/type conjugated to Tetanus Toxoid at ratios of ~3, ~3, ~1.5, and ~3 respectively in 10 mM histidine and 1.6 mM tris buffer containing 160.5-161.1 mM sodium chloride, 0.5 mg/mL aluminum as aluminum phosphate (AlPO4), 0.035 mg/mL polysorbate 80 and 56 mg/mL sucrose at pH of 6.05 for intramuscular injection.

The MenABCWY vaccine is prepared by mixing of two drug products, MenACWY-TT and MnB Bivalent rLP2086. Buffering components and excipients were chosen based on the individual development of each component and are shown to provide the necessary stability profile for extended shelf life.

Dosage verification studies were performed to demonstrate that MenACWY-TT drug product and MnB Bivalent rLP2086 drug product are compatible when mixed together for administration of MenABCWY vaccine and that all drug product and dosing solutions are compatible with the administration components and that dosing solutions are stable in the administration components for a period of time adequate to perform the dose preparation and administration operations. The stability of MenABCWY vaccine prepared by reconstitution of MenACWY-TT drug product with 0.67 mL of MnB Bivalent rLP2086 drug product over the hold time at ambient temperature and light conditions was confirmed in reconstituted vials and in dosing syringes.

Samples representing the dosing solutions of MenABCWY vaccine were tested using stability indicating methods such as RP-HPLC for antigen binding and purity, bioplex activity assay, ELISA, and ICP-MS with predefined acceptance criteria. The results of this study show acceptable stability of MenABCWY vaccine for 24 hours at room temperature and light conditions. These data are shown and described in Examples 5-15 below.

Example 5: Evaluation of the MenABCWY Vaccine

A study was carried out to assess whether there is acceptable physical compatibility and short-term stability when a lyophilized MenACWY-TT composition is reconstituted with the MnB bivalent rLP2086 composition. The lyophilized MenACWY-TT composition and the liquid MnB bivalent rLP2086 composition were combined and stored for up to 24 hours in an uncontrolled room temperature environment to approximate real life conditions. It was demonstrated that lyophilized MenACWY-TT composition could be reconstituted with the liquid MnB bivalent rLP2086 composition with gentle hand mixing and the combined pH and osmolality were within typical range for an injectable. All key attributes for the conjugates and proteins were similar to those of a control for up to 24 hours in the uncontrolled room temperature environment.

The physical compatibility was evaluated through assessing pH, appearance, ease of reconstitution, and osmolality of the combined drug product. The stability of the antigens was evaluated through assessing concentration, purity and the in-vitro relative antigenicity (IVRA) of the rLP2086 subfamily A and subfamily B proteins as well as the concentrations of the conjugated Meningococcal A, C, Y, and W-135 polysaccharides by ELISA.

Example 5 through Example 15 demonstrate that the combination of the lyophilized MenACWY-TT composition and the liquid MnB bivalent rLP2086 composition, i.e., the MenABCWY composition, was found to be compatible and stable for at least 24 hours at room temperature.

ELISAs for Determining Mening A, C, Y, and W-135 Polysaccharide Concentrations in the MenABCWY Composition—Development of the Mening A, C, Y and W-135 ELISA & Screening of the pAb for Detection Six antibodies were selected for screening for use in the ELISA assays. Each of four groups of ten rabbits was immunized with either Men A, C, Y or W-135 polysaccharide TT conjugates with rabbits subsequently exsanguinated after antibody development. Each rabbit was individually screened using Men A, C, Y or W-135 polysaccharides conjugated to a carrier protein $CRM_{197}$ for binding and specificity. Rabbit sera was screened for a positive binding signal, which is equivalent to an absorbance reading greater than three-fold above the background absorbance. Additionally, rabbit sera was screened for low non-specific binding, which was any absorbance readings for sera combinations without antigen, secondary or detection above the absorbance reading for the blank, as well as low cross-reactivity, which was any absorbance readings for heterologous serotypes that was above the background absorbance. Rabbits that met the screening criteria were pooled. The standard curve range was established using CRM conjugates and confirmed with reconstituted the lyophilized MenACWY-TT composition. The standard curve range was established using CRM conjugates and confirmed with reconstituted lyophilized MenACWY-TT composition.

The feasibility of quantitating the A, C, Y and W conjugates in the combined drug product (MenABCWY composition) was established. It was determined that the MnB Bivalent rLP2086 composition alone was not detected in the assay. Additionally, when aluminum phosphate in the MenABCWY composition samples was solubilized, full recovery of conjugates was obtained. Therefore, it was determined that the MnB bivalent rLP2086 composition does not interfere with the quantitation of the MenACWY-TT conjugates by ELISA.

Example 6: Evaluation of Suitability of Methods to Assess the MnB Bivalent rLP2086 Composition in the Presence of the MenACWY-TT Composition IEX-HPLC was evaluated for its suitability to determine the strength of the MnB bivalent rLP2086 composition subfamily A and B proteins in the presence of the MenACWY-TT composition. The total protein and bound protein results for the MnB bivalent rLP2086 composition in the presence of the MenACWY-TT composition and in the absence of the MenACWY-TT composition were accessed. The overlaid chromatograms are shown in FIG. 1.

TABLE 4

| Sample | Subfamily | Bound Protein, % |
| --- | --- | --- |
| the MnB bivalent rLP2086 composition no the MenACWY-TT composition | Protein A (SEQ ID NO: 1) | 107 |
|  | Protein B (SEQ ID NO: 2) | 104 |
| the MnB bivalent rLP2086 composition with the MenACWY-TT composition | Protein A (SEQ ID NO: 1) | 108 |
|  | Protein B (SEQ ID NO: 2) | 103 |

Figure 2:
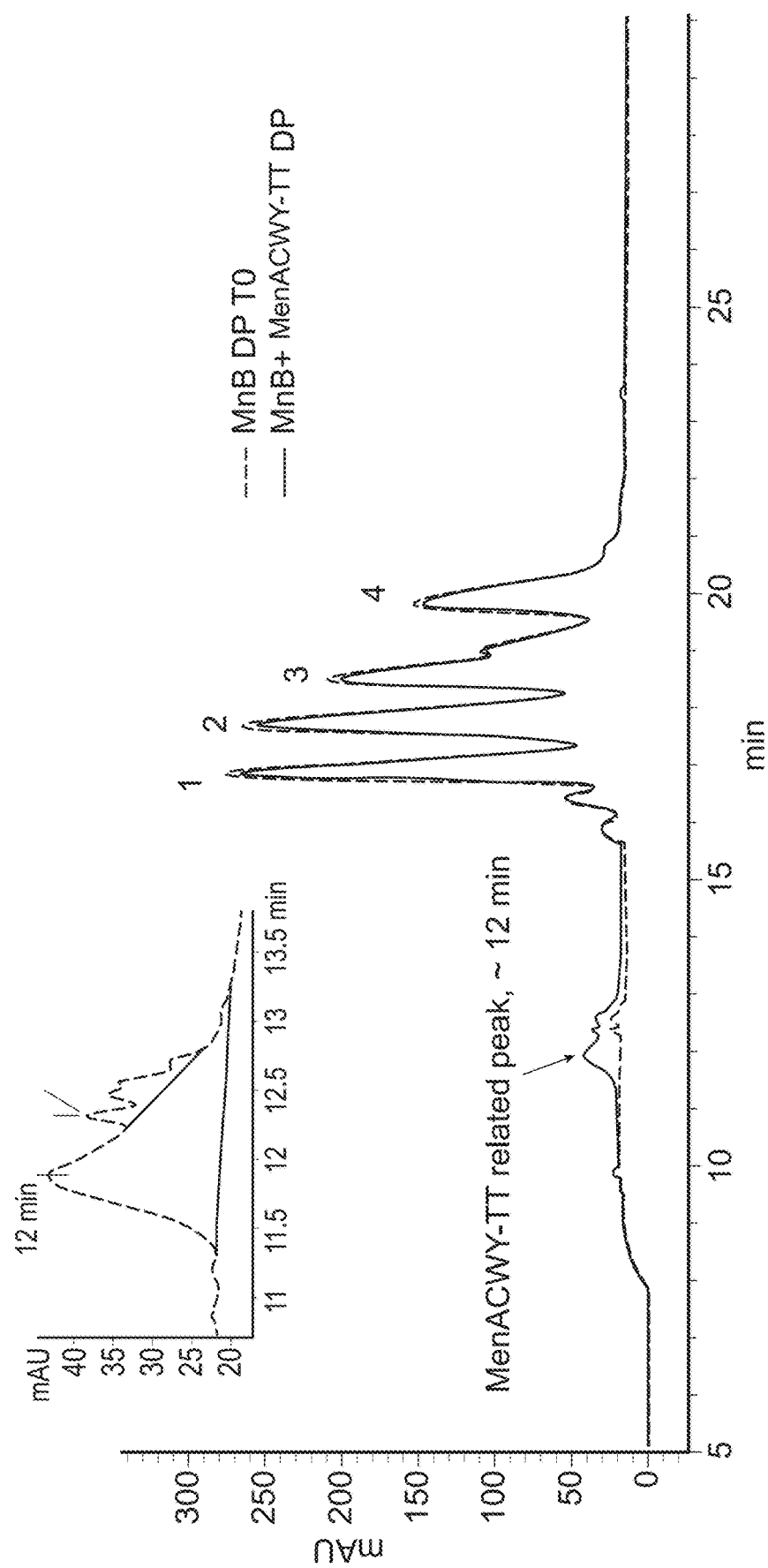
FIG. 2—Overlay of RP-HPLC Chromatograms showing that the presence of the MenACWY-TT composition does not interfere with evaluation of the MnB bivalent rLP2086 composition purity, as described in Example 7.

Example 7: Evaluation of the MnB Bivalent rLP2086 Composition Purity and Peak Ratio in the Presence of the MenACWY-TT Composition RP-HPLC was evaluated for its suitability to determine the purity of the MnB bivalent rLP2086 composition in the presence of the MenACWY-TT composition. The purity results for the MnB bivalent rLP2086 composition in the presence of the MenACWY-TT composition and in the absence of the MenACWY-TT composition were compared. The overlaid chromatograms are shown in FIG. 2. An example of the integration of the impurity peak is shown as an insert in FIG. 2. The evaluation results show that the presence of the MenACWY-TT composition does not interfere with evaluation of the MnB bivalent rLP2086 composition purity using the RP-HPLC method.

Example 8: Evaluation of the MnB Bivalent rLP2086 Composition IVRA in the Presence of the MenACWY-TT Composition The IVRA method was evaluated for its suitability for determination of in-vitro relative antigenicity of the MnB bivalent rLP2086 composition Subfamily A (SEQ ID NO: 1) and Subfamily B (SEQ ID NO: 2) proteins in the presence of the MenACWY-TT composition.

The IVRA results for the MnB bivalent rLP2086 composition Subfamily A and Subfamily B proteins in the presence and in the absence of the MenACWY-TT composition were compared. The feasibility evaluation results show that, within the assay variability the results are comparable and that the presence of the MenACWY-TT composition does not interfere with determination of in-vitro relative antigenicity.

Example 9: Reconstitution of the MenACWY-TT Composition Vials with the MnB Bivalent rLP2086 Composition The MenACWY-TT composition and the MnB bivalent rLP2086 composition drug products were performed using the MenACWY-TT composition vials reconstituted with the MnB bivalent rLP2086 composition drug product. The MenACWY-TT composition vials reconstituted with either saline or the MenACWY-TT composition matrix placebo were used as controls depending on the method.

TABLE 5

| Product | Component | Composition |
| --- | --- | --- |
| The MenACWY-TT composition | *Neisseria meningitidis* | |
| | Group A polysaccharide | 10 µg/mL |
| | Group C polysaccharide | 10 µg/mL |
| | Group W-135 polysaccharide | 10 µg/mL |
| | Group Y polysaccharide | 10 µg/mL |
| | Tetanus toxoid carrier protein | 88 µg/mL |
| | Sucrose | 164 mM |
| | Trometanol | 1.6 mM |
| the MnB bivalent rLP2086 composition | Sub-family A rLP2086 protein (SEQ ID NO: 1) | 120 µg/mL |
| | Sub-family B rLP2086 protein (SEQ ID NO: 2) | 120 µg/mL |
| | AlPO4 | 0.5 mg/mL |
| | Histidine | 10 mM |
| | NaCl | 150 mM |
| | | pH 6.0 |
| the MnB bivalent rLP2086 composition Placebo | AlPO4 | 0.5 mg/mL |
| | Histidine | 10 mM |
| | NaCl | 150 mM |
| | | pH 6.01 |
| Bulk MnB bivalent rLP2086 composition DP | Sub-family A rLP2086 protein (SEQ ID NO: 1) | 120 µg/mL |
| | Sub-family B rLP2086 protein (SEQ ID NO: 2) | 120 µg/mL |
| | AlPO4 | 0.5 mg/mL |
| | Histidine | 10 mM |
| | NaCl | 150 mM |
| | | pH 6.0 |

Determination of Saline Reconstitution Volume for the MenACWY-TT Composition

The NIMENRIX® commercial product package contains both a vial containing the lyophilized MenACWY-TT composition and a syringe containing 0.9% saline used for reconstitution. In order to reproduce the final NIMENRIX® concentration in the commercial vaccine upon reconstitution with the MnB bivalent rLP2086 composition, the amount of saline dispensed using the syringe from the commercial product had to be determined. This same volume of the MnB bivalent rLP2086 composition would then be used for all reconstitution studies.

Reconstitution of the MenACWY-TT Composition Vials with the MnB Bivalent rLP2086 Composition The MnB bivalent rLP2086 composition was pooled in a 10 mL glass vial. Approximately 800 µL of the solution was withdrawn into a 1 mL syringe. The adjusted contents of the syringe were injected into a vial containing the MenACWY-TT composition. The vial was swirled to dissolve the contents.

The pH and appearance were determined on duplicate samples on the MenABCWY composition. Osmolality was measured in triplicate on the MenACWY-TT composition reconstituted with saline and on the MenACWY-TT composition reconstituted with the MnB bivalent rLP2086 composition.

Example 10: SEC-MALLS to Evaluate Mening A, C, Y, and W-135 Polysaccharide Stability in DP Matrix Mening A, C, Y, and W-135 Polysaccharides were used as surrogates to assess if any instability of the conjugated Meningococcal A, C, Y, and W-135 polysaccharides in the combined drug product (the MenABCWY composition) could be expected.

Treatment of Mening A, C, Y, and W-135 Polysaccharides Reagent Preparation ("Full MenABCWY Composition Buffer Matrix")

2.24 g of sucrose and 7.8 mg of Tris (Tromethamine) was added to 20 ml of 2×MnB bivalent rLP2086 composition buffer matrix with MnB rLP2086 proteins (Histidine 20 mM pH 6.0, NaCl 300 mM, PS 80 0.07 mg/ml, AlPO4 1 mg/ml (8 mM), rLP2086 subfamily A (SEQ ID NO: 1) and subfamily B (SEQ ID NO: 2) proteins 240 µg/mL each).

Sample Preparation

Each Mening Polysaccharide was diluted 1:1 with Full MenABCWY composition Buffer Matrix and incubated for 0, 6 and 24 hours at 5° C., 25° C. and 37° C. After incubation the sample suspension was spun for 1 minute at 14,000 r.p.m. The supernatant was analyzed by SEC-MALLS.

Example 11: Stability of the MenABCWY Composition—Evaluation of pH, Appearance, and Osmolality of the Combined MnB Bivalent rLP2086 and MenACWY-TT Compositions The pH and appearance of the combined MnB bivalent rLP2086 composition and the MenACWY-TT composition, i.e., the MenABCWY composition, were evaluated immediately after reconstitution and again after 24 hours.

All results were as expected (Table 6).

TABLE 6

Appearance and pH of the MenABCWY composition

| Sample # | Sample | Time Point, hours | Appearance | pH |
| --- | --- | --- | --- | --- |
| 1 | MenABCWY composition, Rep1 | 0 | Homogeneous white suspension | 5.8 |
| 2 | MenABCWY composition, Rep2 | 0 | Homogeneous white suspension | 5.8 |

TABLE 6-continued

Appearance and pH of the MenABCWY composition

| Sample # | Sample | Time Point, hours | Appearance | pH |
|---|---|---|---|---|
| 3 | MenABCWY composition, Rep 1 | 24 | Homogeneous white suspension | 5.8 |
| 4 | MenABCWY composition, Rep 2 | 24 | Homogeneous white suspension | 5.8 |
| 5 | MenACWY-TT composition w/Saline | 0 | Clear, Colorless | 6.3 |
| 6 | MenACWY-TT composition w/Saline | 24 | Clear, Colorless | 6.4 |

The average osmolality of the MenACWY-TT composition reconstituted with the MnB bivalent rLP2086 composition was within 3% of the average osmolality of the MenACWY-TT composition reconstituted with saline.

TABLE 7

| Vial | Reconstituting Agent | Reading 1 mOsm | Reading 2 mOsm | Reading 3 mOsm | Average mOsm |
|---|---|---|---|---|---|
| MenACWY-TT composition | Saline | 471 | 473 | 478 | 474 |
| MenACWY-TT composition | MnB bivalent rLP2086 composition | 487 | 487 | 489 | 488 |

Example 12: Mening A, C, Y, and W-135 Polysaccharide Conjugate

Concentrations in the Combined Drug Product

The concentration of the Mening A, C, Y and W-135-TT conjugates in the MenABCWY composition was assessed initially and again after 24 hours. The concentrations of the four conjugates were stable over the twenty four hour time period (Table 8).

TABLE 8

Short Term Stability Results of the MnA, C, Y and W Conjugates in the MenABCWY composition by ELISA

| | MenACWY-TT composition + MnB bivalent rLP2086 composition | | | The MenACWY-TT composition + Saline | | |
|---|---|---|---|---|---|---|
| Serotype | Initial, μg/mL | After 24 hrs, μg/mL | Stability Ratio | Initial, μg/mL | After 24 hrs, μg/mL | Stability Ratio |
| A | 6.7 | 6.8 | 1.0 | 6.4 | 6.7 | 1.1 |
| C | 6.9 | 6.6 | 1.0 | 6.5 | 6.7 | 1.0 |
| Y | 8.1 | 8.7 | 1.1 | 9.6 | 9.8 | 1.0 |
| W | 8.5 | 8.8 | 1.0 | 8.8 | 9.0 | 1.0 |

Example 13: Evaluation of the Stability of the MnB Bivalent rLP2086 Proteins in the MenABCWY Composition Total and Bound rLP2086 Subfamily A (SEQ ID NO: 1) and Subfamily B (SEQ ID NO: 2) Protein Concentrations in the Combined Drug Product The MenABCWY composition samples were analyzed by IEX-HPLC to determine the protein concentrations. As shown in Table 9, the total protein, bound protein (to aluminum), and % bound of both MnB bivalent rLP2086 Subfamily A (SEQ ID NO: 1) and Subfamily B (SEQ ID NO: 2) proteins (bound to aluminum) did not change within 24 hours indicating that the rLP2086 Subfamily A and Subfamily B proteins were stable over the twenty four hour time period.

TABLE 9

Total and Bound Protein Stability

| Time Point, hours | Subfamily | Total Protein, μg/mL | Bound Protein, μg/mL | Bound Protein, % |
|---|---|---|---|---|
| 0 | A | 83 | 85 | 102 |
| | B | 88 | 87 | 99 |
| 24 | A | 87 | 88 | 101 |
| | B | 92 | 91 | 99 |

Figure 3:
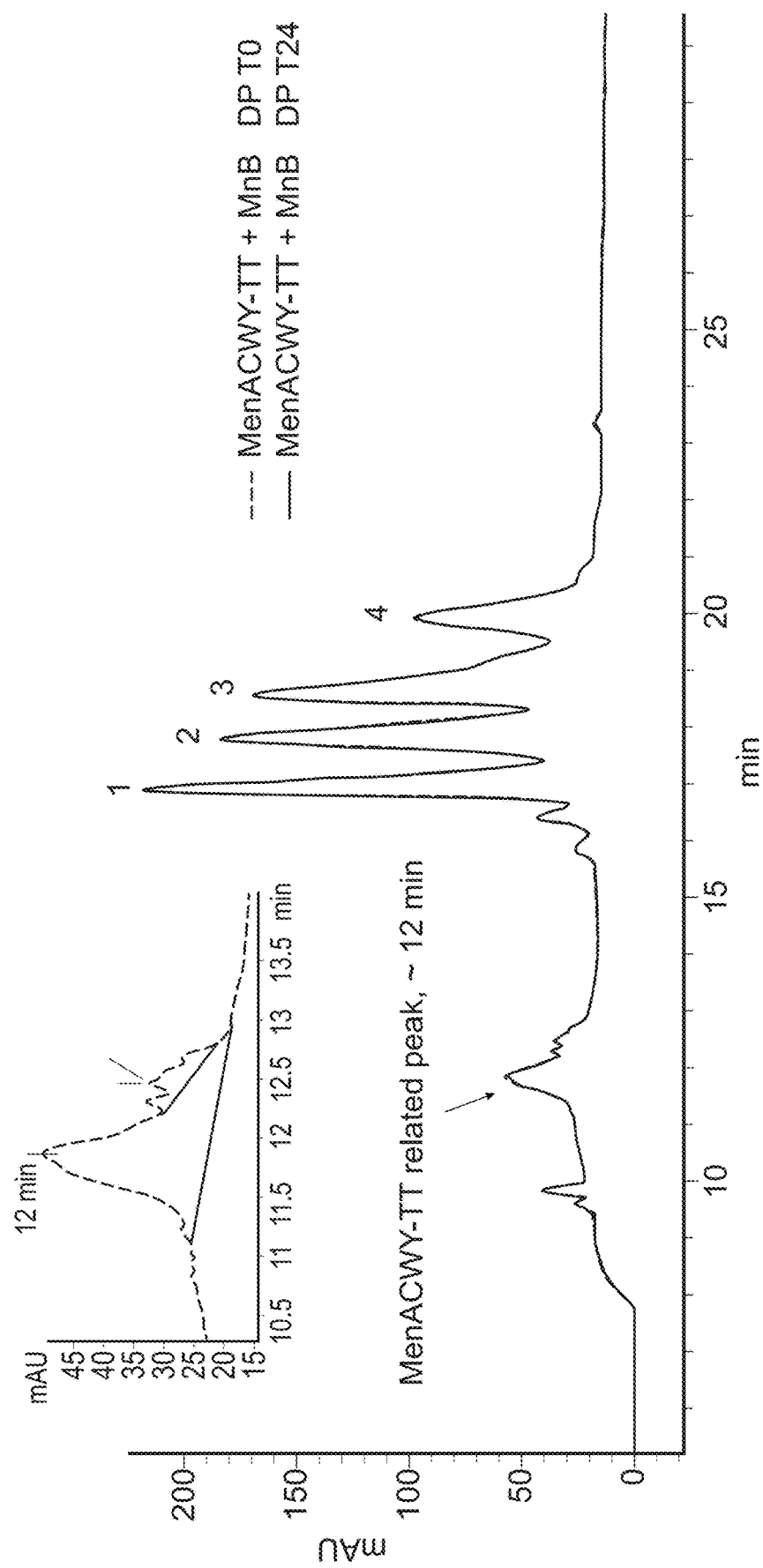
FIG. 3—Overlay of RP-HPLC Chromatograms showing rLP2086 Protein Purity and Peak Ratio in the Combined MenABCWY composition, as described in Example 14.
Figures 4A, 4B:
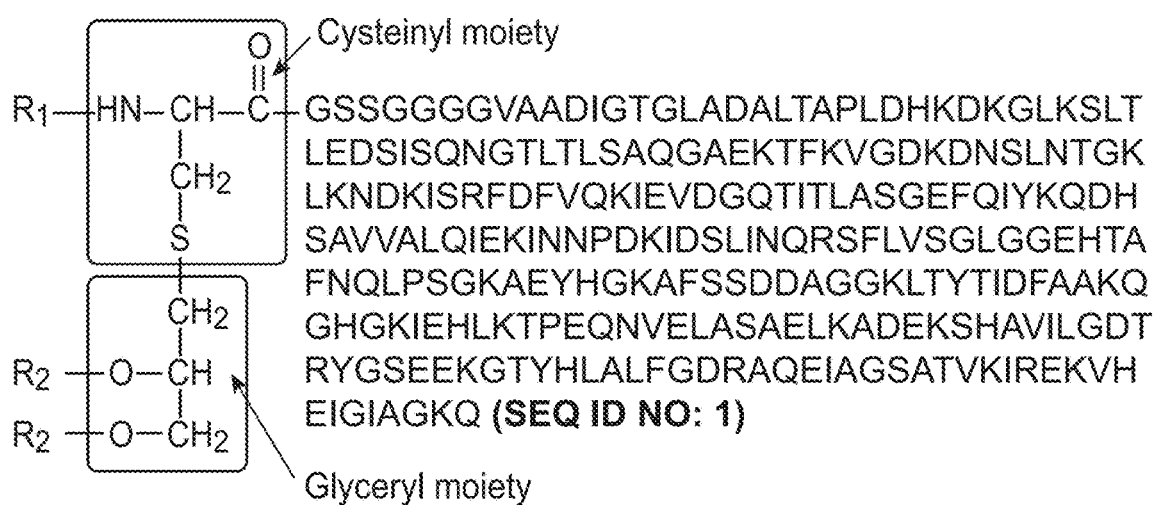
FIG. 4A—Primary Amino Acid Sequence of MnB rLP2086 Subfamily A A05 Protein.
FIG. 4B—Primary Structure of MnB rLP2086 Subfamily A A05 Protein

Example 14: rLP2086 Protein Purity and Peak Ratio in the Combined MenABCWY Composition The MenABCWY composition samples were analyzed by RP-HPLC to determine purity and peak ratios for the rLP2086 proteins. See FIG. 3. The peak at 11.9 min is excluded from the purity calculation.

rLP2086 Subfamily A and Subfamily B Protein IVRA in the Combined Drug Product

The IVRA of the MenABCWY composition samples was assessed for up to 24 hours after mixing. It was determined that the relative antigenicity of the rLP2086 Subfamily A (SEQ ID NO: 1) and Subfamily B (SEQ ID NO: 2) proteins in the MenABCWY composition was stable over the twenty four hour time period.

Example 15: Mening A, C, Y, and W-135 Polysaccharide Stability in Full MenABCWY Composition Buffer Matrix by SEC-MALS Stability of Mening A PS in Full MenABCWY Composition Buffer Matrix by SEC-MALLS after 6 and 24 Hours Incubation at Various Temperatures Mening A, C, W, and Y polysaccharides were mixed with the Full MenABCWY Composition Buffer Matrix and evaluated for stability by SEC-MALS after incubation at 5° C., 25° C. and 37° C. for up to 24 hours. All four polysaccharides appear to be stable for up to 24 hours at 5° C. and 25° C. Some degradation was observed at 37° C. for Mening A and Y. The degree of degradation could not be determined for Mening Y Polysaccharides due to formation of high Mw aggregates under all tested conditions except initial.

TABLE 10

| Sample | Incubation Time, hours | Incubation Temperature | Mw (kDa) | Δ Mw (%) |
|---|---|---|---|---|
| Mening A PS | 0 | NA | 169 | N/A |
| | 24 | 5° C. | 171 | 1 |
| | | 25° C. | 157 | −7 |
| | | 37° C. | 126 | −26 |
| Mening C PS | 0 | NA | 213 | N/A |
| | 24 | 5° C. | 216 | 1 |
| | | 25° C. | 215 | 1 |
| | | 37° C. | 220 | 3 |
| Mening Y PS* | 0 | NA | 294 | N/A |
| | 24 | 5° C. | 734 | 149 |

TABLE 10-continued

| Sample | Incubation Time, hours | Incubation Temperature | Mw (kDa) | Δ Mw (%) |
|---|---|---|---|---|
| | | 25° C. | 756 | 157 |
| | | 37° C. | 696 | 136 |
| Mening W-135 PS | 0 | NA | 205 | N/A |
| | 24 | 5° C. | 230 | 12 |
| | | 25° C. | 211 | 3 |
| | | 37° C. | 219 | 7 |

Example 16: Evaluation of the MnB Bivalent rLP2086 Composition-Induced hSBA Activity Cross Protection Against MENACW Serogroup C There were 49 strains from U. S. and 10 strains from Netherlands in the Serogroup C SBA strain pool. The fHBP sequence is more heterogeneous in serogroup C. The strain pool contains at least 17%, namely 19%, of MenC strains were fHBP A10 expressing strains and 10% A15 expressing strains. The prevalent clonal complexes in this collection of serogroup C strains are ST11/ET-37 complex and ST-103. One strain expressing A10 and three strains expressing A15 with fHBP expression levels above 1100 MFI were selected for further testing. 36 lots of C' were used for C' T30/T0 ratio screening. PMB5180, and PMB5196 expressing A15 for fHBP were excluded since appropriate human serum complement sources that did not non-specifically kill the strain could not be identified according the C' passing rate (Table 12). For PMB5043, the C' passed initial screening test failed in SBA assay due to T30/T0 ratio. PMB5208 met the selection criteria: appropriate complement sources were identified, low baseline seropositivity rates with adolescent preimmune sera were confirmed 17%, and hSBAs was technically feasible.

TABLE 12

| Serogroup C Test Strain Candidates | | | | | | | |
|---|---|---|---|---|---|---|---|
| Strain | fHBP Variant | fHBP Expression[a] | Epidemiological marker | Country of Isolation | C' Pass Rate | hSBA Compatible | Baseline Seropositivity Rate |
| PMB5208 | A10 | 1563 | ST11/ET-37 complex | United States | 56% | Yes[b] | 17%[d] |
| PMB5180 | A15 | 3237 | ST-103 | United States | 0% | ND[e] | ND |
| PMB5196 | A15 | 3353 | ST-103 | United States | 3% | ND | ND |
| PMB5043 | A15 | 2803 | ST-103 | United States | 8% | No[c] | ND |

[a]mean fluorescent intensity as determined in the MEASURE assay
[b]strain formed defined colonies, and was killed by indicator sera, in hSBA
[c]no appropriate complement sources available, failed T30/T0 ratio in SBA
[d]adolescents, prevaccinated sera
[e]not done
The selected Serogroup C strain is indicated in bold font.

Serogroup W

There were 14 strains from U. S., 9 strains from Netherlands and 6 recent outbreak strains from U. K. in the Serogroup W SBA strain pool. The fHBP sequence is more homogeneous in this collection of serogroup W strains. Forty-five percent of the strains in this pool expressed fHBP A19 variant and 45% fHBP A10. The prevalent clonal complex for fHBP A19 variant strains in the serogroup W pool is ST-22 and the prevalent clonal complex for fHBP A10 variant strains is ST-11/ET-37 complex. From the US, one strain expressing A19 and one strain expressing A10 were selected. Two UK outbreak strains expressing A10 with fHBP expression levels above 1100 MFI were selected for further testing. 36 lots of C' were used for C' T30/T0 ratio screening. Four strains all passed this initial C' screening test. Based on the preimmunity rate, PMB5524 and PMB5163 were excluded since the seropositivity rates with adolescent preimmune sera were 74% and 48%, respectively. PMB5248 and PMB5523 met the selection criteria: appropriate complement sources were identified, low baseline seropositivity rates with adolescent preimmune sera e.g. 26%, and 28%, respectively and hSBAs were technically feasible (Table 13).

TABLE 13

Serogroup W Test Strain Candidates

| Strain | fHBP Variant | fHBP Expression[a] | Epidemiological Marker | Country of Isolation | C' Pass Rate | hSBA Compatible | Baseline Seropositivity Rate |
|---|---|---|---|---|---|---|---|
| PMB5248 | A19 | 2684 | ST-22 complex | United States | 14% | Yes[b] | 26%[c] |
| PMB5524 | A10 | 1197 | ST-11/ET-37 complex | U.K. | 34% | Yes | 74%[d] |
| PMB5163 | A10 | 1565 | ST-11 complex/ET-37 complex | United States | 6% | Yes | 48%[d] |
| PMB5523 | A10 | 1796 | ST-11 complex/ET-37 complex | U.K. | 32% | Yes | 28% |

[a]mean fluorescent intensity as determined in the MEASURE assay
[b]strain formed defined colonies, and was killed by indicator sera, in hSBA
[c]adolescents, prevaccinated sera
[d]pre-immunity rate high
The selected Serogroup W strain is indicated in bold font.

Serogroup X

There were 8 strains from Africa and one strain from Netherlands in the Serogroup X SBA strain pool. Five strains from Africa express fHBP B49 variant, three strains had a new fHBP type and the one strain from Netherland expressed fHBP B09. The fHBP expression for all nine strains was over 1100 MFI. Three Africa outbreak strains and one from the Netherlands were selected for further testing. 36 lots of C' were used for C' T30/T0 ratio screening. Four strains all passed C' initial screening test. Based on the preimmunity rate, PMB5467 was excluded since the seropositivity rates with adolescent preimmune sera was 68%. PMB5537, PMB5540 and PMB5539 met the selection criteria: appropriate complement sources were identified, low baseline seropositivity rates with adolescent preimmune sera e.g. 0, and hSBAs were technically feasible (Table 14). PMB5540 was selected for evaluation.

TABLE 14

Serogroup X Test Strain Candidates

| Strain | fHBP Variant | fHBP Expression[a] | Epidemiological Marker | Country of Isolation | C' Pass Rate | hSBA Compatible | Baseline Seropositivity Rate |
|---|---|---|---|---|---|---|---|
| PMB5467 | B09 | 1795 | ST-1157 complex | Netherland | 6% | Yes[b] | 68%[d] |
| PMB5537 | B239 | 4896 | ST-181 complex | Burkina Faso | 8% | Yes[b] | 4%[c] |
| PMB5540 | B49 | 8612 | ST-181 complex | Burkina Faso | 53% | Yes[b] | 0% |
| PMB5539 | B49 | 13706 | To be assigned | Uganda | 83% | Yes[b] | 0% |

[a]mean fluorescent intensity as determined in the MEASURE assay
[b]strain formed defined colonies, and was killed by indicator sera in hSBA
[c]no appropriate complement sources available, failed T30/T0 ratio in SBA
[d]adolescents, prevaccinated sera
[d]pre-immunity rate high
The selected Serogroup X strain is indicated in bold font.

Serogroup Y

There were 87 strains from U. S. and 30 strains from Netherlands in the Serogroup Y SBA strain pool. The fHBP sequence is more homogeneous in this collection of serogroup Y strains. Sixty-six percent of the serogroup Y strains in the pool express fHBP A15. The common clonal complex for fHBP A15 variant expressing strains in this serogroup Y collection is ST-23/Cluster A3. Only 15% of the serogroup Y strains in this collection have fHBP expression levels above 1100 MFI. Three strains from the A15 variant group with fHBP expression levels above 1100 MFI were selected for further testing. 36 lots of C' were used for C' T30/T0 ratio screening. PMB5122, PMB5053 and PMB5050 were excluded since appropriate human serum complement sources that did not non-specifically kill the strain could not be identified according the C' passing rate (Table 15). PMB5187 with fHBP B47 was selected for C' T30/T0 screening and C' sources that did not kill the strain non-specifically could be identified (Table 15). Even though PMB5187 did not express the prevalent fHBP variant for serogroup Y, this strain met the other selection criteria: appropriate complement sources were identified, low baseline seropositivity rates with adolescent preimmune sera e.g. 4%, and hSBAs was technically feasible.

TABLE 15

Serogroup Y Test Strain Candidates:

| Strain | fHBP Variant | fHBP Expression[a] | Epidemiological Marker | Country of Isolation | C' Pass Rate | hSBA Compatible | Baseline Seropositivity Rate |
|---|---|---|---|---|---|---|---|
| PMB5122 | A15 | 1011 | ST-23/ Cluster A3 | United States | 0% | ND[d] | ND |
| PMB5053 | A15 | 1608 | ST-23/ Cluster A3 | United States | 0% | ND | ND |
| PMB5050 | A15 | 1811 | ST-23/ Cluster A3 | United States | 0% | ND | ND |
| PMB5187 | B47 | 5063 | ST-23/ Cluster A3 | United States | 64% | Yes[b] | 4%[c] |

[a]mean fluorescent intensity as determined in the MEASURE assay
[b]strain formed defined colonies, and was killed by indicator sera, in hSBA
[c]adolescents, prevaccinated sera
[d]not done
The selected Serogroup Y strain is indicated in bold font.

MnACYWX strains were selected for hSBA development based on the prevalent variants of fHBP for the respective serogroup, fHBP expression above 1100 MFI and assay feasibility (e.g. identification of human complement and baseline seropositivity). Characteristics of the six selected MnACYWX strains, as well as the median fHBP expression for each variant group are summarized in Table 16.

TABLE 16

MnACYWX Test Strain Characteristics

| Strain | Serogroup | fHBP Variant | fHBP Expression | Clonal Complex | Country of Isolation |
|---|---|---|---|---|---|
| PMB3257 | A | B16 | 1725 | ST-1 complex | South Africa |
| PMB5208 | C | A10 | 1563 | CC11/ET-37 complex | United States |
| PMB5248 | W | A19 | 2684 | CC-22 | United States |
| PMB5523 | W | A10 | 1796 | CC-11/ET-37 complex | U.K. |
| PMB5187 | Y | B47 | 5063 | CC-23/ Cluster A3 | United States |
| PMB5540 | X | B49 | 8612 | ST-181 complex | Burkina Faso |

Immunogenicity Analysis

The MnACYWX test strains were used in hSBAs to assess the immune response elicited in subsets of healthy adolescents aged 10 to <13 years enrolled in the Phase 2 concomitant study B1971015. TRUMENBA-elicited hSBA responses were compared to MENACTRA-elicited (meningococcal A, C, Y and W-135 polysaccharide conjugate vaccine [MCV4]) hSBA responses for the six strains selected (Table 17). Substantial bactericidal antibody responses were observed in a high proportion of vaccinated individuals based on an hSBA titer ≥1:8, a more stringent criterion than the accepted correlate of protection (ie, an hSBA titer ≥1:4) for MenCWYX strains except MenA with 28% from those subjects immunized with TRUMENBA compared to 97% from those immunized with MCV4. The TRUMENBA response reached a peak at one month after dose 2 for two serogroup W strains (PMB5248 100%, PMB5523, 97%) and one month after dose 3 for serogroup C, Y, X strains with response rates of 83%-100%. MCV4 responses reached peak one month after dose 1, with no response for MenX. TRUMENBA elicited antibodies demonstrated the potential to protect against MenX, which is not covered by MCV4. The TRUMENBA response rate (i.e. %≥1:8) after 3 doses against MnC, W or Y strains is comparable to MCV4 response rate after 1 dose. The immunogenicity data obtained from the MnACYWX hSBA test strains provide proof of concept for protection against serogroups other than B.

TABLE 17

The percentage of SBA titers ≥1:8 for MnACWYX strains

| Strain | Serogroup | Sampling Time | Group 2: MCV4 0-month | | | Group 3: Trumenba 0, 2, 6- month | | |
|---|---|---|---|---|---|---|---|---|
| | | | N | n | %(GMT) | N | n | %(GMT) |
| PMB3257 | A | Month 0 | 30 | 1 | 3% (2) | 30 | 1 | 3% (2) |
| | | Month 1 | 30 | 29 | 97% (95) | 30 | 4 | 13% (3) |
| | | Month 3 | 30 | 22 | 73% (31) | 30 | 6 | 20% (4) |
| | | Month 7 | 30 | 14 | 47% (11) | 29 | 8 | 28% (5) |
| PMB5208 | C | Month 0 | 30 | 6 | 20% (3) | 30 | 7 | 23% (4) |
| | | Month 1 | 30 | 27 | 90% (119) | 30 | 16 | 53% (8) |
| | | Month 3 | 30 | 28 | 93% (88) | 30 | 21 | 70% (12) |
| | | Month 7 | 30 | 27 | 90% (38) | 30 | 28 | 93% (29) |
| PMB5248 | W | Month 0 | 30 | 12 | 40% (5) | 30 | 8 | 27% (4) |
| | | Month 1 | 30 | 29 | 97% (88) | 30 | 22 | 73% (18) |
| | | Month 3 | 29 | 28 | 97% (58) | 30 | 30 | 100% (47) |
| | | Month 7 | 29 | 26 | 90% (41) | 30 | 30 | 100% (77) |
| PMB5523 | W | Month 0 | 29 | 16 | 55% (8) | 30 | 13 | 43% (7) |
| | | Month 1 | 30 | 29 | 97% (60) | 30 | 20 | 67% (15) |
| | | Month 3 | 30 | 29 | 97% (58) | 30 | 29 | 97% (21) |
| | | Month 7 | 30 | 29 | 97% (44) | 30 | 30 | 100% (42) |
| PMB5187 | Y | Month 0 | 30 | 4 | 13% (3) | 30 | 3 | 10% (3) |
| | | Month 1 | 30 | 29 | 97% (79) | 30 | 14 | 47% (7) |
| | | Month 3 | 30 | 28 | 93% (58) | 30 | 28 | 93% (31) |
| | | Month 7 | 30 | 27 | 90% (36) | 30 | 30 | 100% (58) |
| PMB5540 | X | Month 0 | 30 | 0 | 0% (2) | 30 | 2 | 7% (2) |
| | | Month 1 | 30 | 0 | 0% (2) | 30 | 5 | 17% (3) |
| | | Month 3 | 30 | 0 | 0% (2) | 30 | 16 | 53% (7) |
| | | Month 7 | 30 | 0 | 0% (2) | 30 | 25 | 83% (20) |

Conclusion

MnACYWX strains were selected for hSBA development based on the prevalent variants of fHBP for the respective serogroup, fHBP expression above the fHBP-expression threshold for MnB and assay feasibility (e.g. identification of human complement and baseline seropositivity). Using sera from subjects immunized with Trumenba in hSBA using MnACYWX strains provided proof for the concept that Trumenba elicited antibodies can provide protection against serogroups other than B. Bivalent rLP2086-elicited responses (e.g. percentage of subjects with titers ≥8) after 3 doses are comparable to MCV4-elicited responses after 1 dose for strains from serogroups C, W and Y, but lower for a serogroup A strain. Moreover, bivalent rLP2086-elicited hSBA titers ≥8 in a high proportion of subjects, indicative of protection against MenX, which is not provided by MCV4.

Example 17: Trumenba Elicits Bactericidal Antibodies Against Non-Serogroup B Meningococci Introduction.

Figures 6F, 7:
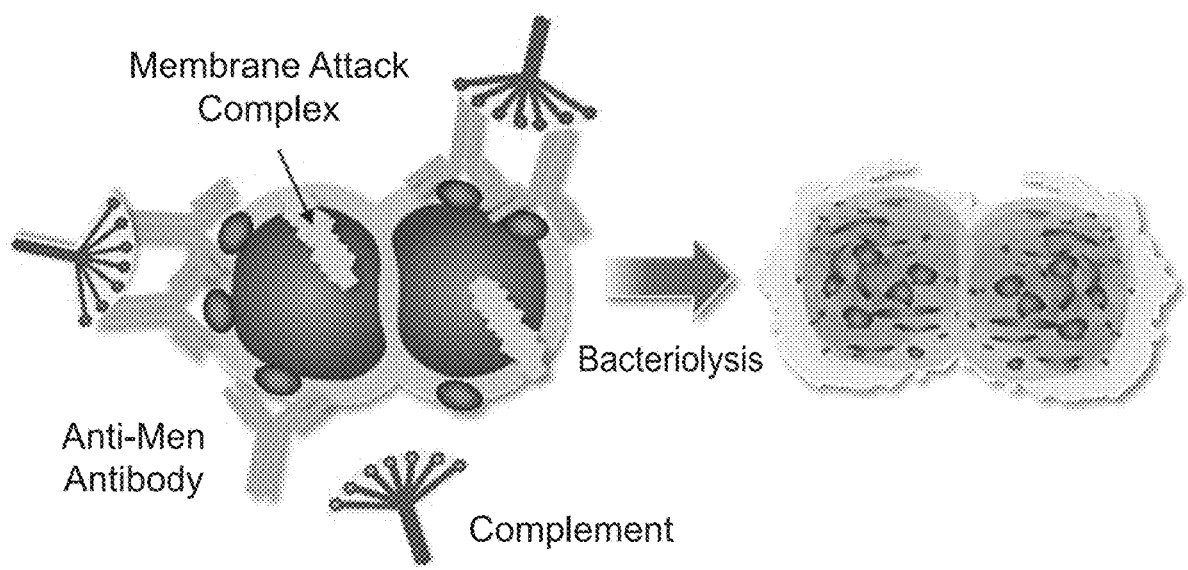

*Neisseria meningitidis* (Men) is the leading cause of bacterial meningitis and septicemia in infants, adolescents, and young adults. There are 5 major disease-causing meningococcal serogroups, A, B, C, Y, and W, with a sixth serogroup, X, emerging in Africa. Quadrivalent meningococcal conjugate vaccines (MCV4) are used to protect from disease caused by meningococcal serogroups A, C, Y, and W in various regions of the world. The recently approved vaccine TRUMENBA® (MenB-FHbp, bivalent rLP2086, Pfizer Inc, Collegeville, Pa.), intended to provide protection against serogroup B disease, consists of 2 recombinant lipoproteins, 1 from each of the 2 factor H binding protein (FHbp) phylogenetic subfamilies.2 The gene coding for FHbp is found in nearly all invasive Men strains, independent of serogroup classification. Preclinical studies have demonstrated the potential for MenB-FHbp to protect against other disease-causing serogroups. In preliminary studies, the Men B vaccine BEXSERO® (MenB-4C; Novartis Inc, Cambridge, Mass.), which includes a single FHbp variant antigen, was able to elicit a bactericidal immune response against MenX and MenW strains. The aim of this study was to extend these observations using exploratory assays to investigate whether antibodies elicited in adolescents by MenB-FHbp are bactericidal against MenA, C, W, Y, and X strains (FIG. 7), thereby providing the potential for protection against meningococcal disease across serogroups.

Experimental Overview.

Figure 8:
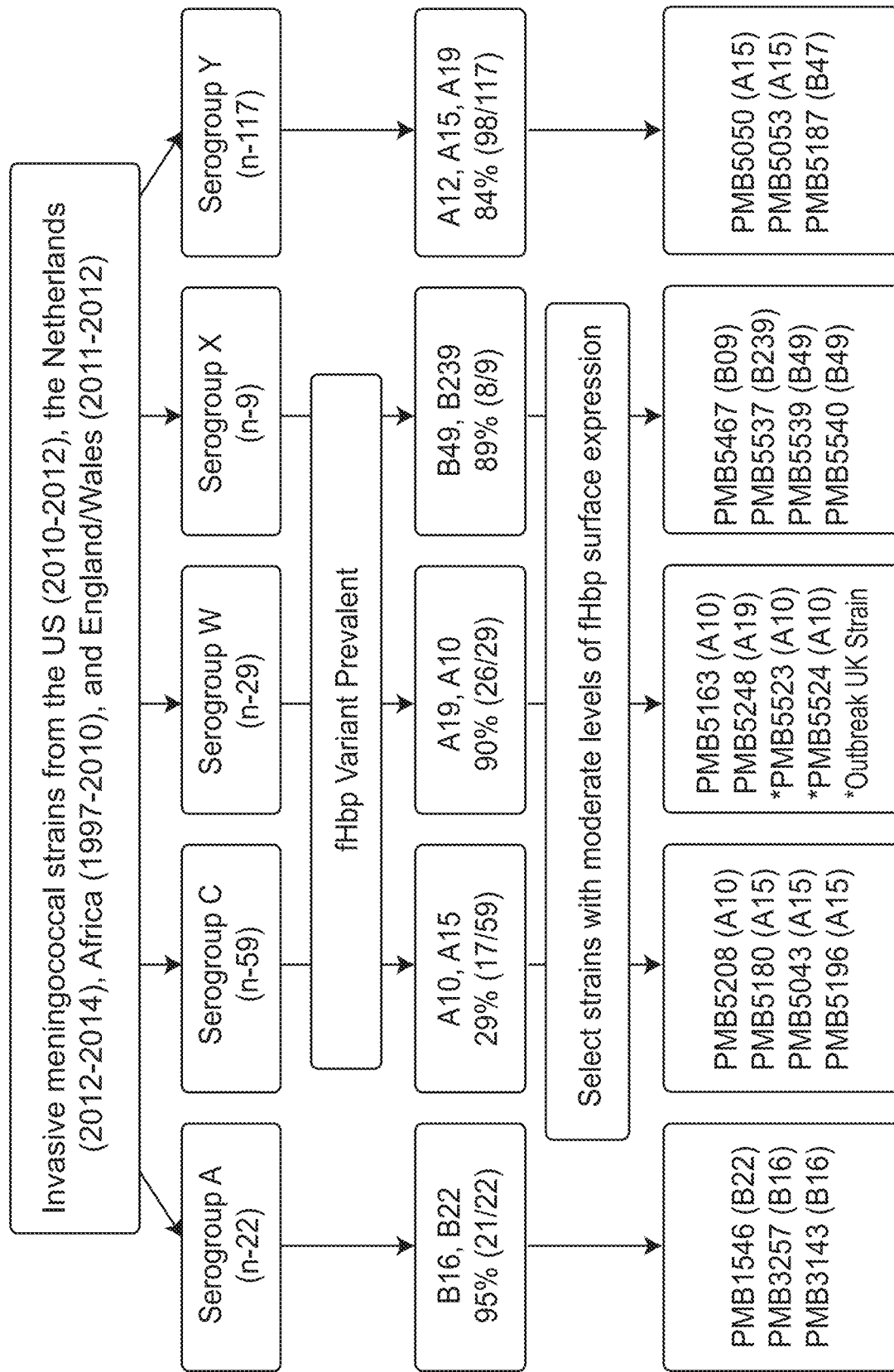

From the candidate strains (FIG. 8), select strains that

Were not susceptible to human complement killing alone

Were killed in hSBA using sera shown to have bactericidal antibodies directed against FHbp expressed by MenB strains Have low baseline titers with prevaccination sera (25 prevaccination sera; see FIG. 9) For the selected strains (Table 18, FIG. 10): Develop exploratory hSBA assays. See FIG. 9 for the sera tested in the hSBA. Response rate=percentage of subjects with hSBA titers ≥8, greater than the established correlate of protection (≥1:4) (FIG. 11-16).

TABLE 18

Characteristics of Selected MenA, MenC, MenY, MenW, and MenX Test Strains

| Strain | Serogroup | fHBP Variant | fHBP Expression (MFI) | Median of fHBP Expression (MFI) for Sergroup | Clonal Complex | Country of Isolation |
|---|---|---|---|---|---|---|
| PMB3257 | A | B16 | 1725 | 1192 | ST-1 complex/ subgroup I/II | South Africa |
| PMB5208 | C | A10 | 1563 | 1563 | ST-11 complex/ ET-37 complex | United States |
| PMB5248 | W | A19 | 2684 | 460 | ST-22 complex | United States |
| PMB5523 | W | A10 | 1796 | 460 | ST-11 complex/ ET-37 complex | England/Wales |
| PMB5187 | Y | B47 | 5063 | 290 | ST-23 complex/ cluster A3 | United States |
| PMB5540 | X | B49 | 8612 | 7555 | ST-181 complex | Burkina Faso |

With reference to FIG. 9, 25 sera from Group A month 0 were used to study preimmunity. Sera from 30 subjects from Group A drawn at month 0 and 1 and Group B drawn at month 0, 1, 3 and 7 were used for hSBA testing. Endpoint of the response rate is the percentage of sera with titers >1:8.

Figure 10:
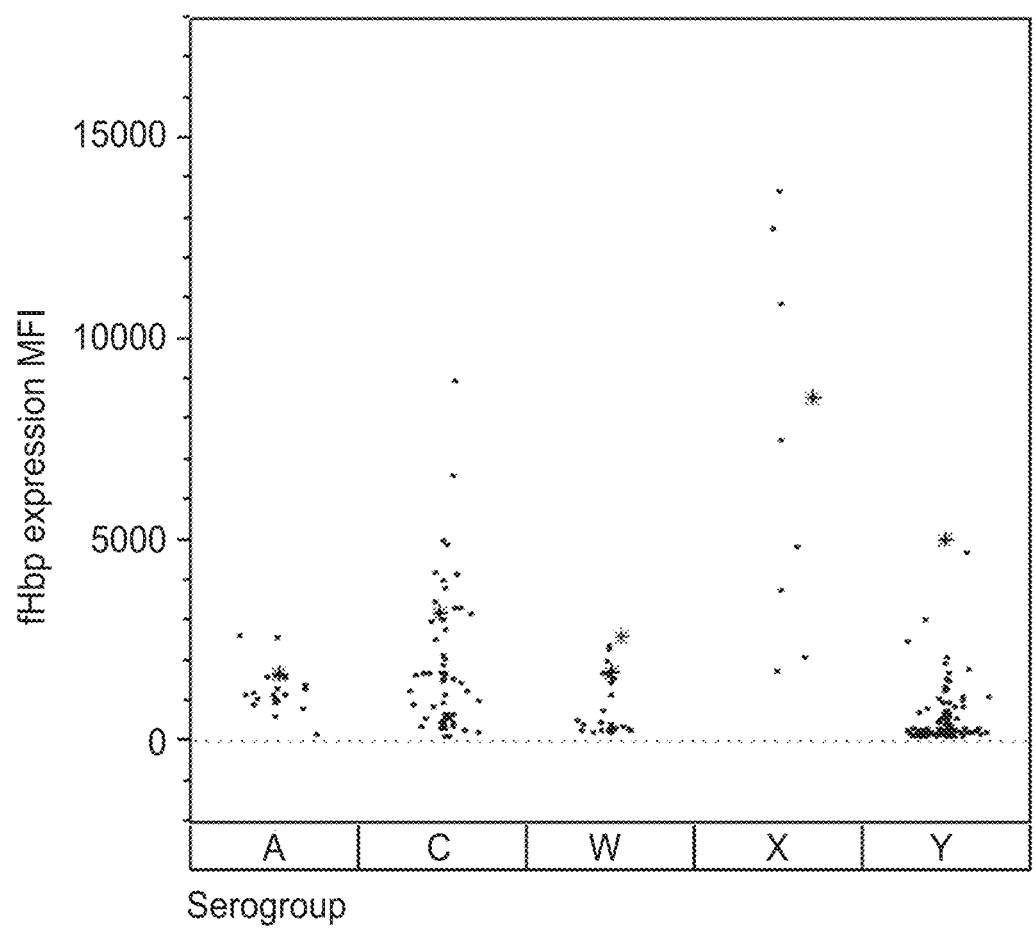

FIG. 10—Distribution of FHbp Surface Expression Levels (MFI) Determined From Flow Cytometric Experiments Using the FHbp Reactive mAb MN 994-11. The FHbp surface expression for each of the strains within a serogroup is noted with a black dot while the FHbp surface expression levels for the selected test strains within each serogroup are noted with a colored star.

Figure 11:
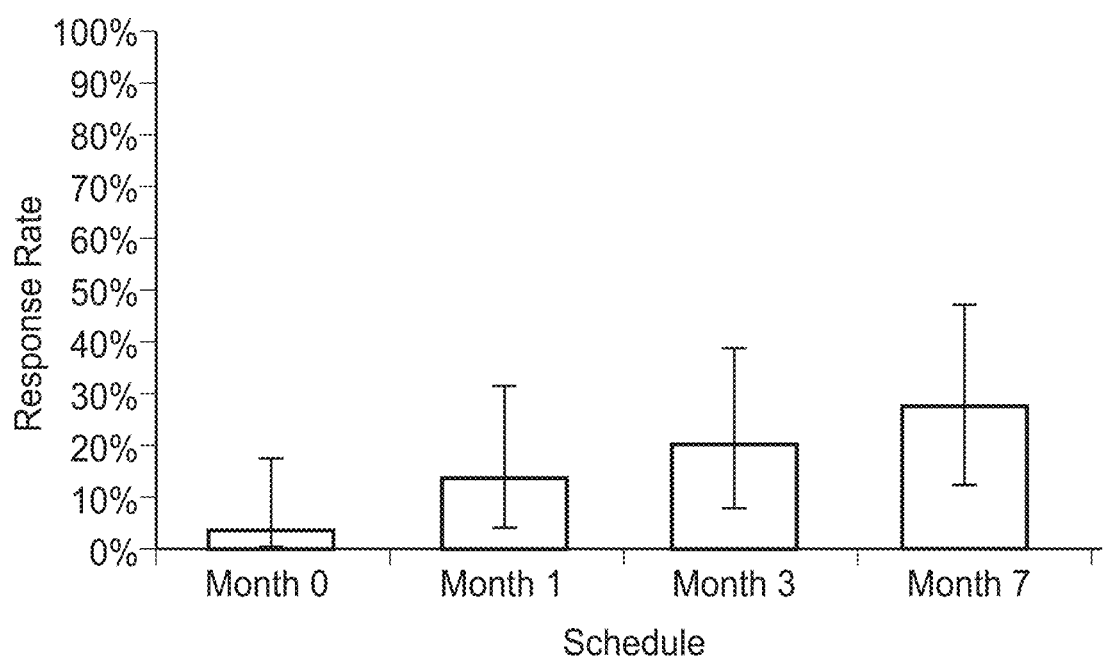

FIG. 11—hSBA Response Rate (Percentage of Subjects With hSBA Titers ≥8) for MenA PMB3257 (B16). Response rates and 95% confidence intervals for sera collected at preimmunization (month 0) and 1 month after doses 1, 2, and 3 for MenBFHbp are shown. The geometric mean titers (GMTs) obtained were 2, 3, 4, and 5, respectively. The response rates for subjects in the positive control group were 3% prior to vaccination and 97% one month after receiving MCV4. The GMTs for the positive control group were 2 and 95, respectively.

Figure 12:
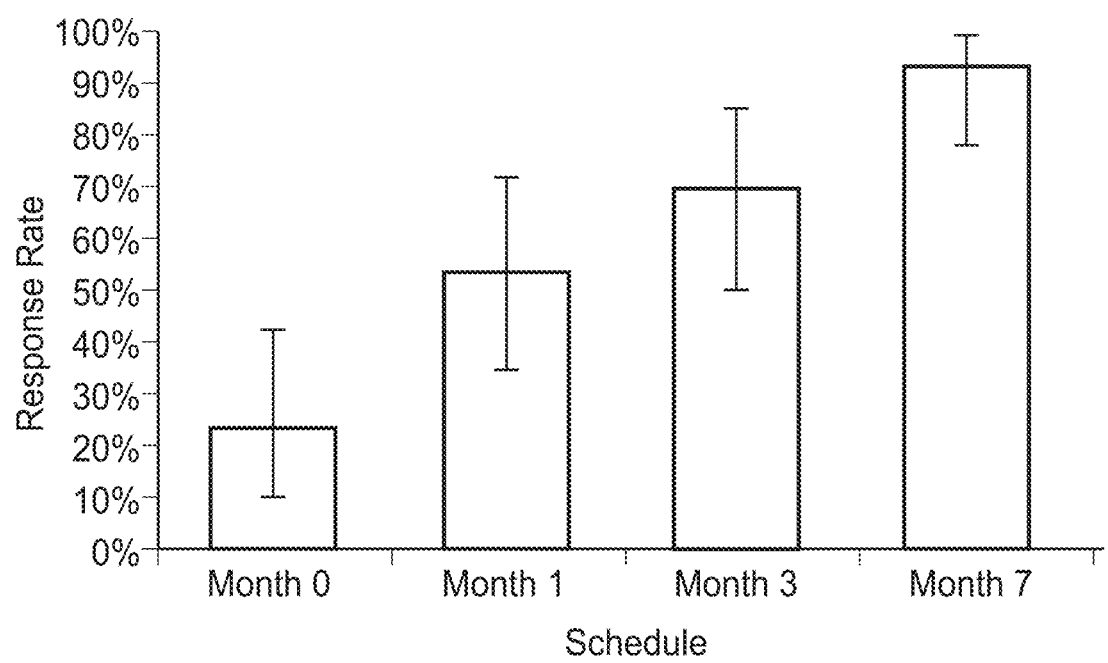

FIG. 12—hSBA Response Rate (Percentage of Subjects With hSBA Titers ≥8) for MenC PMB5208 (A10). Response rates and 95% confidence intervals for sera collected at preimmunization (month 0) and 1 month after doses 1, 2, and 3 for MenBFHbp are shown. The GMTs obtained were 4, 8, 12, and 29, respectively. The response rates for subjects in the positive control group were 20% prior to vaccination and 90% one month after receiving MCV4. The GMTs for the positive control group were 3 and 119, respectively.

Figure 13:
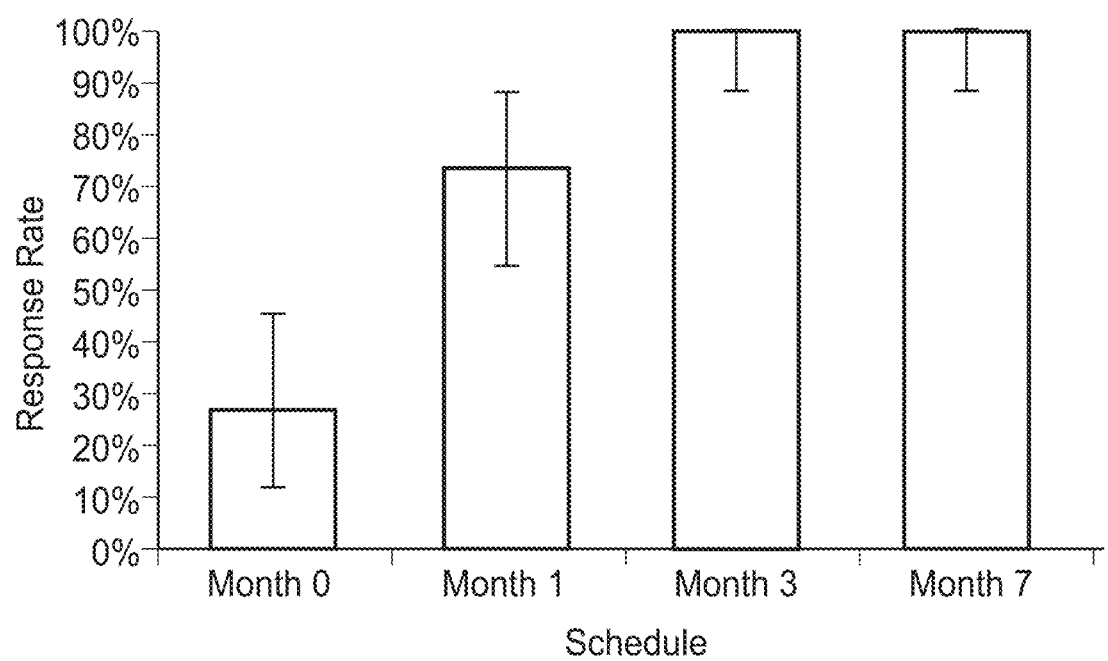

FIG. 13—hSBA Response Rate (Percentage of Subjects With hSBA Titers ≥8) for MenW PMB5248 (A19). Response rates and 95% confidence intervals for sera collected at preimmunization (month 0) and 1 month after doses 1, 2, and 3 for MenBFHbp are shown. The GMTs obtained were 4, 18, 47, and 77, respectively. The response rates for subjects in the positive control group were 40% prior to vaccination and 97% one month after receiving MCV4. The GMTs for the positive control group were 5 and 88, respectively.

Figure 14:
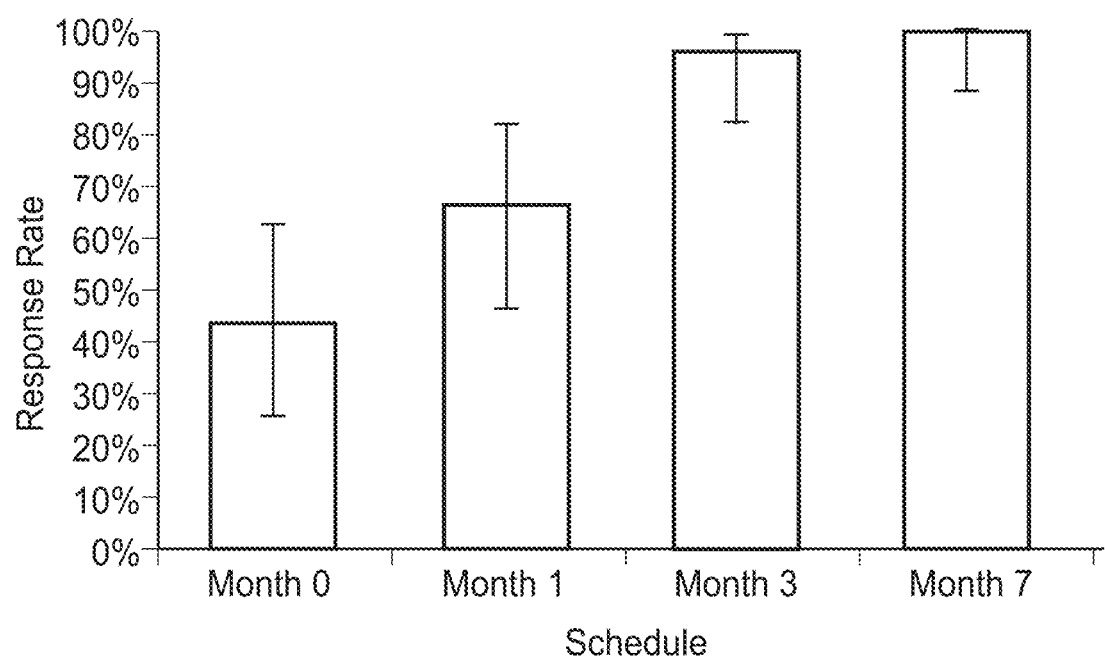

FIG. 14—hSBA Response Rate (Percentage of Subjects With hSBA Titers ≥8) for MenW PMB5523 (A10). Response rates and 95% confidence intervals for sera collected at preimmunization (month 0) and 1 month after doses 1, 2, and 3 for MenBFHbp are shown. The GMTs obtained were 7, 15, 21, and 42, respectively. The response rates for subjects in the positive control group were 55% prior to vaccination and 97% one month after receiving MCV4. The GMTs for the positive control group were 8 and 60, respectively.

Figure 15:
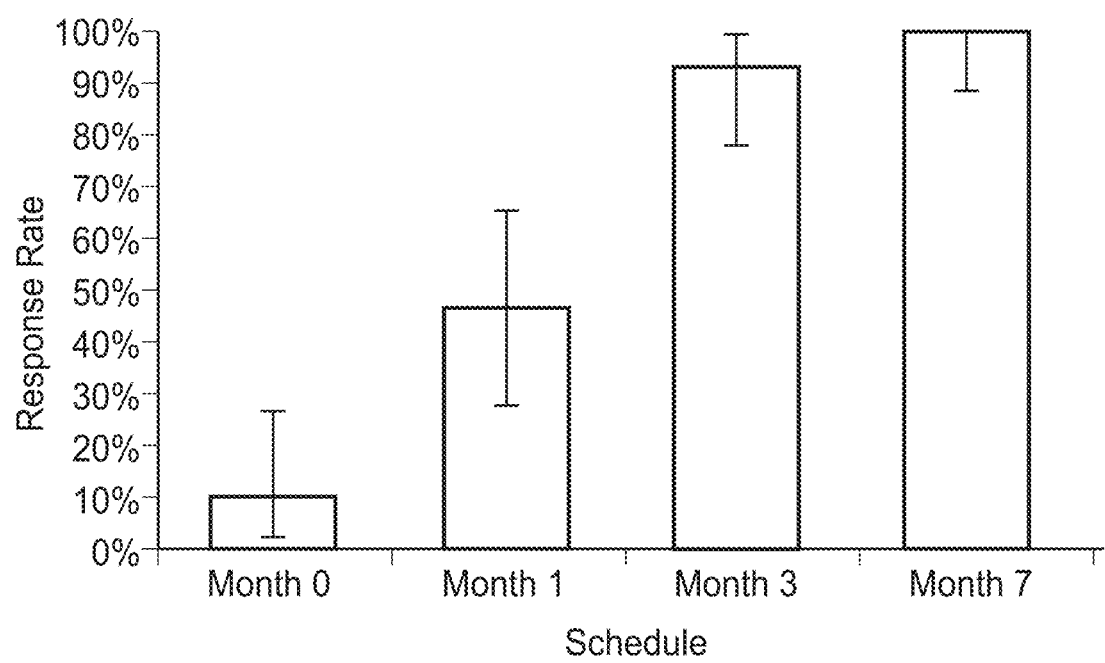

FIG. 15—hSBA Response Rate (Percentage of Subjects With hSBA Titers ≥8) for MenY PMB5187 (B47). Response rates and 95% confidence intervals for sera collected at preimmunization (month 0) and 1 month after doses 1, 2, and 3 for MenBFHbp are shown. The GMTs obtained were 3, 7, 31, and 58, respectively. The response rates for subjects in the positive control group were 13% prior to vaccination and 97% one month after receiving MCV4. The GMTs for the positive control group were 3 and 79, respectively.

Figure 16:
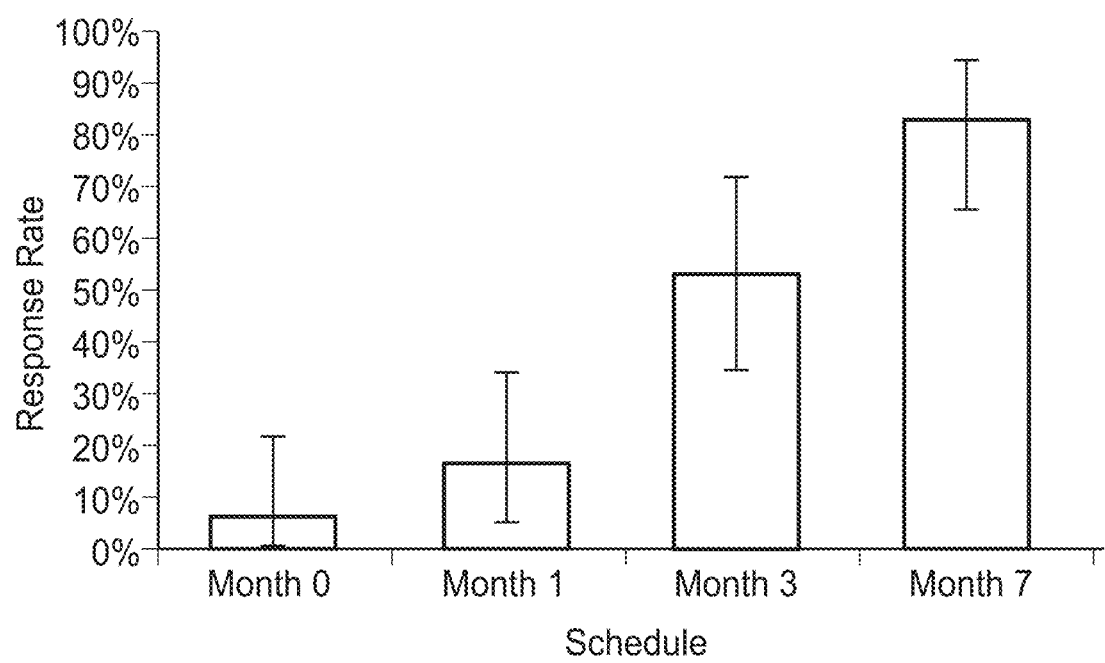

FIG. 16—hSBA Response Rate (Percentage of Subjects With hSBA Titers ≥8) for MenX PMB5540 (B49). Response rates and 95% confidence intervals for sera collected at preimmunization (month 0) and 1 month after doses 1, 2, and 3 for MenBFHbp are shown. The GMTs obtained were 2, 3, 7, and 20, respectively. The response rates for subjects in the positive control group were 0% prior to vaccination and 0% one month after receiving MCV4 vaccine. The GMTs for the positive control group were 2 and 2, respectively.

Summary.

Response rates elicited by MenB-FHbp peaked at 1 month after dose 2 (Month 3) for the MenW strain, PMB5248 (100%), and 1 month after dose 3 (Month 7) for the MenC, MenY, and MenX strains, as well as for the second MenW strain (response rates ranging from 83%-100%).

The response rates measured by hSBA for the MenA test strain were substantially lower, peaking at 28% after 3 doses of MenB-FHbp.

The recognized correlate of protection against meningococcal disease is an hSBA titer ≥4. The ability of MenB-FHbp to elicit hSBA titers of at least 1:8 provides proof of concept that MenB-FHbp may protect against disease caused by meningococcal serogroups other than B, including MenX, which is not covered by MCV4.

Example 18: A Phase 2, Randomized, Controlled, Observer-Blinded Study to Describe the Immunogenicity, Safety, and Tolerability of *Neisseria meningitidis* Serogroup B Bivalent Recombinant Lipoprotein 2086 Vaccine (Bivalent rLP2086, i.e., Now TRUMENBA® Vaccine) in Healthy Subjects Aged ≥24 Months to <10 Years (B1971017-Syn)

Study Design:

This was a Phase 2, randomized, controlled, observer-blinded, multicenter study designed to assess the immunogenicity, safety, and tolerability of bivalent rLP2086 at the 120-μg dose level administered to healthy subjects aged ≥24 months to <10 years as part of a Month 0, 2, and 6 schedule (Table 19). Approximately 400 subjects were planned to be randomly assigned to 1 of 2 groups in a 3:1 ratio. Group 1 received bivalent rLP2086 at Month 0 (Visit 1) followed by subsequent vaccinations at Months 2 and 6. Group 2 received a licensed pediatric hepatitis A virus (HAV) vaccine at Month 0 (Visit 1) and Month 6 and an injection with saline at Month 2 to maintain the study blind. Follow-up visits were conducted 1 month after each vaccination and 6 months after the third vaccination to collect safety data and/or obtain a blood sample. Subjects participated in the study for up to 13 months.

PMB2948 (B24), and PMB2707 (B44), each expressing an factor H binding protein (fHBP) variant heterologous to the vaccine component antigens, were used in the hSBAs for determination of the immunogenicity endpoints in this study. Sera obtained from all subjects prior to the first study vaccination, 1 month after the second study vaccination, and 1 and 6 months after the third study vaccination were used in these assays.

For the primary analyses, 2 of the primary test strains (PMB80 [A22] and PMB2948 [B24]) were tested at each blood sampling time point for half of the subjects (in both groups), and the other 2 primary test strains (PMB2001 [A56] and PMB2707 [B44]) were tested at each blood sampling time point for the remaining half of the subjects.

The primary immunogenicity endpoints were: Proportion of subjects aged ≥24 months to <4 years (at study entry) with hSBA titer lower limit of quantitation (LLOQ) for each of the 4 primary MnB test strains 1 month after the third vaccination with bivalent rLP2086; and Proportion of subjects aged ≥4 years to <10 years (at study entry) with hSBA titer ≥LLOQ for each of the 4 primary MnB test strains 1 month after the third vaccination with bivalent rLP2086.

TABLE 19

Study Design

| | Vaccination 1 | Post-Vaccination 1 Follow-up | Vaccination 2 | Post-Vaccination 2 Blood Draw | Vaccination 3 | Post-Vaccination 3 Blood Draw | Month 12 Follow-up and Blood Draw |
|---|---|---|---|---|---|---|---|
| Visit | 1 | 2 | 3 | 4 | 5 | 6 | 7 |
| Approximate month | 0 | 1 | 2 | 3 | 6 | 7 | 12 |
| Group 1 (300 subjects) | Bivalent rLP2086 | | Bivalent rLP2086 | | Bivalent rLP2086 | | |
| Group 2 (100 subjects) | HAV vaccine | | Saline | | HAV vaccine | | |
| Blood draw (all subjects) | 5-10 mL | | | 5-10 mL | | 5-10 mL | 5-10 mL |

HAV = hepatitis A virus

Vaccines Administered:

Subjects in Group 1 were administered bivalent rLP2086 by intramuscular injection into the upper deltoid muscle of the arm at Months 0, 2, and 6. Subjects in Group 2 were administered HAV vaccine/saline/HAV vaccine into the upper deltoid muscle of the arm at Months 0, 2, and 6, respectively.

Immunogenicity Evaluations:

To facilitate immunogenicity analysis, subjects had approximately 5 to 10 mL (dependent upon age) of blood collected immediately before Vaccination 1, 1 month after Vaccination 2, and 1 and 6 months after Vaccination 3. For assessment of the immune response to bivalent rLP2086, functional antibodies were analyzed in validated hSBAs with 4 primary MnB test strains selected using an unbiased algorithm, and adjusted for epidemiological prevalence based on regulatory input, from Pfizer's MnB serum bactericidal assay (SBA) strain pool. The hSBA measures antibodies in human sera that initiate complement-dependent destruction of the target meningococcal strain. Four (4) primary MnB test strains, PMB80 (A22), PMB2001 (A56), The secondary immunogenicity endpoints were:
In healthy subjects aged ≥24 months to <10 years at study entry:
  Proportion of subjects with hSBA titer ≥LLOQ for each of the 4 primary MnB test strains 1 month after the third vaccination with bivalent rLP2086.
In healthy subjects aged ≥24 months to <4 years at study entry, in healthy subjects aged ≥4 years to <10 years at study entry, and in the combined age stratum:
  Proportion of subjects with hSBA titer ≥LLOQ for each of the 4 primary MnB test strains 1 month after the second vaccination and 1 and 6 months after the third vaccination with bivalent rLP2086.
  Proportions of subjects achieving hSBA titers of ≥1:4, ≥1:8, ≥1:16, ≥1:32, ≥1:64, and ≥1:128 for each of the 4 primary test strains at baseline, 1 month after the second vaccination, and 1 and 6 months after the third vaccination with bivalent rLP2086.
  hSBA GMTs for each of the 4 primary test strains at baseline, 1 month after the second vaccination, and 1 and 6 months after the third vaccination with bivalent rLP2086.

The secondary immunogenicity endpoints were summarized for both the evaluable immunogenicity population and the mITT population.

The following exploratory endpoints were used to describe responses in healthy subjects aged ≥24 months to <4 years at study entry, in healthy subjects aged ≥4 years to <10 years at study entry, and in the combined age stratum:

Proportions of subjects with hSBA titers ≥1:4, ≥1:8, ≥1:16, ≥1:32, ≥1:64, and ≥1:128 at each applicable blood sampling time point.

hSBA GMTs for each of the 4 primary strains at each applicable blood sampling time point.

Proportion of subjects achieving at least a 4-fold increase in hSBA titer from baseline to 1 month after the third vaccination with bivalent rLP2086 for each of the 4 primary test strains:

For subjects with a baseline hSBA titer below the limit of detection (LOD) or an hSBA titer of <1:4, a 4-fold response was defined as an hSBA titer of ≥1:16 or the LLOQ (whichever titer was higher).

For subjects with a baseline hSBA titer of ≥LOD (ie, hSBA titer of ≥4) and <LLOQ, a 4-fold response was defined as an hSBA titer of ≥4 times the LLOQ.

For subjects with a baseline hSBA titer of ≥LLOQ, a 4-fold response was defined as an hSBA titer of ≥4 times the baseline titer.

Results
Subjects:

A total of 400 subjects aged ≥24 months to <10 years were randomized in this study. Of the subjects randomized, 294 subjects were in Group 1 (bivalent rLP2086) and 106 subjects were in Group 2 (HAV/saline). There were 200 subjects randomized in each of the ≥24-month to <4-year and ≥4-year to <10-year age strata.

Of the 400 randomized subjects, 390 (97.5%) subjects completed the vaccination phase (through 1 month after last study vaccination) of the study. A total of 387 (96.8%) subjects completed the 6-month follow-up telephone contact. Only subjects who completed the vaccination phase and the 6-month follow-up telephone contact were considered to have completed the study. Overall, a total of 375 (93.8%) subjects completed all study procedures and completion was similar in each age strata.

A total of 371 (92.8%) subjects were included in the evaluable immunogenicity population, and 29 (7.3%) subjects were excluded from the evaluable immunogenicity population. All 400 randomized subjects were included in the mITT population.

Immunogenicity Results:

The primary objectives of this study were to describe subject immune response to bivalent rLP2086 as measured by hSBA against 4 primary MnB test strains, 2 expressing an LP2086 subfamily A protein and 2 expressing an LP2086 subfamily B protein, measured 1 month after the third vaccination in healthy subjects aged ≥24 months to <4 years and ≥4 years to <10 years. The description of immune responses for the combined age stratum (≥24 months to <10 years) was a secondary objective. The endpoints for the primary objectives were the proportions of subjects in each age stratum achieving hSBA titers ≥LLOQ for each of the 4 primary MnB strains 1 month after the third vaccination.

A robust immune response was observed for children aged ≥24 months to <10 years 1 month after the third dose of bivalent rLP2086, as confirmed by the proportion of subjects achieving an hSBA titer ≥LLOQ (1:8 for A56, B24 and B44; 1:16 for A22) for each of the 4 primary MnB test strains ranging from 80.0% to 100.0% for subjects aged ≥24 months to <4 years and from 78.3% to 100.0% for subjects ≥4 years to <10 years after 3 doses. The proportion of subjects in the combined age stratum with an hSBA titer ≥LLOQ for each of the 4 primary MnB test strains 1 month after the third vaccination ranged from 79.1% to 100.0%. These findings are further supported by substantial GMTs (range 19.1 to 191) and in the proportion of subjects achieving an hSBA titer ≥1:4 (81.5% to 100%) or ≥1:16 (75.4% to 100%) against each of the 4 primary MnB test strains after 3 doses of bivalent rLP2086 compared to baseline across both age strata. Additionally, the proportion of subjects in the combined age stratum achieving an hSBA fold rise ≥4 from baseline to 1 month after the third vaccination for each of the 4 primary MnB test strains ranged from 76.9% to 93.5%.

The secondary objective of the study was to describe immune responses 1 month after the second dose of bivalent rLP2086, as assessed by ≥LLOQ responses, defined hSBA titers and hSBA GMTs for the 2 age strata and the combined age stratum. For the combined age stratum, the proportion of subjects achieving an hSBA titer ≥LLOQ ranged from 48.5% to 100.0% with no meaningful differences observed between the younger and older age strata. These findings are further supported by the combined age stratum with increases in GMTs (range 11.1 to 96.6) and in the proportion of subjects achieving an hSBA titer ≥1:4 (57.7% to 100%) or ≥1:16 (43.1% to 100%) after 2 doses of bivalent rLP2086 compared to baseline against each of the 4 primary MnB test strains. GMTs were similar between the 2 age strata. Additionally, the proportion of subjects in the combined age stratum achieving an hSBA fold rise ≥4 from baseline to 1 month after the second vaccination for each of the 4 primary MnB test strains ranged from 42.3% to 91.0%.

Immunopersistence was also assessed at 6 months after the third dose of bivalent rLP2086 with the proportion of subjects with an hSBA titer ≥LLOQ declining from 79.1% to 100% 1 month after Vaccination 3 to 10.4% to 82.4% at 6 months after the third vaccination for the combined age stratum. No differences between the 2 age strata were observed except for A22, for which older children had a higher proportion of subjects achieving a titer ≥LLOQ than the younger children (46%, 95% CI 33.4, 59.1 vs 19%, 95% CI 10.2, 30.9). However, baseline prevaccination rates of titers ≥LLOQ were greater for A22 in the older age stratum (13.6% vs 4.4%). A similar trend was also observed for the combined age stratum for the proportion of subjects with a protective hSBA titer ≥1:4, ranging from 13.3% to 84.0% and GMTs, ranging from 5.1 to 31.3 at 6 months after the third vaccination.

In summary, bivalent rLP2086 given as 3 doses on a 0-, 2-, and 6-month schedule elicits a robust immune response among toddlers and children aged ≥24 months to <10 years with protective antibody titers achieved as measured by hSBA in a high proportion of subjects after the third dose. No clinically meaningful differences were observed between toddlers aged ≥24 months to <4 years and children aged ≥4 years to <10 years. Antibody responses decline 6 months after the third dose, but remain higher than prevaccination baseline rates.

Conclusion(s):

In conclusion, bivalent rLP2086 administered to toddlers and children aged ≥24 months to <10 years in a 3-dose series on a 0-, 2-, and 6-month schedule elicits a robust immune response by the majority of subjects after the second and third doses, with protective antibody titers achieved after the third dose as measured by hSBAs. hSBA titers decreased 6 months after a 3-dose series. The vaccine, as administered in Example 19: A Phase 2, Randomized, Controlled, Observer-Blinded Study to Describe the Immunogenicity, Safety, and Tolerability of *Neisseria meningitidis* Serogroup B Bivalent Recombinant Lipoprotein 2086 Vaccine (Bivalent rLP2086, i.e., Now TRUMENBA® Vaccine) in Healthy Subjects Aged ≥24 Months to <10 Years (B1971017-CSR)

The initial formulation of bivalent rLP2086 (which did not include polysorbate-80) has been assessed in Phase 1 studies in adults, adolescents, children, and toddlers with satisfactory safety, tolerability, and immunogenicity profiles demonstrated in these populations. The initial formulation has been shown to have an acceptable safety profile up to a dose of 200 µg, and to be immunogenic as measured by hSBA. In toddlers aged 18 to 36 months, the initial formulation has been studied at dose levels of 20 µg, 60 µg, and 200 µg (Study 6108A1-502-AU). In the 6108A1-502-AU study, frequencies of local reactions in each dose group were generally higher than those in the hepatitis A virus (HAV) vaccine/placebo group, but in most cases the reactions were of mild or moderate severity. The incidence of fever tended to increase with increasing dose level. The proportions of subjects reporting any fever after any dose were 36.4% in the 20-µg group, 39.1% in the 60-µg group, and 54.5% in the 200-µg group. The frequencies of other systemic events in each vaccine group were generally comparable to those for HAV/placebo. The majority of subjects had an hSBA response for the MnB strains following the third vaccination.

Compared to the initial formulation, the drug substance manufacturing process and the drug product formulation have undergone enhancements (including the addition of polysorbate-80) designed to increase scalability for manufacture and to ensure long-term stability of the final formulation of the vaccine. Safety data from adults and adolescents participating in studies with the final formulation of bivalent rLP2086 are consistent with the safety of the initial formulation. Local reactions and systemic events were generally mild or moderate in severity in all age groups. Severe events were relatively infrequent. Furthermore, follow-up adverse event (AE) data from immunopersistence studies 6108A1-1002-AU, 6108A1-2001, and B1971033 ranging from 6 months to 48 months after the third dose of bivalent rLP2086 raised no safety concerns. Serious adverse events (SAEs) were infrequent, and mostly considered not related to the study vaccine. There were few withdrawals from the studies due to AEs.

Two (2) Phase 2 studies (B1971017 and B1971035) were conducted to explore the immunogenicity and safety of the vaccine in children (12 months to <10 years) with the final formulation of the vaccine. Study B1971035 is ongoing and designed to assess the safety, tolerability, and immunogenicity of 2 different dose levels (60-µg and 120-µg) among healthy toddlers aged 12 months to <24 months. This study (B1971017) assessed the immunogenicity, safety, and tolerability of bivalent rLP2086 at the 120-µg dose level (final formulation) administered to healthy subjects aged ≥24 months to <10 years as part of a Month 0, 2, and 6 schedule. Approximately 400 subjects were planned to be randomized to 1 of 2 groups in a 3:1 ratio. Group 1 received bivalent rLP2086 at Month 0 (Visit 1) followed by subsequent vaccinations at Months 2 and 6. Group 2 received HAV vaccine at Month 0 (Visit 1) and Month 6 and an injection with saline at Month 2. Randomization was stratified to ensure that equal numbers of subjects were included in the ≥24-month to <4-year and ≥4-year to <10-year age strata. This (B1971017) was a Phase 2, randomized, controlled, observer-blinded, multicenter study in which approximately 400 subjects were planned to be randomly assigned to 1 of 2 groups in a 3:1 ratio. Group 1 received bivalent rLP2086 at Month 0 (Visit 1) followed by subsequent vaccinations at Months 2 and 6. Group 2 received a licensed pediatric HAV vaccine at Month 0 (Visit 1) and Month 6 and an injection with saline at Month 2 to maintain the study blind. Randomization was stratified according to age to ensure that equal numbers of subjects were included in the 24-month to <4-year age stratum and the ≥4-year to <10-year age stratum. The study was planned to enroll approximately 200 subjects aged ≥24 months to <4 years and approximately 200 subjects aged ≥4 years to <10 years.

This study assessed the immunogenicity, safety, and tolerability of bivalent rLP2086 at the 120-µg dose level administered to healthy subjects aged ≥24 months to <10 years as part of a Month 0, 2, and 6 schedule. Follow-up visits were conducted 1 month after each vaccination and 6 months after the third vaccination to collect safety data and/or obtain a blood sample. Subjects participated in the study for up to 13 months. Bivalent rLP2086 (containing 60 µg each of a purified subfamily A and subfamily B rLP2086 protein, adsorbed to aluminum in a sterile buffered isotonic suspension) was provided in a 0.5-mL dose for injection.

A licensed pediatric HAV vaccine was provided in a 0.5-mL dose for injection.

For Group 1, 59.31% of subjects aged ≥24 months to <4 years and 57.05% of subjects aged ≥4 years to <10 years received concomitant treatment. For Group 2, 58.18% of subjects aged ≥24 months to <4 years and 52.94% of subjects aged ≥4 years to <10 years received concomitant treatment. The most common concomitant treatments received during the study were ibuprofen, paracetamol, and amoxicillin.

Bivalent rLP2086 Serum Bactericidal Assay—Primary Test Strains

For assessment of the immune response to bivalent rLP2086, functional antibodies were analyzed in validated hSBAs with 4 primary MnB test strains selected using an unbiased algorithm, and adjusted for epidemiological prevalence based on regulatory input, from Pfizer's MnB serum bactericidal assay (SBA) strain pool. The hSBA measures antibodies in human sera that initiate complement-dependent destruction of the target meningococcal strain. Four (4) primary MnB test strains, PMB80 (A22), PMB2001 (A56), PMB2948 (B24), and PMB2707 (B44), each expressing an fHBP variant heterologous to the vaccine component antigens, were used in the hSBAs for determination of the immunogenicity endpoints in this study. Sera obtained from all subjects prior to the first study vaccination, 1 month after the second study vaccination, and 1 and 6 months after the third study vaccination were used in these assays.

For the primary analyses, 2 of the primary test strains (PMB80 [A22] and PMB2948 [B24]) were tested at each blood sampling time point for half of the subjects (in both groups), and the other 2 test primary strains (PMB2001 [A56] and PMB2707 [B44]) were tested at each blood sampling time point for the remaining half of the subjects.

Immunogenicity Analysis

There was no hypotheses testing for immunogenicity analysis. An estimation approach was used to assess the primary, secondary, and exploratory objectives.

The proportions of subjects in each group achieving hSBA titer ≥lower limit of quantitation (LLOQ) 1 month after the second and third vaccination and 6 months after the third vaccination were computed for each test strain, along with 2-sided 95% exact confidence intervals (CIs), for each of the age strata and the combined age stratum.

Primary Immunogenicity Endpoints

The primary immunogenicity endpoints were:
Proportion of subjects aged ≥24 months to <4 years (at study entry) with hSBA titer ≥LLOQ for each of the 4 primary MnB test strains 1 month after the third vaccination with bivalent rLP2086.
Proportion of subjects aged ≥4 years to <10 years (at study entry) with hSBA titer ≥LLOQ for each of the 4 primary MnB test strains 1 month after the third vaccination with bivalent rLP2086.

Secondary Immunogenicity Endpoints

The secondary immunogenicity endpoints were:
In healthy subjects aged ≥24 months to <10 years at study entry:
Proportion of subjects with hSBA titer ≥LLOQ for each of the 4 primary MnB test strains 1 month after the third vaccination with bivalent rLP2086.
In healthy subjects aged ≥24 months to <4 years at study entry, in healthy subjects aged ≥4 years to <10 years at study entry, and in the combined age stratum:
Proportion of subjects with hSBA titer ≥LLOQ for each of the 4 primary MnB test strains 1 month after the second vaccination and 1 and 6 months after the third vaccination with bivalent rLP2086.
Proportions of subjects achieving hSBA titers of ≥1:4, ≥1:8, ≥1:16, ≥1:32, ≥1:64, and ≥1:128 for each of the 4 primary test strains at baseline, 1 month after the second vaccination, and 1 and 6 months after the third vaccination with bivalent rLP2086.
hSBA GMTs for each of the 4 primary test strains at baseline, 1 month after the second vaccination, and 1 and 6 months after the third vaccination with bivalent rLP2086.

Exploratory Immunogenicity Endpoints

For exploratory endpoints, testing was not performed on all 4 primary MnB test strains. Instead, 50% of subjects were tested using strains PMB2001 (A56) and PMB2707 (B44), but not PMB80 (A22) or PMB2948 (B24). The remaining 50% of subjects were tested using strains PMB80 (A22) or PMB2948 (B24), but not PMB2001 (A56) or PMB2707 (B44). All of the exploratory endpoints specified below may have been applied to hSBA results from all subjects who received bivalent rLP2086 and may have been tested for the appropriate strain at the indicated time point(s).

The following exploratory endpoints were used to describe responses in healthy subjects aged ≥24 months to <4 years at study entry, in healthy subjects aged ≥4 years to <10 years at study entry, and in the combined age stratum:
Proportions of subjects with hSBA titers ≥1:4, ≥1:8, ≥1:16, ≥1:32, ≥1:64, and ≥1:128 at each applicable blood sampling time point.
hSBA GMTs for each of the 4 primary strains at each applicable blood sampling time point.
Proportion of subjects achieving at least a 4-fold increase in hSBA titer from baseline to 1 month after the third vaccination with bivalent rLP2086 for each of the 4 primary test strains:
For subjects with a baseline hSBA titer below the limit of detection (LOD) or an hSBA titer of <1:4, a 4-fold response was defined as an hSBA titer of ≥1:16 or the LLOQ (whichever titer was higher).
For subjects with a baseline hSBA titer of LOD (ie, hSBA titer of ≥4) and <LLOQ, a 4-fold response was defined as an hSBA titer of ≥4 times the LLOQ.
For subjects with a baseline hSBA titer of ≥LLOQ, a 4-fold response was defined as an hSBA titer of ≥4 times the baseline titer.

Methods of Analysis

The primary analysis for immunogenicity included an estimate for the proportion of subjects in each group achieving an hSBA titer ≥LLOQ 1 month after the third vaccination for each test strain, along with 2-sided 95% exact confidence CIs, for each of the age strata and in the combined age stratum.

All of the binary endpoints (including primary endpoints) were summarized with 2-sided 95% CIs using the exact method. GMTs on hSBA results were also summarized with 95% CIs.

The LLOQ was 1:16 for PMB80 (A22), 1:8 for PMB2001 (A56), 1:8 for PMB2707 (B44), and 1:8 for PMB2948 (B24).

For the calculation of GMTs, hSBA results below the LLOQ were set as 0.5×LLOQ for the primary analysis.

Analysis of Primary Endpoints

The primary analysis for the primary objectives was based on the evaluable immunogenicity population. The proportion of subjects in each group achieving hSBA titer ≥LLOQ 1 month after the third vaccination was computed for each test strain with 2-sided 95% exact CIs. To address the 2 primary objectives, these data are presented for the 2 age strata: ≥24 months to <4 years and ≥4 years to <10 years.

All of the binary endpoints (including primary endpoints) were summarized with 2-sided 95% CIs using the exact method. GMTs on hSBA results were also summarized with 95% CIs.

To support the interpretation of the primary analyses, an identical analysis based on the mITT population was conducted.

Analysis of Secondary and Exploratory Endpoints

The following analyses addressed the secondary and exploratory immunogenicity objectives:
The proportions of subjects achieving hSBA titers ≥LLOQ for each of the 4 primary strains at 1 month after the second vaccination and 6 months after the third vaccination were analyzed in the 2 age strata separately and combined, in the evaluable immunogenicity and the mITT populations.
The proportions of subjects achieving hSBA titers of ≥1:4, ≥1:8, ≥1:16, ≥1:32, ≥1:64, and ≥1:128 for each of the 4 primary test strains at baseline, 1 month after the second vaccination, and 1 and 6 months after the third vaccination were analyzed in the 2 age strata separately and combined, in the evaluable immunogenicity and the mITT populations.
The hSBA GMTs for each of the 4 primary test strains at baseline, 1 month after the second vaccination, and 1 and 6 months after the third vaccination were analyzed in the 2 age strata separately and combined, in the evaluable immunogenicity and the mITT populations.

The exploratory endpoints were summarized, in the 2 age strata separately and combined, for each applicable time point for both the evaluable immunogenicity population and the mITT population.

Reverse Cumulative Distribution Curves

The empirical reverse cumulative distribution curves (RCDCs) were assessed graphically for each of the 4 primary strains and at each sampling time point, for the evaluable immunogenicity population.

Immunogenicity Evaluation

Populations Analyzed

The evaluable immunogenicity population was the primary analysis population for the immunogenicity analyses. The mITT population was used as a supportive immunogenicity population for the immunogenicity analyses.

A total of 371 (92.8%) subjects were included in the evaluable immunogenicity population, and 29 (7.3%) subjects were excluded from the evaluable immunogenicity population. Subjects could have been excluded from the immunogenicity populations for more than 1 reason. A total of 21 (5.3%) subjects were excluded from the evaluable immunogenicity population because they did not have baseline blood drawn prior to the first dose of vaccine or after Vaccination 3, 15 (3.8%) subjects did not have a valid and determinate assay result at any visit, 11 (2.8%) subjects were not eligible or became ineligible for the study before or at the 1-month post-Vaccination 3 visit, 11 (2.8%) subjects did not receive vaccine as randomized at all vaccination visits, and 4 (1.0%) subjects had an important protocol deviation as identified by the medical monitor. Overall, the 2 study groups and 2 age strata were comparable with respect to the percentages of subjects who were excluded from the evaluable immunogenicity population.

All 400 randomized subjects were included in the mITT population.

Immunogenicity Results

The results of the analyses for the primary immunogenicity endpoints, secondary immunogenicity endpoints, and exploratory immunogenicity endpoints are provided in the following sections.

Primary and Secondary Endpoints

Proportion of Subjects Achieving an hSBA Titer ≥LLOQ

The primary immunogenicity endpoints were the proportion of subjects aged ≥24 months to <4 years (at study entry), and aged ≥4 years to <10 years (at study entry), with an hSBA titer ≥LLOQ for each of the 4 primary MnB test strains 1 month after the third vaccination with bivalent rLP2086. The proportion of all subjects in the combined age stratum (at study entry) with an hSBA titer ≥LLOQ for each of the 4 primary MnB test strains 1 month after the third vaccination with bivalent rLP2086, along with the proportion of subjects in the individual and combined age strata with an hSBA titer ≥LLOQ for each of the 4 primary MnB test strains 1 month after the second vaccination with bivalent rLP2086, were secondary endpoints.

The proportion of subjects in each age stratum with an hSBA titer ≥LLOQ for each of the 4 primary MnB test strains is presented in Table 20 for the evaluable immunogenicity population.

The proportion of subjects aged ≥24 months to <4 years and ≥4 years to <10 years in Group 1 with an hSBA titer ≥LLOQ at baseline was 4.4% and 13.6%, respectively, for PMB80 (A22); 1.5% and 15.4%, respectively, for PMB2001 (A56); 3.0% and 7.5%, respectively, for PMB2948 (B24); and 0.0%, for both age strata for PMB2707 (B44). Overall, the proportion of subjects in the combined age stratum with an hSBA titer ≥LLOQ at baseline was 9.0% for PMB80 (A22), 8.3% for PMB2001 (A56), 5.2% for PMB2948 (B24), and 0.0% for PMB2707 (B44) in Group 1.

The proportion of subjects aged ≥24 months to <4 years and ≥4 years to <10 years in Group 1 with an hSBA titer ≥LLOQ at 1 month after the second vaccination was 59.4% and 78.8%, respectively, for PMB80 (A22); 100.0% for both age strata for PMB2001 (A56); 49.2% and 65.1%, respectively, for PMB2948 (B24); and 57.1% and 40.3%, respectively, for PMB2707 (B44).

Overall, the proportion of subjects in the combined age stratum with an hSBA titer ≥LLOQ at 1 month after the second vaccination was 69.2% for PMB80 (A22), 100.0% for PMB2001 (A56), 57.0% for PMB2948 (B24), and 48.5% for PMB2707 (B44) in Group 1.

The proportion of subjects aged ≥24 months to <4 years and ≥4 years to <10 years in Group 1 with an hSBA titer ≥LLOQ at 1 month after the third vaccination was 83.8% and 91.0%, respectively, for PMB80 (A22); 100.0% for both age strata for PMB2001 (A56); 85.7% and 92.1%, respectively, for PMB2948 (B24); and 80.0% and 78.3%, respectively, for PMB2707 (B44).

Overall, the proportion of subjects in the combined age stratum with an hSBA titer ≥LLOQ at 1 month after the third vaccination was 87.4% for PMB80 (A22), 100.0% for PMB2001 (A56), 88.9% for PMB2948 (B24), and 79.1% for PMB2707 (B44) in Group 1. In general, the proportion of Group 2 subjects with an hSBA titer ≥LLOQ did not change over time compared to baseline. The proportion of subjects in the combined age stratum with an hSBA titer ≥LLOQ at any time point ranged from 4.4% to 8.5% for PMB80 (A22); 14.9% to 20.9% for PMB2001 (A56); 0.0% to 8.9% for PMB2948 (B24); and 0.0% at each time point for PMB2707 (B44).

Results for the mITT population were similar to those of the evaluable immunogenicity population.

Subgroup analyses of the proportion of subjects with an hSBA titer ≥LLOQ for each of the 4 primary MnB test strains are presented for the evaluable immunogenicity population by sex, race, and country. There were no clinically important differences observed in the subgroup analyses performed.

Immunopersistence: Proportion of Subjects Achieving hSBA Titer ≥LLOQ

6 Months after Third Vaccination

The proportion of subjects aged ≥24 months to <4 years, ≥4 years to <10 years, and in the combined age stratum (≥24 months to <10 years), with an hSBA titer ≥LLOQ for each of the 4 primary MnB test strains 6 months after the third vaccination with bivalent rLP2086 was a secondary immunogenicity endpoint. The proportion of subjects with an hSBA titer ≥LLOQ for each of the 4 primary MnB test strains in each age stratum is presented in Table 20 for the evaluable immunogenicity population.

In general, there was a decline in the proportion of subjects with an hSBA titer ≥LLOQ for each of the 4 primary MnB test strains observed among Group 1 subjects in both age strata at 6 months after the third vaccination.

For subjects aged ≥24 months to <4 years, from 1 month after the third vaccination to 6 months after the third vaccination, the proportion of subjects with an hSBA titer ≥LLOQ decreased from 83.8% to 19.0%, respectively, for PMB80 (A22); 100.0% to 80.3%, respectively, for PMB2001 (A56); 85.7% to 9.2%, respectively for PMB2948 (B24); and 80.0% to 12.1%, respectively, for PMB2707 (B44).

For subjects aged ≥4 years to <10 years, from 1 month after the third vaccination to 6 months after the third vaccination, the proportion of subjects with an hSBA titer ≥LLOQ decreased from 91.0% to 46.0%, respectively, for PMB80 (A22); 100.0% to 84.3%, respectively, for PMB2001 (A56); 92.1% to 21.9%, respectively for PMB2948 (B24); and 78.3% to 8.7%, respectively, for PMB2707 (B44).

Overall for the combined age stratum, from 1 month after the third vaccination to 6 months after the third vaccination, the proportion of subjects with an hSBA titer ≥LLOQ decreased from 87.4% to 32.5% for PMB80 (A22); 100.0% to 82.4% for PMB2001 (A56); 88.9% to 15.5% for PMB2948 (B24); and 79.1% to 10.4% for PMB2707 (B44).

In general, the proportion of Group 2 subjects with an hSBA titer ≥LLOQ did not change over time compared to baseline.

TABLE 20

Subjects With hSBA Titer ≥ LLOQ for Primary Strains - Evaluable Immunogenicity Population

| Strain (Variant) Sampling Time Point Age Strata | Vaccine Group (as Randomized) | | | | | | | |
|---|---|---|---|---|---|---|---|---|
| | Group 1 rLP2086 | | | | Group 2 HAV/Saline | | | |
| | $N^a$ | $n^b$ | (%) | (95% CI)$^c$ | $N^a$ | $n^b$ | (%) | (95% CI)$^c$ |
| PMB80 (A22) Before Vaccination 1 | | | | | | | | |
| ≥24 Months to <10 years | 134 | 12 | (9.0) | (4.7, 15.1) | 47 | 3 | (6.4) | (1.3, 17.5) |
| ≥24 Months to <4 years | 68 | 3 | (4.4) | (0.9, 12.4) | 26 | 1 | (3.8) | (0.1, 19.6) |
| ≥4 Years to <10 years | 66 | 9 | (13.6) | (6.4, 24.3) | 21 | 2 | (9.5) | (1.2, 30.4) |
| 1 Month after Vaccination 2 | | | | | | | | |
| ≥24 Months to <10 years | 130 | 90 | (69.2) | (60.5, 77.0) | 45 | 2 | (4.4) | (0.5, 15.1) |
| ≥24 Months to <4 years | 64 | 38 | (59.4) | (46.4, 71.5) | 24 | 0 | (0.0) | (0.0, 14.2) |
| ≥4 Years to <10 years | 66 | 52 | (78.8) | (67.0, 87.9) | 21 | 2 | (9.5) | (1.2, 30.4) |
| 1 Month after Vaccination 3 | | | | | | | | |
| ≥24 Months to <10 years | 135 | 118 | (87.4) | (80.6, 92.5) | 45 | 3 | (6.7) | (1.4, 18.3) |
| ≥24 Months to <4 years | 68 | 57 | (83.8) | (72.9, 91.6) | 25 | 1 | (4.0) | (0.1, 20.4) |
| ≥4 Years to <10 years | 67 | 61 | (91.0) | (81.5, 96.6) | 20 | 2 | (10.0) | (1.2, 31.7) |
| 6 Months after Vaccination 3 | | | | | | | | |
| ≥24 Months to <10 years | 126 | 41 | (32.5) | (24.5, 41.5) | 47 | 4 | (8.5) | (2.4, 20.4) |
| ≥24 Months to <4 years | 63 | 12 | (19.0) | (10.2, 30.9) | 26 | 2 | (7.7) | (0.9, 25.1) |
| ≥4 Years to <10 years | 63 | 29 | (46.0) | (33.4, 59.1) | 21 | 2 | (9.5) | (1.2, 30.4) |
| PMB2001 (A56) Before Vaccination 1 | | | | | | | | |
| ≥24 Months to <10 years | 132 | 11 | (8.3) | (4.2, 14.4) | 47 | 7 | (14.9) | (6.2, 28.3) |
| ≥24 Months to <4 years | 67 | 1 | (1.5) | (0.0, 8.0) | 24 | 2 | (8.3) | (1.0, 27.0) |
| ≥4 Years to <10 years | 65 | 10 | (15.4) | (7.6, 26.5) | 23 | 5 | (21.7) | (7.5, 43.7) |
| 1 Month after Vaccination 2 | | | | | | | | |
| ≥24 Months to <10 years | 133 | 133 | (100.0) | (97.3, 100.0) | 43 | 7 | (16.3) | (6.8, 30.7) |
| ≥24 Months to <4 years | 66 | 66 | (100.0) | (94.6, 100.0) | 21 | 2 | (9.5) | (1.2, 30.4) |
| ≥4 Years to <10 years | 67 | 67 | (100.0) | (94.6, 100.0) | 22 | 5 | (22.7) | (7.8, 45.4) |
| 1 Month after Vaccination 3 | | | | | | | | |
| ≥24 Months to <10 years | 139 | 139 | (100.0) | (97.4, 100.0) | 43 | 9 | (20.9) | (10.0, 36.0) |
| ≥24 Months to <4 years | 68 | 68 | (100.0) | (94.7, 100.0) | 24 | 1 | (4.2) | (0.1, 21.1) |
| ≥4 Years to <10 years | 71 | 71 | (100.0) | (94.9, 100.0) | 19 | 8 | (42.1) | (20.3, 66.5) |
| 6 Months after Vaccination 3 | | | | | | | | |
| ≥24 Months to <10 years | 131 | 108 | (82.4) | (74.8, 88.5) | 46 | 9 | (19.6) | (9.4, 33.9) |
| ≥24 Months to <4 years | 61 | 49 | (80.3) | (68.2, 89.4) | 24 | 4 | (16.7) | (4.7, 37.4) |
| ≥4 Years to <10 years | 70 | 59 | (84.3) | (73.6, 91.9) | 22 | 5 | (22.7) | (7.8, 45.4) |
| PMB2948 (B24) Before Vaccination 1 | | | | | | | | |
| ≥24 Months to <10 years | 134 | 7 | (5.2) | (2.1, 10.5) | 47 | 2 | (4.3) | (0.5, 14.5) |
| ≥24 Months to <4 years | 67 | 2 | (3.0) | (0.4, 10.4) | 26 | 1 | (3.8) | (0.1, 19.6) |
| ≥4 Years to <10 years | 67 | 5 | (7.5) | (2.5, 16.6) | 21 | 1 | (4.8) | (0.1, 23.8) |
| 1 Month after Vaccination 2 | | | | | | | | |
| ≥24 Months to <10 years | 128 | 73 | (57.0) | (48.0, 65.7) | 45 | 4 | (8.9) | (2.5, 21.2) |
| ≥24 Months to <4 years | 65 | 32 | (49.2) | (36.6, 61.9) | 24 | 2 | (8.3) | (1.0, 27.0) |
| ≥4 Years to <10 years | 63 | 41 | (65.1) | (52.0, 76.7) | 21 | 2 | (9.5) | (1.2, 30.4) |
| 1 Month after Vaccination 3 | | | | | | | | |
| ≥24 Months to <10 years | 126 | 112 | (88.9) | (82.1, 93.8) | 46 | 2 | (4.3) | (0.5, 14.8) |
| ≥24 Months to <4 years | 63 | 54 | (85.7) | (74.6, 93.3) | 26 | 2 | (7.7) | (0.9, 25.1) |
| ≥4 Years to <10 years | 63 | 58 | (92.1) | (82.4, 97.4) | 20 | 0 | (0.0) | (0.0, 16.8) |
| 6 Months after Vaccination 3 | | | | | | | | |
| ≥24 Months to <10 years | 129 | 20 | (15.5) | (9.7, 22.9) | 47 | 0 | (0.0) | (0.0, 7.5) |
| ≥24 Months to <4 years | 65 | 6 | (9.2) | (3.5, 19.0) | 26 | 0 | (0.0) | (0.0, 13.2) |
| ≥4 Years to <10 years | 64 | 14 | (21.9) | (12.5, 34.0) | 21 | 0 | (0.0) | (0.0, 16.1) |

TABLE 20-continued

Subjects With hSBA Titer ≥ LLOQ for Primary Strains - Evaluable Immunogenicity Population

| Strain (Variant) Sampling Time Point Age Strata | Vaccine Group (as Randomized) | | | | | | | |
|---|---|---|---|---|---|---|---|---|
| | Group 1 rLP2086 | | | | Group 2 HAV/Saline | | | |
| | N[a] | n[b] | (%) | (95% CI)[c] | N[a] | n[b] | (%) | (95% CI)[c] |
| PMB2707 (B44) Before Vaccination 1 | | | | | | | | |
| ≥24 Months to <10 years | 138 | 0 | (0.0) | (0.0, 2.6) | 50 | 0 | (0.0) | (0.0, 7.1) |
| ≥24 Months to <4 years | 67 | 0 | (0.0) | (0.0, 5.4) | 26 | 0 | (0.0) | (0.0, 13.2) |
| ≥4 Years to <10 years | 71 | 0 | (0.0) | (0.0, 5.1) | 24 | 0 | (0.0) | (0.0, 14.2) |
| 1 Month after Vaccination 2 | | | | | | | | |
| ≥24 Months to <10 years | 130 | 63 | (48.5) | (39.6, 57.4) | 50 | 0 | (0.0) | (0.0, 7.1) |
| ≥24 Months to <4 years | 63 | 36 | (57.1) | (44.0, 69.5) | 26 | 0 | (0.0) | (0.0, 13.2) |
| ≥4 Years to <10 years | 67 | 27 | (40.3) | (28.5, 53.0) | 24 | 0 | (0.0) | (0.0, 14.2) |
| 1 Month after Vaccination 3 | | | | | | | | |
| ≥24 Months to <10 years | 134 | 106 | (79.1) | (71.2, 85.6) | 50 | 0 | (0.0) | (0.0, 7.1) |
| ≥24 Months to <4 years | 65 | 52 | (80.0) | (68.2, 88.9) | 26 | 0 | (0.0) | (0.0, 13.2) |
| ≥4 Years to <10 years | 69 | 54 | (78.3) | (66.7, 87.3) | 24 | 0 | (0.0) | (0.0, 14.2) |
| 6 Months after Vaccination 3 | | | | | | | | |
| ≥24 Months to <10 years | 135 | 14 | (10.4) | (5.8, 16.8) | 49 | 0 | (0.0) | (0.0, 7.3) |
| ≥24 Months to <4 years | 66 | 8 | (12.1) | (5.4, 22.5) | 26 | 0 | (0.0) | (0.0, 13.2) |
| ≥4 Years to <10 years | 69 | 6 | (8.7) | (3.3, 18.0) | 23 | 0 | (0.0) | (0.0, 14.8) |

Abbreviation: hSBA = serum bactericidal assay using human complement; LLOQ = lower limit of quantitation.
Note:
LLOQ = 1:16 for A22; 1:8 for A56, B24, and B44.
[a]N = number of subjects with valid and determinate hSBA titers for the given strain.
[b]n = Number of subjects with observed hSBA titer ≥ LLOQ for the given strain at the given time point.
[c]Exact 2-sided CI based upon observed proportion of subjects, using the Clopper and Pearson method.
Program ID: Study B1971017/CP IMM_LLOQ.SAS. Date of Reporting Dataset Creation: 1 JUN. 2017. Runtime ID: 16 JUN. 2017 11:22. File ID: T_2_2_IMM_LLOQ_EVL.HTM.

hSBA GMTs.

The hSBA GMTs for each of the 4 primary test strains at baseline, 1 month after the second vaccination, and 1 month after the third vaccination with bivalent rLP2086 was a secondary endpoint. Table 21 provides hSBA GMTs for the 4 primary MnB strains for the evaluable immunogenicity population.

For Group 1 subjects aged ≥24 months to <4 years and aged ≥4 years to <10 years, hSBA GMTs at baseline were 8.3 and 9.1, respectively, for PMB80 (A22); 4.1 and 5.8, respectively, for PMB2001 (A56); 4.3 and 4.6, respectively, for PMB2948 (B24); and 4.0 in both age strata for PMB2707 (B44).

For Group 1 subjects aged ≥24 months to <10 years, hSBA GMTs at baseline were 8.7 for PMB80 (A22), 4.9 for PMB2001 (A56), 4.5 for PMB2948 (B24), and 4.0 for PMB2707 (B44).

For Group 1 subjects aged ≥24 months to <4 years and aged ≥4 years to <10 years, hSBA GMTs at 1 month after Vaccination 2 were 17.4 and 23.1, respectively, for PMB80 (A22); 103.8 and 90.0, respectively, for PMB2001 (A56); 9.1 and 13.7, respectively, for PMB2948 (B24); and 17.1 and 8.2, respectively, for PMB2707 (B44).

For Group 1 subjects aged ≥24 months to <10 years, hSBA GMTs at 1 month after Vaccination 2 were 20.1 for PMB80 (A22), 96.6 for PMB2001 (A56); 11.1 for PMB2948 (B24), and 11.7 for PMB2707 (B44).

For Group 1 subjects aged ≥24 months to <4 years and aged ≥4 years to <10 years, hSBA GMTs at 1 month after Vaccination 3 were 33.7 and 38.2, respectively, for PMB80 (A22); 175.6 and 191.0, respectively, for PMB2001 (A56); 19.1 and 26.8, respectively, for PMB2948 (B24); and 43.6 and 36.5, respectively, for PMB2707 (B44).

For Group 1 subjects aged ≥24 months to <10 years, hSBA GMTs at 1 month after Vaccination 3 were 35.8 for PMB80 (A22), 183.3 for PMB2001 (A56); 22.6 for PMB2948 (B24), and 39.8 for PMB2707 (B44).

In general, the hSBA GMTs for subjects in Group 2 did not change over time compared to baseline. For the combined age stratum, hSBA GMTs at any time point ranged from 8.6 to 8.9 for PMB80 (A22); 5.6 to 6.0 for PMB2001 (A56); 4.0 to 4.8 for PMB2948 (B24); and 4.0 at each time point for PMB2707 (B44).

TABLE 21 hSBA GMTs for Primary Strains - Evaluable Immunogenicity Population

| Strain (Variant) Sampling Time Point Age Strata | Vaccine Group (as Randomized) | | | | | |
|---|---|---|---|---|---|---|
| | Group 1 rLP2086 | | | Group 2 HAV/Saline | | |
| | $N^a$ | $GMT^b$ | (95% CI)$^c$ | $N^a$ | $GMT^b$ | (95% CI)$^c$ |
| PMB80 (A22) | | | | | | |
| Before Vaccination 1 | | | | | | |
| ≥24 Months to <10 years | 134 | 8.7 | (8.3, 9.1) | 47 | 8.9 | (7.8, 10.1) |
| ≥24 Months to <4 years | 68 | 8.3 | (7.9, 8.8) | 26 | 8.2 | (7.8, 8.7) |
| ≥4 Years to <10 years | 66 | 9.1 | (8.3, 9.9) | 21 | 9.8 | (7.2, 13.2) |
| 1 Month after Vaccination 2 | | | | | | |
| ≥24 Months to <10 years | 130 | 20.1 | (17.4, 23.2) | 45 | 8.6 | (7.7, 9.7) |
| ≥24 Months to <4 years | 64 | 17.4 | (14.2, 21.4) | 24 | 8.0 | (NE, NE) |
| ≥4 Years to <10 years | 66 | 23.1 | (18.9, 28.3) | 21 | 9.4 | (7.4, 12.0) |
| 1 Month after Vaccination 3 | | | | | | |
| ≥24 Months to <10 years | 135 | 35.8 | (30.5, 42.2) | 45 | 8.8 | (7.8, 9.8) |
| ≥24 Months to <4 years | 68 | 33.7 | (26.4, 42.9) | 25 | 8.7 | (7.3, 10.3) |
| ≥4 Years to <10 years | 67 | 38.2 | (30.6, 47.6) | 20 | 8.9 | (7.6, 10.4) |
| 6 Months after Vaccination 3 | | | | | | |
| ≥24 Months to <10 years | 126 | 12.4 | (10.9, 14.2) | 47 | 8.7 | (7.9, 9.7) |
| ≥24 Months to <4 years | 63 | 10.9 | (9.0, 13.1) | 26 | 8.4 | (7.8, 9.1) |
| ≥4 Years to <10 years | 63 | 14.2 | (11.8, 17.0) | 21 | 9.1 | (7.4, 11.3) |
| PMB2001 (A56) | | | | | | |
| Before Vaccination 1 | | | | | | |
| ≥24 Months to <10 years | 132 | 4.9 | (4.3, 5.5) | 47 | 5.6 | (4.4, 7.2) |
| ≥24 Months to <4 years | 67 | 4.1 | (3.9, 4.3) | 24 | 4.9 | (3.7, 6.6) |
| ≥4 Years to <10 years | 65 | 5.8 | (4.6, 7.3) | 23 | 6.5 | (4.3, 9.8) |
| 1 Month after Vaccination 2 | | | | | | |
| ≥24 Months to <10 years | 133 | 96.6 | (83.0, 112.5) | 43 | 5.8 | (4.4, 7.6) |
| ≥24 Months to <4 years | 66 | 103.8 | (84.2, 127.9) | 21 | 5.0 | (3.6, 7.1) |
| ≥4 Years to <10 years | 67 | 90.0 | (71.9, 112.7) | 22 | 6.6 | (4.2, 10.5) |
| 1 Month after Vaccination 3 | | | | | | |
| ≥24 Months to <10 years | 139 | 183.3 | (156.7, 214.4) | 43 | 6.0 | (4.6, 7.7) |
| ≥24 Months to <4 years | 68 | 175.6 | (139.1, 221.6) | 24 | 4.5 | (3.5, 5.7) |
| ≥4 Years to <10 years | 71 | 191.0 | (153.9, 237.1) | 19 | 8.6 | (5.4, 13.8) |
| 6 Months after Vaccination 3 | | | | | | |
| ≥24 Months to <10 years | 131 | 31.3 | (25.3, 38.7) | 46 | 6.0 | (4.6, 7.8) |
| ≥24 Months to <4 years | 61 | 27.0 | (19.7, 36.9) | 24 | 6.0 | (4.0, 8.9) |
| ≥4 Years to <10 years | 70 | 35.7 | (26.6, 47.8) | 22 | 6.0 | (4.2, 8.7) |
| PMB2948 (B24) | | | | | | |
| Before Vaccination 1 | | | | | | |
| ≥24 Months to <10 years | 134 | 4.5 | (4.1, 4.9) | 47 | 4.4 | (3.9, 4.9) |
| ≥24 Months to <4 years | 67 | 4.3 | (3.8, 4.9) | 26 | 4.3 | (3.7, 5.1) |
| ≥4 Years to <10 years | 67 | 4.6 | (4.0, 5.2) | 21 | 4.4 | (3.6, 5.4) |
| 1 Month after Vaccination 2 | | | | | | |
| ≥24 Months to <10 years | 128 | 11.1 | (9.2, 13.5) | 45 | 4.8 | (4.0, 5.8) |
| ≥24 Months to <4 years | 65 | 9.1 | (7.0, 11.9) | 24 | 4.8 | (3.7, 6.2) |
| ≥4 Years to <10 years | 63 | 13.7 | (10.3, 18.2) | 21 | 4.9 | (3.6, 6.6) |
| 1 Month after Vaccination 3 | | | | | | |
| ≥24 Months to <10 years | 126 | 22.6 | (19.1, 26.8) | 46 | 4.3 | (3.9, 4.8) |
| ≥24 Months to <4 years | 63 | 19.1 | (14.9, 24.5) | 26 | 4.6 | (3.8, 5.6) |
| ≥4 Years to <10 years | 63 | 26.8 | (21.3, 33.9) | 20 | 4.0 | (NE, NE) |
| 6 Months after Vaccination 3 | | | | | | |
| ≥24 Months to <10 years | 129 | 5.6 | (4.8, 6.5) | 47 | 4.0 | (NE, NE) |
| ≥24 Months to <4 years | 65 | 5.1 | (4.1, 6.3) | 26 | 4.0 | (NE, NE) |
| ≥4 Years to <10 years | 64 | 6.2 | (4.9, 7.7) | 21 | 4.0 | (NE, NE) |
| PMB2707 (B44) | | | | | | |
| Before Vaccination 1 | | | | | | |
| ≥24 Months to <10 years | 138 | 4.0 | (NE, NE) | 50 | 4.0 | (NE, NE) |
| ≥24 Months to <4 years | 67 | 4.0 | (NE, NE) | 26 | 4.0 | (NE, NE) |
| ≥4 Years to <10 years | 71 | 4.0 | (NE, NE) | 24 | 4.0 | (NE, NE) |

TABLE 21-continued hSBA GMTs for Primary Strains - Evaluable Immunogenicity Population

| | Vaccine Group (as Randomized) | | | | | |
|---|---|---|---|---|---|---|
| Strain (Variant) Sampling Time Point | Group 1 rLP2086 | | | Group 2 HAV/Saline | | |
| Age Strata | $N^a$ | $GMT^b$ | (95% CI)$^c$ | $N^a$ | $GMT^b$ | (95% CI)$^c$ |
| 1 Month after Vaccination 2 | | | | | | |
| ≥24 Months to <10 years | 130 | 11.7 | (9.3, 14.7) | 50 | 4.0 | (NE, NE) |
| ≥24 Months to <4 years | 63 | 17.1 | (11.8, 24.8) | 26 | 4.0 | (NE, NE) |
| ≥4 Years to <10 years | 67 | 8.2 | (6.3, 10.6) | 24 | 4.0 | (NE, NE) |
| 1 Month after Vaccination 3 | | | | | | |
| ≥24 Months to <10 years | 134 | 39.8 | (30.6, 51.6) | 50 | 4.0 | (NE, NE) |
| ≥24 Months to <4 years | 65 | 43.6 | (29.9, 63.6) | 26 | 4.0 | (NE, NE) |
| ≥4 Years to <10 years | 69 | 36.5 | (25.2, 52.7) | 24 | 4.0 | (NE, NE) |
| 6 Months after Vaccination 3 | | | | | | |
| ≥24 Months to <10 years | 135 | 5.1 | (4.4, 5.9) | 49 | 4.0 | (NE, NE) |
| ≥24 Months to <4 years | 66 | 5.2 | (4.2, 6.4) | 26 | 4.0 | (NE, NE) |
| ≥4 Years to <10 years | 69 | 5.0 | (4.1, 6.2) | 23 | 4.0 | (NE, NE) |

Abbreviations: GMT = geometric mean titer; hSBA = serum bactericidal assay using human complement; LLOQ = lower limit of quantitation; NE = not estimable.
Note:
LLOQ = 1:16 for A22; 1:8 for A56, B24, and B44. Titers below the LLOQ were set to 0.5 × LLOQ for analysis.
$^a$N = number of subjects with valid and determinate hSBA titers for the given strain.
$^b$GMTs were calculated using all subjects with valid and determinate hSBA titers at the given time point.
$^c$CIs are back transformations of confidence levels based on the Student t distribution for the mean logarithm of the hSBA titers.

Subgroup analyses of hSBA GMTs for each of the 4 primary MnB test strains are presented for the evaluable immunogenicity population by sex, race, and country, and for the mITT population. There were no clinically important differences observed in the subgroup analyses performed.

Immunopersistence: hSBA GMTs

The hSBA GMTs for each of the 4 primary test strains at 6 months after the third vaccination with bivalent rLP2086 was a secondary endpoint. Table 21 provides hSBA GMTs for the 4 primary MnB strains for the evaluable immunogenicity population. Overall, there was a decrease observed from 1 month after the third vaccination to 6 months after the third vaccination in hSBA GMTs for each of the 4 primary test strains for Group 1 subjects in both age strata.

For Group 1 subjects aged ≥24 months to <4 years, from 1 month after the third vaccination to 6 months after the third vaccination, hSBA GMTs decreased from 33.7 to 10.9 for PMB80 (A22), 175.6 to 27.0 for PMB2001(A56), 19.1 to 5.1 for PMB2948 (B24), and 43.6 to 5.2 for PMB2707 (B44).

For Group 1 subjects aged ≥4 years to <10 years, from 1 month after the third vaccination to 6 months after the third vaccination, hSBA GMTs decreased from 38.2 to 14.2 for PMB80 (A22), 191.0 to 35.7 for PMB2001 (A56), 26.8 to 6.2 for PMB2948 (B24), and 36.5 to 5.0 for PMB2707 (B44).

For Group 1 subjects aged ≥24 months to <10 years, from 1 month after the third vaccination to 6 months after the third vaccination, hSBA GMTs decreased from 35.8 to 12.4 for PMB80 (A22), 183.3 to 31.3 for PMB2001(A56), 22.6 to 5.6 for PMB2948 (B24), and 39.8 to 5.1 for PMB2707 (B44).

In general, the hSBA GMTs for subjects in Group 2 did not change over time compared to baseline.

Defined hSBA Titers

The proportions of subjects aged ≥24 months to <4 years, ≥4 years to <10 years, and in the combined age stratum, achieving hSBA titers of ≥1:4, ≥1:8, ≥1:16, ≥1:32, ≥1:64, and ≥1:128 for each of the 4 primary test strains at baseline, 1 month after the second vaccination, and 1 month after the third vaccination with bivalent rLP2086 was a secondary immunogenicity endpoint.

The proportion of subjects achieving defined hSBA titers for the 4 primary MnB strains was assessed for the evaluable immunogenicity population.

Subjects who achieved an hSBA titer ≥1:4 and ≥1:16 are described below. An hSBA titer of ≥1:4 is widely recognized as the correlate of protection against IMD; however, a more conservative hSBA titer of ≥1:16 has been considered a level indicative of a 4-fold vaccine effect for subjects seronegative before vaccination.

The proportion of subjects aged ≥24 months to <4 years, and ≥4 years to <10 years, in Group 1 with an hSBA titer ≥1:4 at baseline was 5.9% and 19.7%, respectively, for PMB80 (A22); 3.0% and 18.5%, respectively, for PMB2001 (A56); 4.5% and 9.0%, respectively, for PMB2948 (B24); and 0.0% and 1.4%, respectively for PMB2707 (B44). Subjects aged ≥24 months to <4 years, and ≥4 years to <10 years, in Group 1 with an hSBA titer ≥1:16 at baseline was 4.4% and 13.6%, respectively, for PMB80 (A22); 1.5% and 15.4%, respectively, for PMB2001 (A56); 3.0% and 6.0%, respectively, for PMB2948 (B24); and 0.0% for both age strata for PMB2707 (B44).

The proportion of Group 1 subjects in the combined age stratum with an hSBA titer □1:4 and □1:16 at baseline was 12.7% and 9.0%, respectively, for PMB80 (A22); 10.6% and 8.3%, respectively, for PMB2001 (A56); 6.7% and 4.5%, respectively, for PMB2948 (B24); and 0.7% and 0.0%, respectively, for PMB2707 (B44).

The proportion of subjects aged ≥24 months to <4 years, and ≥4 years to <10 years, in Group 1 with an hSBA titer ≥1:4 at 1 month after the second vaccination was 65.6% and 83.3%, respectively, for PMB80 (A22); 100.0% for both age strata for PMB2001 (A56); 53.8% and 68.3%, respectively, for PMB2948 (B24); and 49.3% and 66.7%, respectively, for PMB2707 (B44). Subjects aged ≥24 months to <4 years, and ≥4 years to <10 years, in Group 1 with an hSBA titer ≥1:16 at 1 month after the second vaccination was 59.4% and 78.8%, respectively, for PMB80 (A22); 98.5% and 100.0%, respectively, for PMB2001 (A56); 43.1% and 58.7%, respectively, for PMB2948 (B24); and 31.3% and 55.6%, respectively, for PMB2707 (B44).

The proportion of Group 1 subjects in the combined age stratum with an hSBA titer ≥1:4 and ≥1:16 at 1 month after the second vaccination was 74.6% and 69.2%, respectively, for PMB80 (A22); 100.0% and 99.2%, respectively, for PMB2001 (A56); 60.9% and 50.8%, respectively, for PMB2948 (B24); and 57.7% and 43.1%, respectively, for PMB2707 (B44).

The proportion of subjects aged ≥24 months to <4 years, and ≥4 years to <10 years, in Group 1 with an hSBA titer ≥1:4 at 1 month after the third vaccination was 86.8% and 98.5%, respectively, for PMB80 (A22); 100.0% for each age strata for PMB2001 (A56); 90.5% and 95.2% for PMB2948 (B24); and 81.5% and 82.6%, respectively for PMB2707 (B44). Subjects aged ≥24 months to <4 years, and ≥4 years to <10 years, in Group 1 with an hSBA titer ≥1:16 at 1 month after the third vaccination was 83.8% and 91.0%, respectively, for PMB80 (A22); 100.0% for each age stratum for PMB2001 (A56); 81.0% and 88.9%, respectively, for PMB2948 (B24); and 81.5% to 82.6% and 80.0% and 75.4%, respectively, for PMB2707 (B44).

The proportion of Group 1 subjects in the combined age stratum with an hSBA titer ≥1:4 and ≥1:16 at 1 month after the third vaccination was 92.6% and 87.4%, respectively, for PMB80 (A22); 100.0% and 100.0%, respectively, for PMB2001 (A56); 92.9% and 84.9%, respectively, for PMB2948 (B24); and 82.1% and 77.6%, respectively, for PMB2707 (B44).

In general, the proportion of Group 2 subjects achieving defined hSBA titers did not change over time compared to baseline.

Results for the mITT population were similar to those of the evaluable immunogenicity population.

Immunopersistence: Defined hSBA Titers

The proportions of subjects aged ≥24 months to <4 years, ≥4 years to <10 years, and in the combined age stratum, achieving hSBA titers of ≥1:4, ≥1:8, ≥1:16, ≥1:32, ≥1:64, and ≥1:128 for each of the 4 primary test strains at 6 months after the third vaccination with bivalent rLP2086 was a secondary immunogenicity endpoint. The proportion of subjects achieving defined hSBA titers for the 4 primary MnB strains was assessed for the evaluable immunogenicity population.

Overall, there was a decrease observed in the proportion of Group 1 subjects in both age strata who achieved defined hSBA titers from 1 month after the third vaccination to 6 months after the third vaccination.

For Group 1 subjects aged ≥24 months to <4 years and aged ≥4 years to <10 years, from 1 month after the third vaccination to 6 months after the third vaccination, the proportion of subjects with an hSBA titer ≥1:4 decreased from 86.8% to 25.4% and 98.5% to 55.6%, respectively, for PMB80 (A22); 100.0% to 82.0% and 100.0% to 85.7%, respectively for PMB2001 (A56); 90.5% to 13.8% and 95.2% to 26.6%, respectively, for PMB2948 (B24); and 81.5% to 13.6% and 82.6% to 13.0%, respectively, for PMB2707 (B44).

For Group 1 subjects in the combined age stratum, from 1 month after the third vaccination to 6 months after the third vaccination, the proportion of subjects with an hSBA titer ≥1:4 decreased from 92.6% to 40.5% for PMB80 (A22); 100.0% to 84.0% for PMB2001 (A56); 92.9% to 20.2% for PMB2948 (B24); and 82.1% to 13.3% for PMB2707 (B44).

For Group 1 subjects aged ≥24 months to <4 years and aged ≥4 years to <10 years, from 1 month after the third vaccination to 6 months after the third vaccination, the proportion of subjects with an hSBA titer ≥1:16 decreased from 83.8% to 19.0% and 91.0% to 46.0%, respectively, for PMB80 (A22); 100.0% to 77.0% and 100.0% to 82.9%, respectively, for PMB2001 (A56); 81.0% to 9.2% and 88.9% to 20.3%, respectively, for PMB2948 (B24); and 80.0% to 9.1% and 75.4% 7.2%, respectively, for PMB2707 (B44). For Group 1 subjects in the combined age stratum, from 1 month after the third vaccination to 6 months after the third vaccination, the proportion of subjects with an hSBA titer ≥1:16 decreased from 87.4% to 32.5% for PMB80 (A22); 100.0% to 80.2% for PMB2001 (A56); 84.9% to 14.7% for PMB2948 (B24); and 77.6% to 8.1% for PMB2707 (B44).

In general, the proportion of Group 2 subjects achieving defined hSBA titers did not change over time compared to baseline.

Exploratory Immunogenicity Endpoints

The analysis of some exploratory immunogenicity endpoints was based on hSBA results for strains PMB2001 (A56) and PMB2707 (B44) for half of the subjects, and strains PMB80 (A22) and PMB2948 (B24) for the remaining half. The exploratory endpoint analyzed was hSBA titer with a ≥4-fold increase from baseline.

hSBA Titer 4-Fold Increase from Baseline

Table 22 presents the proportion of subjects with hSBA titers with a ≥4-fold rise ≥4 from baseline for the 4 primary test strains.

The proportion of Group 1 subjects aged ≥24 months to <4 years and aged ≥4 years to <10 years achieving a ≥4-fold rise in hSBA titer from baseline to 1 month after Vaccination 2 was 56.3% and 63.6%, respectively for PMB80 (A22); 100.0% and 82.1%, respectively for PMB2001 (A56); 43.1% and 54.0%, respectively, for PMB2948 (B24); and 54.0% and 31.3%, respectively, for PMB2707 (B44).

The proportion of Group 1 subjects in the combined age stratum achieving a ≥4-fold rise in hSBA titer from baseline to 1 month after Vaccination 2 was 60.0% for PMB80 (A22), 91.0% for PMB2001 (A56), 48.4% for PMB2948 (B24), and 42.3% for PMB2707 (B44). The proportion of Group 1 subjects aged ≥24 months to <4 years and aged ≥4 years to <10 years, achieving a ≥4-fold rise in hSBA titer from baseline to 1 month after Vaccination 3 was 79.4% and 77.6%, respectively for PMB80 (A22); 98.5% and 88.7%, respectively for PMB2001 (A56); 77.8% and 82.5%, respectively, for PMB2948 (B24); and 78.5% and 75.4%, respectively, for PMB2707 (B44).

The proportion of Group 1 subjects in the combined age stratum achieving a ≥4-fold rise in hSBA titer from baseline to 1 month after Vaccination 3 was 78.5% for PMB80 (A22), 93.5% for PMB2001 (A56), 80.2% for PMB2948 (B24), and 76.9% for PMB2707 (B44). The proportion of Group 1 subjects aged ≥24 months to <4 years and aged ≥4 years to <10 years achieving a ≥4-fold rise in hSBA titer from baseline to 6 months after Vaccination 3 was 19.0% and 36.5%, respectively for PMB80 (A22); 75.4% and 64.3%, respectively for PMB2001 (A56); 6.2% and 17.2%, respectively, for PMB2948 (B24); and 7.6% and 7.2%, respectively, for PMB2707 (B44).

The proportion of Group 1 subjects in the combined age stratum achieving a ≥4-fold rise in hSBA titer from baseline to 6 months after Vaccination 3 was 27.8% for PMB80 (A22), 69.5% for PMB2001 (A56), 11.6% for PMB2948 (B24), and 7.4% for PMB2707 (B44). Similar results were observed for the mITT population.

TABLE 22

Subjects With hSBA Titer ≥4-Fold Rise for Primary
Strains - Evaluable Immunogenicity Population

| Strain (Variant) Sampling Time Point | Group 1 rLP2086 | | | | Group 2 HAV/Saline | | | |
|---|---|---|---|---|---|---|---|---|
| Age Strata | $N^a$ | $n^b$ | (%) | (95% CI)$^c$ | $N^a$ | $n^b$ | (%) | (95% CI)$^c$ |
| hSBA titer fold rise ≥4 from baseline$^d$ PMB80 (A22) 1 Month after Vaccination 2 | | | | | | | | |
| ≥24 Months to <10 years | 130 | 78 | (60.0) | (51.0, 68.5) | 45 | 0 | (0.0) | (0.0, 7.9) |
| ≥24 Months to <4 years | 64 | 36 | (56.3) | (43.3, 68.6) | 24 | 0 | (0.0) | (0.0, 14.2) |
| ≥4 Years to <10 years | 66 | 42 | (63.6) | (50.9, 75.1) | 21 | 0 | (0.0) | (0.0, 16.1) |
| 1 Month after Vaccination 3 | | | | | | | | |
| ≥24 Months to <10 years | 135 | 106 | (78.5) | (70.6, 85.1) | 45 | 1 | (2.2) | (0.1, 11.8) |
| ≥24 Months to <4 years | 68 | 54 | (79.4) | (67.9, 88.3) | 25 | 1 | (4.0) | (0.1, 20.4) |
| ≥4 Years to <10 years | 67 | 52 | (77.6) | (65.8, 86.9) | 20 | 0 | (0.0) | (0.0, 16.8) |
| 6 Months after Vaccination 3 | | | | | | | | |
| ≥24 Months to <10 years | 126 | 35 | (27.8) | (20.2, 36.5) | 47 | 2 | (4.3) | (0.5, 14.5) |
| ≥24 Months to <4 years | 63 | 12 | (19.0) | (10.2, 30.9) | 26 | 2 | (7.7) | (0.9, 25.1) |
| ≥4 Years to <10 years | 63 | 23 | (36.5) | (24.7, 49.6) | 21 | 0 | (0.0) | (0.0, 16.1) |
| PMB2001 (A56) 1 Month after Vaccination 2 | | | | | | | | |
| ≥24 Months to <10 years | 133 | 121 | (91.0) | (84.8, 95.3) | 43 | 4 | (9.3) | (2.6, 22.1) |
| ≥24 Months to <4 years | 66 | 66 | (100.0) | (94.6, 100.0) | 21 | 1 | (4.8) | (0.1, 23.8) |
| ≥4 Years to <10 years | 67 | 55 | (82.1) | (70.8, 90.4) | 22 | 3 | (13.6) | (2.9, 34.9) |
| 1 Month after Vaccination 3 | | | | | | | | |
| ≥24 Months to <10 years | 139 | 130 | (93.5) | (88.1, 97.0) | 43 | 8 | (18.6) | (8.4, 33.4) |
| ≥24 Months to <4 years | 68 | 67 | (98.5) | (92.1, 100.0) | 24 | 1 | (4.2) | (0.1, 21.1) |
| ≥4 Years to <10 years | 71 | 63 | (88.7) | (79.0, 95.0) | 19 | 7 | (36.8) | (16.3, 61.6) |
| 6 Months after Vaccination 3 | | | | | | | | |
| ≥24 Months to <10 years | 131 | 91 | (69.5) | (60.8, 77.2) | 46 | 6 | (13.0) | (4.9, 26.3) |
| ≥24 Months to <4 years | 61 | 46 | (75.4) | (62.7, 85.5) | 24 | 3 | (12.5) | (2.7, 32.4) |
| ≥4 Years to <10 years | 70 | 45 | (64.3) | (51.9, 75.4) | 22 | 3 | (13.6) | (2.9, 34.9) |
| PMB2948 (B24) 1 Month after Vaccination 2 | | | | | | | | |
| ≥24 Months to <10 years | 128 | 62 | (48.4) | (39.5, 57.4) | 45 | 3 | (6.7) | (1.4, 18.3) |
| ≥24 Months to <4 years | 65 | 28 | (43.1) | (30.8, 56.0) | 24 | 1 | (4.2) | (0.1, 21.1) |
| ≥4 Years to <10 years | 63 | 34 | (54.0) | (40.9, 66.6) | 21 | 2 | (9.5) | (1.2, 30.4) |
| 1 Month after Vaccination 3 | | | | | | | | |
| ≥24 Months to <10 years | 126 | 101 | (80.2) | (72.1, 86.7) | 46 | 2 | (4.3) | (0.5, 14.8) |
| ≥24 Months to <4 years | 63 | 49 | (77.8) | (65.5, 87.3) | 26 | 2 | (7.7) | (0.9, 25.1) |
| ≥4 Years to <10 years | 63 | 52 | (82.5) | (70.9, 90.9) | 20 | 0 | (0.0) | (0.0, 16.8) |
| 6 Months after Vaccination 3 | | | | | | | | |
| ≥24 Months to <10 years | 129 | 15 | (11.6) | (6.7, 18.5) | 47 | 0 | (0.0) | (0.0, 7.5) |
| ≥24 Months to <4 years | 65 | 4 | (6.2) | (1.7, 15.0) | 26 | 0 | (0.0) | (0.0, 13.2) |
| ≥4 Years to <10 years | 64 | 11 | (17.2) | (8.9, 28.7) | 21 | 0 | (0.0) | (0.0, 16.1) |
| PMB2707 (B44) 1 Month after Vaccination 2 | | | | | | | | |
| ≥24 Months to <10 years | 130 | 55 | (42.3) | (33.7, 51.3) | 50 | 0 | (0.0) | (0.0, 7.1) |
| ≥24 Months to <4 years | 63 | 34 | (54.0) | (40.9, 66.6) | 26 | 0 | (0.0) | (0.0, 13.2) |
| ≥4 Years to <10 years | 67 | 21 | (31.3) | (20.6, 43.8) | 24 | 0 | (0.0) | (0.0, 14.2) |
| 1 Month after Vaccination 3 | | | | | | | | |
| ≥24 Months to <10 years | 134 | 103 | (76.9) | (68.8, 83.7) | 50 | 0 | (0.0) | (0.0, 7.1) |
| ≥24 Months to <4 years | 65 | 51 | (78.5) | (66.5, 87.7) | 26 | 0 | (0.0) | (0.0, 13.2) |
| ≥4 Years to <10 years | 69 | 52 | (75.4) | (63.5, 84.9) | 24 | 0 | (0.0) | (0.0, 14.2) |

TABLE 22-continued

Subjects With hSBA Titer ≥4-Fold Rise for Primary
Strains - Evaluable Immunogenicity Population

| | Vaccine Group (as Randomized) | | | | | | | |
|---|---|---|---|---|---|---|---|---|
| Strain (Variant) Sampling Time Point | Group 1 rLP2086 | | | | Group 2 HAV/Saline | | | |
| Age Strata | $N^a$ | $n^b$ | (%) | (95% CI)$^c$ | $N^a$ | $n^b$ | (%) | (95% CI)$^c$ |
| 6 Months after Vaccination 3 | | | | | | | | |
| ≥24 Months to <10 years | 135 | 10 | (7.4) | (3.6, 13.2) | 49 | 0 | (0.0) | (0.0, 7.3) |
| ≥24 Months to <4 years | 66 | 5 | (7.6) | (2.5, 16.8) | 26 | 0 | (0.0) | (0.0, 13.2) |
| ≥4 Years to <10 years | 69 | 5 | (7.2) | (2.4, 16.1) | 23 | 0 | (00) | (0.0, 14.8) |

Abbreviations: hSBA = serum bactericidal assay using human complement; LLOQ = lower limit of quantitation; LOD = limit of detection.
Note:
LLOQ = 1:16 for A22; 1:8 for A56, B24, and B44.
Note:
The 4-fold increase is defined as follows: (1) For subjects with a baseline hSBA titer below the LOD (hSBA titer <1:4), a response is defined as an hSBA titer ≥1:16 or the LLOQ (whichever titer is higher). (2) For subjects with a baseline hSBA titer ≥ LOD and < LLOQ, a response is defined as an hSBA titer ≥4 times the LLOQ. (3) For subjects with a baseline hSBA titer ≥ LLOQ, a response is defined as an hSBA titer ≥4 times the baseline titer.
$^a$For hSBA titer fold rise ≥4 from baseline, N = number of subjects with valid and determinate hSBA titers for the given strain at both the specified time point and baseline.
$^b$For hSBA titer fold rise ≥4 from baseline, n = number of subjects who achieved hSBA titer fold rise ≥4 from baseline for the given strain.
$^c$Exact 2-sided CI based upon observed proportion of subjects, using the Clopper and Pearson method.
$^d$Baseline is defined as the blood draw prior to Vaccination 1.

Additional Immunogenicity Analyses
Assessment of Missing hSBA Data for Primary MnB Test Strains Only valid and determinate hSBA results were included in all immunogenicity analyses. The hSBA results were excluded from the immunogenicity analysis (or considered to be missing) for the following reasons:

The subject withdrew from the study.
The subject did not have blood samples for testing but was not withdrawn from the study.
The quantity of blood was insufficient to perform the assay. This was entered as "quantity not sufficient" for the assay results.
The sample was tested but a numerical titer could not be reliably determined. This was entered as "indeterminate" for the assay results.

Reverse Cumulative Distribution Curves

The RCDCs of the proportions of subjects exhibiting an hSBA response (≥LLOQ) for each of the 4 primary strains and at each sampling time point, for the combined age stratum were assessed. RCDCs for each of the 4 primary strains and at each sampling time point, for subjects aged ≥24 months to <4 years were also assessed. RCDCs for each of the 4 primary strains and at each sampling time point, for subjects aged ≥4 years to <10 years were assessed.

The RCDCs showed the majority of subjects in both age strata exhibited a measurable hSBA response to each of the primary MnB test strains at 1 month after the second and third dose of bivalent rLP2086.

Immunogenicity Conclusions

The primary objectives of this study were to describe subject immune response to bivalent rLP2086 as measured by hSBA against 4 primary MnB test strains, 2 expressing an LP2086 subfamily A protein and 2 expressing an LP2086 subfamily B protein, measured 1 month after the third vaccination in healthy subjects aged ≥24 months to <4 years and ≥4 years to <10 years. The description of immune responses for the combined age stratum (≥24 months to <10 years) was a secondary objective. The endpoints for the primary objectives were the proportions of subjects in each age stratum achieving hSBA titers ≥LLOQ for each of the 4 primary MnB strains 1 month after the third vaccination.

A robust immune response was observed for children aged ≥24 months to <10 years 1 month after the third dose of bivalent rLP2086, as confirmed by the proportion of subjects achieving an hSBA titer ≥LLOQ (1:8 for A56, B24 and B44; 1:16 for A22) for each of the 4 primary MnB test strains ranging from 80.0% to 100.0% for subjects aged ≥24 months to <4 years and from 78.3% to 100.0% for subjects ≥4 years to <10 years after 3 doses. The proportion of subjects in the combined age stratum with an hSBA titer ≥LLOQ for each of the 4 primary MnB test strains 1 month after the third vaccination ranged from 79.1% to 100.0%. These findings are further supported by substantial GMTs (range 19.1 to 191) and in the proportion of subjects achieving an hSBA titer ≥1:4 (81.5% to 100%) or ≥1:16 (75.4% to 100%) against each of the 4 primary MnB test strains after 3 doses of bivalent rLP2086 compared to baseline across both age strata. Additionally, the proportion of subjects in the combined age stratum achieving an hSBA fold rise ≥4 from baseline to 1 month after the third vaccination for each of the 4 primary MnB test strains ranged from 76.9% to 93.5%.

The secondary objective of the study was to describe immune responses 1 month after the second dose of bivalent rLP2086, as assessed by ≥LLOQ responses, defined hSBA titers and hSBA GMTs for the 2 age strata and the combined age stratum. For the combined age stratum, the proportion of subjects achieving an hSBA titer ≥LLOQ ranged from 48.5% to 100.0% with no meaningful differences observed between the younger and older age strata. These findings are further supported by the combined age stratum with increases in GMTs (range 11.1 to 96.6) and in the proportion of subjects achieving an hSBA titer ≥1:4 (57.7% to 100%) or ≥1:16 (43.1% to 100%) after 2 doses of bivalent rLP2086 compared to baseline against each of the 4 primary MnB test strains. GMTs were similar between the 2 age strata. Additionally, the proportion of subjects in the combined age stratum achieving an hSBA fold rise ≥4 from baseline to 1 month after the second vaccination for each of the 4 primary MnB test strains ranged from 42.3% to 91.0%.

Immunopersistence was also assessed at 6 months after the third dose of bivalent rLP2086 with the proportion of subjects with an hSBA titer ≥LLOQ declining from 79.1% to 100% 1 month after Vaccination 3 to 10.4% to 82.4% at 6 months after the third vaccination for the combined age stratum. No differences between the 2 age strata were observed except for A22, for which older children had a higher proportion of subjects achieving a titer ≥LLOQ than the younger children (46%, 95% CI 33.4, 59.1 vs 19%, 95% CI 10.2, 30.9). However, baseline prevaccination rates of titers ≥LLOQ were greater for A22 in the older age stratum (13.6% vs 4.4%). A similar trend was also observed for the combined age stratum for the proportion of subjects with a protective hSBA titer ≥1:4, ranging from 13.3% to 84.0% and GMTs, ranging from 5.1 to 31.3 at 6 months after the third vaccination.

In summary, bivalent rLP2086 given as 3 doses on a 0-, 2-, and 6-month schedule elicits a robust immune response among toddlers and children aged ≥24 months to <10 years with protective antibody titers achieved as measured by hSBA in a high proportion of subjects after the third dose. No clinically meaningful differences were observed between toddlers aged ≥24 months to <4 years and children aged ≥4 years to <10 years. Antibody responses decline 6 months after the third dose, but remain higher than prevaccination baseline rates.

Discussion and Overall Conclusions
Immunogenicity Discussion

Immunogenicity results from this Phase 2 study of a 3-dose regimen (0-, 2-, and 6-month schedule) of bivalent rLP2086 given to toddlers and children aged ≥24 months to <10 years are consistent with previous studies in adolescents and young adults. Immunogenicity responses to bivalent rLP2086 vaccination were measured in validated hSBAs using 4 primary MnB test strains, each expressing fHBP variants heterologous to the vaccine component antigens, using criteria more stringent than the accepted correlate of protection (hSBA titer ≥1:4). Based on an hSBA titer ≥LLOQ for the 4 primary MnB test strains 1 month after Vaccination 3, the toddlers and children participating in this study had similar immune responses compared to adolescents (10 years to <19 years) participating in Study B1971009, with proportions of subjects achieving an hSBA titer ≥LLOQ after the third vaccination (0-, 2-, 6-month schedule) ranging from 79.1% to 100% in this study and 87.1% to 99.5% in Study B1971009. Meaningful differences in the proportion of subjects with an hSBA titer ≥LLOQ for the 4 primary test strains 1 month after Vaccination 3 between these 2 studies are not apparent, despite the fact that Study B1971009 had a much higher proportion of adolescent subjects with a prevaccination hSBA titer ≥LLOQ compared to the toddlers and children in this study, particularly for the A22 (33.2% vs 9%, respectively) and A56 (27.5% vs 8.3%, respectively) test strains. Bivalent rLP2086 appears to be highly immunogenic in the ≥24 months to <10 years age population and is likely to offer protection against MnB infection similarly to that expected for adolescents based on the hSBA correlate of protection.

With regard to the secondary objectives, immune responses in this study for the combined age stratum (≥24 months to <10 years) 1 month after the second dose of bivalent rLP2086 were relatively robust for the 4 primary MnB test strains, with the proportion of subjects achieving an hSBA titer ≥LLOQ ranging from 48.5% to 100%. With exception of strain A56, these responses were lower than immune responses observed among adolescents (10 years to <19 years) participating in Study B1971009 receiving 2 doses of bivalent rLP2086 given 2 months apart, ranging from 64% to 99.1%. Immunopersistence was assessed in this study for toddlers and children by measuring hSBA titers 6 months after Vaccination 3. The proportion of subjects achieving an hSBA titer ≥LLOQ declined from a range of 79.1% to 100% 1 month after Vaccination 3 to a range of 10.4% to 82.4% 6 months after Vaccination 3. GMTs and the proportion of subjects with defined hSBA titers also declined 6 months after Vaccination 3. Although the proportions of subjects achieving an hSBA titer ≥LLOQ 6 months after Vaccination 3 in this study (10.4% to 82.4%) were lower than for adolescents (11 years to <19 years) participating in Study 6108A1-2001 (36.7% to 89.4%), they are still higher than the proportion of subjects aged ≥24 months to <10 years with an hSBA titer ≥LLOQ at baseline (0% to 9%). It is well established that meningococcal colonization rates increase with age through early adulthood. Differences between subjects aged 24 months to <10 years and older age groups may be partially attributable to the proportion of subjects with a baseline titer ≥LLOQ, which were as high as 27.5% (A56) and 33.2% (A22) in Study B1971009, and 7.4% to 13.4% for subfamily A strains in Study 6108A1-2001. Additionally, a recent study showed that carriage of disease-associated serogroup B strains was higher in subjects with protective hSBA titers (before vaccination), and that vaccination did not impact subsequent carriage of those disease-associated strains. This suggests that carriage may impact baseline hSBA titers and that persistence or recolonization after vaccination may be contributing to a greater proportion of subjects with an hSBA titer ≥LLOQ observed among adolescents 6 months after vaccination compared to the toddlers and children in this study, who we speculate are less likely to be colonized and have lower percentages of hSBA titers LLOQ at baseline. Immunopersistence studies with monovalent conjugate meningococcal serogroup C vaccine in infants and children similarly show that protective immunity rapidly wanes. However, even among a cohort of children with percentages of hSBA titers >1:8 for serogroup C at only 46.9% 4 years after completion of the primary dose, a subsequent booster dose provided titers >1:8 in 100% of subjects 1 month and 1 year after the booster. This indicates that even those considered seronegative prior to the booster dose have a strong anamnestic response which persists for up to 1 year after booster vaccination. Post-booster response and persistence studies are therefore warranted among individuals who received their primary series of bivalent rLP2086 as toddlers and children to provide further insights into the utility of a booster dose in providing protection against IMD through adolescence and early adulthood.

In summary, bivalent rLP2086 administered on a 0-, 2-, and 6-month schedule is highly immunogenic among toddlers and children aged ≥24 months to <10 years with protective immune responses achieved as measured by hSBA in a high proportion of subjects after the third dose. Immune responses, as measured in this study, appear to be similar to that observed in prior studies among adolescents 1 month after the second and third doses. The 3-dose regimen appears to provide high rates of protective immunity in toddlers and children aged ≥24 months to <10 years.

Overall Conclusions

In conclusion, bivalent rLP2086 administered to toddlers and children aged ≥24 months to <10 years in a 3-dose series on a 0-, 2-, and 6-month schedule elicits a robust immune response by the majority of subjects after the second and third doses, with protective antibody titers achieved after the third dose as measured by hSBAs. hSBA titers decreased 6 months after a 3-dose series. The vaccine, as administered in this study, was safe and well tolerated with an acceptable safety profile for toddlers and children aged ≥24 months to <10 years.

Example 20: A Phase 2, Randomized, Controlled, Observer-Blinded Study Conducted to Describe the Immunogenicity, Safety, and Tolerability of a *Neisseria meningitidis* Serogroup B Bivalent Recombinant Lipoprotein 2086 Vaccine (Bivalent rLP2086) when Administered to Healthy Toddlers Aged 12 to <18 Months or 18 to <24 Months (B1971035-Syn)

Objectives
Primary Immunogenicity Objectives:
To describe the immune response as measured by serum bactericidal assay using human complement (hSBA) performed with 4 primary *Neisseria meningitidis* serogroup B (MnB) strains, 2 expressing an LP2086 subfamily A protein and 2 expressing an LP2086 subfamily B protein, measured 1 month after the third vaccination with bivalent rLP2086, in healthy toddlers aged 12 to <18 months at study entry.
To describe the immune response as measured by hSBA performed with 4 primary MnB strains, 2 expressing an LP2086 subfamily A protein and 2 expressing an LP2086 subfamily B protein, measured 1 month after the third vaccination with bivalent rLP2086, in healthy toddlers aged 18 to <24 months at study entry.

Primary Safety Objective:
To evaluate the safety profile of bivalent rLP2086 compared to a control (hepatitis A virus [HAV] vaccine), as measured by local reactions, systemic events, adverse events (AEs), serious adverse events (SAEs), newly diagnosed chronic medical conditions (NDCMCs), medically attended events (MAEs), and immediate AEs in healthy toddlers 12 to <18 months and 18 to <24 months of age at study entry, and in both age strata combined.

Secondary Immunogenicity Objectives:
To describe the immune response as measured by hSBA performed with 4 primary MnB test strains, 2 expressing an LP2086 subfamily A protein and 2 expressing an LP2086 subfamily B protein, measured 1 month after the third vaccination with bivalent rLP2086, in healthy toddlers aged 12 to <24 months at study entry (ie, both age strata combined).
To describe the immune response as measured by hSBA performed with 4 primary MnB test strains, 2 expressing an LP2086 subfamily A protein and 2 expressing an LP2086 subfamily B protein, measured 1 month after the second vaccination and 6, 12, 24, 36, and 48 months after the third vaccination in healthy toddlers aged 12 to <18 months and 18 to <24 months at study entry, and in both age strata combined.

Exploratory Immunogenicity Objectives:
To further describe the immune response as measured by hSBA performed with 4 primary MnB test strains, 2 expressing an LP2086 subfamily A protein and 2 expressing an LP2086 subfamily B protein, measured 1 month after the second vaccination and 1, 6, 12, 24, 36, and 48 months after the third vaccination with bivalent rLP2086 in healthy toddlers aged 12 to <18 months and 18 to <24 months at study entry, and in both age strata combined.
To further describe the immune response as measured by hSBA to secondary MnB test strains expressing LP2086 subfamily A and B proteins, at 1 month after the second vaccination and 1, 6, 12, 24, 36, and 48 months after the third vaccination in healthy toddlers aged 12 to <18 months and 18 to <24 months at study entry, and in both age strata combined.

Methods
Study Design:
The study was a Phase 2, randomized, active-controlled, observer-blinded, sponsor-unblinded, multicenter study in which approximately 396 healthy toddlers stratified by age, 12 to <18 months or 18 to <24 months old, were randomly assigned in a 2:1 ratio to receive bivalent rLP2086 (either of 2 dose levels [60 µg or 120 µg]) or a licensed pediatric HAV vaccine (0.5 mL)/sterile saline solution for injection (0.5-mL of 0.85% sodium chloride).

The study was conducted in 2 stages. Stage 1 assessed vaccine immunogenicity, safety, and tolerability across 2 phases: a sentinel-enrollment phase and an expanded-enrollment phase. Stage 2 assessed the duration of the immune response to bivalent rLP2086.

For immunogenicity, all data through 1 month after Vaccination 3 (Visit 7) are presented with the exception of secondary MnB test strain data supporting an exploratory objective. The final report includes all immunogenicity data through the completion of Stage 2 and safety data for the period after Visit 8 until the end of the study (Visit 13, 48 months after Vaccination 3).

The Stage 1 sentinel-enrollment phase was planned to include a total of 4 sentinel cohorts: 2 age strata for each dose level (60 µg or 120 µg) of bivalent rLP2086. The younger-aged sentinel cohorts were composed of subjects aged 12 to <15 months and the older-aged sentinel cohorts were composed of subjects aged 18 to <24 months. Each of the 4 sentinel cohorts was planned to enroll approximately 33 subjects. The sentinel-enrollment phase was staggered with reviews by an IRC at pre-specified points and stopping rules applied. The 120-µg dose level sentinel cohorts did not proceed until the 60-µg dose level was evaluated by the IRC as safe and tolerable in the sentinel cohort of the same age. The younger-aged 120-µg dose level sentinel cohort did not proceed until this dose level was evaluated by the IRC as safe and tolerable in the older-aged 120-µg dose level sentinel cohort.

Prior to the Stage 1 expanded-enrollment phase, the IRC reviewed all post-Vaccination 1, 7-day e-diary and SAE data obtained from sentinel subjects. Based on the review, the IRC selected the 120-µg bivalent rLP2086 dose level to be studied in the Stage 1 expanded-enrollment phase for both age strata. The younger-aged expanded-enrollment cohort (enrolling an additional 132 subjects) was extended to subjects aged 12 to <18 months and stratified by age into 2 subsets: aged 12 to <15 months and aged 15 to <18 months. The older-aged expanded enrollment cohort (enrolling an additional 132 subjects) enrolled subjects aged 18 to <24 months during the expanded-enrollment phase. The total study duration for subjects completing only Stage 1 will be approximately 18 months. The visit schedule for Stage 1 is presented in Table 23.

Stage 2 includes only those subjects randomly assigned to bivalent rLP2086 (irrespective of dose level). The total study duration for subjects who complete Stage 2 will be approximately 4.5 years (54 months). The visit schedule for Stage 2 is presented in Table 24.

Bivalent rLP2086 was administered at Months 0, 2, and 6 (Visits 1, 4, and 6). Pediatric HAV vaccine was administered at Months 0 and 6 (Visits 1 and 6), and saline was administered at Month 2 (Visit 4) to maintain the study blind.

saline was administered as an intramuscular injection into either the deltoid muscle or anterolateral thigh muscle. Only a third-party unblinded medically qualified member of the study staff administered the investigational product. If muscle mass in the deltoid was not adequate for intramuscular injection, then the thigh was the preferred injection site.

TABLE 23

Stage 1 Visit Schedule

| Visit Identifier | 1 | 2 | 3 | 4 | 5 |
|---|---|---|---|---|---|
| Time Period | Month 0 | Week 1 | Month 1 | Month 2 | Month 3 |
| Visit Description | Vaccination 1 | Post-Vaccination 1 Follow-up Visit | Telephone Contact | Vaccination 2 | Post-Vaccination 2 Blood Draw |
| | | | Vaccination Phase | | |
| Vaccination & 30-minute observation[c] | X | | | X | |
| Obtain 5-mL blood sample | X[d] | | | | X |

| Visit Identifier | 6 | 7 | 8 | 9[a] | 10[a] |
|---|---|---|---|---|---|
| Time Period | Month 6 | Month 7 | Month 12 | Month 18 | End of Stage 1 |
| Visit Description | Vaccination 3 | Post-Vaccination 3 Blood Draw | 6-Month Follow-up Visit[b] | Antibody Persistence Blood Draw[b] | Telephone Contact |
| | Vaccination Phase | | Follow-up Phase | | |
| Vaccination & 30-minute observation[c] | X | | | | |
| Obtain 5-mL blood sample | | X | X[e] | X | |

Abbreviations: CRF = case report form; e-diary = electronic diary.
[a] Visits 9 and 10 are not included in this primary analysis clinical study report.
[b] Relative to Vaccination 3.
[c] Injection performed by unblinded administrator; acute reactions assessed by blinded observer. Location of vaccination was noted in the source, the CRF, and the e-diary.
[d] Blood was collected before vaccination and only after eligibility was confirmed.
[e] Immunogenicity results from blood draw at Visit 8 are not included in this primary analysis clinical study report.
Source: Protocol schedule of activities for Stage 2.

TABLE 24

Stage 2 Visit Schedule

| Visit Identifier | 11 | 12 | 13 |
|---|---|---|---|
| Time Period | Month 30 | Month 42 | Month 54 |
| Visit Description (Time After Vaccination 3) | Immunogenicity 1 (24 Months) | Immunogenicity 2 (36 Months) | Immunogenicity 3 (48 Months) |
| Obtain 5-mL blood sample | X | X | X |

Source: Protocol schedule of activities for Stage 2.

Vaccines Administered:

Bivalent rLP2086 (60 µg or 120 µg) was administered 3 times over the course of the study: the first vaccination at Visit 1 (Month 0), second vaccination at Visit 4 (Month 2), and third vaccination at Visit 6 (Month 6). Bivalent rLP2086 was administered as an intramuscular injection into either the deltoid muscle or anterolateral thigh muscle. HAV vaccine was administered twice over the course of the study: the first vaccination at Visit 1 (Month 0) and third vaccination at Visit 6 (Month 6). Saline was administered at the second vaccination (Month 2) time point. HAV vaccine/

Immunogenicity Evaluations:

To facilitate immunogenicity analysis, subjects had approximately 5 mL of blood collected at the following time points during Stage 1: before Vaccination 1 (Visit 1), 1 month after Vaccination 2 (Visit 5), 1 month after Vaccination 3 (Visit 7), 6 months after Vaccination 3 (Visit 8), 12 months after Vaccination 3 (Visit 9). In total, 25 mL was collected over the 18-month period. Local/topical anesthetic could be used prior to blood draws.

To determine duration of immune response, Stage 2 subjects will have approximately 5 mL of blood collected at the following time points: 2 years after Vaccination 3, 3 years after Vaccination 3, and 4 years after Vaccination 3. In total, 15 mL will be collected over approximately 2.5 years.

For assessment of the immune response to bivalent rLP2086, functional antibodies were analyzed in hSBAs with meningococcal serogroup B strains. The hSBA measures antibodies in human sera that result in complement-dependent killing of the target meningococcal strain. Four (4) primary MnB test strains, PMB80 (A22), PMB2001 (A56), PMB2948 (B24), and PMB2707 (B44), each expressing a factor H binding protein (fHBP) variant heterologous to the vaccine component antigens, were used in the hSBAs for determination of the immunogenicity endpoints in this study.

Due to serum volume limitations, 2 of the primary strains (PMB80 [A22] and PMB2948 [B24]) were tested at each blood sampling time point for half of the subjects (in both age strata), and the other 2 primary strains (PMB2001 [A56] and PMB2707 [B44]) were tested at each blood sampling time point for the remaining half of the subjects.

Once all subjects completed enrollment (Visit 1), the independent statistical center (ISC), a statistical team not involved in the conduct of the study, provided 2 subject listings (randomly selected, 50% of subjects to be tested for PMB80 [A22]/PMB2948 [B24] and the remaining 50% of subjects to be tested for PMB2001 [A56]/PMB2707 [B44]) to the sponsor's sample management team. Both listings followed the same randomization ratio (2:1) and age-strata distribution as in the study design. The same strain pair (PMB80 [A22]/PMB2948 [B24] or PMB2001 [A56]/PMB2707 [B44]) was tested across all visits for the same subjects.

Once testing for the primary analyses was completed, and if sufficient volume of sera was available, additional testing to assess the immune response to bivalent rLP2086 could be considered as follows: PMB80 (A22) and PMB2948 (B24) could be tested in serum samples from the 50% of subjects who received bivalent rLP2086 and whose serum samples were originally tested for PMB2001 (A56) and PMB2707 (B44). Conversely, PMB2001 (A56) and PMB2707 (B44) could be tested in serum samples from the 50% of subjects who received bivalent rLP2086 and were originally tested for PMB80 (A22) and PMB2948 (B24). Testing for secondary strains could be performed.

Statistical Methods:

The primary immunogenicity endpoints were:
Proportions of subjects achieving an hSBA titer ≥lower limit of quantitation (LLOQ) 1 month after the third vaccination, for each of the 4 primary MnB test strains in healthy toddlers 12 to <18 months of age at study entry.
Proportions of subjects achieving an hSBA titer ≥LLOQ 1 month after the third vaccination, for each of the 4 primary MnB test strains in healthy toddlers 18 to <24 months of age at study entry.

All secondary immunogenicity endpoints for the entire study are described here but this Example presents results for the immunogenicity endpoints applicable to Visits 1 to 7 only. Subsequent endpoints will be analyzed.

The following endpoint applied to results in healthy subjects 12 months to <24 months of age (i.e., both age strata combined) at study entry:
Proportion of subjects with hSBA titers ≥LLOQ for each of the 4 primary MnB test strains 1 month after the third vaccination with bivalent rLP2086 and 6, 12, 24, 36, and 48 months after the third vaccination with bivalent rLP2016.

The following endpoints applied to results in healthy subjects 12 to <18 months of age and 18 to <24 months of age at study entry, and in both age strata combined:
Proportions of subjects with hSBA titers ≥LLOQ for each of the 4 primary MnB test strains at 1 month after the second vaccination with bivalent rLP2086.
Proportions of subjects with hSBA titers ≥LLOQ, ≥1:4, ≥1:16, ≥1:32, ≥1:64, and ≥1:128 for each of the 4 primary MnB strains at each applicable blood sampling visit.
hSBA geometric mean titers (GMTs) for each of the 4 primary MnB test strains at each applicable blood sampling visit.

All of the exploratory endpoints specified below applied to hSBA results from all healthy subjects 12 to <18 months of age or 18 to <24 months of age at study entry, and in both age strata combined, who received bivalent rLP2086 and were tested for the appropriate strain at the appropriate time point:
Proportions of subjects with hSBA titers ≥LLOQ, ≥1:4, ≥1:16, ≥1:32, ≥1:64, and ≥1:128 at each applicable blood sampling time point.
hSBA GMTs for each of the 4 primary MnB strains at each applicable blood sampling visit.
Proportions of subjects achieving at least a 4-fold increase in hSBA titer from baseline to 1 month after the third vaccination with bivalent rLP2086 for each of the 4 primary test strains:
For subjects with a baseline hSBA titer below the limit of detection (LOD) or an hSBA titer of <1:4, a 4-fold response was defined as an hSBA titer of ≥1:16.
For subjects with a baseline hSBA titer of ≥LOD (ie, hSBA titer of ≥1:4) and <LLOQ, a 4-fold response was defined as an hSBA titer of ≥4 times the LLOQ.
For subjects with a baseline hSBA titer of ≥LLOQ, a 4-fold response was defined as an hSBA titer of ≥4 times the baseline titer.

The following endpoints were planned if there had been sufficient sera available to test each subject for all 4 primary strains and/or to test subjects for the secondary strains.
Proportions of subjects achieving an hSBA titer ≥LLOQ for all 4 primary test strains (PMB80 [A22], PMB2948 [B24], PMB2001 [A56], and PMB2707 [B44]) combined, 1 month after the third vaccination with bivalent rLP2086. This applied only to those subjects who had all 4 primary strains tested.
Additional exploratory assays to test hSBA on the secondary MnB strains as follows:
hSBA GMTs to each secondary MnB strain tested, at 1 month after the second and third vaccinations and/or at each blood sampling time point thereafter.
Proportions of subjects with an hSBA titer ≥LLOQ, to each secondary MnB strain at 1 month after the second and third vaccinations and/or at each blood sampling time point thereafter.

Analysis of Primary Endpoints

The primary analysis for the primary objectives was the proportion of subjects with an hSBA titer ≥LLOQ 1 month after the third vaccination, for each of the 4 primary MnB test strains in healthy toddlers aged 12 to <18 months, and 18 to <24 months, at study entry respectively. The evaluable immunogenicity population was used for this summary and both percentages and confidence intervals (CIs) are displayed.

Analysis of Secondary Endpoints

All of the analyses performed on the mITT population were considered as secondary analyses.

Secondary analyses also included percent of subjects with hSBA titers ≥LLOQ for each of the 4 primary MnB test strains 1 month following the third vaccination for both the evaluable immunogenicity population and for the mITT population.

For this Example, the percentage of subjects with hSBA titers ≥LLOQ for each of the 4 primary MnB test strains 1 month following the second vaccination and 1 month after the third vaccination were analyzed using both the evaluable immunogenicity population and the mITT population. For the final analysis, the percentage of subjects with hSBA titers ≥LLOQ for each of the 4 primary MnB test strains 6, 12, 24, 36, and 48 months after the third vaccination will be analyzed using both the evaluable immunogenicity population and the mITT population.

The percentage of subjects with hSBA titers ≥LLOQ, 1:4, 1:8, 1:16, 1:32, 1:64, 1:128 for each of the 4 primary MnB test strains at each applicable blood sampling visit were analyzed using both the evaluable immunogenicity population and the mITT population.

The GMTs for each of the primary MnB test strains at each applicable blood sampling visit were summarized for the evaluable immunogenicity population and the mITT population.

Analysis of Exploratory Endpoints

The proportion of subjects achieving at least a 4-fold increase in hSBA titer from baseline to 1 month after the second and third vaccinations with bivalent rLP2086 was summarized for the evaluable immunogenicity population and the mITT population.

Subgroup Analysis

Some immunogenicity and safety endpoints were descriptively summarized by sex, by country, and within age strata.

Results

Subject Disposition and Demography:

A total of 396 subjects 12 to <24 months of age were randomized in this study. Of the subjects randomized, a total of 44 subjects received 60 µg of bivalent rLP2086, 220 subjects received 120 µg of bivalent rLP2086, and 132 subjects received HAV vaccine/saline. There were 198 subjects randomized in each of the age strata (12 to <18 months and 18 to <24 months).

Of the 396 randomized subjects, 385 (97.2%) subjects completed the vaccination phase (from the first study vaccination [Visit 1] through 1 month after Vaccination 3 [Visit 7]) of the study. A total of 386 (97.5%) subjects completed the follow-up phase (from Visit 7 to 6 months after Vaccination 3 [Visit 8]). Overall, a total of 381 (96.2%) subjects completed all study visits up to the 6-month follow-up visit (Visit 8) and completion status was similar for each age stratum (189 [95.5%] subjects and 192 [97.0%] subjects in the 12 to <18 months and 18 to <24 months age strata, respectively).

Overall, 52.8% of subjects were female, and the majority of the subjects were white (94.4%) and non-Hispanic/non-Latino (99.5%). The mean age (SD) at first vaccination was 17.3 (3.61) months (range of 12 to 23 months). Demographic characteristics were generally similar among the vaccine groups.

The characteristics of ITT and mITT populations were similar to the characteristics of the safety population.

Immunogenicity Results:

The primary objectives of this study were to describe the immune response to bivalent rLP2086 as measured by hSBA against 4 primary MnB test strains, 2 expressing an LP2086 subfamily A protein and 2 expressing an LP2086 subfamily B protein, measured 1 month after the third vaccination in healthy subjects 12 to <18 months of age and 18 to <24 months of age. The description of immune responses for the combined age stratum (12 to <24 months) was a secondary objective. The primary endpoints for the primary objectives were the proportions of subjects in each age stratum achieving hSBA titers ≥LLOQ for each of the 4 primary MnB strains 1 month after the third vaccination.

A robust immune response was observed at both dose levels for toddlers 12 to <18 months of age and for toddlers 18 to <24 months of age, as well as for the combined age stratum (12 to <24 months) 1 month after the third dose of bivalent rLP2086, as confirmed by the proportion of subjects achieving an hSBA titer ≥LLOQ (1:8 for A56, B24 and B44; 1:16 for A22) for each of the 4 primary MnB test strains. For the 60-µg group, the proportion of subjects achieving an hSBA titer ≥LLOQ ranged from 88.9% to 100.0% for the younger toddlers (12 to <18 months) and from 81.8% to 100.0% for the older toddlers (18 to <24 months) after 3 doses. For the 120-µg group, the proportion of subjects achieving an hSBA titer ≥LLOQ ranged from 71.1% to 100.0% for toddlers 12 to <18 months of age and from 72.0% to 100.0% for toddlers 18 to <24 months of age after 3 doses. For the combined age stratum the proportion of subjects achieving an hSBA titer ≥LLOQ for each of the 4 primary MnB test strains 1 month after the third vaccination ranged from 85.0% to 100.0% for the 60-µg group and from 71.6% to 100.0% for the 120-µg group. These findings are further supported by increases in GMTs (range from 4.0 to 8.5 at baseline to 15.1 to 171.4 at 1 month after Vaccination 3) and in the proportion of subjects achieving an hSBA titer ≥1:4 (71.1% to 100.0%) or ≥1:16 (63.6% to 100.0%) against each of the 4 primary MnB test strains after 3 doses of bivalent rLP2086 compared to baseline across both age strata and dose levels. Additionally, the proportion of subjects for the combined age stratum achieving an hSBA fold rise ≥4 from baseline to 1 month after the third vaccination for each of the 4 primary MnB test strains ranged from 67.4% to 100.0% for both dose levels. In conclusion, 3 doses of either 60 µg or 120 µg of bivalent rLP2086 administered on a 0-, 2-, 6-month schedule, induced robust immune responses in toddlers 12 to <24 months of age (both individual and combined age strata).

The secondary objective of the study was to describe immune responses 1 month after the second dose of bivalent rLP2086, as assessed by ≥LLOQ responses, defined hSBA titers, and hSBA GMTs for the 2 age strata and the combined age stratum. For the combined age stratum, the proportion of subjects achieving an hSBA titer ≥LLOQ after the second dose of bivalent rLP2086 (administered 2 months after the first dose) ranged from 57.9% to 94.7% for subjects in the 60-µg group and from 33.7% to 100.0% for subjects in the 120-µg group.

Similar results were obtained for the 2 individual age strata with no clinically meaningful differences between the younger and older age strata. These findings are supported by increases in GMTs (range 7.2 to 110.6) over baseline and in the proportion of subjects achieving an hSBA titer ≥1:4 (36.0% to 100.0%) or ≥1:16 (32.6% to 100%) against each of the 4 primary MnB test strains after 2 doses of bivalent rLP2086 compared to baseline across both dose levels for the combined age stratum. Similar results were obtained for the 2 individual age strata. Additionally, the proportion of subjects for the combined age stratum achieving an hSBA fold rise ≥4 from baseline to 1 month after the second vaccination for each of the 4 primary MnB test strains ranged from 30.2% to 98.9%. In conclusion, 2 doses of either 60 µg or 120 µg of bivalent rLP2086 administered 2 months apart induced immune responses in toddlers 12 to <24 months of age (both individual and combined age strata). In summary, at both the 60-µg and 120-µg dose levels, bivalent rLP2086 given as 3 doses on a 0-, 2-, and 6-month schedule elicits a robust immune response among toddlers 12 to <24 months of age with protective antibody titers achieved as measured by hSBA in a high proportion of subjects after the third dose.

Conclusions:

In conclusion, the 60-µg and 120-µg dose levels of bivalent rLP2086 when administered to toddlers 12 to <24 months of age on a 0-, 2-, and 6-month schedule elicit protective antibody titers after the third dose as measured by hSBAs. The vaccine, as administered in this study, was safe and well tolerated with an acceptable safety profile for toddlers 12 to <24 months of age.

Example 21: A Phase 2, Randomized, Controlled, Observer-Blinded Study Conducted to Describe the Immunogenicity, Safety, and Tolerability of a *Neisseria meningitidis* Serogroup B Bivalent Recombinant Lipoprotein 2086 Vaccine (Bivalent rLP2086) when Administered to Healthy Toddlers Aged 12 to <18 Months or 18 to <24 Months (B1971035-CSR)

This Phase 2 study was conducted in 2 stages. Stage 1 was designed and conducted to assess the safety, tolerability, and immunogenicity of bivalent rLP2086 in healthy toddlers aged 12 to <24 months through 12 months after the last study vaccination vaccination (Visit 10). Stage 1 was composed of a sentinel-enrollment phase with 4 sentinel cohorts and an expanded-enrollment phase. In the sentinel cohorts, bivalent rLP2086 was administered at 2 dose levels (60 µg and 120 µg) in 2 age strata (12 to <15 months and 18 to <24 months). Selection of dose level for the expanded-enrollment phase was based on an internal review committee (IRC) review of the safety profile of the 2 dose levels. Stage 2 was planned to assess the duration of the immune response up through 4 years after the final study vaccination.

Primary Immunogenicity Objectives

To describe the immune response as measured by hSBA performed with 4 primary MnB strains, 2 expressing an LP2086 subfamily A protein and 2 expressing an LP2086 subfamily B protein, measured 1 month after the third vaccination with bivalent rLP2086, in healthy toddlers aged 12 to <18 months at study entry.

To describe the immune response as measured by hSBA performed with 4 primary MnB strains, 2 expressing an LP2086 subfamily A protein and 2 expressing an LP2086 subfamily B protein, measured 1 month after the third vaccination with bivalent rLP2086, in healthy toddlers aged 18 to <24 months at study entry.

Secondary Immunogenicity Objectives

To describe the immune response as measured by hSBA performed with 4 primary MnB test strains, 2 expressing an LP2086 subfamily A protein and 2 expressing an LP2086 subfamily B protein, measured 1 month after the third vaccination with bivalent rLP2086, in healthy toddlers aged 12 to <24 months at study entry (ie, both age strata combined).

To describe the immune response as measured by hSBA performed with 4 primary MnB test strains, 2 expressing an LP2086 subfamily A protein and 2 expressing an LP2086 subfamily B protein, measured 1 month after the second vaccination and 6, 12, 24, 36, and 48 months after the third vaccination in healthy toddlers aged 12 to <18 months and 18 to <24 months at study entry, and in both age strata combined.

Exploratory Immunogenicity Objectives

To further describe the immune response as measured by hSBA performed with 4 primary MnB test strains, 2 expressing an LP2086 subfamily A protein and 2 expressing an LP2086 subfamily B protein, measured 1 month after the second vaccination and 1, 6, 12, 24, 36, and 48 months after the third vaccination with bivalent rLP2086 in healthy toddlers aged 12 to <18 months and 18 to <24 months at study entry, and in both age strata combined.

To further describe the immune response as measured by hSBA to secondary MnB test strains expressing LP2086 subfamily A and B proteins, at 1 month after the second vaccination and 1, 6, 12, 24, 36, and 48 months after the third vaccination in healthy toddlers aged 12 to <18 months and 18 to <24 months at study entry, and in both age strata combined.

Investigational Plan

Overall Study Design and Plan

The study is a Phase 2, randomized, active-controlled, observer-blinded, sponsor-unblinded, multicenter study in which approximately 396 healthy toddlers stratified by age, 12 to <18 months or 18 to <24 months old, were randomly assigned in a 2:1 ratio to receive bivalent rLP2086 (either of 2 dose levels [60 µg or 120 µg]) or a licensed pediatric HAV vaccine (0.5 mL)/sterile saline solution for injection (0.5-mL of 0.85% sodium chloride). The study was conducted in 2 stages. Stage 1 assessed vaccine immunogenicity, safety, and tolerability across 2 phases: a sentinel-enrollment phase and an expanded-enrollment phase. Stage 2 assessed the duration of the immune response to bivalent rLP2086.

The Stage 1 sentinel-enrollment phase was planned to include a total of 4 sentinel cohorts: 2 age strata for each dose level (60 µg or 120 µg) of bivalent rLP2086. The younger-aged sentinel cohorts were composed of subjects aged 12 to <15 months and the older-aged sentinel cohorts were composed of subjects aged 18 to <24 months. Each of the 4 sentinel cohorts was planned to enroll approximately 33 subjects. The sentinel-enrollment phase was staggered with reviews by an IRC at pre-specified points and stopping rules applied. The 120-µg dose level sentinel cohorts did not proceed until the 60-µg dose level was evaluated by the IRC as safe and tolerable in the sentinel cohort of the same age. The younger-aged 120-µg dose level sentinel cohort did not proceed until this dose level was evaluated by the IRC as safe and tolerable in the older-aged 120-µg dose level sentinel cohort.

Prior to the Stage 1 expanded-enrollment phase, the IRC reviewed all post-Vaccination 1, 7-day e-diary and SAE data obtained from sentinel subjects. Based on the review, the IRC selected the 120-µg bivalent rLP2086 dose level to be studied in the Stage 1 expanded-enrollment phase for both age strata. The younger-aged expanded-enrollment cohort (enrolling an additional 132 subjects) was extended to subjects aged 12 to <18 months and stratified by age into 2 subsets: aged 12 to <15 months and aged 15 to <18 months. The older-aged expanded enrollment cohort (enrolling an additional 132 subjects) enrolled subjects aged 18 to <24 months during the expanded-enrollment phase. The total study duration for subjects completing only Stage 1 will be approximately 18 months.

Stage 2 includes only those subjects randomly assigned to bivalent rLP2086 (irrespective of dose level). The total study duration for subjects who complete Stage 2 will be approximately 4.5 years (54 months).

Bivalent rLP2086 was administered at Months 0, 2, and 6 (Visits 1, 4, and 6). Pediatric HAV vaccine was administered at Months 0 and 6 (Visits 1 and 6), and saline was administered at Month 2 (Visit 4) to maintain the study blind.

Discussion of Study Design, Including Choice of Control Groups

This 2-stage study evaluated the safety, tolerability, and immunogenicity of bivalent rLP2086 at 2 dose levels (60 µg and 120 µg) in healthy toddlers aged 12 to <24 months.

HAV vaccine (at Months 0 and 6) was chosen as the control in this study. In comparison to other recommended vaccines for this age group, HAV vaccine has a better tolerability profile. In addition, HAV vaccine confers a benefit to subjects who might be at increased risk for hepatitis A viral infection either during future travel or during other exposures. The generally recommended regimen for HAV vaccine is 2 doses at Months 0 and 6. In this study, saline was given at Month 2 to maintain the study blind.

Vaccines Administered

Bivalent rLP2086 (60 µg or 120 µg) was administered 3 times over the course of the study: the first vaccination at Visit 1 (Month 0), second vaccination at Visit 4 (Month 2), and third vaccination at Visit 6 (Month 6). Bivalent rLP2086 was administered as an intramuscular injection into either the deltoid muscle or anterolateral thigh muscle. HAV vaccine was administered twice over the course of the study: the first vaccination at Visit 1 (Month 0) and third vaccination at Visit 6 (Month 6). Saline was administered at the second vaccination (Month 2) time point. HAV vaccine/saline was administered as an intramuscular injection into either the deltoid muscle or anterolateral thigh muscle. Only a third-party unblinded medically qualified member of the study staff administered the investigational product. If muscle mass in the deltoid was not adequate for intramuscular injection, then the thigh was the preferred injection site. Site of administration (eg, left/right arm/thigh) was noted in the source notes and on the CRF.

Identity of Investigational Product(s)

Bivalent rLP2086 (containing either 30 µg [60-µg dose level] or 60 µg [120-µg dose level] each of a purified subfamily A and subfamily B rLP2086 protein, adsorbed to aluminum in a sterile buffered isotonic suspension) was provided in a 0.5-mL dose for injection.

A licensed pediatric HAV vaccine was provided in a 0.5-mL dose for injection.

The placebo was sterile saline for injection (0.85% sodium chloride) supplied as a 0.5-mL dose.

The investigational products (bivalent rLP2086, HAV vaccine, and saline) were provided by the sponsor to each study site. Study vaccines were packed and labeled as investigational product in accordance with current guidelines and applicable local and legal regulatory requirements. Each investigational product was labeled with a unique kit number.

Selection of Vaccination Regimen

Bivalent rLP2086 (either 60 µg or 120 µg) was administered on a Month 0, 2, and 6 schedule. The control group of subjects received HAV vaccine at Month 0 and Month 6 and an injection of saline at Month 2 to maintain the study blind.

Bivalent rLP2086 Serum Bactericidal Assay—Primary Test Strains

For assessment of the immune response to bivalent rLP2086, functional antibodies were analyzed in hSBAs with meningococcal serogroup B strains. The hSBA measures antibodies in human sera that mediate complement-dependent killing of the target meningococcal strain. Four (4) primary MnB test strains, PMB80 (A22), PMB2001 (A56), PMB2948 (B24), and PMB2707 (B44), each expressing a factor H binding protein (fHBP) variant heterologous to the vaccine component antigens, were used in the hSBAs for determination of the immunogenicity endpoints in this study.

Due to serum volume limitations, 2 of the primary strains (PMB80 [A22] and PMB2948 [B24]) were tested at each blood sampling time point for half of the subjects (in both age strata), and the other 2 primary strains (PMB2001 [A56] and PMB2707 [B44]) were tested at each blood sampling time point for the remaining half of the subjects.

Once all subjects completed enrollment (Visit 1), the independent statistical center (ISC), a statistical team not involved in the conduct of the study, provided 2 subject listings (randomly selected, 50% of subjects to be tested for PMB80 [A22]/PMB2948 [B24] and the remaining 50% of subjects to be tested for PMB2001 [A56]/PMB2707 [B44]) to the sponsor's sample management team. Both listings followed the same randomization ratio (2:1) and age-strata distribution as in the study design. The same strain pair (PMB80 [A22]/PMB2948 [B24] or PMB2001 [A56]/PMB2707 [B44]) was tested across all visits for the same subjects.

Additional Assays

Once testing for the primary analyses was completed, and if sufficient volume of sera was available, additional testing to assess the immune response to bivalent rLP2086 could be considered as follows: PMB80 (A22) and PMB2948 (B24) could be tested in serum samples from the 50% of subjects who received bivalent rLP2086 and whose serum samples were originally tested for PMB2001 (A56) and PMB2707 (B44). Conversely, PMB2001 (A56) and PMB2707 (B44) could be tested in serum samples from the 50% of subjects who received bivalent rLP2086 and were originally tested for PMB80 (A22) and PMB2948 (B24). Testing for secondary strains could be performed.

Immunogenicity Analysis

Comparisons of Interest and Endpoints—Primary Immunogenicity Endpoints

The primary immunogenicity endpoints were:
  Proportions of subjects achieving an hSBA titer lower limit of quantitation (LLOQ) 1 month after the third vaccination, for each of the 4 primary MnB test strains in healthy toddlers 12 to <18 months of age at study entry.
  Proportions of subjects achieving an hSBA titer ≥LLOQ 1 month after the third vaccination, for each of the 4 primary MnB test strains in healthy toddlers 18 to <24 months of age at study entry.

Comparisons of Interest and Endpoints—Secondary Immunogenicity Endpoints

All secondary immunogenicity endpoints for the entire study are described here but this Example will present results for the immunogenicity endpoints applicable to Visits 1 to 7 (Vaccination 1 to 3 months after Vaccination 3) only.

The following endpoint applied to results in healthy subjects 12 months to <24 months of age (ie, both age strata combined) at study entry:
  Proportion of subjects with hSBA titers ≥LLOQ for each of the 4 primary MnB test strains 1 month after the third vaccination with bivalent rLP2086 and 6, 12, 24, 36, and 48 months after the third vaccination with bivalent rLP2016.

The following endpoints applied to results in healthy subjects 12 to <18 months of age and 18 to <24 months of age at study entry, and in both age strata combined:
  Proportions of subjects with hSBA titers ≥LLOQ for each of the 4 primary MnB test strains at 1 month after the second vaccination with bivalent rLP2086.
  Proportions of subjects with hSBA titers ≥LLOQ, ≥1:4, ≥1:16, ≥1:32, ≥1:64, and ≥1:128 for each of the 4 primary MnB strains at each applicable blood sampling visit.
  hSBA geometric mean titers (GMTs) for each of the 4 primary MnB test strains at each applicable blood sampling visit.

Exploratory Immunogenicity Endpoints

All of the exploratory endpoints specified below applied to hSBA results from all healthy subjects 12 to <18 months of age or 18 to <24 months of age at study entry, and in both age strata combined, who received bivalent rLP2086 and were tested for the appropriate strain at the appropriate time point:

Proportions of subjects with hSBA titers ≥LLOQ, ≥1:4, ≥1:16, ≥1:32, ≥1:64, and ≥1:128 at each applicable blood sampling time point.

hSBA GMTs for each of the 4 primary MnB strains at each applicable blood sampling visit.

Proportions of subjects achieving at least a 4-fold increase in hSBA titer from baseline to 1 month after the third vaccination with bivalent rLP2086 for each of the 4 primary test strains:

For subjects with a baseline hSBA titer below the limit of detection (LOD) or an hSBA titer of <1:4, a 4-fold response was defined as an hSBA titer of ≥1:16.

For subjects with a baseline hSBA titer of ≥LOD (ie, hSBA titer of ≥4) and <LLOQ, a 4-fold response was defined as an hSBA titer of ≥4 times the LLOQ.

For subjects with a baseline hSBA titer of ≥LLOQ, a 4-fold response was defined as an hSBA titer of ≥4 times the baseline titer.

The following endpoints were considered if there had been sufficient sera available to test each subject for all 4 primary strains and/or to test subjects for the secondary strains.

Proportions of subjects achieving an hSBA titer ≥LLOQ for all 4 primary test strains (PMB80 [A22], PMB2948 [B24], PMB2001 [A56], and PMB2707 [B44]) combined, 1 month after the third vaccination with bivalent rLP2086. This applied only to those subjects who had all 4 primary strains tested.

Additional exploratory assays to test hSBA on the secondary MnB strains as follows:

hSBA GMTs to each secondary MnB strain tested, at 1 month after the second and third vaccinations and/or at each blood sampling time point thereafter.

Proportions of subjects with an hSBA titer ≥LLOQ, to each secondary MnB strain at 1 month after the second and third vaccinations and/or at each blood sampling time point thereafter.

Analysis Populations

Modified Intent-to-Treat Population

All randomized subjects who had at least 1 valid and determinate assay result related to a proposed analysis were included in the modified intent-to-treat (mITT) population. This analysis set was for the immunogenicity analysis. Subjects were analyzed according to the investigational product to which they were randomized in the analysis of the mITT population.

Methods of Analysis

The control group and each dose-level group from different cohorts within the same age stratum were pooled for analysis. All of the immunogenicity analyses were summarized for each age stratum separately, as well as for the overall population.

This was not a hypothesis-testing study; thus, an estimation approach was used to assess the primary, secondary, and exploratory objectives in this study.

The LLOQ was 1:16 for PMB80 (A22), 1:8 for PMB2001 (A56), 1:8 for PMB2707 (B44), and 1:8 for PMB2948 (B24).

For the calculation of GMTs, hSBA results below the LLOQ were set to 0.5×LLOQ for the primary analysis.

Analysis of Primary Endpoints

The primary analysis for the primary objectives was the proportion of subjects with an hSBA titer ≥LLOQ 1 month after the third vaccination, for each of the 4 primary MnB test strains in healthy toddlers aged 12 to <18 months, and 18 to <24 months, at study entry respectively. The evaluable immunogenicity population was used for this summary and both percentages and confidence intervals (CIs) are displayed.

Analysis of Secondary Endpoints

All of the analyses performed on the mITT population were considered as secondary analyses.

Analyses for secondary endpoints also included percent of subjects with hSBA titers ≥LLOQ for each of the 4 primary MnB test strains 1 month following the third vaccination for both the evaluable immunogenicity population and for the mITT population.

For this Example, the percentage of subjects with hSBA titers ≥LLOQ for each of the 4 primary MnB test strains at 1 month after Vaccination 2 and 1 month after Vaccination 3 were analyzed using both the evaluable immunogenicity population and the mITT population and presented in this report. The same analysis is planned for subsequent time points (6, 12, 24, 36, and 48 months after the third vaccination).

The percentage of subjects with hSBA titers ≥LLOQ, 1:4, 1:8, 1:16, 1:32, 1:64, 1:128 for each of the 4 primary MnB test strains at 1 month after Vaccination 2 and 1 month after Vaccination 3 were analyzed using both the evaluable immunogenicity population and the mITT population and presented in this report. The same analysis is planned for subsequent time points (6, 12, 24, 36, and 48 months after Vaccination 3).

The GMTs for each of the primary MnB test strains at 1 month following the second vaccination and 1 month after the third vaccination were summarized for the evaluable immunogenicity population and the mITT population and presented in this report. The same analysis is planned for subsequent time points (6, 12, 24, 36, and 48 months after Vaccination 3).

Analysis of Exploratory Endpoints

The proportion of subjects achieving at least a 4-fold increase in hSBA titer from baseline to 1 month after the second and third vaccinations with bivalent rLP2086 was summarized for the evaluable immunogenicity population and the mITT population.

Reverse Cumulative Distribution Curves

The empirical reverse cumulative distribution curves (RCDCs) were also assessed for each of the 4 primary MnB test strains and at 1 month after Vaccination 2 and 1 month after Vaccination 3 for the evaluable immunogenicity population.

Immunogenicity Evaluation

Populations Analyzed

The evaluable immunogenicity population was the primary analysis population for the immunogenicity analyses. The mITT population was used as a supportive immunogenicity population for the immunogenicity analyses.

A total of 348 (87.9%) subjects were included in the evaluable immunogenicity population, and 48 (12.1%) subjects were excluded from the evaluable immunogenicity population. Subjects could have been excluded from the immunogenicity populations for more than 1 reason. A total of 31 (7.8%) subjects were excluded from the evaluable immunogenicity population because they did not have scheduled prevaccination or postvaccination blood drawn (includes subjects who did not have samples taken and subjects with samples taken outside of the protocol-specified window), 13 (3.3%) subjects were not eligible or became ineligible for the study before or at the 1-month post-Vaccination 3 visit, 11 (2.8%) subjects did not receive vaccine as randomized at all vaccination visits, and 16 (4.0%) subjects received prohibited vaccines or treatments. A total of 84.3% of subjects 12 to <18 months of age and 91.4% of subjects 18 to <24 months of age were included in the evaluable immunogenicity population.

Immunogenicity Results

The primary analysis results including all of the immunogenicity data through 1 month after Vaccination 3 (Visit 7) are provided in the following sections. The analysis of immunogenicity endpoints was based on hSBA results for strains PMB2001 (A56) and PMB2707 (B44) for half of the subjects, and strains PMB80 (A22) and PMB2948 (B24) for the remaining half.

Primary and Secondary Endpoints
Proportion of Subjects Achieving an hSBA Titer LLOQ The primary immunogenicity endpoints were the proportions of subjects 12 to <18 months of age (at study entry), and 18 to <24 months of age (at study entry), achieving an hSBA titer ≥LLOQ for each of the 4 primary MnB test strains 1 month after the third vaccination with bivalent rLP2086. The proportion of all subjects in the combined age stratum achieving an hSBA titer ≥LLOQ for each of the 4 primary MnB test strains 1 month after the third vaccination with bivalent rLP2086, along with the proportion of subjects in the individual and combined age strata achieving an hSBA titer ≥LLOQ for each of the 4 primary MnB test strains 1 month after the second vaccination with bivalent rLP2086, were secondary endpoints.

The proportion of subjects in each age stratum achieving an hSBA titer ≥LLOQ for each of the 4 primary MnB test strains is presented in Table for the evaluable immunogenicity population.

For the combined age stratum the proportion of subjects achieving an hSBA titer ≥LLOQ at baseline was 0.0% and 3.1% for PMB80 (A22); 0.0% and 1.1% for PMB2001 (A56); 4.8% and 2.1% for PMB2948 (B24); and 0.0% and 1.1% for PMB2707 (B44) for the 60-μg and 120-μg groups, respectively.

At 1 month after Vaccination 2, the proportion of subjects achieving an hSBA titer ≥LLOQ for the 12 to <18 months age stratum was 90.0% and 64.4% for PMB80 (A22); 100.0% and 100.0% for PMB2001 (A56); 70.0% and 23.8% for PMB2948 (B24); and 77.8% and 72.3% for PMB2707 (B44) for the 60-μg and 120-μg groups, respectively. For the 18 to <24 months age stratum, the proportion of subjects achieving an hSBA titer ≥LLOQ was 66.7% and 84.0% for PMB80 (A22); 90.0% and 100.0% for PMB2001 (A56); 44.4% and 43.2% for PMB2948 (B24); and 60.0% and 63.8% for PMB2707 (B44) for the 60-μg and 120-μg groups, respectively. Overall, for the combined age stratum the proportion of subjects achieving an hSBA titer ≥LLOQ at 1 month after Vaccination 2 was 78.9% and 74.7% for PMB80 (A22); 94.7% and 100.0% for PMB2001 (A56); 57.9% and 33.7% for PMB2948 (B24); and 68.4% and 68.1% for PMB2707 (B44) for the 60-μg and 120-μg groups, respectively.

At 1 month after Vaccination 3, the proportion of subjects achieving an hSBA titer ≥LLOQ for the 12 to <18 months age stratum was 88.9% and 91.1% for PMB80 (A22); 100.0% and 100.0% for PMB2001 (A56); 88.9% and 71.1% for PMB2948 (B24); and 88.9% and 87.2% for PMB2707 (B44) for the 60-μg and 120-μg groups, respectively. In the 18 to <24 months age stratum, the proportion of subjects achieving an hSBA titer ≥LLOQ was 90.9% and 88.2% for PMB80 (A22); 100.0% and 100.0% for PMB2001 (A56); 81.8% and 72.0% for PMB2948 (B24); and 90.0% and 85.1% for PMB2707 (B44) for the 60-μg and 120-μg groups, respectively. Overall, for the combined age stratum the proportion of subjects achieving an hSBA titer ≥LLOQ at 1 month after Vaccination 3 was 90.0% and 89.6% for PMB80 (A22); 100.0% and 100.0% for PMB2001 (A56); 85.0% and 71.6% for PMB2948 (B24); and 89.5% and 86.2% for PMB2707 (B44) for the 60-μg and 120-μg groups, respectively.

In general, the proportion of subjects in the HAV/saline group achieving an hSBA titer ≥LLOQ did not change over time compared to baseline (Table 25).

Results for the mITT population were similar to those of the evaluable immunogenicity population.

Subgroup analyses of the proportion of subjects achieving an hSBA titer ≥LLOQ for each of the 4 primary MnB test strains were assessed for the evaluable immunogenicity population by sex and country. There were no clinically important differences observed in the subgroup analyses performed.

TABLE 25

Subjects With hSBA Titer ≥ LLOQ for Primary Strains - Evaluable Immunogenicity Population

| Strain (Variant) Sampling Time Point Age Strata | \multicolumn{4}{c}{Vaccine Group (as Randomized)} | | | | | | | | |
|---|---|---|---|---|---|---|---|---|---|---|---|---|
| | 60 μg rLP2086 | | | | 120 μg rLP2086 | | | | HAV/Saline | | | |
| | $N^a$ | $n^b$ | (%) | (95% CI)$^c$ | $N^a$ | $n^b$ | (%) | (95% CI)$^c$ | $N^a$ | $n^b$ | (%) | (95% CI)$^c$ |
| PMB80 (A22) Before Vaccination 1 | | | | | | | | | | | | |
| 12 to <24 Months | 20 | 0 | (0.0) | (0.0, 16.8) | 97 | 3 | (3.1) | (0.6, 8.8) | 61 | 1 | (1.6) | (0.0, 8.8) |
| 12 to <18 Months | 9 | 0 | (0.0) | (0.0, 33.6) | 46 | 1 | (2.2) | (0.1, 11.5) | 31 | 0 | (0.0) | (0.0, 11.2) |
| 18 to <24 Months | 11 | 0 | (0.0) | (0.0, 28.5) | 51 | 2 | (3.9) | (0.5, 13.5) | 30 | 1 | (3.3) | (0.1, 17.2) |
| 1 Month after Vaccination 2 | | | | | | | | | | | | |
| 12 to <24 Months | 19 | 15 | (78.9) | (54.4, 93.9) | 95 | 71 | (74.7) | (64.8, 83.1) | 59 | 1 | (1.7) | (0.0, 9.1) |
| 12 to <18 Months | 10 | 9 | (90.0) | (55.5, 99.7) | 45 | 29 | (64.4) | (48.8, 78.1) | 30 | 0 | (0.0) | (0.0, 11.6) |
| 18 to <24 Months | 9 | 6 | (66.7) | (29.9, 92.5) | 50 | 42 | (84.0) | (70.9, 92.8) | 29 | 1 | (3.4) | (0.1, 17.8) |
| 1 Month after Vaccination 3 | | | | | | | | | | | | |
| 12 to <24 Months | 20 | 18 | (90.0) | (68.3, 98.8) | 96 | 86 | (89.6) | (81.7, 94.9) | 60 | 3 | (5.0) | (1.0, 13.9) |
| 12 to <18 Months | 9 | 8 | (88.9) | (51.8, 99.7) | 45 | 41 | (91.1) | (78.8, 97.5) | 31 | 1 | (3.2) | (0.1, 16.7) |
| 18 to <24 Months | 11 | 10 | (90.9) | (58.7, 99.8) | 51 | 45 | (88.2) | (76.1, 95.6) | 29 | 2 | (6.9) | (0.8, 22.8) |

TABLE 25-continued

Subjects With hSBA Titer ≥ LLOQ for Primary Strains - Evaluable Immunogenicity Population

| Strain (Variant) Sampling Time Point Age Strata | 60 μg rLP2086 | | | | Vaccine Group (as Randomized) 120 μg rLP2086 | | | | HAV/Saline | | | |
|---|---|---|---|---|---|---|---|---|---|---|---|---|
| | N[a] | n[b] | (%) | (95% CI)[c] | N[a] | n[b] | (%) | (95% CI)[c] | N[a] | n[b] | (%) | (95% CI)[c] |
| PMB2001 (A56) Before Vaccination 1 | | | | | | | | | | | | |
| 12 to <24 Months | 19 | 0 | (0.0) | (0.0, 17.6) | 95 | 1 | (1.1) | (0.0, 5.7) | 53 | 0 | (0.0) | (0.0, 6.7) |
| 12 to <18 Months | 9 | 0 | (0.0) | (0.0, 33.6) | 46 | 0 | (0.0) | (0.0, 7.7) | 24 | 0 | (0.0) | (0.0, 14.2) |
| 18 to <24 Months | 10 | 0 | (0.0) | (0.0, 30.8) | 49 | 1 | (2.0) | (0.1, 10.9) | 29 | 0 | (0.0) | (0.0, 11.9) |
| 1 Month after Vaccination 2 | | | | | | | | | | | | |
| 12 to <24 Months | 19 | 18 | (94.7) | (74.0, 99.9) | 95 | 95 | (100.0) | (96.2, 100.0) | 52 | 0 | (0.0) | (0.0, 6.8) |
| 12 to <18 Months | 9 | 9 | (100.0) | (66.4, 100.0) | 47 | 47 | (100.0) | (92.5, 100.0) | 23 | 0 | (0.0) | (0.0, 14.8) |
| 18 to <24 Months | 10 | 9 | (90.0) | (55.5, 99.7) | 48 | 48 | (100.0) | (92.6, 100.0) | 29 | 0 | (0.0) | (0.0, 11.9) |
| 1 Month after Vaccination 3 | | | | | | | | | | | | |
| 12 to <24 Months | 19 | 19 | (100.0) | (82.4, 100.0) | 95 | 95 | (100.0) | (96.2, 100.0) | 54 | 1 | (1.9) | (0.0, 9.9) |
| 12 to <18 Months | 9 | 9 | (100.0) | (66.4, 100.0) | 47 | 47 | (100.0) | (92.5, 100.0) | 24 | 0 | (0.0) | (0.0, 14.2) |
| 18 to <24 Months | 10 | 10 | (100.0) | (69.2, 100.0) | 48 | 48 | (100.0) | (92.6, 100.0) | 30 | 1 | (3.3) | (0.1, 17.2) |
| PMB2948 (B24) Before Vaccination 1 | | | | | | | | | | | | |
| 12 to <24 Months | 21 | 1 | (4.8) | (0.1, 23.8) | 97 | 2 | (2.1) | (0.3, 7.3) | 61 | 1 | (1.6) | (0.0, 8.8) |
| 12 to <18 Months | 10 | 0 | (0.0) | (0.0, 30.8) | 46 | 1 | (2.2) | (0.1, 11.5) | 31 | 0 | (0.0) | (0.0, 11.2) |
| 18 to <24 Months | 11 | 1 | (9.1) | (0.2, 41.3) | 51 | 1 | (2.0) | (0.0, 10.4) | 30 | 1 | (3.3) | (0.1, 17.2) |
| 1 Month after Vaccination 2 | | | | | | | | | | | | |
| 12 to <24 Months | 19 | 11 | (57.9) | (33.5, 79.7) | 86 | 29 | (33.7) | (23.9, 44.7) | 59 | 1 | (1.7) | (0.0, 9.1) |
| 12 to <18 Months | 10 | 7 | (70.0) | (34.8, 93.3) | 42 | 10 | (23.8) | (12.1, 39.5) | 30 | 0 | (0.0) | (0.0, 11.6) |
| 18 to <24 Months | 9 | 4 | (44.4) | (13.7, 78.8) | 44 | 19 | (43.2) | (28.3, 59.0) | 29 | 1 | (3.4) | (0.1, 17.8) |
| 1 Month after Vaccination 3 | | | | | | | | | | | | |
| 12 to <24 Months | 20 | 17 | (85.0) | (62.1, 96.8) | 95 | 68 | (71.6) | (61.4, 80.4) | 60 | 3 | (5.0) | (1.0, 13.9) |
| 12 to <18 Months | 9 | 8 | (88.9) | (51.8, 99.7) | 45 | 32 | (71.1) | (55.7, 83.6) | 31 | 1 | (3.2) | (0.1, 16.7) |
| 18 to <24 Months | 11 | 9 | (81.8) | (48.2, 97.7) | 50 | 36 | (72.0) | (57.5, 83.8) | 29 | 2 | (6.9) | (0.8, 22.8) |
| PMB2707 (B44) Before Vaccination 1 | | | | | | | | | | | | |
| 12 to <24 Months | 19 | 0 | (0.0) | (0.0, 17.6) | 95 | 1 | (1.1) | (0.0, 5.7) | 54 | 0 | (0.0) | (0.0, 6.6) |
| 12 to <18 Months | 9 | 0 | (0.0) | (0.0, 33.6) | 46 | 1 | (2.2) | (0.1, 11.5) | 24 | 0 | (0.0) | (0.0, 14.2) |
| 18 to <24 Months | 10 | 0 | (0.0) | (0.0, 30.8) | 49 | 0 | (0.0) | (0.0, 7.3) | 30 | 0 | (0.0) | (0.0, 11.6) |
| 1 Month after Vaccination 2 | | | | | | | | | | | | |
| 12 to <24 Months | 19 | 13 | (68.4) | (43.4, 87.4) | 94 | 64 | (68.1) | (57.7, 77.3) | 52 | 0 | (0.0) | (0.0, 6.8) |
| 12 to <18 Months | 9 | 7 | (77.8) | (40.0, 97.2) | 47 | 34 | (72.3) | (57.4, 84.4) | 23 | 0 | (0.0) | (0.0, 14.8) |
| 18 to <24 Months | 10 | 6 | (60.0) | (26.2, 87.8) | 47 | 30 | (63.8) | (48.5, 77.3) | 29 | 0 | (0.0) | (0.0, 11.9) |
| 1 Month after Vaccination 3 | | | | | | | | | | | | |
| 12 to <24 Months | 19 | 17 | (89.5) | (66.9, 98.7) | 94 | 81 | (86.2) | (77.5, 92.4) | 54 | 0 | (0.0) | (0.0, 6.6) |
| 12 to <18 Months | 9 | 8 | (88.9) | (51.8, 99.7) | 47 | 41 | (87.2) | (74.3, 95.2) | 24 | 0 | (0.0) | (0.0, 14.2) |
| 18 to <24 Months | 10 | 9 | (90.0) | (55.5, 99.7) | 47 | 40 | (85.1) | (71.7, 93.8) | 30 | 0 | (0.0) | (0.0, 11.6) |

Abbreviations: hSBA = serum bactericidal assay using human complement; LLOQ = lower limit of quantitation.
Note:
LLOQ = 1:16 for A22; 1:8 for A56, B24, and B44.
[a]N = number of subjects with valid and determinate hSBA titers for the given strain.
[b]n = Number of subjects with observed hSBA titer ≥ LLOQ for the given strain at the given time point.
[c]Exact 2-sided CI based upon observed proportion of subjects, using the Clopper and Pearson method.

hSBA GMTs

The hSBA GMTs for each of the 4 primary MnB test strains for subjects 12 to <18 months of age, 18 to <24 months of age, and for the combined age stratum, at baseline, 1 month after the second vaccination, and 1 month after the third vaccination with bivalent rLP2086 was a secondary endpoint. Table 26 provides hSBA GMTs for the 4 primary MnB strains for the evaluable immunogenicity population.

For the combined age stratum, the hSBA GMTs at baseline were 8.0 and 8.4 for PMB80 (A22); 4.0 and 4.1 for PMB2001 (A56); 4.4 and 4.1 for PMB2948 (B24); and 4.0 and 4.0 for PMB2707 (B44) for the 60-μg and 120-μg groups, respectively.

At 1 month after Vaccination 2, the hSBA GMTs for the 12 to <18 months age stratum were 42.2 and 24.6 for PMB80 (A22); 101.6 and 117.2 for PMB2001 (A56); 10.6 and 6.0 for PMB2948 (B24); and 23.5 and 22.1 for PMB2707 (B44) for the 60-μg and 120-μg groups, respectively. For the 18 to <24 months age stratum, the hSBA GMTs were 23.5 and 36.8 for PMB80 (A22); 68.6 and 104.6 for PMB2001 (A56); 6.9 and 8.5 for PMB2948 (B24); and 21.1 and 17.0 for PMB2707 (B44) for the 60-μg and 120-μg groups, respectively. Overall, at 1 month after Vaccination 2 the hSBA GMTs for the combined age stratum were 32.0 and 30.4 for PMB80 (A22); 82.6 and 110.6 for PMB2001 (A56); 8.6 and 7.2 for PMB2948 (B24); and 22.2 and 19.4 for PMB2707 (B44) for the 60-µg and 120-µg groups, respectively.

At 1 month after Vaccination 3, the hSBA GMTs for the 12 to <18 months age stratum were 80.6 and 63.0 for PMB80 (A22); 109.7 and 190.6 for PMB2001 (A56); 20.2 and 15.8 for PMB2948 (B24); and 29.6 and 46.3 for PMB2707 (B44) for the 60-µg and 120-µg groups, respectively. For the 18 to <24 months age stratum, the hSBA GMTs were 82.3 and 71.4 for PMB80 (A22); 181.0 and 154.4 for PMB2001 (A56); 17.0 and 14.5 for PMB2948 (B24); and 34.3 and 44.9 for PMB2707 (B44) for the 60-µg and 120-µg groups, respectively.

Overall, at 1 month after Vaccination 3, the hSBA GMTs for the combined age stratum were 81.6 and 67.3 for PMB80 (A22); 142.8 and 171.4 for PMB2001 (A56); 18.4 and 15.1 for PMB2948 (B24); and 32.0 and 45.6 for PMB2707 (B44) for the 60-µg and 120-µg groups, respectively.

In general, the hSBA GMTs for subjects in the HAV/saline group did not change over time compared to baseline.

TABLE 26 hSBA GMTs for Primary Strains - Evaluable Immunogenicity Population

| Strain (Variant) Sampling Time Point | Vaccine Group (as Randomized) | | | | | | | | |
|---|---|---|---|---|---|---|---|---|---|
| | 60 µg rLP2086 | | | 120 µg rLP2086 | | | HAV/Saline | | |
| Age Strata | N[a] | GMT[b] | (95% CI)[c] | N[a] | GMT[b] | (95% CI)[c] | N[a] | GMT[b] | (95% CI)[c] |
| PMB80 (A22) Before Vaccination 1 | | | | | | | | | |
| 12 to <24 Months | 20 | 8.0 | (NE, NE) | 97 | 8.4 | (7.9, 9.0) | 61 | 8.1 | (7.9, 8.3) |
| 12 to <18 Months | 9 | 8.0 | (NE, NE) | 46 | 8.5 | (7.5, 9.6) | 31 | 8.0 | (NE, NE) |
| 18 to <24 Months | 11 | 8.0 | (NE, NE) | 51 | 8.3 | (7.8, 8.9) | 30 | 8.2 | (7.8, 8.6) |
| 1 Month after Vaccination 2 | | | | | | | | | |
| 12 to <24 Months | 19 | 32.0 | (19.7, 52.0) | 95 | 30.4 | (24.3, 38.1) | 59 | 8.3 | (7.7, 8.9) |
| 12 to <18 Months | 10 | 42.2 | (22.6, 79.1) | 45 | 24.6 | (17.8, 34.2) | 30 | 8.0 | (NE, NE) |
| 18 to <24 Months | 9 | 23.5 | (10.1, 54.9) | 50 | 36.8 | (26.9, 50.3) | 29 | 8.6 | (7.4, 10.0) |
| 1 Month after Vaccination 3 | | | | | | | | | |
| 12 to <24 Months | 20 | 81.6 | (46.6, 142.8) | 96 | 67.3 | (53.7, 84.3) | 60 | 8.6 | (7.9, 9.3) |
| 12 to <18 Months | 9 | 80.6 | (30.9, 210.7) | 45 | 63.0 | (44.5, 89.3) | 31 | 8.6 | (7.5, 9.8) |
| 18 to <24 Months | 11 | 82.3 | (36.5, 185.8) | 51 | 71.4 | (52.7, 96.6) | 29 | 8.6 | (7.7, 9.6) |
| PMB2001 (A56) Before Vaccination 1 | | | | | | | | | |
| 12 to <24 Months | 19 | 4.0 | (NE, NE) | 95 | 4.1 | (3.9, 4.3) | 53 | 4.0 | (NE, NE) |
| 12 to <18 Months | 9 | 4.0 | (NE, NE) | 46 | 4.0 | (NE, NE) | 24 | 4.0 | (NE, NE) |
| 18 to <24 Months | 10 | 4.0 | (NE, NE) | 49 | 4.2 | (3.8, 4.5) | 29 | 4.0 | (NE, NE) |
| 1 Month after Vaccination 2 | | | | | | | | | |
| 12 to <24 Months | 19 | 82.6 | (51.4, 132.9) | 95 | 110.6 | (92.0, 133.0) | 52 | 4.0 | (NE, NE) |
| 12 to <18 Months | 9 | 101.6 | (64.0, 161.2) | 47 | 117.2 | (89.7, 153.0) | 23 | 4.0 | (NE, NE) |
| 18 to <24 Months | 10 | 68.6 | (28.2, 166.8) | 48 | 104.6 | (80.4, 136.0) | 29 | 4.0 | (NE, NE) |
| 1 Month after Vaccination 3 | | | | | | | | | |
| 12 to <24 Months | 19 | 142.8 | (85.5, 238.6) | 95 | 171.4 | (141.6, 207.4) | 54 | 4.2 | (3.8, 4.5) |
| 12 to <18 Months | 9 | 109.7 | (70.4, 171.1) | 47 | 190.6 | (146.9, 247.4) | 24 | 4.0 | (NE, NE) |
| 18 to <24 Months | 10 | 181.0 | (68.6, 477.9) | 48 | 154.4 | (116.3, 205.1) | 30 | 4.3 | (3.7, 4.9) |
| PMB2948 (B24) Before Vaccination 1 | | | | | | | | | |
| 12 to <24 Months | 21 | 4.4 | (3.6, 5.4) | 97 | 4.1 | (4.0, 4.3) | 61 | 4.2 | (3.8, 4.6) |
| 12 to <18 Months | 10 | 4.0 | (NE, NE) | 46 | 4.1 | (3.9, 4.4) | 31 | 4.0 | (NE, NE) |
| 18 to <24 Months | 11 | 4.8 | (3.2, 7.4) | 51 | 4.1 | (3.9, 4.3) | 30 | 4.4 | (3.6, 5.3) |
| 1 Month after Vaccination 2 | | | | | | | | | |
| 12 to <24 Months | 19 | 8.6 | (6.1, 12.2) | 86 | 7.2 | (5.9, 8.7) | 59 | 4.1 | (3.9, 4.4) |
| 12 to <18 Months | 10 | 10.6 | (6.2, 18.0) | 42 | 6.0 | (4.7, 7.8) | 30 | 4.0 | (NE, NE) |
| 18 to <24 Months | 9 | 6.9 | (4.1, 11.5) | 44 | 8.5 | (6.4, 11.3) | 29 | 4.3 | (3.7, 5.0) |
| 1 Month after Vaccination 3 | | | | | | | | | |
| 12 to <24 Months | 20 | 18.4 | (11.8, 28.6) | 95 | 15.1 | (12.3, 18.6) | 60 | 4.3 | (3.9, 4.8) |
| 12 to <18 Months | 9 | 20.2 | (11.1, 36.6) | 45 | 15.8 | (11.4, 21.8) | 31 | 4.3 | (3.7, 4.9) |
| 18 to <24 Months | 11 | 17.0 | (8.2, 35.5) | 50 | 14.5 | (11.1, 19.1) | 29 | 4.4 | (3.8, 5.0) |
| PMB2707 (B44) Before Vaccination 1 | | | | | | | | | |
| 12 to <24 Months | 19 | 4.0 | (NE, NE) | 95 | 4.0 | (4.0, 4.1) | 54 | 4.0 | (NE, NE) |
| 12 to <18 Months | 9 | 4.0 | (NE, NE) | 46 | 4.1 | (3.9, 4.2) | 24 | 4.0 | (NE, NE) |
| 18 to <24 Months | 10 | 4.0 | (NE, NE) | 49 | 4.0 | (NE, NE) | 30 | 4.0 | (NE, NE) |
| 1 Month after Vaccination 2 | | | | | | | | | |
| 12 to <24 Months | 19 | 22.2 | (11.2, 43.9) | 94 | 19.4 | (15.1, 24.9) | 52 | 4.0 | (NE, NE) |
| 12 to <18 Months | 9 | 23.5 | (9.3, 59.4) | 47 | 22.1 | (15.5, 31.6) | 23 | 4.0 | (NE, NE) |
| 18 to <24 Months | 10 | 21.1 | (6.5, 68.3) | 47 | 17.0 | (11.8, 24.4) | 29 | 4.0 | (NE, NE) |

TABLE 26-continued hSBA GMTs for Primary Strains - Evaluable Immunogenicity Population

| Strain (Variant) Sampling Time Point | 60 μg rLP2086 | | | 120 μg rLP2086 | | | HAV/Saline | | |
|---|---|---|---|---|---|---|---|---|---|
| Age Strata | N[a] | GMT[b] | (95% CI)[c] | N[a] | GMT[b] | (95% CI)[c] | N[a] | GMT[b] | (95% CI)[c] |
| 1 Month after Vaccination 3 | | | | | | | | | |
| 12 to <24 Months | 19 | 32.0 | (18.3, 55.8) | 94 | 45.6 | (35.2, 59.0) | 54 | 4.0 | (NE, NE) |
| 12 to <18 Months | 9 | 29.6 | (11.6, 75.8) | 47 | 46.3 | (31.6, 67.8) | 24 | 4.0 | (NE, NE) |
| 18 to <24 Months | 10 | 34.3 | (15.0, 78.2) | 47 | 44.9 | (31.3, 64.5) | 30 | 4.0 | (NE, NE) |

Abbreviations: GMT = geometric mean titer; hSBA = serum bactericidal assay using human complement; LLOQ = lower limit of quantitation; NE = not estimable.
Note:
LLOQ =1:16 for A22; 1:8 for A56, B24, and B44. Titers below the LLOQ were set to 0.5 × LLOQ for analysis.
[a]N = number of subjects with valid and determinate hSBA titers for the given strain.
[b]GMTs were calculated using all subjects with valid and determinate hSBA titers at the given time point.
[c]CIs are back transformations of confidence levels based on the Student t distribution for the mean logarithm of the hSBA titers.

Results for the mITT population were similar to those of the evaluable immunogenicity population.

Subgroup analyses of hSBA GMTs for each of the 4 primary MnB test strains were assessed for the evaluable immunogenicity population by sex and country. There were no clinically important differences observed in the subgroup analyses performed.

Defined hSBA Titers

The proportions of subjects 12 to <18 months of age, 18 to <24 months of age, and for the combined age stratum, achieving hSBA titers ≥1:4, ≥1:8, ≥1:16, ≥1:32, ≥1:64, and ≥1:128 for each of the 4 primary MnB test strains at baseline, 1 month after the second vaccination, and 1 month after the third vaccination with bivalent rLP2086 was a secondary immunogenicity endpoint.

The proportion of subjects achieving defined hSBA titers for the 4 primary MnB strains is presented in Table 27 for the evaluable immunogenicity population.

The results for subjects receiving bivalent rLP2086 who achieved an hSBA titer ≥1:4 and ≥1:16 are described below. An hSBA titer of ≥1:4 is widely recognized as the correlate of protection against IMD; however, a more conservative hSBA titer of ≥1:16 has been considered a level indicative of a 4-fold vaccine effect for subjects seronegative before vaccination.

In general, the proportion of subjects in the HAV/saline group achieving defined hSBA titers did not change over time compared to baseline.

Results for the mITT population were similar to those of the evaluable immunogenicity population.

hSBA Titer ≥1:4

At 1 month after Vaccination 2, the proportion of subjects 12 to <18 months of age achieving an hSBA titer ≥1:4 was 90.0% and 64.4% for PMB80 (A22); 100.0% and 100.0% for PMB2001 (A56); 70.0% and 28.6% for PMB2948 (B24); and 77.8% and 72.3% for PMB2707 (B44) for the 60-μg and 120-μg groups, respectively. The proportion of subjects 18 to <24 months of age achieving an hSBA titer ≥1:4 was 66.7% and 86.0% for PMB80 (A22); 100.0% and 100.0% for PMB2001 (A56); 44.4% and 43.2% for PMB2948 (B24); and 70.0% and 63.8% for PMB2707 (B44) for the 60-μg and 120-μg groups, respectively. Overall for the combined age stratum, the proportion of subjects achieving an hSBA titer ≥1:4 at 1 month after Vaccination 2 was 78.9% and 75.8% for PMB80 (A22); 100.0% and 100.0% for PMB2001 (A56); 57.9% and 36.0% for PMB2948 (B24); and 73.7% and 68.1% for PMB2707 (B44) for the 60-μg and 120-μg groups, respectively.

At 1 month after Vaccination 3, the proportion of subjects 12 to <18 months of age achieving an hSBA titer ≥1:4 was 88.9% and 91.1% for PMB80 (A22); 100.0% and 100.0% for PMB2001 (A56); 88.9% and 71.1% for PMB2948 (B24); and 88.9% and 87.2% for PMB2707 (B44) for the 60-μg and 120-μg groups, respectively. The proportion of subjects 18 to <24 months of age achieving an hSBA titer ≥1:4 was 90.9% and 88.2% for PMB80 (A22); 100.0% and 100.0% for PMB2001 (A56); 81.8% and 72.0% for PMB2948 (B24); and 90.0% and 87.2% for PMB2707 (B44) for the 60-μg and 120-μg groups, respectively. Overall for the combined age stratum, the proportion of subjects achieving an hSBA titer ≥1:4 at 1 month after Vaccination 3 was 90.0% and 89.6% for PMB80 (A22); 100.0% and 100.0% for PMB2001 (A56); 85.0% and 71.6% for PMB2948 (B24); and 89.5% and 87.2% for PMB2707 (B44) for the 60-μg and 120-μg groups, respectively.

hSBA Titer ≥1:16

At 1 month after Vaccination 2, the proportion of subjects 12 to <18 months of age achieving an hSBA titer ≥1:16 was 90.0% and 64.4% for PMB80 (A22); 100.0% and 100.0% for PMB2001 (A56); 60.0% and 21.4% for PMB2948 (B24); and 77.8% and 72.3% for PMB2707 (B44) for the 60-μg and 120-μg groups, respectively. The proportion of subjects 18 to <24 months of age achieving an hSBA titer ≥1:16 was 66.7% and 86.0% for PMB80 (A22); 90.0% and 100.0% for PMB2001 (A56); 33.3% and 43.2% for PMB2948 (B24); and 60.0% and 61.7% for PMB2707 (B44) for the 60-μg and 120-μg groups, respectively. Overall for the combined age stratum, the proportion of subjects achieving an hSBA titer ≥1:16 at 1 month after Vaccination 2 was 78.9% and 74.7% for PMB80 (A22); 94.7% and 100.0% for PMB2001 (A56); 47.4% and 32.6% for PMB2948 (B24); and 68.4% and 67.0% for PMB2707 (B44) for the 60-μg and 120-μg groups, respectively.

At 1 month after Vaccination 3, the proportion of subjects 12 to <18 months of age achieving an hSBA titer ≥1:16 was 88.9% and 91.1% for PMB80 (A22); 100.0% and 97.9% for PMB2001 (A56); 88.9% and 66.7% for PMB2948 (B24); and 77.8% and 87.2% for PMB2707 (B44) for the 60-μg and 120-μg groups, respectively. The proportion of subjects 18 to <24 months of age achieving an hSBA titer ≥1:16 was 90.9% and 88.2% for PMB80 (A22); 100.0% and 100.0% for PMB2001 (A56); 63.6% and 68.0% for PMB2948 (B24); and 90.0% and 85.1% for PMB2707 (B44) for the 60-μg and 120-μg groups, respectively. Overall for the combined age stratum, the proportion of subjects achieving an hSBA titer ≥1:16 at 1 month after Vaccination 3 was 90.0% and 89.6% for PMB80 (A22); 100.0% and 98.9% for PMB2001 (A56); 75.0% and 67.4% for PMB2948 (B24); and 84.2% and 86.2% for PMB2707 (B44) for the 60-μg and 120-μg groups, respectively.

TABLE 27

Subjects Achieving Defined hSBA Titers for Primary Strains - Evaluable Immunogenicity Population

| Strain (Variant) Sampling Time Point Age Strata | Titer | Vaccine Group (as Randomized) | | | | | | | | | | |
|---|---|---|---|---|---|---|---|---|---|---|---|---|
| | | 60 μg rLP2086 | | | | 120 μg rLP2086 | | | | HAV/Saline | | | |
| | | $N^a$ | $n^b$ | % | (95% CI)$^c$ | $N^a$ | $n^b$ | % | (95% CI)$^c$ | $N^a$ | $n^b$ | % | (95% CI)$^c$ |
| PMB80 (A22) <br> Before Vaccination 1 | | | | | | | | | | | | | |
| 12 to <24 Months | 4 | 20 | 0 | 0.0 | (0.0, 16.8) | 97 | 4 | 4.1 | (1.1, 10.2) | 61 | 1 | 1.6 | (0.0, 8.8) |
| | 8 | 20 | 0 | 0.0 | (0.0, 16.8) | 97 | 3 | 3.1 | (0.6, 8.8) | 61 | 1 | 1.6 | (0.0, 8.8) |
| | 16 | 20 | 0 | 0.0 | (0.0, 16.8) | 97 | 3 | 3.1 | (0.6, 8.8) | 61 | 1 | 1.6 | (0.0, 8.8) |
| | 32 | 20 | 0 | 0.0 | (0.0, 16.8) | 97 | 2 | 2.1 | (0.3, 7.3) | 61 | 0 | 0.0 | (0.0, 5.9) |
| | 64 | 20 | 0 | 0.0 | (0.0, 16.8) | 97 | 1 | 1.0 | (0.0, 5.6) | 61 | 0 | 0.0 | (0.0, 5.9) |
| | 128 | 20 | 0 | 0.0 | (0.0, 16.8) | 97 | 1 | 1.0 | (0.0, 5.6) | 61 | 0 | 0.0 | (0.0, 5.9) |
| 12 to <18 Months | 4 | 9 | 0 | 0.0 | (0.0, 33.6) | 46 | 2 | 4.3 | (0.5, 14.8) | 31 | 0 | 0.0 | (0.0, 11.2) |
| | 8 | 9 | 0 | 0.0 | (0.0, 33.6) | 46 | 1 | 2.2 | (0.1, 11.5) | 31 | 0 | 0.0 | (0.0, 11.2) |
| | 16 | 9 | 0 | 0.0 | (0.0, 33.6) | 46 | 1 | 2.2 | (0.1, 11.5) | 31 | 0 | 0.0 | (0.0, 11.2) |
| | 32 | 9 | 0 | 0.0 | (0.0, 33.6) | 46 | 1 | 2.2 | (0.1, 11.5) | 31 | 0 | 0.0 | (0.0, 11.2) |
| | 64 | 9 | 0 | 0.0 | (0.0, 33.6) | 46 | 1 | 2.2 | (0.1, 11.5) | 31 | 0 | 0.0 | (0.0, 11.2) |
| | 128 | 9 | 0 | 0.0 | (0.0, 33.6) | 46 | 1 | 2.2 | (0.1, 11.5) | 31 | 0 | 0.0 | (0.0, 11.2) |
| 18 to <24 Months | 4 | 11 | 0 | 0.0 | (0.0, 28.5) | 51 | 2 | 3.9 | (0.5, 13.5) | 30 | 1 | 3.3 | (0.1, 17.2) |
| | 8 | 11 | 0 | 0.0 | (0.0, 28.5) | 51 | 2 | 3.9 | (0.5, 13.5) | 30 | 1 | 3.3 | (0.1, 17.2) |
| | 16 | 11 | 0 | 0.0 | (0.0, 28.5) | 51 | 2 | 3.9 | (0.5, 13.5) | 30 | 1 | 3.3 | (0.1, 17.2) |
| | 32 | 11 | 0 | 0.0 | (0.0, 28.5) | 51 | 1 | 2.0 | (0.0, 10.4) | 30 | 0 | 0.0 | (0.0, 11.6) |
| | 64 | 11 | 0 | 0.0 | (0.0, 28.5) | 51 | 0 | 0.0 | (0.0, 7.0) | 30 | 0 | 0.0 | (0.0, 11.6) |
| | 128 | 11 | 0 | 0.0 | (0.0, 28.5) | 51 | 0 | 0.0 | (0.0, 7.0) | 30 | 0 | 0.0 | (0.0, 11.6) |
| 1 Month after Vaccination 2 | | | | | | | | | | | | | |
| 12 to <24 Months | 4 | 19 | 15 | 78.9 | (54.4, 93.9) | 95 | 72 | 75.8 | (65.9, 84.0) | 59 | 1 | 1.7 | (0.0, 9.1) |
| | 8 | 19 | 15 | 78.9 | (54.4, 93.9) | 95 | 72 | 75.8 | (65.9, 84.0) | 59 | 1 | 1.7 | (0.0, 9.1) |
| | 16 | 19 | 15 | 78.9 | (54.4, 93.9) | 95 | 71 | 74.7 | (64.8, 83.1) | 59 | 1 | 1.7 | (0.0, 9.1) |
| | 32 | 19 | 12 | 63.2 | (38.4, 83.7) | 95 | 56 | 58.9 | (48.4, 68.9) | 59 | 1 | 1.7 | (0.0, 9.1) |
| | 64 | 19 | 7 | 36.8 | (16.3, 61.6) | 95 | 33 | 34.7 | (25.3, 45.2) | 59 | 1 | 1.7 | (0.0, 9.1) |
| | 128 | 19 | 4 | 21.1 | (6.1, 45.6) | 95 | 13 | 13.7 | (7.5, 22.3) | 59 | 0 | 0.0 | (0.0, 6.1) |
| 12 to <18 Months | 4 | 10 | 9 | 90.0 | (55.5, 99.7) | 45 | 29 | 64.4 | (48.8, 78.1) | 30 | 0 | 0.0 | (0.0, 11.6) |
| | 8 | 10 | 9 | 90.0 | (55.5, 99.7) | 45 | 29 | 64.4 | (48.8, 78.1) | 30 | 0 | 0.0 | (0.0, 11.6) |
| | 16 | 10 | 9 | 90.0 | (55.5, 99.7) | 45 | 29 | 64.4 | (48.8, 78.1) | 30 | 0 | 0.0 | (0.0, 11.6) |
| | 32 | 10 | 8 | 80.0 | (44.4, 97.5) | 45 | 23 | 51.1 | (35.8, 66.3) | 30 | 0 | 0.0 | (0.0, 11.6) |
| | 64 | 10 | 5 | 50.0 | (18.7, 81.3) | 45 | 13 | 28.9 | (16.4, 44.3) | 30 | 0 | 0.0 | (0.0, 11.6) |
| | 128 | 10 | 2 | 20.0 | (2.5, 55.6) | 45 | 5 | 11.1 | (3.7, 24.1) | 30 | 0 | 0.0 | (0.0, 11.6) |
| 18 to <24 Months | 4 | 9 | 6 | 66.7 | (29.9, 92.5) | 50 | 43 | 86.0 | (73.3, 94.2) | 29 | 1 | 3.4 | (0.1, 17.8) |
| | 8 | 9 | 6 | 66.7 | (29.9, 92.5) | 50 | 43 | 86.0 | (73.3, 94.2) | 29 | 1 | 3.4 | (0.1, 17.8) |
| | 16 | 9 | 6 | 66.7 | (29.9, 92.5) | 50 | 42 | 84.0 | (70.9, 92.8) | 29 | 1 | 3.4 | (0.1, 17.8) |
| | 32 | 9 | 4 | 44.4 | (13.7, 78.8) | 50 | 33 | 66.0 | (51.2, 78.8) | 29 | 1 | 3.4 | (0.1, 17.8) |
| | 64 | 9 | 2 | 22.2 | (2.8, 60.0) | 50 | 20 | 40.0 | (26.4, 54.8) | 29 | 1 | 3.4 | (0.1, 17.8) |
| | 128 | 9 | 2 | 22.2 | (2.8, 60.0) | 50 | 8 | 16.0 | (7.2, 29.1) | 29 | 0 | 0.0 | (0.0, 11.9) |
| 1 Month after Vaccination 3 | | | | | | | | | | | | | |
| 12 to <24 Months | 4 | 20 | 18 | 90.0 | (68.3, 98.8) | 96 | 86 | 89.6 | (81.7, 94.9) | 60 | 4 | 6.7 | (1.8, 16.2) |
| | 8 | 20 | 18 | 90.0 | (68.3, 98.8) | 96 | 86 | 89.6 | (81.7, 94.9) | 60 | 4 | 6.7 | (1.8, 16.2) |
| | 16 | 20 | 18 | 90.0 | (68.3, 98.8) | 96 | 86 | 89.6 | (81.7, 94.9) | 60 | 3 | 5.0 | (1.0, 13.9) |
| | 32 | 20 | 17 | 85.0 | (62.1, 96.8) | 96 | 81 | 84.4 | (75.5, 91.0) | 60 | 2 | 3.3 | (0.4, 11.5) |
| | 64 | 20 | 14 | 70.0 | (45.7, 88.1) | 96 | 64 | 66.7 | (56.3, 76.0) | 60 | 1 | 1.7 | (0.0, 8.9) |
| | 128 | 20 | 10 | 50.0 | (27.2, 72.8) | 96 | 42 | 43.8 | (33.6, 54.3) | 60 | 0 | 0.0 | (0.0, 6.0) |
| 12 to <18 Months | 4 | 9 | 8 | 88.9 | (51.8, 99.7) | 45 | 41 | 91.1 | (78.8, 97.5) | 31 | 2 | 6.5 | (0.8, 21.4) |
| | 8 | 9 | 8 | 88.9 | (51.8, 99.7) | 45 | 41 | 91.1 | (78.8, 97.5) | 31 | 2 | 6.5 | (0.8, 21.4) |
| | 16 | 9 | 8 | 88.9 | (51.8, 99.7) | 45 | 41 | 91.1 | (78.8, 97.5) | 31 | 1 | 3.2 | (0.1, 16.7) |
| | 32 | 9 | 8 | 88.9 | (51.8, 99.7) | 45 | 37 | 82.2 | (67.9, 92.0) | 31 | 1 | 3.2 | (0.1, 16.7) |
| | 64 | 9 | 6 | 66.7 | (29.9, 92.5) | 45 | 27 | 60.0 | (44.3, 74.3) | 31 | 1 | 3.2 | (0.1, 16.7) |
| | 128 | 9 | 4 | 44.4 | (13.7, 78.8) | 45 | 17 | 37.8 | (23.8, 53.5) | 31 | 0 | 0.0 | (0.0, 11.2) |
| 18 to <24 Months | 4 | 11 | 10 | 90.9 | (58.7, 99.8) | 51 | 45 | 88.2 | (76.1, 95.6) | 29 | 2 | 6.9 | (0.8, 22.8) |
| | 8 | 11 | 10 | 90.9 | (58.7, 99.8) | 51 | 45 | 88.2 | (76.1, 95.6) | 29 | 2 | 6.9 | (0.8, 22.8) |
| | 16 | 11 | 10 | 90.9 | (58.7, 99.8) | 51 | 45 | 88.2 | (76.1, 95.6) | 29 | 2 | 6.9 | (0.8, 22.8) |
| | 32 | 11 | 9 | 81.8 | (48.2, 97.7) | 51 | 44 | 86.3 | (73.7, 94.3) | 29 | 1 | 3.4 | (0.1, 17.8) |
| | 64 | 11 | 8 | 72.7 | (39.0, 94.0) | 51 | 37 | 72.5 | (58.3, 84.1) | 29 | 0 | 0.0 | (0.0, 11.9) |
| | 128 | 11 | 6 | 54.5 | (23.4, 83.3) | 51 | 25 | 49.0 | (34.8, 63.4) | 29 | 0 | 0.0 | (0.0, 11.9) |
| PMB2001 (A56) <br> Before Vaccination 1 | | | | | | | | | | | | | |
| 12 to <24 Months | 4 | 19 | 0 | 0.0 | (0.0, 17.6) | 95 | 2 | 2.1 | (0.3, 7.4) | 53 | 1 | 1.9 | (0.0, 10.1) |
| | 8 | 19 | 0 | 0.0 | (0.0, 17.6) | 95 | 1 | 1.1 | (0.0, 5.7) | 53 | 0 | 0.0 | (0.0, 6.7) |
| | 16 | 19 | 0 | 0.0 | (0.0, 17.6) | 95 | 1 | 1.1 | (0.0, 5.7) | 53 | 0 | 0.0 | (0.0, 6.7) |
| | 32 | 19 | 0 | 0.0 | (0.0, 17.6) | 95 | 1 | 1.1 | (0.0, 5.7) | 53 | 0 | 0.0 | (0.0, 6.7) |
| | 64 | 19 | 0 | 0.0 | (0.0, 17.6) | 95 | 0 | 0.0 | (0.0, 3.8) | 53 | 0 | 0.0 | (0.0, 6.7) |
| | 128 | 19 | 0 | 0.0 | (0.0, 17.6) | 95 | 0 | 0.0 | (0.0, 3.8) | 53 | 0 | 0.0 | (0.0, 6.7) |
| 12 to <18 Months | 4 | 9 | 0 | 0.0 | (0.0, 33.6) | 46 | 0 | 0.0 | (0.0, 7.7) | 24 | 1 | 4.2 | (0.1, 21.1) |
| | 8 | 9 | 0 | 0.0 | (0.0, 33.6) | 46 | 0 | 0.0 | (0.0, 7.7) | 24 | 0 | 0.0 | (0.0, 14.2) |

TABLE 27-continued

Subjects Achieving Defined hSBA Titers for Primary Strains - Evaluable Immunogenicity Population

| Strain (Variant) Sampling Time Point Age Strata | Titer | 60 μg rLP2086 | | | | 120 μg rLP2086 | | | | HAV/Saline | | | |
|---|---|---|---|---|---|---|---|---|---|---|---|---|---|
| | | $N^a$ | $n^b$ | % | (95% CI)$^c$ | $N^a$ | $n^b$ | % | (95% CI)$^c$ | $N^a$ | $n^b$ | % | (95% CI)$^c$ |
| | 16 | 9 | 0 | 0.0 | (0.0, 33.6) | 46 | 0 | 0.0 | (0.0, 7.7) | 24 | 0 | 0.0 | (0.0, 14.2) |
| | 32 | 9 | 0 | 0.0 | (0.0, 33.6) | 46 | 0 | 0.0 | (0.0, 7.7) | 24 | 0 | 0.0 | (0.0, 14.2) |
| | 64 | 9 | 0 | 0.0 | (0.0, 33.6) | 46 | 0 | 0.0 | (0.0, 7.7) | 24 | 0 | 0.0 | (0.0, 14.2) |
| | 128 | 9 | 0 | 0.0 | (0.0, 33.6) | 46 | 0 | 0.0 | (0.0, 7.7) | 24 | 0 | 0.0 | (0.0, 14.2) |
| 18 to <24 Months | 4 | 10 | 0 | 0.0 | (0.0, 30.8) | 49 | 2 | 4.1 | (0.5, 14.0) | 29 | 0 | 0.0 | (0.0, 11.9) |
| | 8 | 10 | 0 | 0.0 | (0.0, 30.8) | 49 | 1 | 2.0 | (0.1, 10.9) | 29 | 0 | 0.0 | (0.0, 11.9) |
| | 16 | 10 | 0 | 0.0 | (0.0, 30.8) | 49 | 1 | 2.0 | (0.1, 10.9) | 29 | 0 | 0.0 | (0.0, 11.9) |
| | 32 | 10 | 0 | 0.0 | (0.0, 30.8) | 49 | 1 | 2.0 | (0.1, 10.9) | 29 | 0 | 0.0 | (0.0, 11.9) |
| | 64 | 10 | 0 | 0.0 | (0.0, 30.8) | 49 | 0 | 0.0 | (0.0, 7.3) | 29 | 0 | 0.0 | (0.0, 11.9) |
| | 128 | 10 | 0 | 0.0 | (0.0, 30.8) | 49 | 0 | 0.0 | (0.0, 7.3) | 29 | 0 | 0.0 | (0.0, 11.9) |
| 1 Month after Vaccination 2 | | | | | | | | | | | | | |
| 12 to <24 Months | 4 | 19 | 19 | 100.0 | (82.4, 100.0) | 95 | 95 | 100.0 | (96.2, 100.0) | 52 | 1 | 1.9 | (0.0, 10.3) |
| | 8 | 19 | 18 | 94.7 | (74.0, 99.9) | 95 | 95 | 100.0 | (96.2, 100.0) | 52 | 0 | 0.0 | (0.0, 6.8) |
| | 16 | 19 | 18 | 94.7 | (74.0, 99.9) | 95 | 95 | 100.0 | (96.2, 100.0) | 52 | 0 | 0.0 | (0.0, 6.8) |
| | 32 | 19 | 18 | 94.7 | (74.0, 99.9) | 95 | 91 | 95.8 | (89.6, 98.8) | 52 | 0 | 0.0 | (0.0, 6.8) |
| | 64 | 19 | 16 | 84.2 | (60.4, 96.6) | 95 | 82 | 86.3 | (77.7, 92.5) | 52 | 0 | 0.0 | (0.0, 6.8) |
| | 128 | 19 | 9 | 47.4 | (24.4, 71.1) | 95 | 54 | 56.8 | (46.3, 67.0) | 52 | 0 | 0.0 | (0.0, 6.8) |
| 12 to <18 Months | 4 | 9 | 9 | 100.0 | (66.4, 100.0) | 47 | 47 | 100.0 | (92.5, 100.0) | 23 | 1 | 4.3 | (0.1, 21.9) |
| | 8 | 9 | 9 | 100.0 | (66.4, 100.0) | 47 | 47 | 100.0 | (92.5, 100.0) | 23 | 0 | 0.0 | (0.0, 14.8) |
| | 16 | 9 | 9 | 100.0 | (66.4, 100.0) | 47 | 47 | 100.0 | (92.5, 100.0) | 23 | 0 | 0.0 | (0.0, 14.8) |
| | 32 | 9 | 9 | 100.0 | (66.4, 100.0) | 47 | 45 | 95.7 | (85.5, 99.5) | 23 | 0 | 0.0 | (0.0, 14.8) |
| | 64 | 9 | 9 | 100.0 | (66.4, 100.0) | 47 | 41 | 87.2 | (74.3, 95.2) | 23 | 0 | 0.0 | (0.0, 14.8) |
| | 128 | 9 | 4 | 44.4 | (13.7, 78.8) | 47 | 28 | 59.6 | (44.3, 73.6) | 23 | 0 | 0.0 | (0.0, 14.8) |
| 18 to <24 Months | 4 | 10 | 10 | 100.0 | (69.2, 100.0) | 48 | 48 | 100.0 | (92.6, 100.0) | 29 | 0 | 0.0 | (0.0, 11.9) |
| | 8 | 10 | 9 | 90.0 | (55.5, 99.7) | 48 | 48 | 100.0 | (92.6, 100.0) | 29 | 0 | 0.0 | (0.0, 11.9) |
| | 16 | 10 | 9 | 90.0 | (55.5, 99.7) | 48 | 48 | 100.0 | (92.6, 100.0) | 29 | 0 | 0.0 | (0.0, 11.9) |
| | 32 | 10 | 9 | 90.0 | (55.5, 99.7) | 48 | 46 | 95.8 | (85.7, 99.5) | 29 | 0 | 0.0 | (0.0, 11.9) |
| | 64 | 10 | 7 | 70.0 | (34.8, 93.3) | 48 | 41 | 85.4 | (72.2, 93.9) | 29 | 0 | 0.0 | (0.0, 11.9) |
| | 128 | 10 | 5 | 50.0 | (18.7, 81.3) | 48 | 26 | 54.2 | (39.2, 68.6) | 29 | 0 | 0.0 | (0.0, 11.9) |
| 1 Month after Vaccination 3 | | | | | | | | | | | | | |
| 12 to <24 Months | 4 | 19 | 19 | 100.0 | (82.4, 100.0) | 95 | 95 | 100.0 | (96.2, 100.0) | 54 | 5 | 9.3 | (3.1, 20.3) |
| | 8 | 19 | 19 | 100.0 | (82.4, 100.0) | 95 | 95 | 100.0 | (96.2, 100.0) | 54 | 1 | 1.9 | (0.0, 9.9) |
| | 16 | 19 | 19 | 100.0 | (82.4, 100.0) | 95 | 94 | 98.9 | (94.3, 100.0) | 54 | 1 | 1.9 | (0.0, 9.9) |
| | 32 | 19 | 18 | 94.7 | (74.0, 99.9) | 95 | 91 | 95.8 | (89.6, 98.8) | 54 | 1 | 1.9 | (0.0, 9.9) |
| | 64 | 19 | 17 | 89.5 | (66.9, 98.7) | 95 | 85 | 89.5 | (81.5, 94.8) | 54 | 0 | 0.0 | (0.0, 6.6) |
| | 128 | 19 | 13 | 68.4 | (43.4, 87.4) | 95 | 79 | 83.2 | (74.1, 90.1) | 54 | 0 | 0.0 | (0.0, 6.6) |
| 12 to <18 Months | 4 | 9 | 9 | 100.0 | (66.4, 100.0) | 47 | 47 | 100.0 | (92.5, 100.0) | 24 | 2 | 8.3 | (1.0, 27.0) |
| | 8 | 9 | 9 | 100.0 | (66.4, 100.0) | 47 | 47 | 100.0 | (92.5, 100.0) | 24 | 0 | 0.0 | (0.0, 14.2) |
| | 16 | 9 | 9 | 100.0 | (66.4, 100.0) | 47 | 46 | 97.9 | (88.7, 99.9) | 24 | 0 | 0.0 | (0.0, 14.2) |
| | 32 | 9 | 9 | 100.0 | (66.4, 100.0) | 47 | 46 | 97.9 | (88.7, 99.9) | 24 | 0 | 0.0 | (0.0, 14.2) |
| | 64 | 9 | 9 | 100.0 | (66.4, 100.0) | 47 | 44 | 93.6 | (82.5, 98.7) | 24 | 0 | 0.0 | (0.0, 14.2) |
| | 128 | 9 | 5 | 55.6 | (21.2, 86.3) | 47 | 42 | 89.4 | (76.9, 96.5) | 24 | 0 | 0.0 | (0.0, 14.2) |
| 18 to <24 Months | 4 | 10 | 10 | 100.0 | (69.2, 100.0) | 48 | 48 | 100.0 | (92.6, 100.0) | 30 | 3 | 10.0 | (2.1, 26.5) |
| | 8 | 10 | 10 | 100.0 | (69.2, 100.0) | 48 | 48 | 100.0 | (92.6, 100.0) | 30 | 1 | 3.3 | (0.1, 17.2) |
| | 16 | 10 | 10 | 100.0 | (69.2, 100.0) | 48 | 48 | 100.0 | (92.6, 100.0) | 30 | 1 | 3.3 | (0.1, 17.2) |
| | 32 | 10 | 9 | 90.0 | (55.5, 99.7) | 48 | 45 | 93.8 | (82.8, 98.7) | 30 | 1 | 3.3 | (0.1, 17.2) |
| | 64 | 10 | 8 | 80.0 | (44.4, 97.5) | 48 | 41 | 85.4 | (72.2, 93.9) | 30 | 0 | 0.0 | (0.0, 11.6) |
| | 128 | 10 | 8 | 80.0 | (44.4, 97.5) | 48 | 37 | 77.1 | (62.7, 88.0) | 30 | 0 | 0.0 | (0.0, 11.6) |
| PMB2948 (B24) Before Vaccination 1 | | | | | | | | | | | | | |
| 12 to <24 Months | 4 | 21 | 1 | 4.8 | (0.1, 23.8) | 97 | 2 | 2.1 | (0.3, 7.3) | 61 | 1 | 1.6 | (0.0, 8.8) |
| | 8 | 21 | 1 | 4.8 | (0.1, 23.8) | 97 | 2 | 2.1 | (0.3, 7.3) | 61 | 1 | 1.6 | (0.0, 8.8) |
| | 16 | 21 | 1 | 4.8 | (0.1, 23.8) | 97 | 2 | 2.1 | (0.3, 7.3) | 61 | 1 | 1.6 | (0.0, 8.8) |
| | 32 | 21 | 1 | 4.8 | (0.1, 23.8) | 97 | 0 | 0.0 | (0.0, 3.7) | 61 | 1 | 1.6 | (0.0, 8.8) |
| | 64 | 21 | 0 | 0.0 | (0.0, 16.1) | 97 | 0 | 0.0 | (0.0, 3.7) | 61 | 1 | 1.6 | (0.0, 8.8) |
| | 128 | 21 | 0 | 0.0 | (0.0, 16.1) | 97 | 0 | 0.0 | (0.0, 3.7) | 61 | 0 | 0.0 | (0.0, 5.9) |
| 12 to <18 Months | 4 | 10 | 0 | 0.0 | (0.0, 30.8) | 46 | 1 | 2.2 | (0.1, 11.5) | 31 | 0 | 0.0 | (0.0, 11.2) |
| | 8 | 10 | 0 | 0.0 | (0.0, 30.8) | 46 | 1 | 2.2 | (0.1, 11.5) | 31 | 0 | 0.0 | (0.0, 11.2) |
| | 16 | 10 | 0 | 0.0 | (0.0, 30.8) | 46 | 1 | 2.2 | (0.1, 11.5) | 31 | 0 | 0.0 | (0.0, 11.2) |
| | 32 | 10 | 0 | 0.0 | (0.0, 30.8) | 46 | 0 | 0.0 | (0.0, 7.7) | 31 | 0 | 0.0 | (0.0, 11.2) |
| | 64 | 10 | 0 | 0.0 | (0.0, 30.8) | 46 | 0 | 0.0 | (0.0, 7.7) | 31 | 0 | 0.0 | (0.0, 11.2) |
| | 128 | 10 | 0 | 0.0 | (0.0, 30.8) | 46 | 0 | 0.0 | (0.0, 7.7) | 31 | 0 | 0.0 | (0.0, 11.2) |
| 18 to <24 Months | 4 | 11 | 1 | 9.1 | (0.2, 41.3) | 51 | 1 | 2.0 | (0.0, 10.4) | 30 | 1 | 3.3 | (0.1, 17.2) |
| | 8 | 11 | 1 | 9.1 | (0.2, 41.3) | 51 | 1 | 2.0 | (0.0, 10.4) | 30 | 1 | 3.3 | (0.1, 17.2) |
| | 16 | 11 | 1 | 9.1 | (0.2, 41.3) | 51 | 1 | 2.0 | (0.0, 10.4) | 30 | 1 | 3.3 | (0.1, 17.2) |
| | 32 | 11 | 1 | 9.1 | (0.2, 41.3) | 51 | 0 | 0.0 | (0.0, 7.0) | 30 | 1 | 3.3 | (0.1, 17.2) |
| | 64 | 11 | 0 | 0.0 | (0.0, 28.5) | 51 | 0 | 0.0 | (0.0, 7.0) | 30 | 1 | 3.3 | (0.1, 17.2) |
| | 128 | 11 | 0 | 0.0 | (0.0, 28.5) | 51 | 0 | 0.0 | (0.0, 7.0) | 30 | 0 | 0.0 | (0.0, 11.6) |

TABLE 27-continued

Subjects Achieving Defined hSBA Titers for Primary Strains - Evaluable Immunogenicity Population

| Strain (Variant) | | | | | Vaccine Group (as Randomized) | | | | | | | |
|---|---|---|---|---|---|---|---|---|---|---|---|---|
| Sampling Time Point | | 60 μg rLP2086 | | | | 120 μg rLP2086 | | | | HAV/Saline | | |
| Age Strata | Titer | $N^a$ | $n^b$ | % | (95% CI)$^c$ | $N^a$ | $n^b$ | % | (95% CI)$^c$ | $N^a$ | $n^b$ | % | (95% CI)$^c$ |

| Age Strata | Titer | $N^a$ | $n^b$ | % | (95% CI)$^c$ | $N^a$ | $n^b$ | % | (95% CI)$^c$ | $N^a$ | $n^b$ | % | (95% CI)$^c$ |
|---|---|---|---|---|---|---|---|---|---|---|---|---|---|
| 1 Month after Vaccination 2 | | | | | | | | | | | | | |
| 12 to <24 Months | 4 | 19 | 11 | 57.9 | (33.5, 79.7) | 86 | 31 | 36.0 | (26.0, 47.1) | 59 | 1 | 1.7 | (0.0, 9.1) |
|  | 8 | 19 | 11 | 57.9 | (33.5, 79.7) | 86 | 29 | 33.7 | (23.9, 44.7) | 59 | 1 | 1.7 | (0.0, 9.1) |
|  | 16 | 19 | 9 | 47.4 | (24.4, 71.1) | 86 | 28 | 32.6 | (22.8, 43.5) | 59 | 1 | 1.7 | (0.0, 9.1) |
|  | 32 | 19 | 1 | 5.3 | (0.1, 26.0) | 86 | 12 | 14.0 | (7.4, 23.1) | 59 | 1 | 1.7 | (0.0, 9.1) |
|  | 64 | 19 | 0 | 0.0 | (0.0, 17.6) | 86 | 3 | 3.5 | (0.7, 9.9) | 59 | 0 | 0.0 | (0.0, 6.1) |
|  | 128 | 19 | 0 | 0.0 | (0.0, 17.6) | 86 | 1 | 1.2 | (0.0, 6.3) | 59 | 0 | 0.0 | (0.0, 6.1) |
| 12 to <18 Months | 4 | 10 | 7 | 70.0 | (34.8, 93.3) | 42 | 12 | 28.6 | (15.7, 44.6) | 30 | 0 | 0.0 | (0.0, 11.6) |
|  | 8 | 10 | 7 | 70.0 | (34.8, 93.3) | 42 | 10 | 23.8 | (12.1, 39.5) | 30 | 0 | 0.0 | (0.0, 11.6) |
|  | 16 | 10 | 6 | 60.0 | (26.2, 87.8) | 42 | 9 | 21.4 | (10.3, 36.8) | 30 | 0 | 0.0 | (0.0, 11.6) |
|  | 32 | 10 | 1 | 10.0 | (0.3, 44.5) | 42 | 4 | 9.5 | (2.7, 22.6) | 30 | 0 | 0.0 | (0.0, 11.6) |
|  | 64 | 10 | 0 | 0.0 | (0.0, 30.8) | 42 | 1 | 2.4 | (0.1, 12.6) | 30 | 0 | 0.0 | (0.0, 11.6) |
|  | 128 | 10 | 0 | 0.0 | (0.0, 30.8) | 42 | 1 | 2.4 | (0.1, 12.6) | 30 | 0 | 0.0 | (0.0, 11.6) |
| 18 to <24 Months | 4 | 9 | 4 | 44.4 | (13.7, 78.8) | 44 | 19 | 43.2 | (28.3, 59.0) | 29 | 1 | 3.4 | (0.1, 17.8) |
|  | 8 | 9 | 4 | 44.4 | (13.7, 78.8) | 44 | 19 | 43.2 | (28.3, 59.0) | 29 | 1 | 3.4 | (0.1, 17.8) |
|  | 16 | 9 | 3 | 33.3 | (7.5, 70.1) | 44 | 19 | 43.2 | (28.3, 59.0) | 29 | 1 | 3.4 | (0.1, 17.8) |
|  | 32 | 9 | 0 | 0.0 | (0.0, 33.6) | 44 | 8 | 18.2 | (8.2, 32.7) | 29 | 1 | 3.4 | (0.1, 17.8) |
|  | 64 | 9 | 0 | 0.0 | (0.0, 33.6) | 44 | 2 | 4.5 | (0.6, 15.5) | 29 | 0 | 0.0 | (0.0, 11.9) |
|  | 128 | 9 | 0 | 0.0 | (0.0, 33.6) | 44 | 0 | 0.0 | (0.0, 8.0) | 29 | 0 | 0.0 | (0.0, 11.9) |
| 1 Month after Vaccination 3 | | | | | | | | | | | | | |
| 12 to <24 Months | 4 | 20 | 17 | 85.0 | (62.1, 96.8) | 95 | 68 | 71.6 | (61.4, 80.4) | 60 | 3 | 5.0 | (1.0, 13.9) |
|  | 8 | 20 | 17 | 85.0 | (62.1, 96.8) | 95 | 68 | 71.6 | (61.4, 80.4) | 60 | 3 | 5.0 | (1.0, 13.9) |
|  | 16 | 20 | 15 | 75.0 | (50.9, 91.3) | 95 | 64 | 67.4 | (57.0, 76.6) | 60 | 3 | 5.0 | (1.0, 13.9) |
|  | 32 | 20 | 8 | 40.0 | (19.1, 63.9) | 95 | 34 | 35.8 | (26.2, 46.3) | 60 | 1 | 1.7 | (0.0, 8.9) |
|  | 64 | 20 | 3 | 15.0 | (3.2, 37.9) | 95 | 13 | 13.7 | (7.5, 22.3) | 60 | 0 | 0.0 | (0.0, 6.0) |
|  | 128 | 20 | 1 | 5.0 | (0.1, 24.9) | 95 | 2 | 2.1 | (0.3, 7.4) | 60 | 0 | 0.0 | (0.0, 6.0) |
| 12 to <18 Months | 4 | 9 | 8 | 88.9 | (51.8, 99.7) | 45 | 32 | 71.1 | (55.7, 83.6) | 31 | 1 | 3.2 | (0.1, 16.7) |
|  | 8 | 9 | 8 | 88.9 | (51.8, 99.7) | 45 | 32 | 71.1 | (55.7, 83.6) | 31 | 1 | 3.2 | (0.1, 16.7) |
|  | 16 | 9 | 8 | 88.9 | (51.8, 99.7) | 45 | 30 | 66.7 | (51.0, 80.0) | 31 | 1 | 3.2 | (0.1, 16.7) |
|  | 32 | 9 | 4 | 44.4 | (13.7, 78.8) | 45 | 17 | 37.8 | (23.8, 53.5) | 31 | 1 | 3.2 | (0.1, 16.7) |
|  | 64 | 9 | 1 | 11.1 | (0.3, 48.2) | 45 | 8 | 17.8 | (8.0, 32.1) | 31 | 0 | 0.0 | (0.0, 11.2) |
|  | 128 | 9 | 0 | 0.0 | (0.0, 33.6) | 45 | 1 | 2.2 | (0.1, 11.8) | 31 | 0 | 0.0 | (0.0, 11.2) |
| 18 to <24 Months | 4 | 11 | 9 | 81.8 | (48.2, 97.7) | 50 | 36 | 72.0 | (57.5, 83.8) | 29 | 2 | 6.9 | (0.8, 22.8) |
|  | 8 | 11 | 9 | 81.8 | (48.2, 97.7) | 50 | 36 | 72.0 | (57.5, 83.8) | 29 | 2 | 6.9 | (0.8, 22.8) |
|  | 16 | 11 | 7 | 63.6 | (30.8, 89.1) | 50 | 34 | 68.0 | (53.3, 80.5) | 29 | 2 | 6.9 | (0.8, 22.8) |
|  | 32 | 11 | 4 | 36.4 | (10.9, 69.2) | 50 | 17 | 34.0 | (21.2, 48.8) | 29 | 0 | 0.0 | (0.0, 11.9) |
|  | 64 | 11 | 2 | 18.2 | (2.3, 51.8) | 50 | 5 | 10.0 | (3.3, 21.8) | 29 | 0 | 0.0 | (0.0, 11.9) |
|  | 128 | 11 | 1 | 9.1 | (0.2, 41.3) | 50 | 1 | 2.0 | (0.1, 10.6) | 29 | 0 | 0.0 | (0.0, 11.9) |
| PMB2707 (B44) Before Vaccination 1 | | | | | | | | | | | | | |
| 12 to <24 Months | 4 | 19 | 0 | 0.0 | (0.0, 17.6) | 95 | 1 | 1.1 | (0.0, 5.7) | 54 | 0 | 0.0 | (0.0, 6.6) |
|  | 8 | 19 | 0 | 0.0 | (0.0, 17.6) | 95 | 1 | 1.1 | (0.0, 5.7) | 54 | 0 | 0.0 | (0.0, 6.6) |
|  | 16 | 19 | 0 | 0.0 | (0.0, 17.6) | 95 | 0 | 0.0 | (0.0, 3.8) | 54 | 0 | 0.0 | (0.0, 6.6) |
|  | 32 | 19 | 0 | 0.0 | (0.0, 17.6) | 95 | 0 | 0.0 | (0.0, 3.8) | 54 | 0 | 0.0 | (0.0, 6.6) |
|  | 64 | 19 | 0 | 0.0 | (0.0, 17.6) | 95 | 0 | 0.0 | (0.0, 3.8) | 54 | 0 | 0.0 | (0.0, 6.6) |
|  | 128 | 19 | 0 | 0.0 | (0.0, 17.6) | 95 | 0 | 0.0 | (0.0, 3.8) | 54 | 0 | 0.0 | (0.0, 6.6) |
| 12 to <18 Months | 4 | 9 | 0 | 0.0 | (0.0, 33.6) | 46 | 1 | 2.2 | (0.1, 11.5) | 24 | 0 | 0.0 | (0.0, 14.2) |
|  | 8 | 9 | 0 | 0.0 | (0.0, 33.6) | 46 | 1 | 2.2 | (0.1, 11.5) | 24 | 0 | 0.0 | (0.0, 14.2) |
|  | 16 | 9 | 0 | 0.0 | (0.0, 33.6) | 46 | 0 | 0.0 | (0.0, 7.7) | 24 | 0 | 0.0 | (0.0, 14.2) |
|  | 32 | 9 | 0 | 0.0 | (0.0, 33.6) | 46 | 0 | 0.0 | (0.0, 7.7) | 24 | 0 | 0.0 | (0.0, 14.2) |
|  | 64 | 9 | 0 | 0.0 | (0.0, 33.6) | 46 | 0 | 0.0 | (0.0, 7.7) | 24 | 0 | 0.0 | (0.0, 14.2) |
|  | 128 | 9 | 0 | 0.0 | (0.0, 33.6) | 46 | 0 | 0.0 | (0.0, 7.7) | 24 | 0 | 0.0 | (0.0, 14.2) |
| 18 to <24 Months | 4 | 10 | 0 | 0.0 | (0.0, 30.8) | 49 | 0 | 0.0 | (0.0, 7.3) | 30 | 0 | 0.0 | (0.0, 11.6) |
|  | 8 | 10 | 0 | 0.0 | (0.0, 30.8) | 49 | 0 | 0.0 | (0.0, 7.3) | 30 | 0 | 0.0 | (0.0, 11.6) |
|  | 16 | 10 | 0 | 0.0 | (0.0, 30.8) | 49 | 0 | 0.0 | (0.0, 7.3) | 30 | 0 | 0.0 | (0.0, 11.6) |
|  | 32 | 10 | 0 | 0.0 | (0.0, 30.8) | 49 | 0 | 0.0 | (0.0, 7.3) | 30 | 0 | 0.0 | (0.0, 11.6) |
|  | 64 | 10 | 0 | 0.0 | (0.0, 30.8) | 49 | 0 | 0.0 | (0.0, 7.3) | 30 | 0 | 0.0 | (0.0, 11.6) |
|  | 128 | 10 | 0 | 0.0 | (0.0, 30.8) | 49 | 0 | 0.0 | (0.0, 7.3) | 30 | 0 | 0.0 | (0.0, 11.6) |
| 1 Month after Vaccination 2 | | | | | | | | | | | | | |
| 12 to <24 Months | 4 | 19 | 14 | 73.7 | (48.8, 90.9) | 94 | 64 | 68.1 | (57.7, 77.3) | 52 | 0 | 0.0 | (0.0, 6.8) |
|  | 8 | 19 | 13 | 68.4 | (43.4, 87.4) | 94 | 64 | 68.1 | (57.7, 77.3) | 52 | 0 | 0.0 | (0.0, 6.8) |
|  | 16 | 19 | 13 | 68.4 | (43.4, 87.4) | 94 | 63 | 67.0 | (56.6, 76.4) | 52 | 0 | 0.0 | (0.0, 6.8) |
|  | 32 | 19 | 11 | 57.9 | (33.5, 79.7) | 94 | 53 | 56.4 | (45.8, 66.6) | 52 | 0 | 0.0 | (0.0, 6.8) |
|  | 64 | 19 | 6 | 31.6 | (12.6, 56.6) | 94 | 23 | 24.5 | (16.2, 34.4) | 52 | 0 | 0.0 | (0.0, 6.8) |
|  | 128 | 19 | 2 | 10.5 | (1.3, 33.1) | 94 | 10 | 10.6 | (5.2, 18.7) | 52 | 0 | 0.0 | (0.0, 6.8) |
| 12 to <18 Months | 4 | 9 | 7 | 77.8 | (40.0, 97.2) | 47 | 34 | 72.3 | (57.4, 84.4) | 23 | 0 | 0.0 | (0.0, 14.8) |
|  | 8 | 9 | 7 | 77.8 | (40.0, 97.2) | 47 | 34 | 72.3 | (57.4, 84.4) | 23 | 0 | 0.0 | (0.0, 14.8) |
|  | 16 | 9 | 7 | 77.8 | (40.0, 97.2) | 47 | 34 | 72.3 | (57.4, 84.4) | 23 | 0 | 0.0 | (0.0, 14.8) |

TABLE 27-continued

Subjects Achieving Defined hSBA Titers for Primary Strains - Evaluable Immunogenicity Population

| Strain (Variant) Sampling Time Point Age Strata | Titer | 60 μg rLP2086 | | | | 120 μg rLP2086 | | | | HAV/Saline | | | |
|---|---|---|---|---|---|---|---|---|---|---|---|---|---|
| | | $N^a$ | $n^b$ | % | (95% CI)$^c$ | $N^a$ | $n^b$ | % | (95% CI)$^c$ | $N^a$ | $n^b$ | % | (95% CI)$^c$ |
| | 32 | 9 | 5 | 55.6 | (21.2, 86.3) | 47 | 29 | 61.7 | (46.4, 75.5) | 23 | 0 | 0.0 | (0.0, 14.8) |
| | 64 | 9 | 3 | 33.3 | (7.5, 70.1) | 47 | 13 | 27.7 | (15.6, 42.6) | 23 | 0 | 0.0 | (0.0, 14.8) |
| | 128 | 9 | 1 | 11.1 | (0.3, 48.2) | 47 | 5 | 10.6 | (3.5, 23.1) | 23 | 0 | 0.0 | (0.0, 14.8) |
| 18 to <24 Months | 4 | 10 | 7 | 70.0 | (34.8, 93.3) | 47 | 30 | 63.8 | (48.5, 77.3) | 29 | 0 | 0.0 | (0.0, 11.9) |
| | 8 | 10 | 6 | 60.0 | (26.2, 87.8) | 47 | 30 | 63.8 | (48.5, 77.3) | 29 | 0 | 0.0 | (0.0, 11.9) |
| | 16 | 10 | 6 | 60.0 | (26.2, 87.8) | 47 | 29 | 61.7 | (46.4, 75.5) | 29 | 0 | 0.0 | (0.0, 11.9) |
| | 32 | 10 | 6 | 60.0 | (26.2, 87.8) | 47 | 24 | 51.1 | (36.1, 65.9) | 29 | 0 | 0.0 | (0.0, 11.9) |
| | 64 | 10 | 3 | 30.0 | (6.7, 65.2) | 47 | 10 | 21.3 | (10.7, 35.7) | 29 | 0 | 0.0 | (0.0, 11.9) |
| | 128 | 10 | 1 | 10.0 | (0.3, 44.5) | 47 | 5 | 10.6 | (3.5, 23.1) | 29 | 0 | 0.0 | (0.0, 11.9) |
| 1 Month after Vaccination 3 | | | | | | | | | | | | | |
| 12 to <24 Months | 4 | 19 | 17 | 89.5 | (66.9, 98.7) | 94 | 82 | 87.2 | (78.8, 93.2) | 54 | 0 | 0.0 | (0.0, 6.6) |
| | 8 | 19 | 17 | 89.5 | (66.9, 98.7) | 94 | 81 | 86.2 | (77.5, 92.4) | 54 | 0 | 0.0 | (0.0, 6.6) |
| | 16 | 19 | 16 | 84.2 | (60.4, 96.6) | 94 | 81 | 86.2 | (77.5, 92.4) | 54 | 0 | 0.0 | (0.0, 6.6) |
| | 32 | 19 | 12 | 63.2 | (38.4, 83.7) | 94 | 72 | 76.6 | (66.7, 84.7) | 54 | 0 | 0.0 | (0.0, 6.6) |
| | 64 | 19 | 7 | 36.8 | (16.3, 61.6) | 94 | 55 | 58.5 | (47.9, 68.6) | 54 | 0 | 0.0 | (0.0, 6.6) |
| | 128 | 19 | 4 | 21.1 | (6.1, 45.6) | 94 | 30 | 31.9 | (22.7, 42.3) | 54 | 0 | 0.0 | (0.0, 6.6) |
| 12 to <18 Months | 4 | 9 | 8 | 88.9 | (51.8, 99.7) | 47 | 41 | 87.2 | (74.3, 95.2) | 24 | 0 | 0.0 | (0.0, 14.2) |
| | 8 | 9 | 8 | 88.9 | (51.8, 99.7) | 47 | 41 | 87.2 | (74.3, 95.2) | 24 | 0 | 0.0 | (0.0, 14.2) |
| | 16 | 9 | 7 | 77.8 | (40.0, 97.2) | 47 | 41 | 87.2 | (74.3, 95.2) | 24 | 0 | 0.0 | (0.0, 14.2) |
| | 32 | 9 | 5 | 55.6 | (21.2, 86.3) | 47 | 35 | 74.5 | (59.7, 86.1) | 24 | 0 | 0.0 | (0.0, 14.2) |
| | 64 | 9 | 4 | 44.4 | (13.7, 78.8) | 47 | 27 | 57.4 | (42.2, 71.7) | 24 | 0 | 0.0 | (0.0, 14.2) |
| | 128 | 9 | 2 | 22.2 | (2.8, 60.0) | 47 | 14 | 29.8 | (17.3, 44.9) | 24 | 0 | 0.0 | (0.0, 14.2) |
| 18 to <24 Months | 4 | 10 | 9 | 90.0 | (55.5, 99.7) | 47 | 41 | 87.2 | (74.3, 95.2) | 30 | 0 | 0.0 | (0.0, 11.6) |
| | 8 | 10 | 9 | 90.0 | (55.5, 99.7) | 47 | 40 | 85.1 | (71.7, 93.8) | 30 | 0 | 0.0 | (0.0, 11.6) |
| | 16 | 10 | 9 | 90.0 | (55.5, 99.7) | 47 | 40 | 85.1 | (71.7, 93.8) | 30 | 0 | 0.0 | (0.0, 11.6) |
| | 32 | 10 | 7 | 70.0 | (34.8, 93.3) | 47 | 37 | 78.7 | (64.3, 89.3) | 30 | 0 | 0.0 | (0.0, 11.6) |
| | 64 | 10 | 3 | 30.0 | (6.7, 65.2) | 47 | 28 | 59.6 | (44.3, 73.6) | 30 | 0 | 0.0 | (0.0, 11.6) |
| | 128 | 10 | 2 | 20.0 | (2.5, 55.6) | 47 | 16 | 34.0 | (20.9, 49.3) | 30 | 0 | 0.0 | (0.0, 11.6) |

Abbreviations: hSBA = serum bactericidal assay using human complement.
$^a$N = number of subjects with valid and determinate hSBA titers for the given strain.
$^b$n = Number of subjects with observed hSBA titer ≥ the defined titer for the given strain at the given time point.
$^c$Exact 2-sided CI based upon observed proportion of subjects, using the Clopper and Pearson method.

Exploratory Immunogenicity Endpoints
hSBA Titer ≥4-Fold Increase from Baseline

Table 28 presents the proportion of subjects with hSBA titers with a ≥4-fold rise ≥4 from baseline for the 4 primary MnB test strains.

At 1 month after Vaccination 2, the proportion of subjects 12 to <18 months of age achieving a ≥4-fold rise in hSBA titer from baseline was 80.0% and 62.2% for PMB80 (A22); 100.0% and 97.9% for PMB2001 (A56); 60.0% and 19.0% for PMB2948 (B24); and 77.8% and 70.2% for PMB2707 (B44) for the 60-μg and 120-μg groups, respectively. For the 18 to <24 months age stratum, the proportion of subjects achieving a ≥4-fold rise in hSBA titer from baseline was 66.7% and 80.0% for PMB80 (A22); 90.0% and 100.0% for PMB2001 (A56); 33.3% and 40.9% for PMB2948 (B24); and 60.0% and 61.7% for PMB2707 (B44) for the 60-μg and 120-μg groups, respectively. Overall, for the combined age stratum, the proportion of subjects achieving a ≥4-fold rise in hSBA titer from baseline at 1 month after Vaccination 2 was 73.7% and 71.6% for PMB80 (A22); 94.7% and 98.9% for PMB2001 (A56); 47.4% and 30.2% for PMB2948 (B24); and 68.4% and 66.0% for PMB2707 (B44) for the 60-μg and 120-μg groups, respectively.

At 1 month after Vaccination 3, the proportion of subjects 12 to <18 months of age achieving a ≥4-fold rise in hSBA titer from baseline was 77.8% and 86.7% for PMB80 (A22); 100.0% and 95.7% for PMB2001 (A56); 88.9% and 66.7% for PMB2948 (B24); and 77.8% and 85.1% for PMB2707 (B44) for the 60-μg and 120-μg groups, respectively. For the 18 to <24 months age stratum, the proportion of subjects achieving a ≥4-fold rise in hSBA titer from baseline was 90.9% and 88.2% for PMB80 (A22); 100.0% and 100.0% for PMB2001 (A56); 63.6% and 68.0% for PMB2948 (B24); and 90.0% and 85.1% for PMB2707 (B44) for the 60-μg and 120-μg groups, respectively. Overall, for the combined age stratum, the proportion of subjects achieving a ≥4-fold rise in hSBA titer from baseline at 1 month after Vaccination 3 was 85.0% and 87.5% for PMB80 (A22); 100.0% and 97.9% for PMB2001 (A56); 75.0% and 67.4% for PMB2948 (B24); and 84.2% and 85.1% for PMB2707 (B44) for the 60-μg and 120-μg groups, respectively.

The proportion of subjects in the HAV/saline group (combined age stratum) achieving a ≥4-fold rise in hSBA titer at 1 month after Vaccination 3 was 5.0% for PMB80 (A22), 1.9% for PMB2001 (A56), 3.3% for PMB2948 (B24), and 0.0% for PMB2707 (B44).

TABLE 28

Subjects Achieving ≥4-Fold Rise in hSBA Titer for Primary Strains - Evaluable Immunogenicity Population

| Strain (Variant) | Vaccine Group (as Randomized) | | | | | | | | | | | |
|---|---|---|---|---|---|---|---|---|---|---|---|---|
| Sampling Time Point | 60 μg rLP2086 | | | | 120 μg rLP2086 | | | | HAV/Saline | | | |
| Age Strata | $N^a$ | $n^b$ (%) | (%) | (95% CI)$^c$ | $N^a$ | $n^b$ (%) | (%) | (95% CI)$^c$ | $N^a$ | $n^b$ (%) | (%) | (95% CI)$^c$ |
| PMB80 (A22) | | | | | | | | | | | | |
| 1 Month after Vaccination 2 | | | | | | | | | | | | |
| 12 to <24 Months | 19 | 14 | (73.7) | (48.8, 90.9) | 95 | 68 | (71.6) | (61.4, 80.4) | 59 | 1 | (1.7) | (0.0, 9.1) |
| 12 to <18 Months | 10 | 8 | (80.0) | (44.4, 97.5) | 45 | 28 | (62.2) | (46.5, 76.2) | 30 | 0 | (0.0) | (0.0, 11.6) |
| 18 to <24 Months | 9 | 6 | (66.7) | (29.9, 92.5) | 50 | 40 | (80.0) | (66.3, 90.0) | 29 | 1 | (3.4) | (0.1, 17.8) |
| 1 Month after Vaccination 3 | | | | | | | | | | | | |
| 12 to <24 Months | 20 | 17 | (85.0) | (62.1, 96.8) | 96 | 84 | (87.5) | (79.2, 93.4) | 60 | 3 | (5.0) | (1.0, 13.9) |
| 12 to <18 Months | 9 | 7 | (77.8) | (40.0, 97.2) | 45 | 39 | (86.7) | (73.2, 94.9) | 31 | 1 | (3.2) | (0.1, 16.7) |
| 18 to <24 Months | 11 | 10 | (90.9) | (58.7, 99.8) | 51 | 45 | (88.2) | (76.1, 95.6) | 29 | 2 | (6.9) | (0.8, 22.8) |
| PMB2001 (A56) | | | | | | | | | | | | |
| 1 Month after Vaccination 2 | | | | | | | | | | | | |
| 12 to <24 Months | 19 | 18 | (94.7) | (74.0, 99.9) | 95 | 94 | (98.9) | (94.3, 100.0) | 52 | 0 | (0.0) | (0.0, 6.8) |
| 12 to <18 Months | 9 | 9 | (100.0) | (66.4, 100.0) | 47 | 46 | (97.9) | (88.7, 99.9) | 23 | 0 | (0.0) | (0.0, 14.8) |
| 18 to <24 Months | 10 | 9 | (90.0) | (55.5, 99.7) | 48 | 48 | (100.0) | (92.6, 100.0) | 29 | 0 | (0.0) | (0.0, 11.9) |
| 1 Month after Vaccination 3 | | | | | | | | | | | | |
| 12 to <24 Months | 19 | 19 | (100.0) | (82.4, 100.0) | 95 | 93 | (97.9) | (92.6, 99.7) | 54 | 1 | (1.9) | (0.0, 9.9) |
| 12 to <18 Months | 9 | 9 | (100.0) | (66.4, 100.0) | 47 | 45 | (95.7) | (85.5, 99.5) | 24 | 0 | (0.0) | (0.0, 14.2) |
| 18 to <24 Months | 10 | 10 | (100.0) | (69.2, 100.0) | 48 | 48 | (100.0) | (92.6, 100.0) | 30 | 1 | (3.3) | (0.1, 17.2) |
| PMB2948 (B24) | | | | | | | | | | | | |
| 1 Month after Vaccination 2 | | | | | | | | | | | | |
| 12 to <24 Months | 19 | 9 | (47.4) | (24.4, 71.1) | 86 | 26 | (30.2) | (20.8, 41.1) | 59 | 0 | (0.0) | (0.0, 6.1) |
| 12 to <18 Months | 10 | 6 | (60.0) | (26.2, 87.8) | 42 | 8 | (19.0) | (8.6, 34.1) | 30 | 0 | (0.0) | (0.0, 11.6) |
| 18 to <24 Months | 9 | 3 | (33.3) | (7.5, 70.1) | 44 | 18 | (40.9) | (26.3, 56.8) | 29 | 0 | (0.0) | (0.0, 11.9) |
| 1 Month after Vaccination 3 | | | | | | | | | | | | |
| 12 to <24 Months | 20 | 15 | (75.0) | (50.9, 91.3) | 95 | 64 | (67.4) | (57.0, 76.6) | 60 | 2 | (3.3) | (0.4, 11.5) |
| 12 to <18 Months | 9 | 8 | (88.9) | (51.8, 99.7) | 45 | 30 | (66.7) | (51.0, 80.0) | 31 | 1 | (3.2) | (0.1, 16.7) |
| 18 to <24 Months | 11 | 7 | (63.6) | (30.8, 89.1) | 50 | 34 | (68.0) | (53.3, 80.5) | 29 | 1 | (3.4) | (0.1, 17.8) |
| PMB2707 (B44) | | | | | | | | | | | | |
| 1 Month after Vaccination 2 | | | | | | | | | | | | |
| 12 to <24 Months | 19 | 13 | (68.4) | (43.4, 87.4) | 94 | 62 | (66.0) | (55.5, 75.4) | 52 | 0 | (0.0) | (0.0, 6.8) |
| 12 to <18 Months | 9 | 7 | (77.8) | (40.0, 97.2) | 47 | 33 | (70.2) | (55.1, 82.7) | 23 | 0 | (0.0) | (0.0, 14.8) |
| 18 to <24 Months | 10 | 6 | (60.0) | (26.2, 87.8) | 47 | 29 | (61.7) | (46.4, 75.5) | 29 | 0 | (0.0) | (0.0, 11.9) |
| 1 Month after Vaccination 3 | | | | | | | | | | | | |
| 12 to <24 Months | 19 | 16 | (84.2) | (60.4, 96.6) | 94 | 80 | (85.1) | (76.3, 91.6) | 54 | 0 | (0.0) | (0.0, 6.6) |
| 12 to <18 Months | 9 | 7 | (77.8) | (40.0, 97.2) | 47 | 40 | (85.1) | (71.7, 93.8) | 24 | 0 | (0.0) | (0.0, 14.2) |
| 18 to <24 Months | 10 | 9 | (90.0) | (55.5, 99.7) | 47 | 40 | (85.1) | (71.7, 93.8) | 30 | 0 | (0.0) | (0.0, 11.6) |

Abbreviations: hSBA = serum bactericidal assay using human complement; LLOQ = lower limit of quantitation; LOD = limit of detection;
Note:
LLOQ = 1:16 for A22; 1:8 for A56, B24, and B44.
Note:
The 4-fold increase is defined as follows: (1) For subjects with a baseline hSBA titer below the LOD (hSBA titer <1:4), a response is defined as an hSBA titer ≥1:16 or the LLOQ (whichever titer is higher). (2) For subjects with a baseline hSBA titer ≥ LOD and < LLOQ, a response is defined as an hSBA titer ≥4 times the LLOQ. (3) For subjects with a baseline hSBA titer ≥ LLOQ, a response is defined as an hSBA titer ≥4 times the baseline titer.
$^a$For hSBA titer fold rise ≥4 from baseline, N = number of subjects with valid and determinate hSBA titers for the given strain at both the specified time point and baseline.
$^b$For hSBA titer fold rise ≥4 from baseline, n = number of subjects who achieved hSBA titer fold rise ≥4 from baseline for the given strain.
$^c$Exact 2-sided CI based upon observed proportion of subjects, using the Clopper and Pearson method.

Similar results were observed for the mITT population.

Subgroup analyses of the proportion of subjects achieving a ≥4-fold rise in hSBA titer for each of the 4 primary MnB test strains were assessed for the evaluable immunogenicity population by sex and country. There were no clinically important differences observed in the subgroup analyses performed.

Reverse Cumulative Distribution Curves for the Primary MnB Test Strains

The RCDCs of the proportions of subjects exhibiting an hSBA response LLOQ) for each of the 4 primary MnB test strains and at each sampling time point, for the combined age stratum were assessed for PMB80 [A22], PMB2001 [A56], PMB2948 [B24], and PMB2707 [B44]. The RCDCs showed that the immune responses were higher after Vaccination 2 and Vaccination 3 for the bivalent rLP2086 groups versus the HAV/saline group. The immune responses for the bivalent rLP2086 groups increased with each vaccination.

Immunogenicity Conclusions

The primary objectives of this study were to describe the immune response to bivalent rLP2086 as measured by hSBA against 4 primary MnB test strains, 2 expressing an LP2086 subfamily A protein and 2 expressing an LP2086 subfamily B protein, measured 1 month after the third vaccination in healthy subjects 12 to <18 months of age and 18 to <24 months of age. The description of immune responses for the combined age stratum (12 to <24 months) was a secondary objective. The primary endpoints for the primary objectives were the proportions of subjects in each age stratum achieving hSBA titers ≥LLOQ for each of the 4 primary MnB strains 1 month after the third vaccination.

A robust immune response was observed at both dose levels for toddlers 12 to <18 months of age and for toddlers 18 to <24 months of age, as well as for the combined age stratum (12 to <24 months) 1 month after the third dose of bivalent rLP2086, as confirmed by the proportion of subjects achieving an hSBA titer ≥LLOQ (1:8 for A56, B24 and B44; 1:16 for A22) for each of the 4 primary MnB test strains. For the 60-μg group, the proportion of subjects achieving an hSBA titer ≥LLOQ ranged from 88.9% to 100.0% for the younger toddlers (12 to <18 months) and from 81.8% to 100.0% for the older toddlers (18 to <24 months) after 3 doses. For the 120-μg group, the proportion of subjects achieving an hSBA titer ≥LLOQ ranged from 71.1% to 100.0% for toddlers 12 to <18 months of age and from 72.0% to 100.0% for toddlers 18 to <24 months of age after 3 doses. For the combined age stratum the proportion of subjects achieving an hSBA titer ≥LLOQ for each of the 4 primary MnB test strains 1 month after the third vaccination ranged from 85.0% to 100.0% for the 60-μg group and from 71.6% to 100.0% for the 120-μg group. These findings are further supported by increases in GMTs (range from 4.0 to 8.5 at baseline to 15.1 to 171.4 at 1 month after Vaccination 3) and in the proportion of subjects achieving an hSBA titer ≥1:4 (71.1% to 100.0%) or ≥1:16 (63.6% to 100.0%) against each of the 4 primary MnB test strains after 3 doses of bivalent rLP2086 compared to baseline across both age strata and dose levels. Additionally, the proportion of subjects for the combined age stratum achieving an hSBA fold rise ≥4 from baseline to 1 month after the third vaccination for each of the 4 primary MnB test strains ranged from 67.4% to 100.0% for both dose levels. In conclusion, 3 doses of either 60 μg or 120 μg of bivalent rLP2086 administered on a 0-, 2-, 6-month schedule, induced robust immune responses in toddlers 12 to <24 months of age (both individual and combined age strata).

The secondary objective of the study was to describe immune responses 1 month after the second dose of bivalent rLP2086, as assessed by ≥LLOQ responses, defined hSBA titers, and hSBA GMTs for the 2 age strata and the combined age stratum. For the combined age stratum, the proportion of subjects achieving an hSBA titer ≥LLOQ after the second dose of bivalent rLP2086 (administered 2 months after the first dose) ranged from 57.9% to 94.7% for subjects in the 60-μg group and from 33.7% to 100.0% for subjects in the 120-μg group. Similar results were obtained for the 2 individual age strata with no clinically meaningful differences between the younger and older age strata. These findings are supported by increases in GMTs (range 7.2 to 110.6) over baseline and in the proportion of subjects achieving an hSBA titer ≥1:4 (36.0% to 100.0%) or ≥1:16 (32.6% to 100%) against each of the 4 primary MnB test strains after 2 doses of bivalent rLP2086 compared to baseline across both dose levels for the combined age stratum. Similar results were obtained for the 2 individual age strata.

Additionally, the proportion of subjects for the combined age stratum achieving an hSBA fold rise ≥4 from baseline to 1 month after the second vaccination for each of the 4 primary MnB test strains ranged from 30.2% to 98.9%. In conclusion, 2 doses of either 60 μg or 120 μg of bivalent rLP2086 administered 2 months apart induced immune responses in toddlers 12 to <24 months of age (both individual and combined age strata).

In summary, at both the 60-μg and 120-μg dose levels, bivalent rLP2086 given as 3 doses on a 0-, 2-, and 6-month schedule elicits a robust immune response among toddlers 12 to <24 months of age with protective antibody titers achieved as measured by hSBA in a high proportion of subjects after the third dose.

Discussion and Overall Conclusions

Immunogenicity Discussion.

Immunogenicity results from this Phase 2 study of a 3-dose regimen (0-, 2-, and 6-month schedule) of bivalent rLP2086 (at 2 dose levels) given to toddlers 12 to <24 months of age are consistent with previous studies in adolescents and young adults at the 120-μg dose level.

Immunogenicity responses to bivalent rLP2086 vaccination were measured in validated hSBAs using 4 primary MnB test strains, each expressing fHBP variants heterologous to the vaccine component antigens, using criteria more stringent than the accepted correlate of protection (hSBA titer ≥1:4). Based on an hSBA titer ≥LLOQ for the 4 primary MnB test strains 1 month after Vaccination 3, the toddlers participating in this study (at either dose level) had similar immune responses compared to adolescents (10 years to <19 years) participating in Study B1971009 and toddlers and children participating in Study B1971017 (≥24 months to <10 years), with proportions of subjects achieving an hSBA titer ≥LLOQ after the third vaccination (0-, 2-, 6-month schedule) ranging from 71.6% to 100.0% for the 120-μg group (12 to <24 months age) in this study, 87.1% to 99.5% in Study B1971009, and 79.1% to 100.0% in Study B1971017. Clinically meaningful differences in the proportion of subjects achieving an hSBA titer ≥LLOQ for the 4 primary MnB test strains 1 month after Vaccination 3 between these 3 studies are not apparent, despite the fact that Study B1971009 had a much higher proportion of adolescent subjects with a prevaccination hSBA titer ≥LLOQ compared to the toddlers in this study. Bivalent rLP2086 appears to be highly immunogenic in the 12 to <24 months age population and is likely to offer protection against MnB infection similarly to that expected for adolescents based on the hSBA correlate of protection. After 3 doses for the individual age strata and for both age strata combined, responses to the 60-μg dose level were not meaningfully different than responses to the 120-μg dose level.

With regard to the secondary objectives, immune responses in this study for the combined age stratum (12 to <24 months) 1 month after the second dose of bivalent rLP2086 (either dose level), the proportion of subjects achieving an hSBA titer ≥LLOQ ranged from 33.7% to 100.0% compared to adolescents (10 years to <19 years) participating in Study B1971009 receiving 2 doses of bivalent rLP2086 given 2 months apart, which ranged from 64.2% to 99.1% and toddlers and children (≥24 months to <10 years) participating in Study B1971017 which ranged from 48.5% to 100.0%. For both age strata and the combined age stratum, immune responses after 2 doses of 60 μg bivalent rLP2086 were not meaningfully different than responses following 2 doses of 120 μg bivalent rLP2086. It should be noted that the smaller sample size in the 60-μg group make definitive conclusions difficult when comparing response rates between 60-μg and 120-μg dose levels.

In summary, at both the 60-μg and 120-μg dose levels, bivalent rLP2086 administered on a 0-, 2-, and 6-month schedule is highly immunogenic among toddlers 12 to <24 months of age with protective immune responses achieved as measured by hSBA in a high proportion of subjects after the third dose. Immune responses, as measured in this study, appear to be similar to that observed in prior studies among adolescents and children 1 month after the third dose. The 3-dose regimen appears to provide high rates of protective immunity in toddlers 12 to <24 months of age.

Overall Conclusions.

In conclusion, the 60-µg and 120-µg dose levels of bivalent rLP2086 when administered to toddlers 12 to <24 months of age on a 0-, 2-, and 6-month schedule elicit protective antibody titers after the third dose as measured by hSBAs. The vaccine, as administered in this study, was safe and well tolerated with an acceptable safety profile for toddlers 12 to <24 months of age.

Example 22: Assessment of the *Neisseria meningitidis* Serogroup B Immunogenicity of Mn Pentavalent and Trumenba® Vaccines in CBA/J Mice The immune response to *Neisseria meningitidis* serogroup B fHBP following vaccination with either bivalent Mn B fHBP vaccine, Trumenba, or the bivalent Mn B fHBP vaccine formulated with quadrivalent ACWY polysaccharide conjugate vaccine (Mn Pentavalent ABCWY) was evaluated in CBA/J mice. Groups of CBA/J mice were immunized with 3 different vaccines: Pentavalent (ABCYW), Trumenba® (MnB) and Nimenrix® (ACYW) (Table 29).

TABLE 29

Study Design: Dose Levels for each Vaccine

| | Dose Levels, µg/0.25 mL Dose | | | |
|---|---|---|---|---|
| Dilution Factor | Mn Pentavalent (ABCWY) | TRUMENBA ® (B) | NIMENRIX ® (ACWY) | AlPO$_4$ (diluent) |
| 1 | 8 + 1.33 | 8 | 1.33 | 125 |
| 2 | 4 + 0.67 | 4 | 0.67 | 125 |
| 4 | 2 + 0.33 | 2 | 0.33 | 125 |
| 8 | 1 + 0.17 | 1 | 0.17 | 125 |

For each arm, CBA/J mice (25/group) were subcutaneously immunized in the scruff of the neck using 2-fold dilution dose levels of the respective vaccine (Table 29). Mice were primed with the vaccine at time 0 and boosted at week 2. Sera were collected PD2 at week 3 for testing using two different serum bactericidal assays that utilized human complement (hSBA). One hSBA used an fHBP subfamily A expressing strain (M98250771) and the other an fHBP subfamily B expressing strain (CDC1127).

The hSBA measures antibody-dependent, complement mediated bactericidal activity against *N meningitidis* serogroup B strains. Briefly, test sera at the appropriate dilution were mixed in 96-well microtiter assay plates with freshly prepared bacterial cultures of the *N meningitidis* B strains (subfamily A or B) and human complement. Assay plates were placed on an orbital shaker and mixed for 30 min in a humidified incubator (37° C./5% CO$_2$). Subsequently, aliquots of the assay reaction from each well were transferred to 96-well filter plates for enumeration of surviving bacteria.

Response rates to vaccination were calculated as the percentage of mice in each dosing group (n=25) that respond in hSBAs. When tested at a predetermined dilution level, mouse serum samples that kill ≥50% of the T$_{30}$ control meningococcal bacteria are considered responders. The T$_{30}$ control wells contain bacteria and complement but no test serum and are counted at the end of the 30 minute assay incubation.

Table 30 and Table 31 show comparable dose-dependent response rates induced by either TRUMENBA® or Mn Pentavalent for both subfamily A and subfamily B of the *N meningitidis* serotype B strains. As expected, NIMENRIX™ did not induce a functional immune response to Mn B strains.

TABLE 30

Subfamily A hSBA responses (% responders)

| Dilution Factor [a] | TRUMENBA | NIMENRIX | Penta |
|---|---|---|---|
| 8 | 24% | 0% | 8% |
| 4 | 40% | 0% | 16% |
| 2 | 52% | 0% | 56% |
| 1 | 80% | 0% | 92% |

[a] See corresponding dose levels in Table 29

TABLE 31

Subfamily B hSBA responses (% responders)

| Dilution Factor [a] | TRUMENBA | NIMENRIX | Penta |
|---|---|---|---|
| 8 | 28% | 0% | 36% |
| 4 | 56% | 0% | 60% |
| 2 | 60% | 0% | 76% |
| 1 | 72% | 0% | 76% |

[a] See corresponding dose levels in Table 29

The following clauses describe additional embodiments of the invention:

C1. A composition comprising a polypeptide and a *Neisseria meningitidis* serogroup A (MenA) capsular saccharide conjugate; a *Neisseria meningitidis* serogroup C (MenC) capsular saccharide conjugate; a *Neisseria meningitidis* serogroup W$_{135}$ (MenW) capsular saccharide conjugate; and a *Neisseria meningitidis* serogroup Y (MenY) capsular saccharide conjugate.

C2. The composition of clause C1, wherein the MenA capsular saccharide is conjugated to a carrier protein; the MenC capsular saccharide is conjugated to a carrier protein; the MenW capsular saccharide is conjugated to a carrier protein; and the MenY capsular saccharide is conjugated to a carrier protein.

C3. The composition of clause C1, wherein the composition further includes a *Neisseria meningitidis* serogroup X (MenX) capsular saccharide conjugate.

C4. The composition of clause C1, wherein the polypeptide is a factor H binding protein (fHBP).

C5. The composition of clause C1, wherein the polypeptide comprises an amino acid sequence having at least 70% identity to the amino acid sequence set forth in any one of SEQ ID NO: 1, SEQ ID NO: 2, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO:

48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

C6. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2; and
 c. a *Neisseria meningitidis* serogroup A (MenA) capsular saccharide conjugated to a carrier protein.

C7. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2; and
 c. a *Neisseria meningitidis* serogroup C (MenC) capsular saccharide conjugated to a carrier protein.

C8. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2; and
 c. a *Neisseria meningitidis* serogroup W-135 (MenW) capsular saccharide conjugated to a carrier protein.

C9. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2; and
 c. a *Neisseria meningitidis* serogroup Y (MenY) capsular saccharide conjugated to a carrier protein.

C10. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2;
 c. a *Neisseria meningitidis* serogroup A (MenA) capsular saccharide conjugated to a carrier protein;
 d. a *Neisseria meningitidis* serogroup C (MenC) capsular saccharide conjugated to a carrier protein;
 e. a *Neisseria meningitidis* serogroup $W_{135}$ (MenW) capsular saccharide conjugated to a carrier protein; and
 f. a *Neisseria meningitidis* serogroup Y (MenY) capsular saccharide conjugated to a carrier protein.

C11. A composition comprising
 a. a first lipidated polypeptide comprising the amino acid sequence set forth in SEQ ID NO: 1;
 b. a second lipidated polypeptide comprising the amino acid sequence set forth in SEQ ID NO: 2;
 c. a *Neisseria meningitidis* serogroup A (MenA) capsular saccharide conjugated to tetanus toxoid carrier protein (TT);
 d. a *Neisseria meningitidis* serogroup C (MenC) capsular saccharide conjugated to tetanus toxoid carrier protein (TT);
 e. a *Neisseria meningitidis* serogroup $W_{135}$ (MenW) capsular saccharide conjugated to tetanus toxoid carrier protein (TT); and
 f. a *Neisseria meningitidis* serogroup Y (MenY) capsular saccharide conjugated to tetanus toxoid carrier protein (TT).

C12. The composition according to clause C1, wherein the MenA capsular saccharide is conjugated to an adipic acid dihydrazide (ADH) linker by 1-cyano-4-dimethylamino pyridinium tetrafluoroborate chemistry, and wherein the linker is conjugated to tetanus toxoid carrier protein (TT) by carbodiimide chemistry (MenA$_{AH}$-TT conjugate).

C13. The composition according to clause C1, wherein the MenC capsular saccharide is conjugated to an ADH linker by 1-cyano-4-dimethylamino pyridinium tetrafluoroborate chemistry, and wherein the linker is conjugated to tetanus toxoid carrier protein (TT) by carbodiimide chemistry (MenC$_{AH}$-TT conjugate).

C14. The composition according to clause C1, wherein the MenW capsular saccharide is directly conjugated to tetanus toxoid carrier protein (TT) by 1-cyano-4-dimethylamino pyridinium tetrafluoroborate chemistry, in the absence of a linker (MenW-TT conjugate).

C15. The composition according to clause C1, wherein the MenY capsular saccharide is directly conjugated to tetanus toxoid carrier protein (TT) by 1-cyano-4-dimethylamino pyridinium tetrafluoroborate chemistry, in the absence of a linker (MenY-TT conjugate).

C16. The composition according to clause C1, further comprising Tris-HCl.

C17. The composition according to clause C1, further comprising sodium chloride.

C18. The composition according to clause C1, further comprising sucrose.

C19. The composition according to clause C1, further comprising Histidine.

C20. The composition according to clause C1, further comprising polysorbate 80.

C21. The composition according to clause C1, further comprising aluminum.

C22. The composition according to clause C1, further comprising aluminum phosphate.

C23. The composition according to clause C1, wherein the composition comprises about 120 μg/ml of the first polypeptide; about 120 μg/ml of the second polypeptide; about 0.5 mg/ml aluminum as aluminum phosphate; about 0.02 mg polysorbate-80; about 10 mM histidine; and about 150 mM sodium chloride.

C24. The composition according to clause C1, wherein the composition comprises about 60 μg of the first polypeptide; about 60 μg of the second polypeptide; about 5 μg of the MenA capsular saccharide conjugated to about 7.5 μg TT; about 5 μg of the MenC capsular saccharide conjugated to about 7.5 μg TT; about 5 μg of the MenW capsular saccharide conjugated to about 3.75 μg TT; about 5 μg of the MenY capsular saccharide conjugated to about 3.25 μg TT; about 97 μg Tris-HCl, pH 6.8±0.3; 4.69-4.71 mg of sodium chloride; about 28 mg of sucrose; about 0.78 mg of L-Histidine; about 0.02 mg polysorbate-80; about 0.25 mg aluminum; and further comprising 0.5 mL water, per dose.

C25. The composition according to clause C1, wherein the composition is suitable for use in a patient aged 12 to <18 Months or 18 to <24 Months.

C26. The composition according to clause C1, wherein the composition is suitable for use in a patient aged 18 to <24 Months.

C27. The composition according to clause C1, wherein the composition is suitable for use in a patient aged ≥24 Months to <10 Years.

C28. The composition according to clause C20, wherein the composition comprises at least 0.010 mg polysorbate-80 and at most 0.018 mg polysorbate-80.

C29. The composition according to clause C20, wherein the composition comprises at least 0.01 mg polysorbate-80 and at most 0.02 mg polysorbate-80.

C30. The composition according to clause C1, wherein the composition does not further comprise a polypeptide having less than 100% sequence identity to SEQ ID NO: 1.
C31. The composition according to clause C1, wherein the first polypeptide has a total of 258 amino acids.
C32. The composition according to clause C1, wherein the composition does not further comprise a polypeptide having less than 100% sequence identity to SEQ ID NO: 2.
C33. The composition according to clause C1, wherein the second polypeptide has a total of 261 amino acids.
C34. The composition according to clause C1, wherein the composition comprises at most two lipidated polypeptides.
C35. The composition according to clause C1, wherein the composition does not comprise a hybrid protein.
C36. The composition according to clause C1, wherein the composition does not comprise a chimeric protein.
C37. The composition according to clause C1, wherein the composition does not comprise a fusion protein.
C38. The composition according to clause C1, wherein the composition is not lyophilized.
C39. The composition according to clause C1, wherein the composition does not comprise formaldehyde.
C40. The composition according to clause C1, wherein the composition does not comprise diphtheria toxoid or CRM.
C41. The composition according to clause C1, wherein the composition does not comprise a MenA capsular saccharide in the absence of an adipic acid dihydrazide (ADH) linker.
C42. The composition according to clause C1, wherein the composition does not comprise a MenC capsular saccharide in the absence of an adipic acid dihydrazide (ADH) linker.
C43. The composition according to clause C1, wherein the composition is a liquid composition.
C44. The composition according to clause C1, wherein the composition does not further comprise any one of the following immunogenic compositions: MENACTRA®, MENVEO®, ADACEL®, HAVRIX®, GARDASIL®, REPEVAX, or any combination thereof.
C45. The composition according to clause C1, wherein the composition does not further comprise a meningococcal A, C, Y and W-135 polysaccharide conjugate (MCV4) composition, wherein the carrier protein is diphtheria toxoid.
C46. The composition according to clause C1, wherein the composition does not further comprise a meningococcal A, C, Y and W-135 polysaccharide conjugate (MCV4) composition, wherein the carrier protein is CRM197.
C47. The composition according to clause C1, wherein the composition does not further comprise a NIMENRIX vaccine.
C48. The composition according to clause C1, wherein the composition does not further comprise a NIMENRIX vaccine, wherein NIMENRIX comprises of a diluent consisting of sodium chloride and water.
C49. A kit comprising (a) a first composition comprising a lipidated MenB rLP2086 subfamily A polypeptide and a lipidated MenB rLP2086 subfamily B polypeptide; and (b) a second composition comprising a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup $W_{135}$ (MenW) capsular saccharide conjugated to tetanus toxoid carrier protein (TT); and a *Neisseria meningitidis* serogroup Y (MenY) capsular saccharide conjugated to tetanus toxoid carrier protein (TT).
C50. The kit according to clause C49, wherein the first composition is a liquid composition and the second composition is a lyophilized composition.
C51. The kit according to clause C49, wherein the lyophilized composition does not comprise polysorbate 80.
C52. The kit according to clause C49, wherein the kit does not further comprise any one of the following immunogenic compositions: MENACTRA®, MENVEO®, ADACEL®, HAVRIX®, GARDASIL®, REPEVAX, or any combination thereof.
C53. The kit according to clause C49, wherein the kit does not further comprise a meningococcal A, C, Y and W-135 polysaccharide conjugate (MCV4) composition, wherein the carrier protein is diphtheria toxoid.
C54. The kit according to clause C49, wherein the kit does not further comprise a meningococcal A, C, Y and W-135 polysaccharide conjugate (MCV4) composition, wherein the carrier protein is CRM197.
C55. The kit according to clause C49, wherein the kit does not further comprise a NIMENRIX vaccine.
C56. The kit according to clause C49, wherein the kit does not further comprise a NIMENRIX® vaccine, wherein NIMENRIX® comprises of a diluent consisting of sodium chloride and water.
C57. A kit comprising:
  a. a liquid composition comprising
    i. a first lipidated polypeptide comprising the amino acid sequence set forth in SEQ ID NO: 1; and
    ii. a second lipidated polypeptide comprising the amino acid sequence set forth in SEQ ID NO: 2; and
  b. a lyophilized composition comprising
    i. a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenA$_{AH}$-TT conjugate);
    ii. a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate);
    iii. a *Neisseria meningitidis* serogroup $W_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); and
    iv. a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).
C58. The kit according to clause C57, wherein the liquid composition further comprises sodium chloride.
C59. The kit according to clause C57, wherein the liquid composition further comprises L-Histidine.
C60. The kit according to clause C57, wherein the liquid composition further comprises polysorbate 80.

C61. The kit according to clause C57, wherein the liquid composition further comprises aluminum phosphate.

C62. The kit according to clause C57, wherein the liquid composition does not further comprise Tris-HCl.

C63. The kit according to clause C57, wherein the liquid composition does not further comprise sucrose.

C64. The kit according to clause C57, wherein the lyophilized composition further comprises sodium chloride.

C65. The kit according to clause C57, wherein the lyophilized composition does not comprise polysorbate-80.

C66. The kit according to clause C60, wherein the liquid composition comprises at least 0.010 mg polysorbate-80 and at most 0.018 mg polysorbate-80.

C67. The kit according to clause C60, wherein the liquid composition comprises at least 0.010 mg polysorbate-80 and at most 0.02 mg polysorbate-80.

C68. An immunogenic composition comprising:
  a. a liquid composition comprising (i) a first lipidated polypeptide comprising the amino acid sequence set forth in SEQ ID NO: 1; and (ii) a second lipidated polypeptide comprising the amino acid sequence set forth in SEQ ID NO: 2; and
  b. a lyophilized composition comprising
    i. a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenAAH-TT conjugate);
    ii. a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate);
    iii. a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); and
    iv. a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).

C69. The immunogenic composition according to clause C68, wherein the lyophilized composition is reconstituted with the liquid composition.

C70. The immunogenic composition according to clause C68, wherein the liquid composition further comprises histidine.

C71. The immunogenic composition according to clause C68, wherein the liquid composition further comprises polysorbate-80.

C72. The immunogenic composition according to clause C68, wherein the liquid composition further comprises aluminum phosphate.

C73. The immunogenic composition according to clause C68, wherein the liquid composition further comprises sodium chloride.

C74. The immunogenic composition according to clause C68, wherein the composition is suitable for use in a patient aged 12 to <18 Months or 18 to <24 Months.

C75. The immunogenic composition according to clause C68, wherein the composition is suitable for use in a patient aged 18 to <24 Months.

C76. The immunogenic composition according to clause C68, wherein the composition is suitable for use in a patient aged ≥24 Months to <10 Years.

C77. An immunogenic composition comprising:
  a. a liquid composition comprising (i) a first lipidated polypeptide comprising the amino acid sequence set forth in SEQ ID NO: 1; and (ii) a second lipidated polypeptide comprising the amino acid sequence set forth in SEQ ID NO: 2; and
  b. a lyophilized composition comprising
    i. a *Neisseria meningitidis* serogroup A (MenA) capsular saccharide conjugated to an adipic acid dihydrazide (ADH) linker by 1-cyano-4-dimethylamino pyridinium tetrafluoroborate chemistry, wherein the linker is conjugated to tetanus toxoid carrier protein (TT) by carbodiimide chemistry (MenAAH-TT conjugate);
    ii. a *Neisseria meningitidis* serogroup C (MenC) capsular saccharide conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate);
    iii. a *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate); and
    iv. a *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate)
    wherein the lyophilized composition is reconstituted with the liquid composition to produce the immunogenic composition.

C78. The immunogenic composition according to clause C77, wherein the liquid composition further comprises aluminum.

C79. The immunogenic composition according to clause C77, wherein the liquid composition further comprises aluminum phosphate.

C80. The immunogenic composition according to clause C77, wherein the lyophilized composition further comprises sodium chloride.

C81. The immunogenic composition according to clause C77, wherein the immunogenic composition comprises at least 0.010 mg polysorbate-80 and at most 0.018 mg polysorbate-80.

C82. The immunogenic composition according to clause C77, wherein the immunogenic composition comprises at least 0.01 mg polysorbate-80 and at most 0.02 mg polysorbate-80.

C83. The immunogenic composition according to clause C77, wherein the lyophilized composition does not contain aluminum.

C84. The immunogenic composition according to clause C78, wherein the first polypeptide and the second polypeptide are bound to the aluminum.

C85. The immunogenic composition according to clause C78, wherein the first polypeptide and the second polypeptide are bound to the aluminum in the immunogenic composition.

C86. The immunogenic composition according to clause C78, wherein the concentration of polypeptides bound to the aluminum in the immunogenic composition is not decreased after 24 hours, as compared to the concentration of polypeptides bound to the aluminum in the liquid composition prior to reconstituting the lyophilized composition.

C87. The immunogenic composition according to clause C77, wherein the concentration of MenA$_{AH}$-TT conjugate in the immunogenic composition is not decreased after 24 hours, as compared to the concentration of the MenA$_{AH}$-TT conjugate in the lyophilized composition.

C88. The immunogenic composition according to clause C77, wherein the concentration of MenC$_{AH}$-TT conjugate in the immunogenic composition is not decreased after 24 hours, as compared to the concentration of the MenC$_{AH}$-TT conjugate in the lyophilized composition.

C89. The immunogenic composition according to clause C77, wherein the concentration of MenW-TT conjugate in the immunogenic composition is not decreased after 24 hours, as compared to the concentration of the MenW-TT conjugate in the lyophilized composition.

C90. The immunogenic composition according to clause C77, wherein the concentration of MenY-TT conjugate in the immunogenic composition is not decreased after 24 hours, as compared to the concentration of the MenY-TT conjugate in the lyophilized composition.

C91. The immunogenic composition according to clause C86, wherein the concentration is decreased by at most 1% after 24 hours, as compared to the respective concentration in the liquid composition prior to reconstitution.

C92. The immunogenic composition according to clause C86, wherein the concentration is decreased by at most 5% after 24 hours, as compared to the respective concentration in the liquid composition prior to reconstitution.

C93. The immunogenic composition according to clause C86, wherein the concentration is decreased by at most 10% after 24 hours, as compared to the respective concentration in the liquid composition prior to reconstitution.

C94. The immunogenic composition according to clause C87-C90, wherein the concentration is decreased by at most 1% after 24 hours, as compared to the respective concentration in the lyophilized composition prior to reconstitution.

C95. The immunogenic composition according to clause C87-C90, wherein the concentration is decreased by at most 5% after 24 hours, as compared to the respective concentration in the lyophilized composition prior to reconstitution.

C96. The immunogenic composition according to clause C87-C90, wherein the concentration is decreased by at most 10% after 24 hours, as compared to the respective concentration in the lyophilized composition prior to reconstitution.

C97. The immunogenic composition according to clause C68 or clause C77, wherein the pH of the reconstituted immunogenic composition is less than the pH of the lyophilized composition, when reconstituted with sodium chloride.

C98. A composition comprising a) a first lipidated polypeptide comprising the amino acid sequence set forth in SEQ ID NO: 1, and b) a second lipidated polypeptide comprising the amino acid sequence set forth in SEQ ID NO: 2.

C99. The composition according to clause C98, wherein the composition further comprises polysorbate-80, aluminum, histidine, and sodium chloride.

C100. The composition according to clause C98, wherein the composition comprises 60 µg of the first lipidated polypeptide and 60 µg of the second lipidated polypeptide.

C101. A method of inducing a bactericidal immune response against a *Neisseria meningitidis* serogroup B subfamily A strain and against a *Neisseria meningitidis* serogroup B subfamily B strain in human, comprising administering to the human an effective amount of the composition according to clause C1.

C102. A method of inducing a bactericidal immune response against a *Neisseria meningitidis* serogroup B subfamily A strain and against a *Neisseria meningitidis* serogroup B subfamily B strain in human, comprising administering to the human an effective amount of the composition according to clause C68.

C103. A method of inducing a bactericidal immune response against a *Neisseria meningitidis* serogroup B subfamily A strain and against a *Neisseria meningitidis* serogroup B subfamily B strain in human, comprising administering to the human an effective amount of the composition according to clause C77.

C104. A method of inducing a bactericidal immune response against a *Neisseria meningitidis* serogroup A, a *Neisseria meningitidis* serogroup C, a *Neisseria meningitidis* serogroup W, and/or a *Neisseria meningitidis* serogroup Y strain in a human, comprising administering to the human an effective amount of the composition according to clause C1.

C105. A method of inducing a bactericidal immune response against a *Neisseria meningitidis* serogroup A, a *Neisseria meningitidis* serogroup C, a *Neisseria meningitidis* serogroup W, and/or a *Neisseria meningitidis* serogroup Y strain in a human, comprising administering to the human an effective amount of the composition according to clause C68.

C106. A method of inducing a bactericidal immune response against a *Neisseria meningitidis* serogroup A, a *Neisseria meningitidis* serogroup C, a *Neisseria meningitidis* serogroup W, and/or a *Neisseria meningitidis* serogroup Y strain in a human, comprising administering to the human an effective amount of the composition according to clause C77.

C107. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, and/or a *Neisseria meningitidis* serogroup Y strain in a human, comprising administering to the human an effective amount of the composition according to clause C1.

C108. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, and/or a *Neisseria meningitidis* serogroup Y strain in a human, comprising administering to the human an effective amount of the composition according to clause C68.

C109. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, and/or a *Neisseria meningitidis* serogroup Y strain in a human, comprising administering to the human an effective amount of the composition according to clause C77.

C110. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and a *Neisseria meningitidis* serogroup X strain in a human, comprising administering to the human an effective amount of the composition according to clause C1.

C111. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and a *Neisseria meningitidis* serogroup X strain in a human, comprising administering to the human an effective amount of the composition according to clause C68.

C112. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and a *Neisseria meningitidis* serogroup X strain in a human, comprising administering to the human an effective amount of the composition according to clause C77.

C113. A method of inducing a bactericidal immune response against a *Neisseria meningitidis* serogroup A, *Neisseria meningitidis* serogroup B, a *Neisseria meningitidis* serogroup C, a *Neisseria meningitidis* serogroup W, a *Neisseria meningitidis* serogroup Y strain, and a *Neisseria meningitidis* serogroup X strain in a human, comprising administering to the human an effective amount of the composition according to clause C98.

C114. A method of inducing a bactericidal immune response against *N. meningitidis* serogroup C strain expressing factor H binding protein A10 in a human, the method comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C115. A method of inducing a bactericidal immune response against *N. meningitidis* serogroup W strain expressing factor H binding protein A10 in a human, comprising administering to the human a composition comprising a polypeptide comprising the amino acid sequence set forth in SEQ ID NO: 1.

C116. A method of inducing a bactericidal immune response against *N. meningitidis* serogroup W strain expressing factor H binding protein A19 in a human, comprising administering to the human a composition comprising a polypeptide comprising the amino acid sequence set forth in SEQ ID NO: 1.

C117. A method of inducing a bactericidal immune response against *N. meningitidis* serogroup A strain expressing factor H binding protein B16 in a human, comprising administering to the human a composition comprising a polypeptide comprising the amino acid sequence set forth in SEQ ID NO: 2.

C118. A method of inducing a bactericidal immune response against *N. meningitidis* serogroup Y strain expressing factor H binding protein B47 in a human, comprising administering to the human a composition comprising a polypeptide comprising the amino acid sequence set forth in SEQ ID NO: 2.

C119. A method of inducing a bactericidal immune response against *N. meningitidis* serogroup C strain expressing factor H binding protein A10 in a human, the method comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C120. A method of inducing a bactericidal immune response against *N. meningitidis* serogroup W strain expressing factor H binding protein A10 in a human, comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C121. A method of inducing a bactericidal immune response against *N. meningitidis* serogroup W strain expressing factor H binding protein A19 in a human, comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C122. A method of inducing a bactericidal immune response against *N. meningitidis* serogroup A strain expressing factor H binding protein B16 in a human, comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C123. A method of inducing a bactericidal immune response against *N. meningitidis* serogroup Y strain expressing factor H binding protein B47 in a human, comprising administering to the human a composition comprising a first lipidated polypeptide comprising the amino acid sequence set forth in SEQ ID NO: 1; a second lipidated polypeptide comprising the amino acid sequence set forth in SEQ ID NO: 2

C124. A method of inducing a bactericidal immune response against a *Neisseria meningitidis* serogroup X strain in a human, comprising administering to the human an effective amount of a polypeptide having at least 70% identity to the amino acid sequence selected from the group consisting of SEQ ID NO: 1, SEQ ID NO: 2, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62.

C125. A method of inducing a bactericidal immune response against a *Neisseria meningitidis* serogroup X strain in a human, comprising administering to the human an effective amount of the composition according to clause C1.

C126. A method of inducing a bactericidal immune response against a *Neisseria meningitidis* serogroup X strain in a human, comprising administering to the human an effective amount of the composition according to clause C68.

C127. A method of inducing a bactericidal immune response against a *Neisseria meningitidis* serogroup X strain in a human, comprising administering to the human an effective amount of the composition according to clause C77.

C128. A method of inducing a bactericidal immune response against a *Neisseria meningitidis* serogroup X strain in a human, comprising administering to the human an effective amount of the composition according to clause C98.

C129. A method of inducing a bactericidal immune response against *N. meningitidis* serogroup X strain expressing factor H binding protein B49 in a human, comprising administering to the human a composition according to clause C98.

C130. A method of inducing a bactericidal immune response against *N. meningitidis* serogroup X strain expressing factor H binding protein B49 in a human, comprising administering to the human a composition comprising a first lipidated polypeptide comprising the amino acid sequence set forth in SEQ ID NO: 1; a second lipidated polypeptide comprising the amino acid sequence set forth in SEQ ID NO: 2.

C131. The method according to any one of clauses C101-C130, wherein the composition induces a bactericidal titer of serum immunoglobulin that is at least 2-fold higher in the human after receiving the first dose than a bactericidal titer of serum immunoglobulin in the human prior to receiving the first dose, when measured under identical conditions in a serum bactericidal assay using human complement.

C132. The method according to any one of clauses C101-C130, wherein the composition induces a bactericidal titer of serum immunoglobulin that is at least 4-fold higher in the human after receiving the first dose than a bactericidal titer of serum immunoglobulin in the human prior to receiving the first dose, when measured under identical conditions in a serum bactericidal assay using human complement.

C133. The method according to any one of clauses C101-C132, wherein the composition induces a bactericidal titer of serum immunoglobulin that is at least 8-fold higher in the human after receiving the first dose than a bactericidal titer of serum immunoglobulin in the human prior to receiving the first dose, when measured under identical conditions in a serum bactericidal assay using human complement.

C134. The method according to any one of clauses C101-C132, wherein the patient is aged 12 to <18 Months or 18 to <24 Months.

C135. The method according to any one of clauses C101-C132, wherein the patient is aged 18 to <24 Months.

C136. The method according to any one of clauses C101-C132, wherein the patient is aged ≥24 Months to <10 Years.

C137. A method for eliciting an immune response in a patient, comprising: (a) administering an immunogenic composition to the patient when the patient is aged between 12 and 18 months; wherein the immunogenic composition comprises a first lipidated polypeptide comprising the amino acid sequence set forth in SEQ ID NO: 1; and a second lipidated polypeptide comprising the amino acid sequence set forth in SEQ ID NO: 2.

C138. A method for eliciting an immune response in a patient, comprising: (a) administering an immunogenic composition to the patient when the patient is aged between 18 and 24 months; wherein the immunogenic composition comprises a first lipidated polypeptide comprising the amino acid sequence set forth in SEQ ID NO: 1; and a second lipidated polypeptide comprising the amino acid sequence set forth in SEQ ID NO: 2.

C139. A method for eliciting an immune response in a patient, comprising: (a) administering an immunogenic composition to the patient when the patient is aged between 24 months and 10 years; wherein the immunogenic composition comprises a first lipidated polypeptide comprising the amino acid sequence set forth in SEQ ID NO: 1; and a second lipidated polypeptide comprising the amino acid sequence set forth in SEQ ID NO: 2.

C140. The method according to any one of clauses C137-C139, wherein the composition further comprises polysorbate-80, aluminum, histidine, and sodium chloride.

---

What is claimed is:

1. A kit comprising (a) a first composition comprising aluminum, a lipidated MenB rLP2086 subfamily A polypeptide set forth as SEQ ID NO: 1 and a lipidated MenB rLP2086 subfamily B polypeptide set forth as SEQ ID NO: 2; and (b) a second composition comprising a *Neisseria meningitidis* serogroup A (MenA) capsular saccharide conjugated to tetanus toxoid carrier protein (TT); a *Neisseria meningitidis* serogroup C (MenC) capsular saccharide conjugated to tetanus toxoid carrier protein (TT); a *Neisseria meningitidis* serogroup W135 (MenW) capsular saccharide conjugated to tetanus toxoid carrier protein (TT); and a *Neisseria meningitidis* serogroup Y (MenY) capsular saccharide conjugated to tetanus toxoid carrier protein (TT).

2. The kit according to claim 1, wherein the first composition is a liquid composition.

3. The kit according to claim 1, wherein the second composition is a lyophilized composition.

4. The kit according to claim 3, wherein the lyophilized composition does not comprise polysorbate 80.

5. The kit according to claim 1, wherein the *Neisseria meningitidis* serogroup A (MenA) capsular saccharide is conjugated to an adipic acid dihydrazide (ADH) linker by 1-cyano-4-dimethylamino pyridinium tetrafluoroborate chemistry, and wherein the linker is conjugated to tetanus toxoid carrier protein (TT) by carbodiimide chemistry (MenA$_{AH}$-TT conjugate).

6. The kit according to claim 1, wherein the *Neisseria meningitidis* serogroup C (MenC) capsular saccharide is conjugated to an ADH linker by 1-cyano-4-dimethylamino pyridinium tetrafluoroborate chemistry, wherein the linker is conjugated to tetanus toxoid carrier protein (TT) by carbodiimide chemistry (MenC$_{AH}$-TT conjugate).

7. The kit according to claim 1, wherein the *Neisseria meningitidis* serogroup W$_{135}$ (MenW) capsular saccharide directly conjugated to tetanus toxoid carrier protein (TT) by 1-cyano-4-dimethylamino pyridinium tetrafluoroborate chemistry, in the absence of a linker (MenW-TT conjugate).

8. The kit according to claim 1, wherein the *Neisseria meningitidis* serogroup Y (MenY) capsular saccharide directly conjugated to tetanus toxoid carrier protein (TT) by 1-cyano-4-dimethylamino pyridinium tetrafluoroborate chemistry, in the absence of a linker (MenY-TT conjugate).

9. The kit according to claim 1, wherein the first composition further comprises sodium chloride.

10. The kit according to claim 1, wherein the first composition further comprises L-Histidine.

11. The kit according to claim 1, wherein the first composition further comprises polysorbate 80.

12. The kit according to claim 11, wherein the molar ratio of the polysorbate-80 to rLP2086 polypeptide is between 1.4 to 4.2.

13. The kit according to claim 1, wherein the first composition comprises aluminum phosphate.

14. The kit according to claim 1, wherein the first composition does not further comprise Tris-HCl.

15. The kit according to claim 1, wherein the first composition does not further comprise sucrose.

16. The kit according to claim 1, wherein the second composition further comprises sodium chloride.

17. The kit according to claim 1, wherein the second composition does not comprise polysorbate-80.

18. The kit according to claim 1, wherein the second composition comprises at least 0.010 mg polysorbate-80 and at most 0.018 mg polysorbate-80.

19. The kit according to claim 1, wherein the second composition comprises at least 0.010 mg polysorbate-80 and at most 0.02 mg polysorbate-80.

* * * * *